US007432378B2

(12) United States Patent
Edwards et al.

(10) Patent No.: US 7,432,378 B2
(45) Date of Patent: Oct. 7, 2008

(54) BENZOIMIDAZOLE COMPOUNDS

(75) Inventors: James P. Edwards, San Diego, CA (US); Michael D. Hack, San Diego, CA (US); David E. Kindrachuk, Cardiff by the Sea, CA (US); Jennifer D. Venable, Solana Beach, CA (US)

(73) Assignee: Janssen Pharmaceutica, N.V. (BE)

( * ) Notice: Subject to any disclaimer, the term of this patent is extended or adjusted under 35 U.S.C. 154(b) by 390 days.

(21) Appl. No.: 10/952,989

(22) Filed: Sep. 29, 2004

(65) Prior Publication Data

US 2005/0070550 A1    Mar. 31, 2005

Related U.S. Application Data

(60) Provisional application No. 60/507,236, filed on Sep. 30, 2003.

(51) Int. Cl.
*C07D 211/68* (2006.01)
*C07D 211/80* (2006.01)
*C07D 213/02* (2006.01)
(52) U.S. Cl. .................................... 546/193
(58) Field of Classification Search ................ 546/193
See application file for complete search history.

(56) References Cited

FOREIGN PATENT DOCUMENTS

WO    WO 00/26192    *    5/2000
WO    WO 00/26192 A       5/2000
WO    WO 02/072548 A      9/2002

OTHER PUBLICATIONS

Anadol, D., et al., Treatment of Hydatid Disease, Paediatric Drugs 2001, 3 (2), 123-135.*
Teggi, A., et al., Therapy of Human Hydatid Disease with Mebendazole and Albendazole, Antimicrobial Agents and Chemotherapy, Aug. 1993, 1679-1684, vol. 37, No. 8.*
Kato, Y. et al., A Novel Benzoimidazole Derivative, M50367, Modulates Helper T Type I/II Responses in Atopic Dermatitis Mice and Intradermal Melanoma-Bearing Mice, Biol. Pharm. Bull., 28(1), 78-82 (2005).*
Wright J. et al.: "Discovery of Selective Dopamine D3 Ligands: II. 2-'4-'3-(-4-aryl-1-piperazinyl) propoxy]phenyl]benzimidazole partial agonists" Bioorganic & Medicinal Chemistry Letters, Oxford, GB, vol. 5, No. 21, Nov. 2, 1995, pp. 2547-2550.
Arrang, J.-M. et al. Auto-inhibition of Brain Histamine Release Mediated by a Novel Class ($H_3$) of Histamine Receptor. Nature (1983) 302:832-837.
Ash, A.S.F.; Schild, H.O. Receptors Mediating Some Actions of Histamine. Br. J. Pharmac. Chemother. (1966) 27:427-439.
Barger, G.; Dale, H.H. Chemical Structure and Sympathomimetic Action of Amines. J. Physiol. (1910) 41:19-59 Reprinted in Adventures in Physiology; Sir Henry H. Dale, Ed.; The Wellcome Trust: London, 1965; pp. 67-98.
Benoist, C. et al. Mast Cells in Autoimmune Disease. Nature (2002) 420(6917):875-878.

Berge, S.M. et al. Pharmaceutical Salts. J. Pharm. Sci. (1977) 66(1):1-19.
Black, J.W. et al. Definition and Antagonism of Histamine H2-Receptors. Nature (1972) 236:385-390.
Cohen, J. The Immunopathogenesis of Sepsis. Nature (2002) 420(6917):885-891.
Coussens, L.M. et al. Inflammation and Cancer. Nature (2002) 420(6917):860-867.
Gantz, I. et al. Molecular Cloning of a Gene Encoding the Histamine H2 Receptor. Proc. Natl. Acad. Sci. USA (1991) 88(2):429-433.
Hill, S.J. et al. International Union of Pharmacology. XIII. Classification of Histamine Receptors. Pharmacol. Rev. (1997) 49(3):253-278.
Hofstra, C.L. et al. Histamine $H_4$ Receptor Mediates Chemotaxis and Calcium Mobilization of Mast Cells. J. Pharmacol. Exp. Ther. (2003) 305(3):1212-1221.
Libby, P. Inflammation in Atherosclerosis. Nature (2002) 420(6917):868-874.
Liu, C. et al. Cloning and Pharmacological Characterization of a Fourth Histamine Receptor ($H_4$) Expressed in Bone Marrow. Mol. Pharmacol. (2001) 59(3):420-426.
Lovenberg, T.W. et al. Cloning and Functional Expression of the Human Histamine $H_3$ Receptor. Mol. Pharmacol. (1999) 55(6):1101-1107.
Morse, K.L. et al. Cloning and Characterization of a Novel Human Histamine Receptor. J. Pharmacol. Exp. Ther. (2001) 296(3):1058-1066.
Nathan, C. Points of Control in Inflammation. Nautre (2002) 420(6917):846-852.
Nguyen, T. et al. Discovery of a Novel Member of the Histamine Receptor Family. Mol. Pharmacol. (2001) 59(3):427-433.
Oda, T. et al. Molecular Cloning and Characterization of a Novel Type of Histamine Receptor Preferentially Expressed in Leukocytes. J. Biol. Chem. (2000) 275(47):36781-36786.
Raible, D.G. et al. Pharmacologic Characterization of a Novel Histamine Receptor on Human Eosinophils. Am. J. Respir. Crit. Care Med. (1994) 149:1506-1511.
Schneider, E. et al. Trends in Histamine Research: New Functions During Immune Responses and Hematopoiesis. Trends Immunol. (2002) 23(5):255-263.
Stark, H. Recent Advances in Histamine $H_3/H_4$ Receptor Ligands. Expert Opin. Ther. Patents (2003) 13(6):851-865.
Steinberg, D. Atherogenesis in Perspective: Hypercholesterolemia and Inflammation as Partners in Crime. Nature Med. (2002) 8(11):1211-1217.
Tracey, K.J. The Inflammatory Relfex. Nature (2002) 420(6917):853-859.
Weiner, H.L. et al. Inflammation and Therapeutic Vaccination in CNS Diseases. Nature (2002) 420(6917):879-884.
Yamashita, M. et al. Expression Cloning of a cDNA Encoding the Bovine Histamine $H_1$ Receptor. Proc. Natl. Acad. Sci. USA (1991) 88(24):11515-11519.
Zhu, Y. et al. Cloning, Expression, and Pharmacological Characterization of a Novel Human Histamine Receptor. Mol. Pharmacol. (2001) 59(3):434-441.

* cited by examiner

*Primary Examiner*—James O. Wilson
*Assistant Examiner*—Erich A Leeser

(57) ABSTRACT

Benzoimidazole compounds, compositions, and methods of using them in leukocyte recruitment inhibition, in modulating $H_4$ receptor, and in treating conditions such as inflammation, $H_4$ receptor-mediated conditions, and related conditions.

25 Claims, No Drawings

BENZOIMIDAZOLE COMPOUNDS

This application claims priority to U.S. provisional patent application Ser. No. 60/507,236, filed on Sep. 30, 2003, which is incorporated herein by reference in its entirety.

FIELD OF THE INVENTION

The invention relates to novel, pharmaceutically active, fused heterocyclic compounds, more particularly benzoimidazole compounds, and methods of using them to treat or prevent disorders and conditions mediated by the histamine $H_4$ receptor.

BACKGROUND OF THE INVENTION

Histamine was first identified as a hormone (G. Barger and H. H. Dale, *J. Physiol.* (*London*) 1910, 41:19-59) and has since been demonstrated to play a major role in a variety of physiological processes, including the inflammatory "triple response" via $H_1$ receptors (A. S. F. Ash and H. O. Schild, *Br. J. Pharmac. Chemother.* 1966, 27:427-439), gastric acid secretion via $H_2$ receptors (J. W. Black et al., *Nature* 1972, 236:385-390), and neurotransmitter release in the central nervous system via $H_3$ receptors (J. -M. Arrang et al., *Nature* 1983, 302:832-837) (for review see S. J. Hill et al., *Pharmacol. Rev.* 1997, 49(3):253-278). All three histamine receptor subtypes have been demonstrated to be members of the superfamily of G protein-coupled receptors (I. Gantz et al., *Proc. Natl. Acad. Sci. U.S.A.* 1991, 88:429-433; T. W. Lovenberg et al., *Mol. Pharmacol.* 1999, 55(6):1101-1107; M. Yamashita et al. *Proc. Natl. Acad. Sci. U.S.A.* 1991, 88:11515-11519). There are, however, additional functions of histamine that have been reported, for which no receptor has been identified. For example, in 1994, Raible et al., demonstrated that histamine and R-α-methylhistamine could activate calcium mobilization in human eosinophils (D. G. Raible et al., *Am. J. Respir. Crit. Care Med.* 1994, 149:1506-1511). These responses were blocked by the $H_3$-receptor antagonist thioperamide. However, R-α-methylhistamine was significantly less potent than histamine, which was not consistent with the involvement of known $H_3$ receptor subtypes. Therefore, Raible et al. hypothesized the existence of a novel histamine receptor on eosinophils that was non-$H_1$, non-$H_2$, and non-$H_3$. Most recently several groups (T. Oda et al., *J. Biol. Chem.* 2000, 275(47):36781-36786; C. Liu et al., *Mol. Pharmacol.* 2001, 59(3):420-426; T. Nguyen et al., *Mol. Pharmacol.* 2001, 59(3):427-433; Y. Zhu et al., *Mol. Pharmacol.* 2001, 59(3):434-441; K. L. Morse et al., *J. Pharmacol. Exp. Ther.* 2001, 296(3):1058-1066) have identified and characterized a fourth histamine receptor subtype, the $H_4$ receptor. This receptor is a 390 amino acid, seven-transmembrane, G protein-coupled receptor with approximately 40% homology to the histamine $H_3$ receptor. In contrast to the $H_3$ receptor, which is primarily located in the brain, the $H_4$ receptor is expressed at greater levels in eosinophils and mast cells, among other cells, as reported by Liu et al. (see above) and C. L. Hofstra et al. (*J. Pharmacol. Exp. Ther.* 2003, 305(3):1212-1221). Because of its preferential expression on immunocompetent cells, this $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast-cell de-granulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast-cell activation initiates allergic ($H_1$) inflammatory responses, which in turn cause the recruitment of other effector cells that further contribute to the inflammatory response. The histamine $H_2$ receptors modulate gastric acid secretion, and the histamine $H_3$ receptors affect neurotransmitter release in the central nervous system.

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have $H_4$ receptor modulating properties. Compounds according to the present invention have leukocyte recruitment inhibiting properties. Compounds according to the present invention have anti-inflammatory properties.

Examples of textbooks on the subject of inflammation include J. I. Gallin and R. Snyderman, *Inflammation: Basic Principles and Clinical Correlates*, $3^{rd}$ Edition, (Lippincott Williams & Wilkins, Philadelphia, 1999); V. Stvrtinova, J. Jakubovsky and I. Hulin, "Inflammation and Fever", *Pathophysiology Principles of Diseases* (Textbook for Medical Students, Academic Press, 1995); Cecil et al., *Textbook Of Medicine*, $18^{th}$ Edition (W. B. Saunders Company, 1988); and Steadmans Medical Dictionary.

Background and review material on inflammation and conditions related with inflammation can be found in articles such as the following: C. Nathan, Points of control in inflammation, *Nature* 2002, 420:846-852; K. J. Tracey, The inflammatory reflex, *Nature* 2002, 420:853-859; L. M. Coussens and Z. Werb, Inflammation and cancer, *Nature* 2002, 420: 860-867; P. Libby, Inflammation in atherosclerosis, *Nature* 2002, 420:868-874; C. Benoist and D. Mathis, Mast cells in autoimmune disease, *Nature* 2002, 420:875-878; H. L. Weiner and D. J. Selkoe, Inflammation and therapeutic vaccination in CNS diseases, *Nature* 2002, 420:879-884; J. Cohen, The immunopathogenesis of sepsis, *Nature* 2002, 420:885-891; D. Steinberg, Atherogenesis in perspective: Hypercholesterolemia and inflammation as partners in crime, *Nature Medicine* 2002, 8(11):1211-1217.

Inflammation herein refers to the response that develops as a consequence of histamine release, which in turn is caused by at least one stimulus. Examples of such stimuli are immunological stimuli and non-immunological stimuli.

Inflammation is due to any one of a plurality of conditions such as allergy, asthma, chronic obstructed pulmonary disease (COPD), atherosclerosis, rheumatoid arthritis, multiple sclerosis, inflammatory bowel diseases (including Crohn's disease and ulcerative colitis), psoriasis, allergic rhinitis, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligo, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome. Regarding the onset and evolution of inflammation, inflammatory diseases or inflammation-mediated diseases or conditions include, but are not limited to, acute inflammation, allergic inflammation, and chronic inflammation.

Cited references are incorporated herein by reference.

SUMMARY OF THE INVENTION

The invention features a compound of formula (I) or (II):

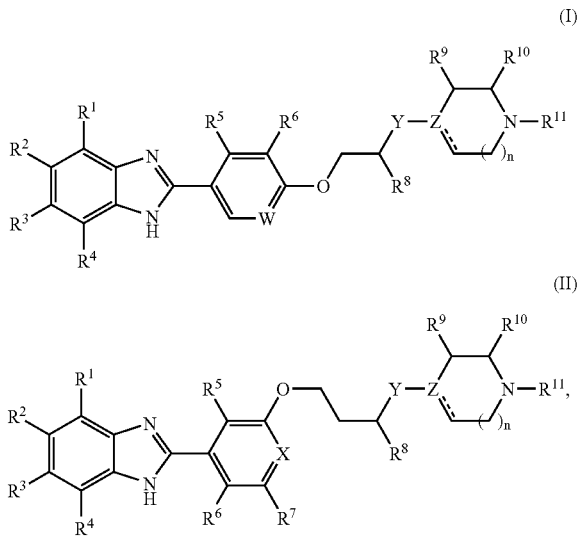

wherein

W is, independently from other member and substituent assignments, N or $CR^7$;

X is, independently from other member and substituent assignments, N or CH;

Y is, independently from other member and substituent assignments, O, $NR^{12}$, or $CR^{12}R^{13}$;

Z is, independently from other member and substituent assignments, N or $CR^{14}$, in which case the solid/dash feature (====)

in any one of formulae (I) and (II) is a single bond; or Z is C, in which case the solid/dash feature (====)

in any one of formulae (I) and (II) is a double bond;

n is, independently from member and substituent assignments, 0, 1, or 2;

each of $R^{1-4}$ is, independently from other member and substituent assignments, H, $C_{1-4}$alkyl, $C_{2-5}$alkenyl, $C_{2-5}$alkynyl, $C_{3-6}$cycloalkyl, —$C_{1-4}$alkoxy, —$C_{1-4}$alkylamino, —$C_{1-4}$alkylthio, —$C_{1-4}$alkylsulfonyl, —$OC_{3-6}$cycloalkyl, —$OCH_2Ph$, cyano, —$CF_3$, F, Cl, Br, I, nitro, —$OCF_3$, —$SCF_3$, —$OR^c$, —$SR^c$, —$S(O)R^c$, —$SO_2R^c$, —$C(O)R^c$, phenyl, benzyl, phenethyl, —$C(O)NR^aR^b$, —$C(O)OR^c$, —$NR^aR^b$, —$CH_2NR^aR^b$ or —$CH_2OR^c$; wherein each of $R^a$, $R^b$ and $R^c$ is, independently from other substituent assignments, selected from H, $C_{1-4}$alkyl, $C_{3-6}$cycloalkyl, phenyl, ($C_{3-6}$cycloalkyl)$C_{1-2}$alkyl-, benzyl and phenethyl, or $R^a$ and $R^b$ taken together with the nitrogen to which they are attached, form a 4-7 membered heterocyclic ring HetCyc1, wherein said ring HetCyc1 has 0 or 1 additional heteroatoms selected from O, S, >NH and >$NC_{1-6}$alkyl, and wherein any phenyl, phenethyl, benzyl, alkyl or cycloalkyl moiety in any of said $R^{1-4}$, $R^a$, $R^b$, $R^c$, and said ring HetCyc1 is optionally, and independently from other substituent assignments, substituted with 1, 2 or 3 substituents selected from $C_{1-3}$alkyl, halo, hydroxy, amino, and $C_{1-3}$alkoxy;

each of $R^{5-7}$ is, independently from other member and substituent assignments, H, $C_{1-6}$alkyl, F, Cl, Br, I, $CF_3$, —$OCF_3$, —$OR^c$, —$C_{1-3}$alkyl$OR^c$, —$C_{1-3}$alkyl$SR^c$, —$SR^c$, —$S(O)R^c$, —$SO_2R^c$, $C_{1-4}$alkoxy, cyano, nitro, —$C(O)NR^aR^b$, —$NR^aR^b$, —$C_{1-3}$alkyl$NR^aR^b$, —$C(O)$phenyl, —$C(O)C_{1-6}$alkyl, —$S(O)C_{1-6}$alkyl, or —$SO_2C_{1-4}$alkyl; or, $R^5$ and $R^6$ for a compound of formula (I) taken together with the carbon atoms to which they are attached form a cyclic structure Cyc1 selected from aryl, heteroaryl, 5- or 6-membered carbocycle, and 5- or 6-membered heterocycle with 1 or 2 heteroatoms, wherein said cyclic structure Cyc1 is, independently from other substituent assignments, substituted with 0, 1, or 2 substituents selected from $C_{1-3}$alkyl, halo, hydroxy, amino, and $C_{1-3}$alkoxy; or, $R^7$ and $R^6$ for a compound of formula (II) taken together with the carbon atoms to which they are attached form a cyclic structure Cyc2 selected from aryl, heteroaryl, 5- or 6-membered carbocycle, and 5- or 6-membered heterocycle with 1 or 2 heteroatoms, wherein said cyclic structure Cyc2 is, independently from other substituent assignments, substituted with 0, 1, or 2 substituents selected from $C_{1-3}$alkyl, halo, hydroxy, amino, and $C_{1-3}$alkoxy;

$R^8$ is, independently from other member and substituent assignments, H, $C_{1-6}$alkyl, $C_{1-4}$alkoxy, or OH;

each of $R^9$ and $R^{10}$ is, independently from other member and substituent assignments, H or $C_{1-6}$alkyl, or $R^9$ and $R^{10}$ taken together form a 5-6 membered cyclic structure Cyc3, wherein said cyclic structure Cyc3 is a 5- or 6-membered carbocycle or a 5- or 6-membered heterocycle with 1 or 2 heteroatoms, and wherein said cyclic structure Cyc3 is, independently from other substituent assignments, substituted with 0, 1, or 2 substituents selected from $C_{1-3}$alkyl, halo, hydroxy, amino, and $C_{1-3}$alkoxy;

$R^{11}$ is, independently from other member and substituent assignments, H or $C_{1-4}$alkyl;

each of $R^{12}$ and $R^{13}$ is, independently from other member and substituent assignments, H or $C_{1-4}$alkyl; or, when Y is $CR^{12}R^{13}$, $R^{12}$ and $R^{13}$ taken together with the carbon member to which they are attached form an optionally substituted cyclic structure Cyc4, wherein said cyclic structure Cyc4 is a 3- to 6-membered carbocycle or a 3- to 6-membered heterocycle with 0 or 1 additional heteroatoms, or $CR^{12}R^{13}$ is C=O;

$R^{14}$ is, independently from other member and substituent assignments, H, $C_{1-4}$alkyl, OH, or $C_{1-4}$alkoxy;

an enantiomer, diastereomer, racemate thereof, or a pharmaceutically acceptable salt, amide or ester thereof;

with the following provisos:

when Y is O or NR$^{12}$, then Z is CR$^{14}$ and R$^8$ is not OH or C$_{1-4}$alkoxy;

when Z is N, Y is CR$^{12}$R$^{13}$; and none of R$^{1-4}$ is C(O)NH$_2$.

Isomeric forms of the compounds of formulae (I) and (II), and of their pharmaceutically acceptable salts, amides and esters, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture.

Whether stated explicitly or not in any part of the written description and claims, it is understood that each substituent and member assignment in the context of this invention is made independently of any other member and substituent assignment, unless stated otherwise. By way of a first example on substituent terminology, if substituent S$^1_{example}$ is one of S$_1$ and S$_2$, and substituent S$^2_{example}$ is one of S$_3$ and S$_4$, then these assignments refer to embodiments of this invention given according to the choices S$^1_{example}$ is S$_1$ and S$^2_{example}$ is S$_3$; S$^1_{example}$ is S$_1$ and S$^2_{example}$ is S$_4$; S$^1_{example}$ is S$_2$ and S$^2_{example}$ is S$_3$; S$^1_{example}$ is S$_2$ and S$^2_{example}$ is S$_4$; and equivalents of each one of such choices. The shorter terminology "S$^1_{example}$ is one of S$_1$ and S$_2$, and S$^2_{example}$ is one of S$_3$ and S$_4$" is accordingly used herein for the sake of brevity, but not by way of limitation. The foregoing first example on substituent terminology, which is stated in generic terms, is meant to illustrate the various substituent R assignments described herein. The foregoing convention given herein for substituents extends, when applicable, to members such as X, Y, Z, and W, and the index n.

Furthermore, when more than one assignment is given for any member or substituent, embodiments of this invention comprise the various groupings that can be made from the listed assignments and equivalents thereof. By way of a second example on substituent terminology, if it is herein described that substituent S$_{example}$ is one of S$_1$, S$_2$, and S$_3$, this listing refers to embodiments of this invention for which S$_{example}$ is S$_1$; S$_{example}$ is S$_2$; S$_{example}$ is S$_3$; S$_{example}$ is one of S$_1$ and S$_2$; S$_{example}$ is one of S$_1$ and S$_3$; S$_{example}$ is one of S$_2$ and S$_3$; S$_{example}$ is one of S$_1$, S$_2$ and S$_3$; and S$_{example}$ is any equivalent of each one of these choices. The shorter terminology "S$_{example}$ is one of S$_1$, S$_2$, and S$_3$" is accordingly used herein for the sake of brevity, but not by way of limitation. The foregoing second example on substituent terminology, which is stated in generic terms, is meant to illustrate the various substituent R assignments described herein. The foregoing convention given herein for substituents extends, when applicable, to members such as X, Y, Z, and W, and the index n.

The nomenclature "C$_{i-j}$" with j>i, when applied herein to a class of substituents, is meant to refer to embodiments of this invention for which each and every one of the number of carbon members, from i to j including i and j, is realized. By way of example, the term C$_{1-3}$ refers independently to embodiments that have one carbon member (C$_1$), embodiments that have two carbon members (C$_2$), and embodiments that have three carbon members (C$_3$).

When any variable referring to a substituent, compound member or index, occurs more than once, the full range of assignments is meant to apply to each occurrence, independently of the specific assignment(s) to any other occurrence of such variable.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention also features a pharmaceutical composition for treating or preventing an H$_4$ receptor-mediated condition in a subject, comprising a therapeutically effective amount of at least one H$_4$ receptor modulator selected from compounds of formulae (I) and (II), enantiomers, diastereomers, racemates thereof, pharmaceutically acceptable salts, amides and esters thereof. In addition, the invention features a pharmaceutical composition for inhibiting leukocyte recruitment in a subject, comprising a therapeutically effective amount of at least one leukocyte recruitment inhibitor selected from compounds of formulae (I) and (II), enantiomers, diastereomers, racemates thereof, pharmaceutically acceptable salts, amides and esters thereof. The invention additionally features an anti-inflammatory composition, comprising a therapeutically effective amount of at least one anti-inflammatory compound selected from compounds of formulae (I) and (II), enantiomers, diastereomers, racemates thereof, pharmaceutically acceptable salts, amides and esters thereof.

The invention features methods for treating or preventing inflammation in a subject, comprising administering to the subject in connection with an inflammatory response a pharmaceutical composition that comprises a therapeutically effective amount of at least one anti-inflammatory compound selected from compounds of formulae (I) and (II), enantiomers, diastereomers, racemates thereof, pharmaceutically acceptable salts, amides and esters thereof. The invention also features methods for treating or preventing an H$_4$ receptor-mediated condition in a subject, comprising administering to the subject a pharmaceutical composition that comprises a therapeutically effective amount of at least one H$_4$ receptor modulator selected from compounds of formulae (I) and (II), enantiomers, diastereomers, racemates thereof, pharmaceutically acceptable salts, amides and esters thereof. In addition, the invention features methods for modulating an H$_4$ receptor, comprising exposing an H$_4$ receptor to at least one compound selected from compounds of formulae (I) and (II), enantiomers, diastereomers, racemates thereof, pharmaceutically acceptable salts, amides and esters thereof. Furthermore, the invention features methods for inhibiting leukocyte recruitment in a subject, comprising administering to the subject a pharmaceutical composition that comprises a therapeutically effective amount of at least one leukocyte recruitment inhibitor selected from compounds of formulae (I) and (II), enantiomers, diastereomers, racemates thereof, pharmaceutically acceptable salts, amides and esters thereof.

DETAILED DESCRIPTION

The present invention is directed to compounds of formula (I) or (II), enantiomers, diastereomers, racemates thereof, pharmaceutically acceptable salts, amides and esters thereof, as herein defined, pharmaceutical compositions that contain at least one of such compounds, methods of using, including treatment and/or prevention of conditions such as those that are mediated by the H$_4$ receptor, and methods of making such pharmaceutical compositions.

The following terms are defined below, and by their usage throughout the disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Unless indicated otherwise by the prefix that indicates the number of carbon members, alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on.

"Alkynyl" includes straight chain and branched hydrocarbon radicals as above with at least one carbon-carbon triple bond (sp). Unless indicated otherwise by the prefix that indicates the number of carbon members, alkynyls include ethynyl, propynyls, butynyls, and pentynyls. Hydrocarbon radicals having a mixture of double bonds and triple bonds, such as 2-penten-4-ynyl, are grouped as alkynyls herein.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

Unless indicated otherwise by the prefix that indicates the number of carbon members, "cycloalkyl" includes cyclopropyl, cyclobutyl, cyclopentyl, cyclohexyl, cycloheptyl, cyclooctyl, and so on.

Unless indicated otherwise by the prefix that indicates the number of members in the cyclic structure, "heterocyclyl", "heterocyclic" or "heterocycle" is a 3- to 8-member aromatic, saturated, or partially saturated single or fused ring system that comprises carbon atoms wherein the heteroatoms are selected from N, O, and S. Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imidazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Carbocycle is a cycloalkyl or a partially saturated cycloalkyl that is not benzo

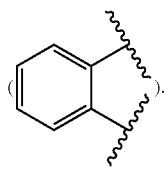

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridged, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on. Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Halo" includes fluoro, chloro, bromo, and iodo, and is preferably fluoro or chloro.

As in standard chemical nomenclature, the group phenyl is herein referred to as "phenyl" or as "Ph".

"Patient" or "subject" includes mammals such as human beings and animals (e.g., dogs, cats, horses, rats, rabbits, mice, non-human primates) in need of observation, experiment, treatment or prevention in connection with the relevant disease or condition. Preferably, the patient is a human being.

"Composition" includes a product comprising the specified ingredients in the specified amounts, including in the effective amounts, as well as any product that results directly or indirectly from combinations of the specified ingredients in the specified amounts.

"Therapeutically effective amount" or "effective amount" and grammatically related terms mean that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

| Table of Acronyms | |
|---|---|
| Term | Acronym |
| Tetrahydrofuran | THF |
| N,N-Dimethylformamide | DMF |
| N,N-Dimethylacetamide | DMA |
| Dimethyl sulfoxide | DMSO |
| tert-Butylcarbamoyl | BOC |
| Bovine serum albumin | BSA |
| High-pressure liquid chromatography | HPLC |
| Thin layer chromatography | TLC |

Particular preferred compounds of the invention comprise a benzoimidazole compound of formula (I) or (II), or an enantiomer, diastereomer, racemate thereof, or a pharmaceutically acceptable salt, amide or ester thereof, wherein $R^{1-14}$, X, Y, Z, W, and n have any of the meanings defined hereinabove and equivalents thereof, or at least one of the following assignments and equivalents thereof. Such assignments may be used where appropriate with any of the definitions, claims or embodiments defined herein:

Preferably, W is N or $CR^7$.

Preferably, X is N or CH.

Preferably, Y is $CR^{12}R^{13}$.

More preferably, Y is $CH_2$.

Preferably, Z is N or CH.

Preferably, n=1 or 2.

More preferably, n=1.

Preferably, $R^1$ is selected from the group consisting of H, methyl, ethyl, isopropyl, cyclopropyl, F, Cl, Br, cyano, phenyl, carboxymethyl, dimethylcarboxamido, or $CH_2OMe$.

More preferably, $R^1$ is H, methyl, F, or Cl.

Preferably, $R^2$ is independently selected from the group consisting of H, methyl, ethyl, isopropyl, t-butyl, cyclopropyl, $CF_3$, $OCF_3$, F, Cl, Br, cyano, phenyl, carboxymethyl, dimethylcarboxamido, or benzoyl.

More preferably, $R^2$ is H, F, Cl, methyl, $CF_3$, $OCF_3$, or t-butyl.

Preferably, $R^3$ is independently selected from the group consisting of H, methyl, ethyl, isopropyl, t-butyl, cyclopropyl, $CF_3$, $OCF_3$, F, Cl, Br, cyano, phenyl, carboxymethyl, dimethylcarboxamido, or benzoyl.

More preferably, $R^3$ is H, F, Cl, methyl, $CF_3$, $OCF_3$, or t-butyl.

Preferably, $R^4$ is selected from the group consisting of H, methyl, ethyl, isopropyl, cyclopropyl, R, Cl, Br, cyano, phenyl, carboxymethyl, dimethylcarboxamido, or $CH_2OMe$.

More preferably, $R^4$ is H, methyl, F, or Cl.

Most preferably, one or two of $R^{1-4}$ are not H.

Preferably, $R^5$ is H, F, Cl, methyl, or ethyl.

More preferably, $R^5$ is F, Cl, methyl, hydroxymethyl, hydroxyethyl, pyrrolidinylmethyl, or diethylaminomethyl.

More preferably, $R^6$ is H, F, Cl, or methyl.

More preferably, $R^7$ is H, F, Cl, or methyl.

Most preferably, $R^5$ is Cl, methyl, or hydroxymethyl.

Preferably, $R^8$ is H, methyl, or OH.

More preferably, $R^8$ is H.

Preferably, $R^9$ and $R^{10}$ are, independently, selected from the group consisting of
a) H,
b) methyl, ethyl, propyl, isopropyl, and
c) trifluoromethyl.

Most preferably, $R^9$ and $R^{10}$ are, independently, H or methyl.

Preferably, $R^{11}$ is H, methyl, or ethyl.

More preferably, $R^{11}$ is methyl.

Compounds of formula (I) or (II) also comprise compounds that satisfy any one of the combinations of definitions given herein and equivalents thereof.

It is understood that some compounds referred to herein are chiral and/or have geometric isomeric centers, for example E- and Z-isomers. The present invention encompasses all such optical, including stereoisomers and racemic mixtures, diastereomers, and geometric isomers that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention. Compounds according to the present invention that have been modified to be detectable by some analytic technique are also within the scope of this invention. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Another example of such compounds is an isotopically labeled compound, such as a deuterium and/or tritium labeled compound that may be used in reaction kinetic studies.

It is understood that substitutions and combinations of substitutions recited herein, whether stated explicitly or not, refer to substitutions that are consistent with the valency of the member being substituted. For example, a substitution applied to a carbon member refers to the tetravalency of C; it refers to the trivalency of N when applied to a nitrogen member; and it refers to the tetravalency of a nitrogen member that is conventionally characterized with a positive electric charge. Valence allowed options are part of the ordinary skill in the art.

The "pharmaceutically acceptable salts, amides and/or esters thereof" refer to those salts, amides and ester forms of the compounds of the present invention that would be apparent to the pharmaceutical chemist, i.e., those that are non-toxic and that would favorably affect the pharmacological properties of said compounds of the present invention. Those compounds having favorable pharmacological properties would be apparent to the pharmaceutical chemist, i.e., those that are non-toxic and that possess such pharmacological properties to provide sufficient palatability, absorption, distribution, metabolism and excretion. Other factors, more practical in nature, that are also important in the selection are cost of raw materials, ease of crystallization, yield, stability, hygroscopicity, and flowability of the resulting bulk drug.

Representative acids and bases that may be used in the preparation of pharmaceutically acceptable salts include the following:

acids including acetic acid, 2,2-dichlorolactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

See, for example, S. M. Berge, et al., "Pharmaceutical Salts", J. Pharm. Sci. 1977, 66:1-19, which is incorporated herein by reference. Examples of suitable esters include $C_{1-7}$alkyl, $C_{5-7}$cycloalkyl, phenyl, substituted phenyl, and phenyl$C_{1-6}$-alkyl-esters. Preferred esters include methyl esters.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but that converts to the specified compound in vivo after administration to the patient. Analogously, the term "compound", when applied to compounds within the scope of this invention, shall encompass in addition to a specific compound of formual (I) or (II), a compound (or prodrug) that converts to the specifically disclosed compound in vivo after administration, even if such prodrug is not explicitly disclosed herein. Conventional procedures for the selection and preparation of suitable prodrug derivatives are described, for example, in "Design of Prodrugs", ed. H. Bundgaard, Elsevier, 1985.

Compounds where W is $CR^7$ were made according to the synthetic methods outlined in Schemes 1 and 2 and examples of such compounds are provided in the group:

| EX | Compound |
|---|---|
| 1 | 2-{2-Chloro-4-[3-(4-methyl-piperazin-1-yl)-propoxy]-phenyl}-4,5-dimethyl-1H-benzoimidazole; |
| 2 | 2-{2-Chloro-4-[3-(1-methyl-piperidin-4-yl)-propoxy]-phenyl}-4-methyl-1H-benzoimidazole; |
| 3 | 2-{2-Chloro-4-[3-(4-methyl-piperazin-1-yl)-propoxy]-phenyl}-5-trifluoromethoxy-1H-benzoimidazole; |
| 4 | 5-tert-Butyl-2-{3-chloro-4-[3-(4-methyl-[1,4]diazepan-1-yl)-propoxy]-phenyl}-1H-benzoimidazole; |
| 5 | 5-tert-Butyl-2-{3-chloro-4-[3-(4-methyl-piperazin-1-yl)-propoxy]-phenyl}-1H-benzoimidazole; |
| 6 | 4,5-Dimethyl-2-{3-methyl-4-[3-(4-methyl-piperazin-1-yl)-propoxy]-phenyl}-1H-benzoimidazole; |
| 7 | 5-tert-Butyl-2-{3-[4-(4-methyl-piperazin-1-yl)-butoxy]-phenyl}-1H-benzoimidazole; |
| 8 | 5-tert-Butyl-2-{3-[4-(4-methyl-[1,4]diazepan-1-yl)-butoxy]-phenyl}-1H-benzoimidazole; |
| 9 | (1-{3-[4-(5-tert-Butyl-1H-benzoimidazol-2-yl)-2-chloro-phenoxy]-propyl}-pyrrolidin-3-yl)-dimethylamine; |
| 10 | 5-Chloro-2-{3-chloro-4-[3-(4-methyl-[1,4]diazepan-1-yl)-propoxy]-phenyl}-6-methyl-1H-benzoimidazole; |
| 11 | 2-{3-Fluoro-4-[3-(4-methyl-piperazin-1-yl)-propoxy]-phenyl}-4-methyl-1H-benzoimidazole; |
| 12 | 5-Methyl-2-{4-[3-(4-methyl-piperazin-1-yl)-propoxy]-naphthalen-1-yl}-1H-benzoimidazole; |
| 13 | 4-[3-(5-tert-Butyl-1H-benzoimidazol-2-yl)-phenoxy]-1-(4-methyl-piperazin-1-yl)-butan-1-one; |
| 14 | 5-Chloro-2-[3-chloro-4-(3-piperazin-1-yl-propoxy)-phenyl]-6-fluoro-1H-benzoimidazole; |
| 15 | 5-tert-Butyl-2-{3-methyl-4-[3-(4-methyl-piperazin-1-yl)-propoxy]-phenyl}-1H-benzoimidazole; |
| 16 | 2-{2-Chloro-4-[3-(1-methyl-piperidin-4-yl)-propoxy]-phenyl}-4,6-dimethyl-1H-benzoimidazole; |
| 17 | 2-{2-Chloro-4-[2-methyl-3-(4-methyl-piperazin-1-yl)-propoxy]-phenyl}-4-methyl-1H-benzoimidazole; |
| 18 | 5-Chloro-2-{3-chloro-4-[3-(4-methyl-piperazin-1-yl)-propoxy]-phenyl}-6-methyl-1H-benzoimidazole; |
| 19 | 6-Chloro-2-{2-chloro-4-[3-(4-methyl-piperazin-1-yl)-propoxy]-phenyl}-4-methyl-1H-benzoimidazole; |
| 20 | 5-tert-Butyl-2-{3-chloro-4-[3-(4-methyl-piperazin-1-yl)-propoxy]-phenyl}-1H-benzoimidazole; |
| 21 | 5-Chloro-2-{3-fluoro-4-[3-(4-methyl-piperazin-1-yl)-propoxy]-phenyl}-1H-benzoimidazole; |
| 22 | 2-{2-Chloro-4-[3-(4-methyl-[1,4]diazepan-1-yl)-propoxy]-phenyl}-4,6-dimethyl-1H-benzoimidazole; |
| 23 | 5-Chloro-6-methyl-2-{3-[4-(4-methyl-piperazin-1-yl)-butoxy]-phenyl}-1H-benzoimidazole; |
| 24 | 5-Chloro-6-fluoro-2-{3-fluoro-4-[3-(4-methyl-piperazin-1-yl)-propoxy]-phenyl}-1H-benzoimidazole; |
| 25 | 2-{3-Fluoro-4-[3-(4-methyl-piperazin-1-yl)-propoxy]-phenyl}-5-methyl-1H-benzoimidazole; |
| 26 | 5,6-Difluoro-2-{3-fluoro-4-[3-(4-methyl-piperazin-1-yl)-propoxy]-phenyl}-1H-benzoimidazole; |
| 27 | 2-{3-Fluoro-4-[3-(4-methyl-piperazin-1-yl)-propoxy]-phenyl}-1H-benzoimidazole; |
| 28 | 2-{2-Chloro-4-[3-(4-methyl-[1,4]diazepan-1-yl)-propoxy]-phenyl}-4,5-dimethyl-1H-benzoimidazole; |
| 29 | 5,6-Dimethyl-2-{3-[4-(4-methyl-piperazin-1-yl)-butoxy]-phenyl}-1H-benzoimidazole; |
| 30 | 2-{2-Chloro-4-[3-(4-methyl-piperazin-1-yl)-propoxy]-phenyl}-4,6-dimethyl-1H-benzoimidazole; |
| 31 | 2-{2-Chloro-4-[3-(4-methyl-[1,4]diazepan-1-yl)-propoxy]-phenyl}-4-methyl-1H-benzoimidazole; |
| 32 | 5-tert-Butyl-2-{2-chloro-4-[3-(4-methyl-piperazin-1-yl)-propoxy]-phenyl}-1H-benzoimidazole; |
| 33 | 2-{3-Methoxy-4-[3-(4-methyl-piperazin-1-yl)-propoxy]-phenyl}-5-trifluoromethyl-1H-benzoimidazole; |
| 34 | 5-Chloro-2-{3-chloro-4-[3-(4-methyl-piperazin-1-yl)-propoxy]-phenyl}-6-fluoro-1H-benzoimidazole; |
| 35 | 5,6-Dichloro-2-{2-chloro-4-[3-(4-methyl-piperazin-1-yl)-propoxy]-phenyl}-1H-benzoimidazole; |
| 36 | 5-Chloro-2-{2-chloro-4-[3-(4-methyl-piperazin-1-yl)-propoxy]-phenyl}-1H-benzoimidazole; |
| 37 | 5-Chloro-2-{2-chloro-4-[3-(4-methyl-piperazin-1-yl)-propoxy]-phenyl}-6-fluoro-1H-benzoimidazole; |
| 38 | 5-Chloro-2-{3-methyl-4-[3-(4-methyl-piperazin-1-yl)-propoxy]-phenyl}-1H-benzoimidazole; |
| 39 | 2-{3-Chloro-4-[3-(4-methyl-piperazin-1-yl)-propoxy]-phenyl}-5-methyl-1H-benzoimidazole; |
| 40 | 5,6-Dichloro-2-{3-chloro-4-[3-(4-methyl-piperazin-1-yl)-propoxy]-phenyl}-1H-benzoimidazole; |
| 41 | 5-Chloro-6-methyl-2-{3-methyl-4-[3-(4-methyl-piperazin-1-yl)-propoxy]-phenyl}-1H-benzoimidazole; |
| 42 | 2-{2-Chloro-4-[3-(4-methyl-piperazin-1-yl)-propoxy]-phenyl}-5-methyl-1H-benzoimidazole; |
| 43 | 5-Chloro-2-{3-chloro-4-[3-(4-methyl-piperazin-1-yl)-propoxy]-phenyl}-1H-benzoimidazole; |
| 44 | 2-{3-Chloro-4-[3-(4-methyl-piperazin-1-yl)-propoxy]-phenyl}-5-trifluoromethyl-1H-benzoimidazole; |
| 45 | 5-Chloro-6-fluoro-2-{3-methyl-4-[3-(4-methyl-piperazin-1-yl)-propoxy]-phenyl}-1H-benzoimidazole; |
| 46 | 5-Methyl-2-{3-methyl-4-[3-(4-methyl-piperazin-1-yl)-propoxy]-phenyl}-1H-benzoimidazole; |
| 47 | 2-{3-Chloro-4-[3-(4-methyl-piperazin-1-yl)-propoxy]-phenyl}-1H-benzoimidazole; |
| 48 | 2-{3-Methyl-4-[3-(4-methyl-piperazin-1-yl)-propoxy]-phenyl}-1H-benzoimidazole; |
| 49 | 2-{2-Chloro-4-[3-(4-methyl-piperazin-1-yl)-propoxy]-phenyl}-1H-benzoimidazole; |
| 50 | 5-Chloro-6-fluoro-2-{3-methoxy-4-[3-(4-methyl-piperazin-1-yl)-propoxy]-phenyl}-1H-benzoimidazole; |
| 51 | 2-{3-Chloro-4-[3-(4-methyl-piperazin-1-yl)-propoxy]-phenyl}-5-methoxy-1H-benzoimidazole; |
| 52 | 5-tert-Butyl-2-{3,5-dibromo-4-[3-(4-methyl-piperazin-1-yl)-propoxy]-phenyl}-1H-benzoimidazole; |
| 53 | 2-{2-Methoxy-4-[3-(4-methyl-piperazin-1-yl)-propoxy]-phenyl}-5-trifluoromethyl-1H-benzoimidazole; |
| 54 | 2-{2-Chloro-4-[3-(4-methyl-piperazin-1-yl)-propoxy]-phenyl}-5-trifluoromethyl-1H-benzoimidazole; |
| 55 | 2-{3-[3-(4-Methyl-piperazin-1-yl)-propoxy]-phenyl}-1H-benzoimidazole; |
| 56 | (2-{3-[4-(4-Methyl-piperazin-1-yl)-butoxy]-phenyl}-1H-benzoimidazol-5-yl)-phenyl-methanone; |
| 57 | 6-Chloro-2-{2-chloro-4-[3-(1-methyl-piperidin-4-yl)-propoxy]-phenyl}-4-methyl-1H-benzoimidazole; |
| 58 | 5-tert-Butyl-2-{3-chloro-4-[3-(1-methyl-piperidin-4-yl)-propoxy]-phenyl}-1H-benzoimidazole; |
| 59 | 2-{2-Chloro-4-[3-(1-methyl-piperidin-4-yl)-propoxy]-phenyl}-4,5-dimethyl-1H-benzoimidazole; |
| 60 | 5-Chloro-6-methyl-2-{4-[3-(1-methyl-piperidin-4-yl)-propoxy]-phenyl}-1H-benzoimidazole; |
| 61 | 5-Chloro-2-{4-[3-(1-methyl-piperidin-4-yl)-propoxy]-phenyl}-1H-benzoimidazole; |
| 62 | 5-Chloro-6-fluoro-2-{4-[3-(1-methyl-piperidin-4-yl)-propoxy]-phenyl}-1H-benzoimidazole; |
| 63 | 5-tert-Butyl-2-{4-[3-(1-methyl-piperidin-4-yl)-propoxy]-phenyl}-1H-benzoimidazole; |
| 64 | 5-Methyl-2-{4-[3-(1-methyl-piperidin-4-yl)-propoxy]-phenyl}-1H-benzoimidazole; |
| 65 | 2-{4-[3-(1-Methyl-piperidin-4-yl)-propoxy]-phenyl}-1H-benzoimidazole; |
| 66 | 6-Chloro-2-{2-fluoro-4-[3-(1-methyl-piperidin-4-yl)-propoxy]-phenyl}-4-methyl-1H-benzoimidazole; |
| 67 | 5-Fluoro-2-{2-methyl-4-[3-(1-methyl-piperidin-4-yl)-propoxy]-phenyl}-1H-benzoimidazole; |
| 68 | 4-Chloro-2-{2-methyl-4-[3-(1-methyl-piperidin-4-yl)-propoxy]-phenyl}-1H-benzoimidazole; |
| 69 | 6-Chloro-4-methyl-2-{2-methyl-4-[3-(1-methyl-piperidin-4-yl)-propoxy]-phenyl}-1H-benzoimidazole; |
| 70 | 5-Chloro-2-{2-chloro-4-[3-(1-methyl-piperidin-4-yl)-propoxy]-phenyl}-6-fluoro-1H-benzoimidazole; |
| 71 | 2-{2-Chloro-4-[3-(1-methyl-piperidin-4-yl)-propoxy]-phenyl}-3H-naphtho[1,2-d]imidazole; |
| 72 | 4,6-Dimethyl-2-{2-methyl-4-[3-(4-methyl-piperazin-1-yl)-propoxy]-phenyl}-1H-benzoimidazole; |
| 73 | 2-{2-Chloro-4-[3-(4-methyl-piperazin-1-yl)-propoxy]-phenyl}-4-methyl-1H-benzoimidazole; |
| 74 | 2-{2-Chloro-4-[3-(4-methyl-piperazin-1-yl)-propoxy]-phenyl}-5-fluoro-4-methyl-1H-benzoimidazole; |
| 75 | 2-{2-Chloro-4-[3-(4-methyl-piperazin-1-yl)-propoxy]-phenyl}-3H-naphtho[1,2-d]imidazole; |
| 76 | 6-{2-Chloro-4-[3-(4-methyl-piperazin-1-yl)-propoxy]-phenyl}-5H-[1,3]dioxolo[4',5':4,5]benzo[1,2-d]imidazole; |

| EX | Compound |
|---|---|
| 77 | 6-Chloro-2-{2-chloro-4-[3-(4-methyl-[1,4]diazepan-1-yl)-propoxy]-phenyl}-4-methyl-1H-benzoimidazole; |
| 78 | 2-{3-Chloro-4-[3-(4-methyl-[1,4]diazepan-1-yl)-propoxy]-phenyl}-4-methyl-1H-benzoimidazole; |
| 79 | 4,6-Dimethyl-2-{3-[4-(4-methyl-[1,4]diazepan-1-yl)-butoxy]-phenyl}-1H-benzoimidazole; |
| 80 | 5-Chloro-2-{4-[3-(4-methyl-piperazin-1-yl)-propoxy]-phenyl}-1H-benzoimidazole; |
| 81 | 2-{4-[3-(4-Methyl-piperazin-1-yl)-propoxy]-phenyl}-1H-benzoimidazole; |
| 82 | {2-(6-Chloro-4-methyl-1H-benzoimidazol-2-yl)-5-[3-(1-methyl-piperidin-4-yl)-propoxy]-benzyl}-dimethyl-amine; |
| 83 | {2-(5-Fluoro-4-methyl-1H-benzoimidazol-2-yl)-5-[3-(1-methyl-piperidin-4-yl)-propoxy]-benzyl}-dimethyl-amine; |
| 84 | 4-{3-[4-(6-Chloro-4-methyl-1H-benzoimidazol-2-yl)-3-methyl-phenoxy]-propyl}-[1,4]diazepan-5-one; |
| 85 | 4-{3-[4-(5-tert-Butyl-1H-benzoimidazol-2-yl)-3-methyl-phenoxy]-propyl}-1-methyl-[1,4]diazepan-5-one; |
| 86 | 5-tert-Butyl-2-{2-methyl-4-[3-(2-methyl-piperazin-1-yl)-propoxy]-phenyl}-1H-benzoimidazole; |
| 87 | 5-tert-Butyl-2-{2-methyl-4-[3-(2-methyl-piperazin-1-yl)-propoxy]-phenyl}-1H-benzoimidazole; |
| 88 | 6-Chloro-4-methyl-2-[2-methyl-4-(3-piperidin-4-yl-propoxy)-phenyl]-1H-benzoimidazole; |
| 89 | 5-Fluoro-4-methyl-2-[2-methyl-4-(3-piperidin-4-yl-propoxy)-phenyl]-1H-benzoimidazole; |
| 90 | 6-Chloro-2-{4-[3-(1-ethyl-piperidin-4-yl)-propoxy]-2-methyl-phenyl}-4-methyl-1H-benzoimidazole; |
| 91 | {2-[3-Chloro-4-(4-methyl-1H-benzoimidazol-2-yl)-phenoxy]-ethyl}-methyl-(1-methyl-piperidin-4-yl)-amine; |
| 92 | 6-Chloro-4-methyl-2-{2-methyl-4-[2-(1-methyl-piperidin-4-yloxy)-ethoxy]-phenyl}-1H-benzoimidazole; |
| 93 | 6-Chloro-4-methyl-2-{2-methyl-4-[3-(1-methyl-1,2,3,6-tetrahydro-pyridin-4-yl)-propoxy]-phenyl}-1H-benzoimidazole; |
| 94 | 5-Fluoro-4-methyl-2-{2-methyl-4-[3-(1-methyl-1,2,3,6-tetrahydro-pyridin-4-yl)-propoxy]-phenyl}-1H-benzoimidazole; |
| 95 | 6-Fluoro-7-methyl-2-{3-[4-(1-methyl-piperidin-4-yl)-butoxy]-phenyl}-1H-benzoimidazole; |
| 96 | 7-Methyl-2-{3-[4-(1-methyl-piperidin-4-yl)-butoxy]-phenyl}-1H-benzoimidazole; |
| 97 | 6,7-Dimethyl-2-{3-[4-(1-methyl-piperidin-4-yl)-butoxy]-phenyl}-1H-benzoimidazole; |
| 98 | 5-Chloro-7-methyl-2-{3-[4-(1-methyl-piperidin-4-yl)-butoxy]-phenyl}-1H-benzoimidazole; |
| 99 | 5,7-Dimethyl-2-{2-methyl-3-[4-(1-methyl-piperidin-4-yl)-butoxy]-phenyl}-1H-benzoimidazole; |
| 100 | 5-Chloro-7-methyl-2-{2-methyl-3-[4-(1-methyl-piperidin-4-yl)-butoxy]-phenyl}-1H-benzoimidazole; |
| 101 | 6-Fluoro-7-methyl-2-{2-methyl-3-[4-(1-methyl-piperidin-4-yl)-butoxy]-phenyl}-1H-benzoimidazole; |
| 102 | 6-Fluoro-7-methyl-2-{3-[3-(1-methyl-piperidin-4-yloxy)-propoxy]-phenyl}-1H-benzoimidazole; and |
| 176 | {2-(5-Fluoro-4-methyl-1H-benzoimidazol-2-yl)-5-[3-(1-methyl-piperidin-4-yl)-propoxy]-phenyl}-methanol. |

Compounds where W is N were made according to the synthetic methods outlined in Schemes 1 through 6 and examples of such compounds are provided in the group:

| EX | Compound |
|---|---|
| 103 | 6-Chloro-4-methyl-2-{6-[3-(4-methyl-piperazin-1-yl)-propoxy]-pyridin-3-yl}-1H-benzoimidazole; |
| 104 | 4-Methyl-2-{6-[3-(4-methyl-piperazin-1-yl)-propoxy]-pyridin-3-yl}-1H-benzoimidazole; |
| 105 | 5-Fluoro-4-methyl-2-{6-[3-(4-methyl-piperazin-1-yl)-propoxy]-pyridin-3-yl}-1H-benzoimidazole; |
| 106 | 4-Methyl-2-{6-[3-(1-methyl-piperidin-4-yl)-propoxy]-pyridin-3-yl}-1H-benzoimidazole; |
| 107 | 4,5-Dimethyl-2-{6-[3-(1-methyl-piperidin-4-yl)-propoxy]-pyridin-3-yl}-1H-benzoimidazole; |
| 108 | 4-Chloro-2-{6-[3-(1-methyl-piperidin-4-yl)-propoxy]-pyridin-3-yl}-1H-benzoimidazole; |
| 109 | 6-Chloro-4-methyl-2-{4-methyl-6-[3-(1-methyl-piperidin-4-yl)-propoxy]-pyridin-3-yl}-1H-benzoimidazole; |
| 110 | 4-Methyl-2-{4-methyl-6-[3-(1-methyl-piperidin-4-yl)-propoxy]-pyridin-3-yl}-1H-benzoimidazole; |
| 111 | 5-Fluoro-4-methyl-2-{4-methyl-6-[3-(1-methyl-piperidin-4-yl)-propoxy]-pyridin-3-yl}-1H-benzoimidazole; |
| 112 | 4,5-Dimethyl-2-{4-methyl-6-[3-(1-methyl-piperidin-4-yl)-propoxy]-pyridin-3-yl}-1H-benzoimidazole; |
| 113 | 4,6-Dimethyl-2-{4-methyl-6-[3-(1-methyl-piperidin-4-yl)-propoxy]-pyridin-3-yl}-1H-benzoimidazole; |
| 114 | 4-Chloro-2-{4-methyl-6-[3-(1-methyl-piperidin-4-yl)-propoxy]-pyridin-3-yl}-1H-benzoimidazole; |
| 115 | 2-{4-Chloro-6-[3-(1-methyl-piperidin-4-yl)-propoxy]-pyridin-3-yl}-5-fluoro-4-methyl-1H-benzoimidazole; |
| 116 | 2-{4-Chloro-6-[3-(1-methyl-piperidin-4-yl)-propoxy]-pyridin-3-yl}-4-methyl-1H-benzoimidazole; |
| 117 | 6-Chloro-2-{4-chloro-6-[3-(1-methyl-piperidin-4-yl)-propoxy]-pyridin-3-yl}-4-methyl-1H-benzoimidazole; |
| 118 | 2-{4-Chloro-6-[3-(1-methyl-piperidin-4-yl)-propoxy]-pyridin-3-yl}-4,6-dimethyl-1H-benzoimidazole; |
| 119 | 2-{4-Methoxy-6-[3-(1-methyl-piperidin-4-yl)-propoxy]-pyridin-3-yl}-4-methyl-1H-benzoimidazole; |
| 120 | 5-Fluoro-2-{4-methoxy-6-[3-(1-methyl-piperidin-4-yl)-propoxy]-pyridin-3-yl}-4-methyl-1H-benzoimidazole; |
| 121 | 5-Fluoro-4-methyl-2-{6-[3-(1-methyl-1,2,3,6-tetrahydro-pyridin-4-yl)-propoxy]-pyridin-3-yl}-1H-benzoimidazole; |
| 122 | 4-Methyl-2-{6-[3-(1-methyl-1,2,3,6-tetrahydro-pyridin-4-yl)-propoxy]-pyridin-3-yl}-1H-benzoimidazole; |
| 123 | 6-Chloro-4-methyl-2-{6-[3-(1-methyl-1,2,3,6-tetrahydro-pyridin-4-yl)-propoxy]-pyridin-3-yl}-1H-benzoimidazole; |
| 124 | 4,5-Dimethyl-2-{6-[3-(1-methyl-1,2,3,6-tetrahydro-pyridin-4-yl)-propoxy]-pyridin-3-yl}-1H-benzoimidazole; |
| 125 | 4,6-Dimethyl-2-{6-[3-(1-methyl-1,2,3,6-tetrahydro-pyridin-4-yl)-propoxy]-pyridin-3-yl}-1H-benzoimidazole; |
| 126 | 5-Chloro-4-methyl-2-{6-[3-(1-methyl-1,2,3,6-tetrahydro-pyridin-4-yl)-propoxy]-pyridin-3-yl}-1H-benzoimidazole; |
| 127 | 5-Fluoro-4-methyl-2-{6-[3-(1-methyl-piperidin-4-yl)-propoxy]-4-pyrrolidin-1-ylmethyl-pyridin-3-yl}-1H-benzoimidazole; |
| 128 | 2-{5-Bromo-2-[4-(1-methyl-piperidin-4-yl)-butoxy]-pyridin-4-yl}-4-methyl-1H-benzoimidazole; |
| 129 | 2-{5-Bromo-2-[4-(1-methyl-piperidin-4-yl)-butoxy]-pyridin-4-yl}-5-fluoro-4-methyl-1H-benzoimidazole; |
| 130 | 2-{5-Bromo-2-[4-(1-methyl-piperidin-4-yl)-butoxy]-pyridin-4-yl}-6-chloro-4-methyl-1H-benzoimidazole; |
| 131 | 2-{5-Bromo-2-[4-(1-methyl-piperidin-4-yl)-butoxy]-pyridin-4-yl}-4,6-dimethyl-1H-benzoimidazole; |
| 132 | 2-{5-Bromo-2-[4-(1-methyl-piperidin-4-yl)-butoxy]-pyridin-4-yl}-4,5-dimethyl-1H-benzoimidazole; |
| 133 | 2-{5-Bromo-2-[4-(1-methyl-piperidin-4-yl)-butoxy]-pyridin-4-yl}-5-chloro-4-methyl-1H-benzoimidazole; |
| 134. | 2-{5-Bromo-2-[4-(1-methyl-piperidin-4-yl)-butoxy]-pyridin-4-yl}-5-tert-butyl-1H-benzoimidazole; |
| 135 | 5-tert-Butyl-2-{2-[4-(1-methyl-piperidin-4-yl)-butoxy]-pyridin-4-yl}-1H-benzoimidazole; |
| 136 | 2-{5-Chloro-2-[4-(1-methyl-piperidin-4-yl)-butoxy]-pyridin-4-yl}-5-fluoro-4-methyl-1H-benzoimidazole; |
| 137 | 2-{5-Chloro-2-[4-(1-methyl-piperidin-4-yl)-butoxy]-pyridin-4-yl}-4,5-dimethyl-1H-benzoimidazole; |
| 138 | 4,6-Dimethyl-2-{2-[4-(4-methyl-piperazin-1-yl)-butoxy]-pyridin-4-yl}-1H-benzoimidazole; |
| 139 | 4-Methyl-2-{2-[4-(4-methyl-piperazin-1-yl)-butoxy]-pyridin-4-yl}-1H-benzoimidazole; |
| 140 | 4,5-Dimethyl-2-{2-[4-(4-methyl-piperazin-1-yl)-butoxy]-pyridin-4-yl}-1H-benzoimidazole; |
| 141 | 5-Fluoro-4-methyl-2-{2-[4-(4-methyl-piperazin-1-yl)-butoxy]-pyridin-4-yl}-1H-benzoimidazole; |
| 142 | 6-Chloro-4-methyl-2-{2-[4-(4-methyl-piperazin-1-yl)-butoxy]-pyridin-4-yl}-1H-benzoimidazole; |
| 143 | 5-Fluoro-4-methyl-2-{2-[4-(4-methyl-[1,4]diazepan-1-yl)-butoxy]-pyridin-4-yl}-1H-benzoimidazole; |
| 144 | 4,5-Dimethyl-2-{2-[4-(4-methyl-[1,4]diazepan-1-yl)-butoxy]-pyridin-4-yl}-1H-benzoimidazole; |
| 145 | 4,6-Dimethyl-2-{2-[4-(1-methyl-piperidin-4-yl)-butoxy]-pyridin-4-yl}-1H-benzoimidazole; |
| 146 | 4-Methyl-2-{2-[4-(1-methyl-piperidin-4-yl)-butoxy]-pyridin-4-yl}-1H-benzoimidazole; |

-continued

| EX | Compound |
|---|---|
| 147 | 5-Fluoro-4-methyl-2-{2-[4-(1-methyl-piperidin-4-yl)-butoxy]-pyridin-4-yl}-1H-benzoimidazole; |
| 148 | 4-Chloro-2-{2-[4-(1-methyl-piperidin-4-yl)-butoxy]-pyridin-4-yl}-1H-benzoimidazole; |
| 149 | 4,5-Dimethyl-2-{2-[4-(1-methyl-piperidin-4-yl)-butoxy]-pyridin-4-yl}-1H-benzoimidazole; |
| 150 | 6-Chloro-4-methyl-2-{2-[4-(1-methyl-piperidin-4-yl)-butoxy]-pyridin-4-yl}-1H-benzoimidazole; |
| 151 | 5-Chloro-4-methyl-2-{2-[4-(1-methyl-piperidin-4-yl)-butoxy]-pyridin-4-yl}-1H-benzoimidazole; |
| 152 | 5-tert-Butyl-2-[2-(4-piperidin-4-yl-butoxy)-pyridin-4-yl]-1H-benzoimidazole; |
| 153 | 4,6-Dimethyl-2-[2-(4-piperidin-4-yl-butoxy)-pyridin-4-yl]-1H-benzoimidazole; |
| 154 | 2-{2-[4-(1-Ethyl-piperidin-4-yl)-butoxy]-pyridin-4-yl}-4,5-dimethyl-1H-benzoimidazole; |
| 155 | 4,6-Dimethyl-2-{3-methyl-2-[4-(1-methyl-piperidin-4-yl)-butoxy]-pyridin-4-yl}-1H-benzoimidazole; |
| 156 | 4-Methyl-2-{3-methyl-2-[4-(1-methyl-piperidin-4-yl)-butoxy]-pyridin-4-yl}-1H-benzoimidazole; |
| 157 | 6-Chloro-4-methyl-2-{3-methyl-2-[4-(1-methyl-piperidin-4-yl)-butoxy]-pyridin-4-yl}-1H-benzoimidazole; |
| 158 | 2-{3-Chloro-2-[4-(1-methyl-piperidin-4-yl)-butoxy]-pyridin-4-yl}-4-methyl-1H-benzoimidazole; |
| 159 | 2-{3-Chloro-2-[4-(1-methyl-piperidin-4-yl)-butoxy]-pyridin-4-yl}-4,5-dimethyl-1H-benzoimidazole; |
| 160 | 4-Chloro-2-{3-chloro-2-[4-(1-methyl-piperidin-4-yl)-butoxy]-pyridin-4-yl}-1H-benzoimidazole; |
| 161 | 2-{3-Chloro-2-[4-(1-methyl-piperidin-4-yl)-butoxy]-pyridin-4-yl}-5-fluoro-4-methyl-1H-benzoimidazole; |
| 162 | 2-{3-Chloro-2-[4-(1-methyl-piperidin-4-yl)-butoxy]-pyridin-4-yl}-4,6-dimethyl-1H-benzoimidazole; |
| 163 | 6-Chloro-2-{3-chloro-2-[4-(1-methyl-piperidin-4-yl)-butoxy]-pyridin-4-yl}-4-methyl-1H-benzoimidazole; |
| 164 | 5-Chloro-2-{3-chloro-2-[4-(1-methyl-piperidin-4-yl)-butoxy]-pyridin-4-yl}-4-methyl-1H-benzoimidazole; |
| 165 | 5-Fluoro-4-methyl-2-{5-methyl-2-[4-(1-methyl-piperidin-4-yl)-butoxy]-pyridin-4-yl}-1H-benzoimidazole; |
| 166 | 5-Chloro-6-fluoro-2-{5-methyl-2-[4-(1-methyl-piperidin-4-yl)-butoxy]-pyridin-4-yl}-1H-benzoimidazole; |
| 167 | 5-tert-Butyl-2-{5-methyl-2-[4-(1-methyl-piperidin-4-yl)-butoxy]-pyridin-4-yl}-1H-benzoimidazole; |
| 168 | 4,5-Dimethyl-2-{5-methyl-2-[4-(1-methyl-piperidin-4-yl)-butoxy]-pyridin-4-yl}-1H-benzoimidazole; |
| 169 | 2-{5-Chloro-2-[4-(1-methyl-piperidin-4-yl)-butoxy]-pyridin-4-yl}-4,6-dimethyl-1H-benzoimidazole; |
| 170 | 5-Chloro-2-{5-chloro-2-[4-(1-methyl-piperidin-4-yl)-butoxy]-pyridin-4-yl}-1H-benzoimidazole; |
| 171 | 5-Chloro-2-{5-chloro-2-[4-(1-methyl-piperidin-4-yl)-butoxy]-pyridin-4-yl}-6-fluoro-1H-benzoimidazole; |
| 172 | 5-tert-Butyl-2-{5-chloro-2-[4-(1-methyl-piperidin-4-yl)-butoxy]-pyridin-4-yl}-1H-benzoimidazole; |
| 173 | 2-{5-Bromo-2-[4-(1-methyl-piperidin-4-yl)-butoxy]-pyridin-4-yl}-4-chloro-1H-benzoimidazole; |
| 174 | 2-{5-Bromo-2-[4-(1-methyl-piperidin-4-yl)-butoxy]-pyridin-4-yl}-5-chloro-6-fluoro-1H-benzoimidazole; |
| 175 | 2-{5-Bromo-2-[4-(1-methyl-piperidin-4-yl)-butoxy]-pyridin-4-yl}-5-chloro-1H-benzoimidazole; and |
| 177 | {4-(4,6-Dimethyl-1H-benzoimidazol-2-yl)-6-[4-(1-methyl-piperidin-4-yl)-butoxy]-pyridin-3-yl}-methanol. |

Embodiments of pharmaceutical compositions and methods of use of compounds according to this invention are provided by pharmaceutical compositions that comprise, and by methods of use of, any of the compounds described herein and combinations thereof.

Embodiments of pharmaceutical compositions for treating or preventing an $H_4$ receptor-mediated condition in a subject that comprise a therapeutically effective amount of at least one $H_4$ receptor modulator selected from compounds of formulae (I) and (II), enantiomers, diastereomers, racemates thereof, pharmaceutically acceptable salts, amides and esters thereof, further comprise a pharmaceutically acceptable carrier.

Embodiments of pharmaceutical compositions for inhibiting leukocyte recruitment in a subject that comprise a therapeutically effective amount of at least one leukocyte recruitment inhibitor selected from compounds of formulae (I) and (II), enantiomers, diastereomers, racemates thereof, pharmaceutically acceptable salts, amides and esters thereof, further comprise a pharmaceutically acceptable carrier.

Embodiments of anti-inflammatory compositions that comprise a therapeutically effective amount of at least one anti-inflammatory compound selected from compounds of formulae (I) and (II), enantiomers, diastereomers, racemates thereof, pharmaceutically acceptable salts, amides and esters thereof, further comprise a pharmaceutically acceptable carrier.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates thereof, pharmaceutically acceptable salts, amides and esters thereof, include methods wherein said inflammatory response is a response to at least one of the conditions: inflammatory disorders, allergic disorders, dermatological disorders, autoimmune disease, lymphatic disorders, itchy skin, and immunodeficiency disorders.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates thereof, pharmaceutically acceptable salts, amides and esters thereof, include methods wherein said inflammatory response is a response to chemotherapy.

Embodiments of methods for treating or preventing inflammation in a subject that comprise administering to the subject in connection with an inflammatory response a pharmaceutical composition comprising a therapeutically effective amount of at least one anti-inflammatory compound selected from compounds of formulae (I) and (II), enantiomers, diastereomers, racemates thereof, pharmaceutically acceptable salts, amides and esters thereof, include methods wherein at least one of the following is satisfied: said inflammatory response is a response to a physical stimulus; said inflammatory response is a response to a chemical stimulus; said inflammatory response is a response to infection; said inflammatory response is a response to an invasion by a body that is foreign to said subject; said inflammatory response is a response to an immunological stimulus; said inflammatory response is a response to a non-immunological stimulus; said inflammatory response is a response to at least one of the conditions: allergy, asthma, chronic obstructed pulmonary disease (COPD), atherosclerosis, rheumatoid arthritis, multiple sclerosis, inflammatory bowel disease, and more specifically wherein said inflammatory bowel disease is at least one of Crohn's disease and ulcerative colitis, psoriasis, allergic rhinitis, scleroderma, autoimmune thyroid disease, immune-mediated diabetes mellitus, and lupus; said inflammatory response is a response to at least one of the conditions: myasthenia gravis, autoimmune neuropathy, and more specifically wherein said autoimmune neuropathy is Guillain-Barré neuropathy, autoimmune uveitis, autoimmune hemolytic anemia, pernicious anemia, autoimmune thrombocytopenia, temporal arteritis, anti-phospholipid syndrome, vasculitides, and more specifically wherein said vasculitides is Wegener's granulomatosis, Behcet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathy, and more specifically wherein said spondyloarthropathy is ankylosing spondylitis, and Sjogren's syndrome; said inflammatory response is acute inflammation; said inflammatory response is allergic inflammation; and said inflammatory response is chronic inflammation. Administration in connection with an inflammatory response according to the present invention includes administration at a time that is at least one of prior to, at the onset of, and after inflammation is detected.

Embodiments of methods for modulating an $H_4$ receptor that comprise exposing an $H_4$ receptor to at least one compound selected from compounds of formulae (I) and (II), enantiomers, diastereomers, racemates thereof, pharmaceutically acceptable salts, amides and esters thereof, include methods wherein at least one of the following is satisfied: said at least one compound modulates the $H_4$ receptor as a receptor antagonist, and said at least one compound of modulates the $H_4$ receptor as a receptor partial agonist.

If more than one active agent is administered, such as a compound of formula (I) or (II), the therapeutically effective amount may be a jointly effective amount.

An illustration of the invention is a pharmaceutical composition made by mixing at least one benzoimidazole compound selected from compounds of formulae (I) and (II), enantiomers, diastereomers, racemates thereof, pharmaceutically acceptable salts, amides and esters thereof, and a pharmaceutically acceptable carrier. Illustrating the invention is a process for making a pharmaceutical composition comprising mixing at least one benzoimidazole compound selected from compounds of formulae (I) and (II), enantiomers, diastereomers, racemates thereof, pharmaceutically acceptable salts, amides and esters thereof, and a pharmaceutically acceptable carrier.

Another example of the invention is the use of a composition that comprises at least one benzoimidazole compound selected from compounds of formulae (I) and (II), enantiomers, diastereomers, racemates thereof, pharmaceutically acceptable salts, amides and esters thereof, in the preparation of a medication for treating any one of the conditions referred to herein; one of such conditions is inflammation. Another example of the invention is the use of a composition that comprises at least one benzoimidazole compound selected from compounds of formulae (I) and (II), enantiomers, diastereomers, racemates thereof, pharmaceutically acceptable salts, amides and esters thereof, in the treatment or prevention of any one of the conditions referred to herein; one of such conditions is inflammation.

Compounds according to the present invention may be made according to processes within the skill of the art and/or according to processes of this invention, such as those described in the schemes and examples that follow and by matrix or combinatorial methods. To obtain the various compounds herein, starting materials may be employed that carry the ultimately desired substituents though the reaction scheme with or without protection as appropriate. Starting materials may be obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. Any product containing a chiral center may be separated into its enantiomers by conventional techniques. Those of ordinary skill in the art will be able to modify and adapt the guidance provided herein to make compounds according to the present invention.

Embodiments of processes illustrated herein include, when chemically meaningful, one or more steps such as hydrolysis, halogenation, protection, and deprotection. These steps can be implemented in light of the teachings provided herein and the ordinary skill in the art.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

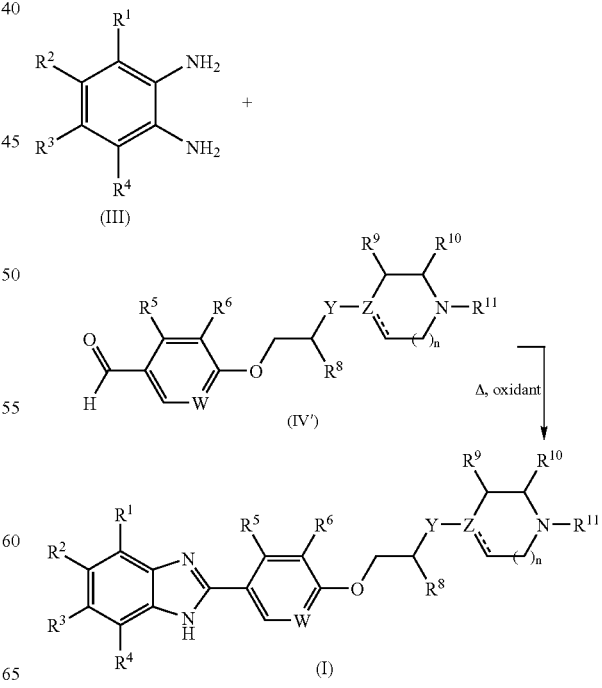

Scheme 1

SCHEME 2

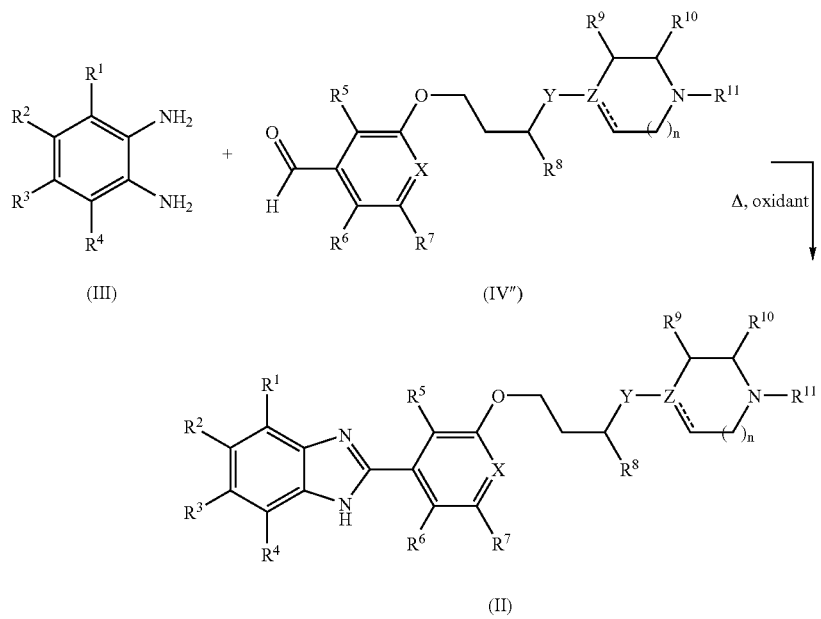

Referring to Schemes 1 and 2, there are disclosed the following notes and additions. The starting materials for the steps described below regarding Schemes 1 and 2 are commercially available or easily accessible to those skilled in the art.

Compounds of formula (I) or (II) are prepared by condensing a suitably substituted diamino benzene (III) under oxidizing conditions with a suitably substituted benzaldehyde (IV') or (IV'') to form a compound of formula (I) when the benzaldehyde (IV') has a para ether substitution with respect to the aldehyde group (Scheme 1), or a compound of formula (II) when the benzaldehyde (IV'') has a meta ether substitution with respect to the aldehyde group (Scheme 2). Suitable oxidants for this step include air, $Na_2S_2O_5$, Oxone, and chemically compatible oxidants that have a similar oxidizing power, and mixtures thereof.

This condensation is preferably performed in a heated medium in a chemically compatible solvent. Reaction medium temperatures range preferably from about 40° C. to about 150° C., more preferably about 80° C. to about 100° C. Solvents that can be used for this reaction include dioxane, THF, benzotrifluoride, toluene, 1,2-dichloroethane, DMA, and DMSO, preferably DMF, and mixtures thereof.

Suitably substituted benzaldehydes (IV') and (IV'') can be prepared according to procedures known in the art. In one preparation procedure, a suitably substituted hydroxy benzaldehyde is reacted with a suitably substituted moiety to form the ether link in compounds (IV') and (IV''). Reaction with suitably substituted 4-hydroxy benzaldehyde leads to the formation of compound (IV'), and reaction with a suitably substituted 3-hydroxy benzaldehyde leads to the formation of compound (IV'').

Regarding the following Schemes 3 through 6, the starting materials for the steps described below are commercially available or easily accessible to those skilled in the art.

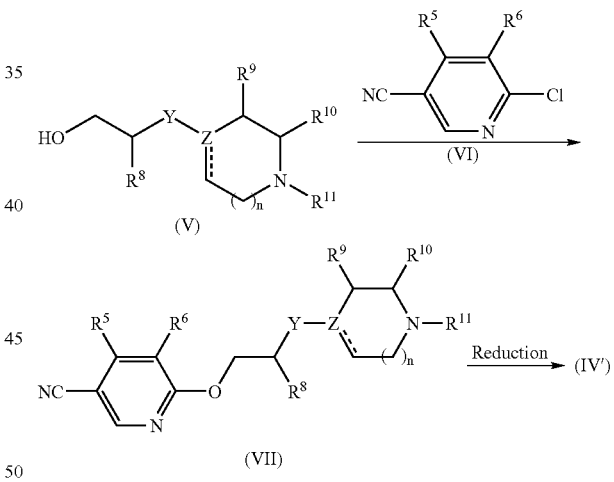

Particular aldehydes (IV') may prepared as shown in Scheme 3. A suitable primary alcohol (V) is treated with a base such as sodium hydride, potassium hydride, potassium t-butoxide, or lithium diisopropylamide (LDA), in a polar solvent such as DMF or THF. Preferred conditions include sodium hydride in DMF. The resulting alkoxide is then treated with an optionally substituted 6-chloronicotinonitrile to form an aryl ether of formula (VII). The reaction may be performed without heating or with heating up to about 60° C. Where $R^5$ is H, compounds of formula (VII) may be further reacted to install a non-hydrogen substituent at that position. Compounds of formula (VII) are treated with a strong base such as LDA, lithium 2,2,6,6-tetramethylpiperidine (LTMP), or lithium bis(trimethylsilyl)amide (LHMDS), at low temperatures of between about −78° C. and about −50° C., in a solvent such as THF, diethyl ether, or toluene. Preferred conditions include the use of LDA or LTMP in THF. The resulting lithiated species is treated with a suitable electrophile, at temperatures between about −78° C. and room temperature. Preferred electrophiles are methyl iodide and hexachloroethane. When R⁵ is then chloride, additional substituents may be introduced at that position using nucleophilic substitution. Suitable nucleophiles include $C_{1-3}$alkoxides and primary and secondary amines. In a particular embodiment, the preferred nucleophile is methoxide. Once the desired substituents are in place, the nitrile functionality in compounds of formula (VII) is then reduced with a suitable reducing agent, such as diisobutylaluminum hydride, in a solvent such as toluene or THF, to form aldehydes of formula (IV') where W is N.

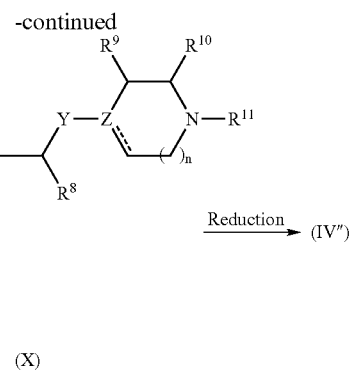

Referring to Scheme 4, a suitable primary alcohol of formula (VIII) is reacted with an appropriately substituted 2-chloropyridine of formula (IX) to generate pyridyl ethers of formula (X), as shown in Scheme 3. Preferred reaction conditions employ sodium hydride in DMF. Where R⁵ is hydrogen, additional substituents may be introduced at that position by reaction of ethers of formula (X) with a strong, hindered base followed by a suitable electrophile as described in Scheme 3. Preferred electrophiles include methyl iodide and hexachloroethane. Once the desired substituents are in place, nitriles of formula (X) may be reduced to aldehydes of formula (IV''), where W is N as shown, through reduction of the nitrile group as described in Scheme 3. Preferred reducing agents include diisobutylaluminum hydride.

Scheme 4

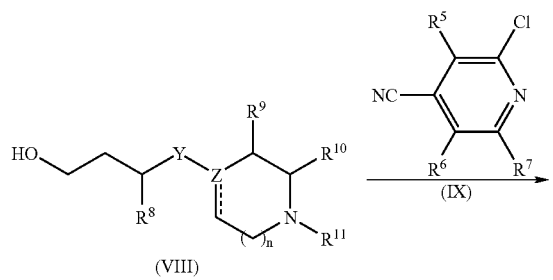

Scheme 5

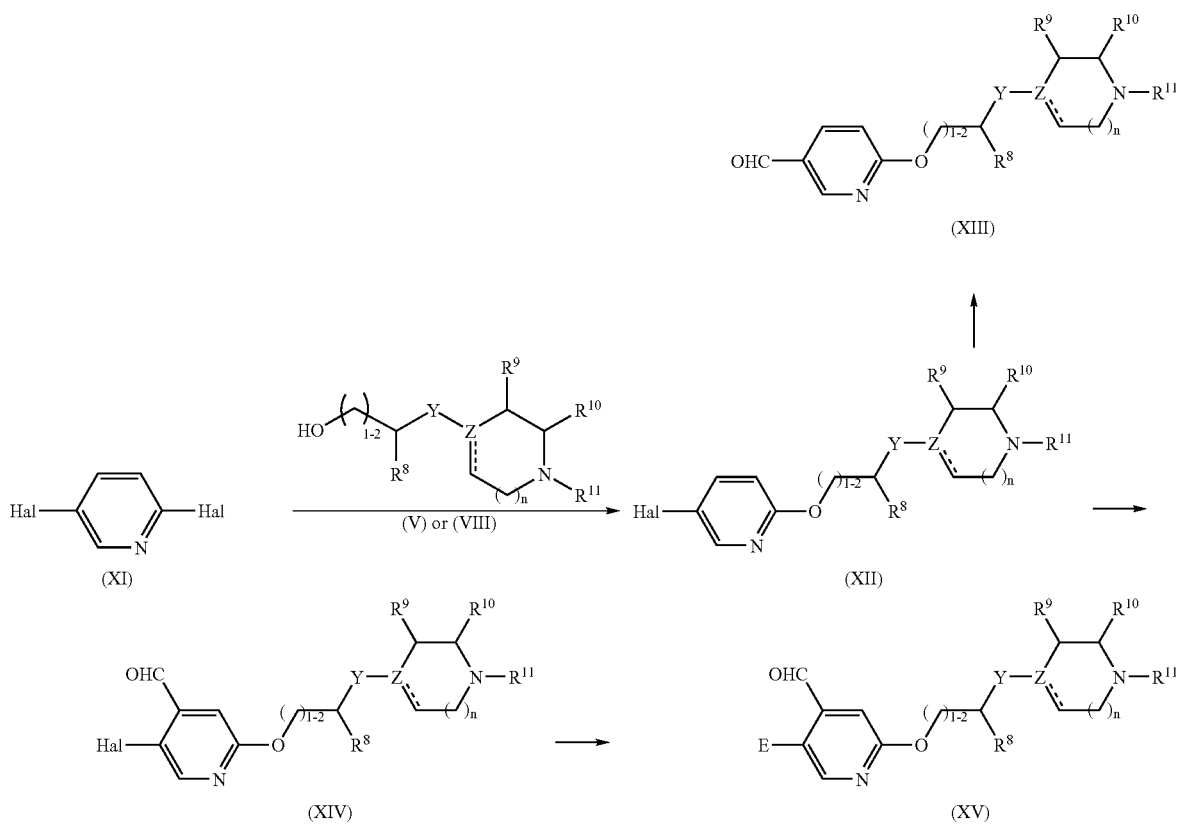

Referring to Scheme 5, dihalopyridines of formula (XI), where Hal is either Cl or Br, are reacted with primary alcohols of formulae (V) or (VII), using conditions described above, to form pyrido ethers of formula (XII). The resulting 3-halopyridines can then be converted to the corresponding 3-formylpyridines of formula (XIII) by halogen-metal exchange with a suitable alkyllithium reagent, in a suitable solvent such as THF or diethyl ether, followed by quenching with a formyl equivalent, such as DMF, N-formylpiperidine, or ethyl chloroformate. Preferred conditions employ n-BuLi or t-BuLi in THF, and a preferred electrophile is DMF. Alternatively, 3-halopyridines of formula (XII) may be converted into aldehydes of formula (XIV) according to the directed lithiation and formyl trapping procedures described in Schemes 3 and 4. Aldehydes of formula (XIV), where Hal is Br, may be further processed through a three-step sequence to provide aldehydes of formula (XV). To that end, the aldehyde is first protected as a suitable group, such as an acetal. The bromide may then reacted via halogen-metal exchange using an alkyllithium reagent and electrophilic trapping, as described above in the current scheme, to introduce substituents E. Preferred electrophilic reagents include methyl iodide and hexachloroethane, to produce compounds of formula (XV) where E is methyl or chloro, respectively. Aldehydes of formulae (XIII), (XIV), and (XV) may then be processed into compound of the invention as shown in Schemes 1 and 2 above.

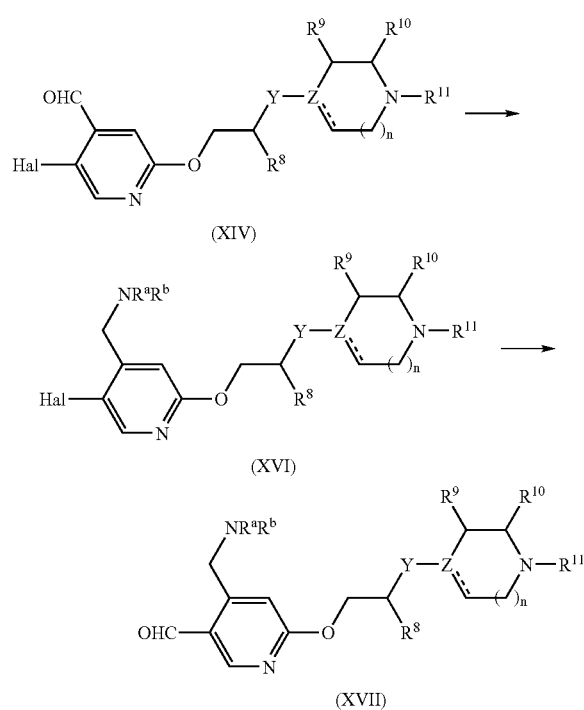

Referring to Scheme 6, aldehydes of formula (XIV) may be converted to aminomethyl analogs of formula (XVI) via reductive amination, using a suitable reducing agent such as $NaCNBH_3$ or $Na(OAc_3)BH$, in a suitable solvent such as 1,2-dichloroethane or methanol. Optional additives may include acetic acid or a Lewis acid such as $ZnCl_2$. Amines of formula (XVI) may then be transformed into aldehydes of formula (XVII) by performing halogen-metal exchange and quenching procedures as described above. Aldehydes of formula (XVII) may be processed into compounds of the invention according to Scheme 1.

Where the processes for the preparation of the compounds according to the invention give rise to mixture of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be separated using a chiral HPLC column.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The expression of the $H_4$ receptor in immune cells, including some leukocytes and mast cells, establishes it as an important target for therapeutic intervention in a range of immunological and inflammatory disorders (such as allergic, chronic, or acute inflammation). Specifically $H_4$ receptor ligands are expected to be useful for the treatment or prevention of various mammalian disease states.

Thus, according to the invention, the disclosed compounds, whether partial agonists or antagonists of the $H_4$ receptor, and compositions are useful for the amelioration of symptoms associated with, the treatment of, and the prevention of, the following conditions and diseases: inflammatory disorders, allergic disorders, dermatological disorders, autoimmune disease, lymphatic disorders, and immunodeficiency disorders, including the more specific conditions and diseases given above. The disclosed compounds may also be useful as adjuvants in chemotherapy or in the treatment of itchy skin.

Aspects of the invention include (a) a pharmaceutical composition comprising a benzoimidazole compound selected from compounds of formulae (I) and (II), enantiomers, diastereomers, racemates thereof, pharmaceutically acceptable salts, amides and esters thereof, and a preferred compound as described herein, and a pharmaceutically acceptable carrier; (b) a packaged drug comprising (1) a pharmaceutical composition comprising at least one benzoimidazole compound selected from compounds of formulae (I) and (II), enantiomers, diastereomers, racemates thereof, pharmaceutically acceptable salts, amides and esters thereof, or one or more preferred compounds as described herein, and a pharmaceutically acceptable carrier, and (2) instructions for the administration of said composition for the treatment or prevention of an $H_4$-mediated disease or condition.

Embodiments of this invention provide methods for treating an $H_4$-mediated condition in a patient, said methods comprising administering to the patient a pharmaceutically effective amount of a composition comprising at least one benzoimidazole compound selected from compounds of formulae (I) and (II), enantiomers, diastereomers, racemates thereof, pharmaceutically acceptable salts, amides and esters thereof, and other disclosed or preferred compounds. In these conditions, the action of the $H_4$ receptor is involved. For example, the invention features a method for treating an $H_4$ mediated condition in a patient, said method comprising administering to the patient a pharmaceutically effective $H_4$-antagonizing amount of a composition comprising at least one benzoimidazole compound selected from compounds of formulae (I) and (II), enantiomers, diastereomers, racemates thereof, pharmaceutically acceptable salts, amides and esters thereof. As used herein, "treating" a disorder, and grammatically related terms, mean eliminating or otherwise ameliorating the cause and/or effects thereof. Terms such as to "inhibit", and grammatically related terms, the onset of a disorder or event, and to "prevent" a disorder or condition, and grammatically related terms, mean preventing, delaying or reducing the likelihood of such onset.

The effect of an antagonist may also be produced by an inverse agonist. Inverse agonism describes the property of a compound to actively turn off a receptor that displays constitutive activity. Constitutive activity can be identified in cells that have been forced to over-express the human $H_4$ receptor. Constitutive activity can be measured by examining cAMP levels or by measuring a reporter gene sensitive to cAMP levels after a treatment with a cAMP-stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as $H_4$ inverse agonists will dose-dependently stimulate cAMP levels in $H_4$-expressing cells. Compounds that behave as $H_4$ antagonists will block either $H_4$ agonist-induced inhibition of cAMP or $H_4$ inverse agonist-induced increases in cAMP.

Further embodiments of the invention include disclosed compounds that are inhibitors of a mammalian histamine $H_4$ receptor function, inhibitors of inflammation or inflammatory responses in vivo or in vitro, modulators of the expression of a mammalian histamine $H_4$ receptor protein, inhibitors of polymorphonuclear leukocyte activation in vivo or in vitro, or combinations of the above, and corresponding methods of treatment, prophylaxis, and diagnosis comprising the use of a disclosed compound.

The terms "unit dose" and their grammatical equivalent forms are used herein to refer to physically discrete units suitable as unitary dosages for human patients and other animals, each unit containing a predetermined effective, pharmacologic amount of the active ingredient calculated to produce the desired pharmacological effect. The specifications for the novel unit dosage forms of this invention are determined by, and are directly dependent on, the characteristics of the active ingredient, and on the limitations inherent in the art of compounding such an active ingredient for therapeutic use in humans and other animals.

The pharmaceutical compositions can be prepared using conventional pharmaceutical excipients and compounding techniques. Examples of suitable unit dosage forms are tablets, capsules, pills, powders, powder packets, granules, wafers, and the like, segregated multiples of any unit dosage form, as well as liquid solutions, and suspensions. Some liquid forms are aqueous, whereas other embodiments of liquid forms are non-aqueous. Oral dosage forms may be elixirs, syrups, capsules, tablets and the like. Examples of solid carriers include those materials usually employed in the manufacture of pills or tablets, such as lactose, starch, glucose, methylcellulose, magnesium stearate, dicalcium phosphate, mannitol and the like, thickeners such as tragacanth and methylcellulose USP, finely divided $SiO_2$, polyvinylpyrrolidone, magnesium stearate, and the like. Typical liquid oral excipients include ethanol, glycerol, water and the like. All excipients may be mixed as needed with diluents (for example, sodium and calcium carbonates, sodium and calcium phosphates, and lactose), disintegrants (for example, cornstarch and alginic acid), granulating agents, lubricants (for example, magnesium stearate, stearic acid, and talc), binders (for example, starch and gelatin), thickeners (for example, paraffin, waxes, and petrolatum), flavoring agents, coloring agents, preservatives, and the like by conventional techniques known to those of ordinary skill in the art of preparing dosage forms. Coatings can be present and include, for example, glyceryl monostearate and/or glyceryl diestearate. Capsules for oral use include hard gelatin capsules in which the active ingredient is mixed with a solid diluent, and soft gelatin capsules, in which the active ingredient is mixed with water or an oil, such as peanut oil, liquid paraffin, or olive oil.

Parenteral dosage forms may be prepared using water or another sterile carrier. Parenteral solutions can be packaged in containers adapted for subdivision into individual doses. For intramuscular, intraperitoneal, subcutaneous, and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone, and gum tragacanth, and a wetting agent, such as lecithin. Suitable preservatives for aqueous suspensions include ethyl and n-propyl p-hydroxybenzoate. Parenteral formulations include pharmaceutically acceptable aqueous or non-aqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

Physiologically acceptable carriers are well known in the art. Examples of liquid carriers are solutions in which compounds according to the present invention form solutions, emulsions, and dispersions. Compatible antioxidants, such as methylparaben and propylparaben, can be present in solid and/or liquid compositions, as can sweeteners.

Pharmaceutical compositions according to the present invention may include suitable emulsifiers typically used in emulsion compositions. Such emulsifiers are described in standard publications such as H. P. Fiedler, 1989, Lexikon der Hilfsstoffe für Pharmazie, Kosmetic und agrenzende Gebiete, Cantor ed., Aulendorf, Germany, and in Handbook of Pharmaceutical Excipients, 1986, American Pharmaceutical Association, Washington, D.C., and the Pharmaceutical Society of Great Britain, London, UK, which are incorporated herein by reference. Gelling agents may also be added to compositions according to this invention. Polyacrylic acid derivatives, such as carbomers, are examples of gelling agents, and more particularly, various types of carbopol, which are typically used in amounts from about 0.2% to about 2%. Suspensions may be prepared as a cream, an ointment, including a water-free ointment, a water-in-oil emulsion, an oil-in-water emulsion, an emulsion gel, or a gel.

It is anticipated that the compounds of the invention can be administered by oral or parenteral routes, including intravenous, intramuscular, intraperitoneal, subcutaneous, rectal, intracisternal, intravaginal, intravesical, topical or local administration, and by inhalation (bucal or nasal, preferably in the form of a spray). For oral administration, the compounds of the invention will generally be provided in the form of tablets, capsules, or as a solution or suspension. Other methods of administration include controlled release formulations, such as subcutaneous implants and dermal patches.

Effective doses of the compounds of the present invention may be ascertained by conventional methods. The specific dosage level required for any particular patient will depend on a number of factors, including severity of the condition, type of symptoms needing treatment, the route of administration, the weight, age, and general condition of the patient, and the administration of other medicaments.

In general, it is anticipated that the daily dose (whether administered as a single dose or as divided doses) will be in the range from about 0.01 mg to about 1000 mg per day, more usually from about 1 mg to about 500 mg per day, and most usually form about 10 mg to about 200 mg per day. Expressed as dosage per unit body weight, a typical dose will be expected to be between about 0.0001 mg/kg and about 15 mg/kg, especially between about 0.01 mg/kg and about 7 mg/kg, and most especially between about 0.15 mg/kg and 2.5 mg/kg.

Anticipated oral dose ranges include from about 0.01 to 500 mg/kg, daily, more preferably from about 0.05 to about 100 mg/kg, taken in 1-4 separate doses. Some compounds of the invention may be orally dosed in the range of about 0.05 to about 50 mg/kg daily, while others may be dosed at 0.05 to about 20 mg/kg daily. Infusion doses can range from about 1.0 to about $1.0 \times 10^4$ μg/(kg.min) of inhibitor, admixed with a pharmaceutical carrier over a period ranging from several minutes to several days. For topical administration, compounds of the present invention may be mixed with a pharmaceutical carrier at a concentration from about 0.1 to about 10% of drug to vehicle. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods. Daily dosages are envisaged to be, for example, between 10 mg and 5000 mg for an adult human being of normal weight.

EXAMPLES

General Experimental

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on a Hewlett Packard (Agilent) series 1100 MSD using electrospray ionization (ESI) in either positive or negative mode as indicated. The "mass calculated" for a molecular formula is the monoisotopic mass of the compound.

Purification Method 1: Reversed-phase HPLC

HPLC retention times are reported in minutes, using the methods and conditions reported below.

Instrument: Agilent HP-1100
Solvent: Acetonitrile (0.05% TFA)/H$_2$O (0.05% TFA)
Flow rate: 0.75 mL/min
Gradient: 1 min at 1% H$_2$O; 7 min linear ramp to 99% H$_2$O; 4 min at 99% H$_2$O.
Column: Zorbax Eclipse XDB-C8 (5 um, 4.6×150 mm)
Temperature: 35° C.
Wavelength: Dual detection at 220 nM and 254 nM.

Purification Method 2: Normal-phase Chromatography

2-Arylbenzimidazoles were purified by chromatography on silica gel eluting with dichloromethane, then 10% methanol in dichloromethane, and subsequently 10% (2.0 M ammonia in methanol) in dichloromethane. The reaction mixtures were loaded on the silica gel without work-up.

Example 1

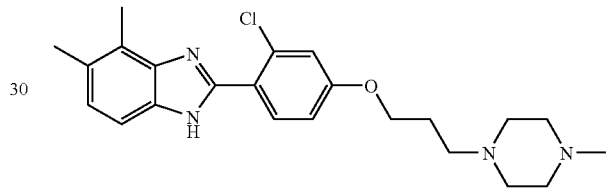

2-{2-Chloro-4-[3-(4-methyl-piperazin-1-yl)-propoxy]-phenyl}-4,5-dimethyl-1H-benzoimidazole General Procedure 1.

A. 2-Chloro-4-(3-chloro-propoxy)-benzaldehyde. 1-Bromo-3-chloropropane (2.55 g, 16.2 mmol, 1.0 equiv) was added to a solution of the 2-chloro-4-hydroxybenzaldehyde (2.54 g, 16.2 mmol, 1.0 equiv) and K$_2$CO$_3$ (4.48 g, 32.4 mmol, 2.0 equiv) in acetonitrile (41 mL). The mixture was heated at 65° C. for 18 h, then cooled to room temperature (rt) and filtered through diatomaceous earth. The filtrate was concentrated under reduced pressure yielding crude product, which was purified by column chromatography (silica gel, 5% ethyl acetate in hexanes) to afford 3.19 g of a colorless oil (66%). $^1$H NMR (400 MHz, CD$_3$OD): 10.3 (s, 1H), 7.87 (d, J=8.0 Hz, 1H), 7.10 (d, J=4.0 Hz, 1H), 7.03 (dd, J=8.0, 4.0 Hz, 1H), 4.23 (t, J=8.0 Hz, 2H), 3.76 (t, J=8.0 Hz, 2H), 2.31-2.22 (m, 2H).

General Procedure 2.

B. 2-Chloro-4-[3-(4-methyl-piperazin-1-yl)-propoxy]-benzaldehyde. N-Methylpiperazine (2.16 g, 21.5 mmol, 2.0 equiv), 2-chloro-4-(3-chloro-propoxy)-benzaldehyde (3.19 g, 10.8 mmol, 1.0 equiv), K$_2$CO$_3$ (4.46 g, 32.3 mmol, 3.0 equiv), and KI (1.02 g, 5.38 mmol, 0.5 equiv) were stirred in n-butanol (22 mL) at 90° C. for 18 h. The reaction mixture was diluted with water and then extracted three times with ethyl acetate. The combined extracts were dried (Na$_2$SO$_4$), filtered, and concentrated, yielding the crude product, which was purified by Method 2 to afford 2.04 g (63%) of an orange oil. $^1$H NMR (400 MHz, CD$_3$OD): 10.3 (s, 1H), 7.86 (d, J=8.0

Hz, 1H), 7.08 (d, J=2.0 Hz, 1H), 7.00 (dd, J=8.0, 2.0 Hz, 1H), 4.15 (t, J=8.0 Hz, 2H), 3.00-2.30 (br s, 10H), 2.29 (s, 3H), 2.05-1.90 (m, 2H).

General Procedure 3.

C. 2-{2-Chloro-4-[3-(4-methyl-piperazin-1-yl)-propoxy]-phenyl}-4,5-dimethyl-1H-benzoimidazole. 2-Chloro-4-[3-(4-methyl-piperazin-1-yl)-propoxy]-benzaldehyde (91.5 mg, 0.31 mmol, 1.0 equiv) and 3,4-dimethyl-benzene-1,2-diamine (42 mg, 0.31 mmol, 1.0 equiv) were stirred with $Na_2S_2O_5$ (76 mg, 0.40 mmol, 1.3 equiv) in DMF (0.25 M) at 90° C. for 12 h. The reaction mixture was loaded directly on silica gel and purified according to Method 2, which afforded 98 mg (76%) of the title compound. MS (electrospray): mass calculated for $C_{23}H_{29}ClN_4O$, 412.20; m/z found, 413.4 [M+H]$^+$. $^1$H NMR (400 MHz, CD$_3$OD): 7.68 (brs, 1H), 7.33 (brs, 1H), 7.15 (d, J=2.5 Hz, 1H), 7.07 (d, J=8.7, 2.5 Hz, 1H), 7.03 (dd, J=8.7, 2.5 Hz, 1H), 4.13 (t, J=6.1 Hz, 2H), 2.60-2.39 (m, 13H), 2.39 (s, 3H), 2.30 (s, 3H), 2.05-1.95 (m, 2H).

Example 2

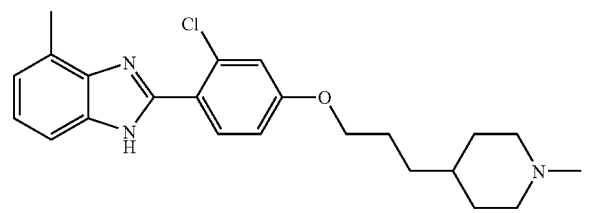

2-{2-Chloro-4-[3-(1-methyl-piperidin-4-yl)-propoxy]-phenyl}-4-methyl-1H-benzoimidazole A. 3-(1-Methyl-piperidin-4-yl)-propan-1-ol. To a refluxing solution of 1 N lithium aluminum hydride in THF (40 mmol) was added dropwise a solution of N-BOC-4-piperidinepropionic acid (3.0 g, 11.6 mmol) in THF (30 mL). The reaction mixture was heated for 3 h and then cooled to rt. Upon further cooling to 0° C., water (1.5 mL) was added slowly, and the reaction mixture was allowed to warm to rt over 15 min. The mixture was again cooled to 0° C., and 10% NaOH (1.5 mL) was added slowly. Upon warming up to rt over 15 min, the mixture was again cooled to 0° C. and more water (4.5 mL) was added. The resultant mixture was allowed to warm to rt over 18 h, and was then filtered through a diatomaceous earth pad. The filtrate was concentrated under reduced pressure, and the residue was purified by Method 2 to afford 1.9 g (100%) of 3-(1-methyl-piperidin-4-yl)-propan-1-ol as a yellow oil. MS (electrospray): mass calculated for $C_9H_{19}NO$, 157.15; m/z found, 158.1 [M+H]$^+$. $^1$H NMR (400 MHz, CD$_3$OD): 3.45-3.41 (m, 2H), 2.77-2.74 (m, 2H), 1.89-1.85 (m, 2H), 1.64-1.61 (m, 2H), 1.47-1.43 (m, 2H), 1.21-1.12 (m, 5H).

B. 2-Chloro-4-[3-(1-methyl-piperidin-4-yl)-propoxy]-benzaldehyde. To an ice-cooled solution of 2-chloro-4-hydroxybenzaldehyde (507 mg, 3.2 mmol, 1.0 equiv), triphenylphosphine (1.02 g, 3.9 mmol, 1.2 equiv), and 3-(1-methyl-piperidin-4-yl)-propan-1-ol (508 mg, 3.9 mmol, 1.2 equiv) in THF (15 mL) was added diethyl azodicarboxylate (DEAD; 0.6 mL, 3.2 mmol, 1.0 equiv). The reaction mixture was allowed to warm to rt and was stirred for 16 h. The mixture was diluted with water and extracted three times with ethyl acetate. The combined extracts were dried (Na$_2$SO$_4$) and concentrated. Purification by Method 2 afforded 768 mg (80%) of the desired aldehyde. MS (electrospray): mass calculated for $C_{16}H_{23}NO_2$, 261.17; m/z found, 262.2 [M+H]$^+$. $^1$H NMR (400 MHz, CDCl$_3$): 9.85 (s, 1H), 7.80 (d, J=8.6 Hz, 2H), 6.97 (d, J=8.6 Hz, 2H), 4.01 (t, J=6.4 Hz, 2H), 2.84-2.82 (m, 2H), 2.25 (s, 3H), 1.92-1.78 (m, 4H), 1.71-1.69 (m, 2H), 1.41-1.37 (m, 2H), 1.29-1.26 (m, 3H).

C. 2-{2-Chloro-4-[3-(1-methyl-piperidin-4-yl)-propoxy]-phenyl}-4-methyl-1H-benzoimidazole. 2-Chloro-4-[3-(1-methyl-piperidin-4-yl)-propoxy]-benzaldehyde and 3-methyl-benzene-1,2-diamine were stirred with Na$_2$S$_2$O$_5$ in DMF at 90° C. for 12 h. Purification of the reaction mixture by Method 2 afforded 129 mg (73%) of the title compound. MS (electrospray): mass calculated for $C_{23}H_{28}ClN_3O$, 397.19; m/z found, 398.4 [M+H]$^+$. $^1$H NMR (400 MHz, CD$_3$OD): 7.69 (d, J=8.5 Hz, 1H), 7.46-7.35 (m, 1H), 7.17-7.13 (m, 2H), 7.06-7.01 (m, 2H), 4.06 (t, J=6.4 Hz, 2H), 2.95-2.85 (m, 2H), 2.59 (s, 3H), 2.27 (s, 3H), 2.10-1.95 (m, 2H), 1.86-1.76 (m, 4H), 1.50-1.49 (m, 2H), 1.32-1.25 (m, 3H).

Example 3

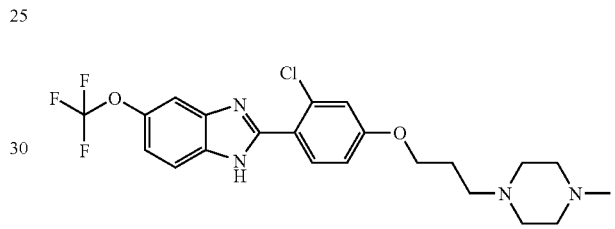

2-{2-Chloro-4-[3-(4-methyl-piperazin-1-yl)-propoxy]-phenyl}-5-trifluoromethoxy-1H-benzoimidazole This compound was prepared by the method described in General Procedure 3 using 2-chloro-4-[3-(4-methyl-piperazin-1-yl)-propoxy]-benzaldehyde (200 mg, 0.68 mmol, 1.0 equiv), 4-trifluoromethoxy-benzene-1,2-diamine (119 mg, 0.62 mmol, 0.92 equiv) and Na$_2$S$_2$O$_5$ (167 mg, 0.88 mmol, 1.3 equiv). Purification by Method 2 afforded 72 mg (23%) of the title compound. MS (electrospray): mass calculated for $C_{22}H_{24}ClF_3N_4O_2$, 468.15; m/z found, 469.4 [M+H]$^+$. $^1$H NMR (400 MHz, CD$_3$OD): 7.82 (d, J=8.7 Hz, 1H), 7.69 (d, J=8.8 Hz, 1H), 7.55 (s, 1H), 7.23 (d, J=8.5 Hz, 1H), 7.21 (d, J=1.6 Hz, 1H), 7.1 (dd, J=8.6, 2.2 Hz, 1H), 4.17 (t, J=5.7 Hz, 2H), 2.88-2.38 (m, 10H), 2.32 (s, 3H), 2.10-1.95 (m, 2H).

Example 4

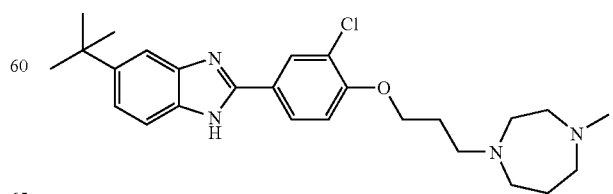

5-tert-Butyl-2-{3-chloro-4-[3-(4-methyl-[1,4]diazepan-1-yl)-propoxy]-phenyl}-1H-benzoimidazole This compound was prepared by the method described in Example 1, using 3-chloro-4-[3-(4-methyl-[1,4]diazepan-1-yl)-propoxy]-benzaldehyde (62 mg, 0.20 mmol, 1.0 equiv), 4-tert-butyl-benzene-1,2-diamine (33 mg, 0.20 mmol, 1.0 equiv), and $Na_2S_2O_5$ (50 mg, 0.26 mmol, 1.3 equiv) in General Procedure 3. Purification by Method 2 afforded 31 mg (34%) of the title compound. MS (electrospray): mass calculated for $C_{26}H_{35}ClN_4O$, 454.25; m/z found, 455.3 [M+H]$^+$. $^1$H NMR (400 MHz, CD$_3$OD): 8.12 (d, J=2.2 Hz, 1H), 7.98 (dd, J=8.6, 2.3 Hz, 1H), 7.6 (s, 1H), 7.52 (d, J=8.5 Hz, 1H), 7.37 (dd, J=8.6, 1.8 Hz, 1H), 7.22 (d, J=8.7 Hz, 1H), 4.19 (t, J=6.0 Hz, 2H), 2.84-2.74 (m, 10H), 2.40 (s, 3H), 2.08-1.97 (m, 2H), 1.90-1.83 (m, 2H), 1.41 (s, 9H).

Example 5

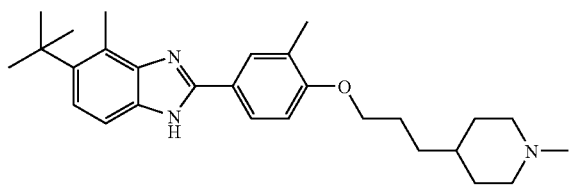

5-tert-Butyl-2-{3-chloro-4-[3-(4-methyl-piperazin-1-yl)-propoxy]-phenyl}-1H-benzoimidazole This compound was prepared by the method described in Example 2, using 3-methyl-4-[3-(1-methyl-piperidin-4-yl)-propoxy]-benzaldehyde (98.6 mg, 0.36 mmol, 1.0 equiv), 4-tert-butyl-benzene-1,2-diamine (59 mg, 0.36 mmol, 1.0 equiv), and $Na_2S_2O_5$ (89 mg, 0.47 mmol, 1.3 equiv) in Step C. Purification by Method 2 afforded 116 mg (77%) of the title compound. MS (electrospray): mass calculated for $C_{27}H_{37}N_3O$, 419.29; m/z found, 420.2 [M+H]$^+$. $^1$H NMR (400 MHz, CD$_3$OD): 7.90-7.82 (m, 2H), 7.60-7.50 (m, 1H), 7.52-7.40 (m, 1H), 7.33 (dd, J=8.5, 1.8 Hz, 1H), 7.02 (d, J=9.1 Hz, 1H), 4.07 (t, J=6.2 Hz, 2H), 2.92-2.85 (m, 2H), 2.30 (s, 3H), 2.28 (s, 3H), 2.10-2.00 (m, 2H), 1.90-1.80 (m, 2H), 1.80-1.70 (m, 2H), 1.55-1.45 (m, 2H), 1.49 (s, 9H), 1.49-1.26 (m, 3H).

Example 6

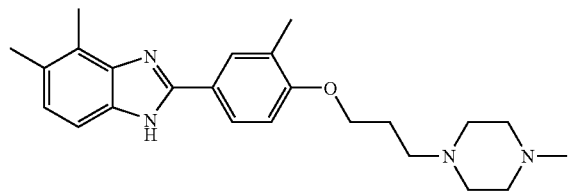

4,5-Dimethyl-2-{3-methyl-4-[3-(4-methyl-piperazin-1-yl)-propoxy]-phenyl}-1H-benzoimidazole This compound was prepared by the method described in Example 1, using 3-methyl-4-[3-(4-methyl-piperazin-1-yl)-propoxy]-benzaldehyde (180 mg, 0.65 mmol, 1.0 equiv), 3,4-dimethyl-benzene-1,2-diamine (89 mg, 0.65 mmol, 1.0 equiv), and $Na_2S_2O_5$ (161 mg, 0.85 mmol, 1.3 equiv) in General Procedure 3. Purification by Method 2 afforded 192 mg (75%) of the title compound. MS (electrospray): mass calculated for $C_{24}H_{32}N_4O$, 392.26; m/z found, 393.5 [M+H]$^+$. $^1$H NMR (400 MHz, CD$_3$OD): 7.95-7.85 (m, 2H), 7.35-7.23 (m, 1H), 7.08-7.00 (m, 2H), 4.12 (t, J=6.0 Hz, 2H), 2.64-2.37 (m, 16H), 2.29 (s, 6H), 2.10-2.00 (m, 2H).

Example 7

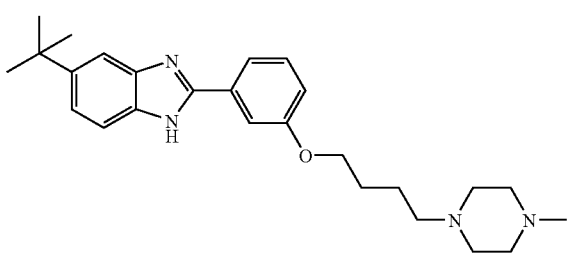

5-tert-Butyl-2-{3-[4-(4-methyl-piperazin-1-yl)-butoxy]-phenyl}-1H-benzoimidazole This compound was prepared by the method described in Example 1, using 3-[4-(4-methyl-piperazin-1-yl)-butoxy]-benzaldehyde (53 mg, 0.19 mmol, 1.0 equiv), 4-tert-butyl-benzene-1,2-diamine (32 mg, 0.19 mmol, 1.0 equiv), and $Na_2S_2O_5$ (48 mg, 0.25 mmol, 1.3 equiv) in General Procedure 3. Purification by Method 2 afforded 75 mg (92%) of the title compound. MS (electrospray): mass calculated for $C_{26}H_{36}N_4O$, 420.29; m/z found, 421.2 [M+H]$^+$. $^1$H NMR (400 MHz, CD$_3$OD): 7.68-7.56 (m, 3H), 7.54 (br d, J=8.2 Hz, 1H), 7.44-7.36 (m, 2H), 7.02 (dd, J=8.2, 2.2 Hz, 1H), 4.07 (t, J=6.1 Hz, 2H), 3.00-2.26 (m, 10H), 2.26 (s, 3H), 1.85-1.75 (m, 2H), 1.75-1.65 (m, 2H), 1.40 (s, 9H).

Example 8

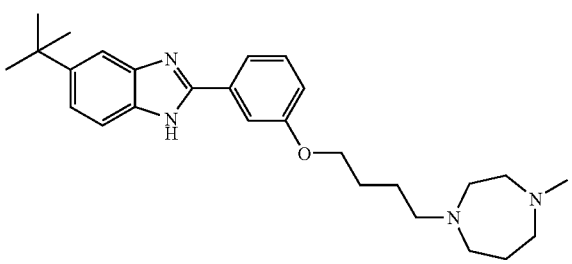

5-tert-Butyl-2-{3-[4-(4-methyl-[1,4]diazepan-1-yl)-butoxy]-phenyl}-1H-benzoimidazole A. 3-(4-Chloro-butoxy)-benzaldehyde. This intermediate was prepared by the method described in General Procedure 1 using 3-hydroxybenzaldehyde (2.0 g, 16.4 mmol, 1.0 equiv), 1-bromo-4-chlorobutane (1.62 mL, 16.4 mmol, 1.0 equiv), and $K_2CO_3$ (4.53 g, 33 mmol, 1.0 equiv). Purification afforded 2.57 g (79%) of the desired product. $^1$H NMR (400

MHz, CDCl₃): 9.98 (s, 1H), 7.47-7.43 (m, 2H), 7.40-7.37 (m, 1H), 7.27-7.25 (m, 1H), 4.09-4.03 (m, 2H), 3.66-3.58 (m, 2H), 2.03-1.93 (m, 4H).

B. 5-tert-Butyl-2-[3-(4-chloro-butoxy)-phenyl]-1H-benzoimidazole. This intermediate was prepared by the method described in General Procedure 3 using 3-(4-chloro-butoxy)-benzaldehyde (500 mg, 2.52 mmol, 1.0 equiv), 4-tert-butyl-benzene-1,2-diamine (414 mg, 2.52 mmol, 1.0 equiv), and Na₂S₂O₅ (622 mg, 3.3 mmol, 1.3 equiv). The reaction mixture was loaded on a silica gel column and purified by flash chromatography (25% ethyl acetate in hexanes) to afford 348 mg (40%) of the desired product. ¹H NMR (400 MHz, CDCl₃): 7.72-7.48 (m, 4H), 7.47-7.35 (m, 2H), 7.08-7.03 (m, 1H), 4.17-4.10 (m, 2H), 3.70-3.64 (m, 2H), 2.03-1.96 (m, 4H), 1.41 (s, 9H).

C. 5-tert-Butyl-2-{3-[4-(4-methyl-[1,4]diazepan-1-yl)-butoxy]-phenyl}-1H-benzoimidazole. This compound was prepared by the method described in General Procedure 2 using 5-tert-butyl-2-[3-(4-chloro-butoxy)-phenyl]-1H-benzoimidazole (51.2 mg, 0.15 mmol, 1.0 equiv), N-methyl-homo-piperazine (19 µL, 0.15 mmol, 1.0 equiv), K₂CO₃ (40 mg, 0.30 mmol, 2.0 equiv), and KI (12 mg, 0.08 mmol, 0.5 equiv). Purification by Method 2 afforded 19 mg (23%) of the title compound. MS (electrospray): mass calculated for C₂₇H₃₈N₄O, 434.30; m/z found, 435.3 [M+H]⁺. ¹H NMR (400 MHz, CD₃OD): 7.66-7.62 (m, 3H), 7.52 (d, J=8.6 Hz, 1H), 7.45-7.35 (m, 1H), 7.37 (dd, J=8.6, 1.8 Hz, 1H), 7.06-7.02 (m, 1H), 4.11 (t, J=6.2 Hz, 2H), 2.78-2.75 (m, 4H), 2.69-2.65 (m, 4H), 2.60-2.55 (m, 2H), 2.32 (s, 3H), 1.85-1.79 (m, 4H), 1.75-1.68 (m, 2H), 1.40 (s, 9H).

Example 9

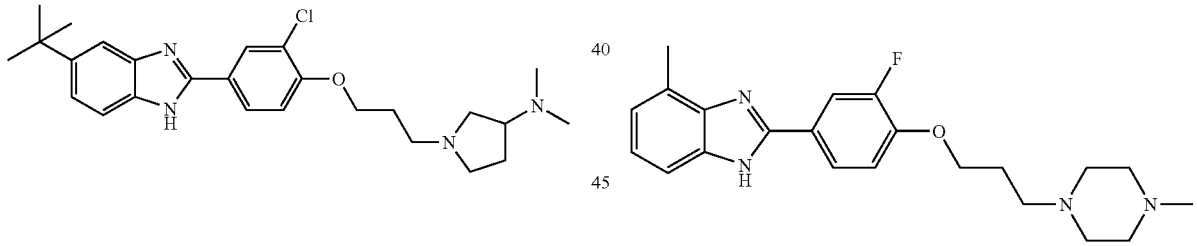

(1-{3-[4-(5-tert-Butyl-1H-benzoimidazol-2-yl)-2-chloro-phenoxy]-propyl}-pyrrolidin-3-yl)-dimethylamine This compound was prepared by the method described in Example 1, using 5-tert-butyl-2-[3-(4-chloro-butoxy)-phenyl]-1H-benzoimidazole (206 mg, 0.55 mmol, 1.0 equiv), dimethyl-pyrrolidin-3-yl-amine (125 mg, 1.09 mmol, 2.0 equiv), K₂CO₃ (227 mg, 1.64 mmol, 3.0 equiv), and KI (46 mg, 0.27 mmol, 0.5 equiv) in General Procedure 3. Purification by Method 2 afforded 137 mg (55%) of the title compound. MS (electrospray): mass calculated for C₂₆H₃₅ClN₄O, 454.25; m/z found, 455.5 [M+H]⁺. ¹H NMR (400 MHz, CD₃OD): 8.11 (d, J=2.2 Hz, 1H), 7.97 (dd, J=8.6, 2.2 Hz, 1H), 7.58 (br s, 1H), 7.65-7.45 (m, 1H), 7.36 (dd, J=8.6, 1.7 Hz, 1H), 7.24 (d, J=8.7 Hz, 1H), 4.21 (t, J=6.0 Hz, 2H), 3.04-2.99 (m, 1H), 2.91-2.65 (m, 4H), 2.56-2.49 (m, 1H), 2.36-2.29 (m, 1H), 2.24 (s, 6H), 2.10-1.99 (m, 3H), 1.79-1.70 (m, 1H), 1.40 (s, 9H).

Example 10

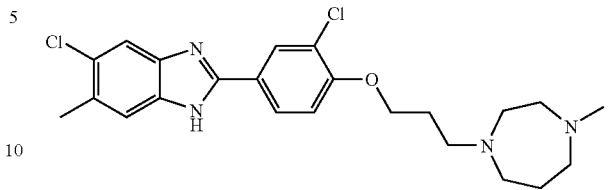

5-Chloro-2-{3-chloro-4-[3-(4-methyl-[1,4]diazepan-1-yl)-propoxy]-phenyl}-6-methyl-1H-benzoimidazole This compound was prepared by the method described in Example 1, using 3-chloro-4-[3-(4-methyl-[1,4]diazepan-1-yl)-propoxy]-benzaldehyde (61 mg, 0.20 mmol, 1.0 equiv), 4-chloro-5-methyl-benzene-1,2-diamine (31 mg, 0.20 mmol, 1.0 equiv), and Na₂S₂O₅ (48 mg, 0.25 mmol, 1.3 equiv) in General Procedure 3. Purification by Method 2 afforded 7.1 mg (8%) of the title compound. MS (electrospray): mass calculated for C₂₃H₂₈Cl₂N₄O, 446.16; m/z found, 447.3 [M+H]⁺. ¹H NMR (400 MHz, CD₃OD): 7.96 (d, J=2.2 Hz, 1H), 7.83 (dd, J=8.6, 2.2 Hz, 1H), 7.45 (s, 1H), 7.34 (s, 1H), 7.10 (d, J=8.7 Hz, 1H), 4.08 (t, J=6.0 Hz, 2H), 2.76-2.64 (m, 10H), 2.36 (s, 3H), 2.30 (s, 3H), 1.96-1.88 (m, 2H), 1.80-1.73 (m, 2H).

Example 11

2-{3-Fluoro-4-[3-(4-methyl-piperazin-1-yl)-propoxy]-phenyl}-4-methyl-1H-benzoimidazole This compound was prepared by the method described in Example 1, using 3-fluoro-4-[3-(4-methyl-piperazin-1-yl)-propoxy]-benzaldehyde (94 mg, 0.34 mmol, 1.0 equiv), 3-methyl-benzene-1,2-diamine (42 mg, 0.34 mmol, 1.0 equiv), and Na₂S₂O₅ (84 mg, 0.44 mmol, 1.3 equiv) in General Procedure 3. Purification by Method 2 afforded 130 mg (100%) of the title compound. MS (electrospray): mass calculated for C₂₂H₂₇FN₄O, 382.22; m/z found, 383.2 [M+H]⁺. ¹H NMR (400 MHz, CD₃OD): 7.86-7.78 (m, 2H), 7.40-7.37 (m, 1H), 7.12-6.97 (m, 3H), 3.99 (t, J=6.1 Hz, 2H), 3.00-2.30 (m, 13H), 2.25 (s, 3H), 1.94-1.90 (m, 2H).

Example 12

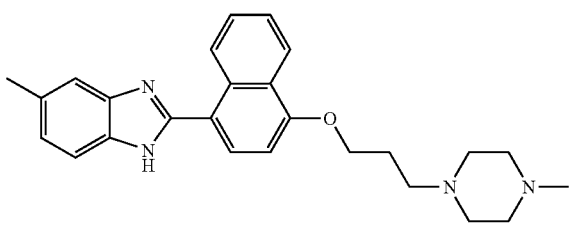

5-Methyl-2-{4-[3-(4-methyl-piperazin-1-yl)-propoxy]-naphthalen-1-yl}-1H-benzoimidazole This compound was prepared by the method described in Example 1, using 4-[3-(4-methyl-piperazin-1-yl)-propoxy]-naphthalene-1-carbaldehyde (63 mg, 0.20 mmol, 1.0 equiv), 4-methyl-benzene-1,2-diamine (24 mg, 0.20 mmol, 1.0 equiv), and $Na_2S_2O_5$ (49 mg, 0.26 mmol, 1.3 equiv) in General Procedure 3. The desired product was isolated from the reaction mixture using Method 1 and was subsequently re-purified by Method 2 to afford 54.6 mg (66%) of the title compound. MS (electrospray): mass calculated for $C_{26}H_{30}N_4O$, 414.24; m/z found, 415.62 [M+H]+. 1H NMR (400 MHz, $CD_3OD$): 8.48 (d, J=8.0 Hz, 1H), 8.10 (d, J=8.4 Hz, 1H), 8.0 (d, J=8.2 Hz, 1H), 7.78-7.65 (m, 4H), 7.50 (d, J=8.4 Hz, 1H), 7.21 (d, J=8.2 Hz, 1H), 4.43 (t, J=6.0 Hz, 2H), 3.40 (br s, 4H), 3.30-3.00 (m, 6H), 2.88 (s, 3H), 2.59 (s, 3H), 2.36-2.30 (m, 2H).

Example 13

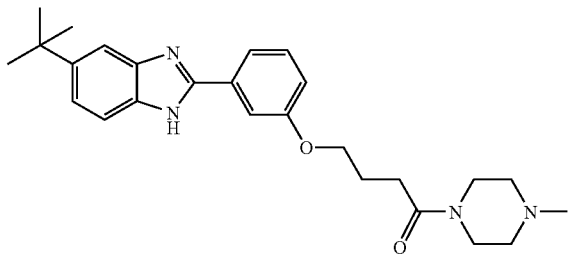

4-[3-(5-tert-Butyl-1H-benzoimidazol-2-yl)-phenoxy]-1-(4-methyl-piperazin-1-yl)-butan-1-one A. 3-[4-(4-Methyl-piperazin-1-yl)-4-oxo-butoxy]-benzaldehyde. To a solution of 4-(3-formyl-phenoxy)-butyric acid (981 mg, 4.72 mmol, 1.0 equiv) and N-methylpiperazine (576 mg, 5.19 mmol, 1.1 equiv) in dichloromethane at 0° C. was added 1-(3-dimethylaminopropyl)-3-ethylcarbodiimide (EDCI; 1.18 g, 6.14 mmol, 1.3 equiv) and 1-hydroxybenzotriazole hydrate (HOBT; 701 mg, 5.19 mmol, 1.1 equiv). The reaction mixture, which was allowed to warm to rt, was stirred for 2.0 h and then poured into water. This mixture was extracted three times with ethyl acetate. The combined extracts were dried ($Na_2SO_4$), filtered, and concentrated under reduced pressure. The crude residue was purified by column chromatography (silica gel, 5% MeOH in dichloromethane) to afford 847 mg (62%) of the desired product. 1H NMR (400 MHz, $CD_3OD$): 9.72 (s, 1H), 7.29-7.23 (m, 2H), 7.22-7.19 (m, 1H), 7.05-6.98 (m, 1H), 3.87 (t, J=6.1 Hz, 2H), 3.43-3.31 (m, 4H), 2.39 (t, J=7.2 Hz, 2H), 2.27-2.17 (m, 4H), 2.08 (s, 3H), 1.92-1.80 (m, 2H).

B. 4-[3-(5-tert-Butyl-1H-benzoimidazol-2-yl)-phenoxy]-1-(4-methyl-piperazin-1-yl)-butan-1-one. This compound was prepared by the method described in General Procedure 3 using 3-[4-(4-methyl-piperazin-1-yl)-4-oxo-butoxy]-benzaldehyde (81.2 mg, 0.28 mmol, 1.0 equiv), 4-tert-butyl-benzene-1,2-diamine (46 mg, 0.28 mmol, 1.0 equiv), and $Na_2S_2O_5$ (69 mg, 0.36 mmol, 1.3 equiv). Purification by Method 2 afforded 77 mg (64%) of the title compound. MS (electrospray): mass calculated for $C_{26}H_{34}N_4O_2$, 434.27; m/z found, 435.0 [M+H]+. 1H NMR (400 MHz, $CD_3OD$): 7.69-7.62 (m, 3H), 7.54 (d, J=8.6 Hz, 1H), 7.45-7.37 (m, 2H), 7.06 (dd, J=8.2, 2.2 Hz, 1H), 4.13 (t, J=6.1 Hz, 2H), 3.70-3.50 (m, 4H), 2.62 (t, J=7.3 Hz, 2H), 2.49-2.40 (m, 4H), 2.32 (s, 3H), 2.16-2.09 (m, 2H), 1.41 (s, 9H).

Example 14

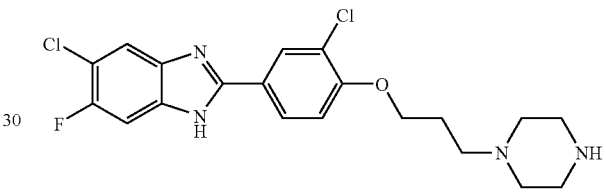

5-Chloro-2-[3-chloro-4-(3-piperazin-1-yl-propoxy)-phenyl]-6-fluoro-1H-benzoimidazole A. 4-{3-[2-Chloro-4-(5-chloro-6-fluoro-1H-benzoimidazol-2-yl)-phenoxy]-propyl}-piperazine-1-carboxylic acid tert-butyl ester. This compound was prepared by the method described in Example 1, using 4-[3-(2-chloro-4-formyl-phenoxy)-propyl]-piperazine-1-carboxylic acid tert-butyl ester (1.0 g, 2.6 mmol, 1.0 equiv), 4-chloro-5-fluoro-benzene-1,2-diamine (421 mg, 2.6 mmol, 1.0 equiv), and $Na_2S_2O_5$ (648 mg, 3.4 mmol, 1.3 equiv) in General Procedure 3. Purification by Method 2 afforded 256 mg (15%) of the title compound. MS (electrospray): mass calculated for $C_{25}H_{29}Cl_2FN_4O_3$, 522.16; m/z found, 545.3 [M+Na]+.

B. 5-Chloro-2-[3-chloro-4-(3-piperazin-1-yl-propoxy)-phenyl]-6-fluoro-1H-benzoimidazole. To a suspension of 4-{3-[2-chloro-4-(5-chloro-6-fluoro-1H-benzoimidazol-2-yl)-phenoxy]-propyl}-piperazine-1-carboxylic acid tert-butyl ester (52.7 mg, 0.10 mmol) in dichloromethane (1.0 mL) at rt was added TFA (1.0 mL), and the reaction mixture was stirred for 50 min. The mixture was concentrated under reduced pressure, and the solid residue was washed four times with dichloromethane. The title compound was obtained in quantitative yield as the TFA salt. MS (electrospray): mass calculated for $C_{20}H_{21}Cl_2FN_4O$, 422.11; m/z found, 423.2 [M+H]+. 1H NMR (400 MHz, $CD_3OD$): 8.17 (d, J=2.3 Hz, 1H), 8.03 (dd, J=8.7, 2.3 Hz, 1H), 7.81 (d, J=6.4 Hz, 1H), 7.59 (d, J=8.7 Hz, 1H), 7.36 (d, J=8.8 Hz, 1H), 4.33 (t, J=5.8 Hz, 2H), 3.50-3.47 (m, 4H), 3.36 (br s, 4H), 3.25 (t, J=7.4 Hz, 2H), 2.33-2.26 (m, 2H).

Example 15

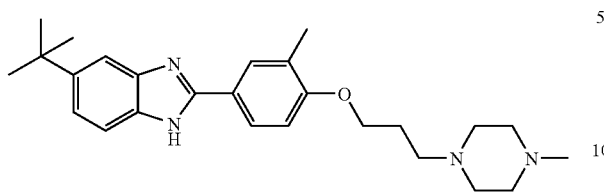

5-tert-Butyl-2-{3-methyl-4-[3-(4-methyl-piperazin-1-yl)-propoxy]-phenyl}-1H-benzoimidazole This compound was prepared by the method described in Example 1, using 3-methyl-4-[3-(4-methyl-piperazin-1-yl)-propoxy]-benzaldehyde (516 mg, 1.87 mmol, 1.0 equiv), 4-tert-butyl-benzene-1,2-diamine (307 mg, 1.87 mmol, 1.0 equiv), and $Na_2S_2O_5$ (461 mg, 2.43 mmol, 1.3 equiv) in General Procedure 3. Purification by Method 2 afforded 633 mg (81%) of the title compound. MS (electrospray): mass calculated for $C_{26}H_{36}N_4O$, 420.29; m/z found, 421.5 [M+H]$^+$. $^1$H NMR (400 MHz, CD$_3$OD): 7.90-7.85 (m, 2H), 7.65-7.40 (m, 2H), 7.33 (d, J=8.5 Hz, 1H), 7.04 (d, J=8.1 Hz, 1H), 4.14-4.11 (m, 2H), 2.90-2.28 (m, 16H), 2.06-2.03 (m, 2H), 1.39 (s, 9H).

Example 16

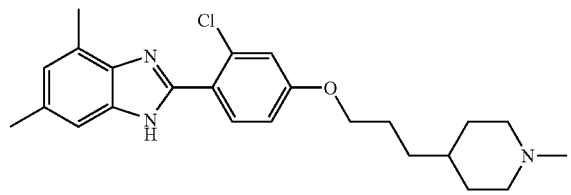

2-{2-Chloro-4-[3-(1-methyl-piperidin-4-yl)-propoxy]-phenyl}-4,6-dimethyl-1H-benzoimidazole This compound was prepared by the method described in Example 2, using 2-chloro-4-[3-(1-methyl-piperidin-4-yl)-propoxy]-benzaldehyde (106 mg, 0.36 mmol, 1.0 equiv), 3,5-dimethyl-benzene-1,2-diamine (49 mg, 0.36 mmol, 1.0 equiv), and $Na_2S_2O_5$ (88 mg, 0.47 mmol, 1.3 equiv) in Step C. Purification by Method 2 afforded 128 mg (87%) of the title compound. MS (electrospray): mass calculated for $C_{24}H_{30}ClN_3O$, 411.21; m/z found, 412.4 [M+H]$^+$. $^1$H NMR (400 MHz, CD$_3$OD): 7.68 (d, J=8.5 Hz, 1H), 7.21 (br s, 1H), 7.12 (d, J=2.4 Hz, 1H), 7.01 (dd, J=8.7, 2.5 Hz, 1H), 6.90 (s, 1H), 4.05 (t, J=6.3 Hz, 2H), 2.92-2.88 (m, 2H), 2.54 (s, 3H), 2.43 (s, 3H), 2.29 (s, 3H), 2.09-2.03 (m, 2H), 1.85-1.76 (m, 4H), 1.47-1.11 (m, 5H).

The following compounds in Examples 17-56 were prepared using General Procedures 1, 2, and 3 as exemplified above.

Example 17

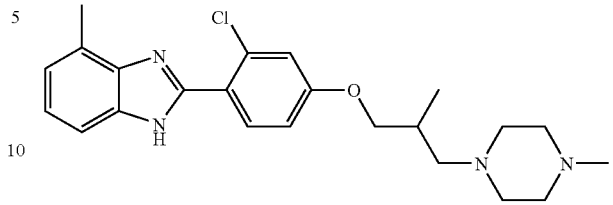

2-{2-Chloro-4-[2-methyl-3-(4-methyl-piperazin-1-yl)-propoxy]-phenyl}-4-methyl-1H-benzoimidazole MS (electrospray): mass calculated for $C_{23}H_{29}ClN_4O$, 412.20; m/z found, 413.2 [M+H]$^+$. $^1$H NMR (400 MHz, CD$_3$OD): 7.75-7.65 (m, 1H), 7.50-7.35 (m, 1H), 7.20-7.13 (m, 2H), 7.15-7.02 (m, 2H), 4.06 (dd, J=9.2, 4.5 Hz, 1H), 3.94 (dd, J=9.2, 6.0 Hz, 1H), 2.80-2.35 (m, 13H), 2.35-2.20 (m, 4H), 2.28 (d, J=4.5 Hz, 3H).

Example 18

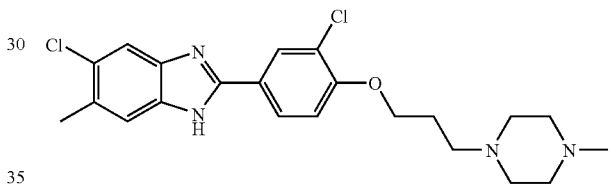

5-Chloro-2-{3-chloro-4-[3-(4-methyl-piperazin-1-yl)-propoxy]-phenyl}-6-methyl-1H-benzoimidazole MS (electrospray): mass calculated for $C_{22}H_{26}Cl_2N_4O$, 432.15; m/z found, 432.8 [M+H]$^+$. $^1$H NMR (400 MHz, CD$_3$OD): 8.19 (d, J=2.2 Hz, 1H), 8.05 (dd, J=8.6, 2.2 Hz, 1H), 7.66 (br s, 1H), 7.55 (br s, 1H), 7.32 (d, J=8.7 Hz, 1H), 4.30 (t, J=6.0 Hz, 2H), 3.00-2.43 (m, 13H), 2.42 (s, 3H), 2.18-2.14 (m, 2H).

Example 19

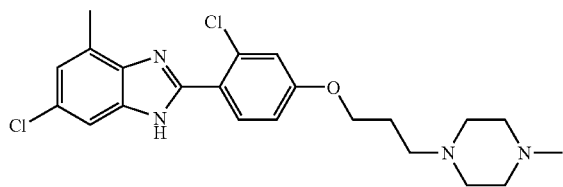

6-Chloro-2-{2-chloro-4-[3-(4-methyl-piperazin-1-yl)-propoxy]-phenyl}-4-methyl-1H-benzoimidazole MS (electrospray): mass calculated for $C_{22}H_{26}Cl_2N_4O$, 432.15; m/z found, 433.1 [M+H]$^+$. $^1$H NMR (400 MHz, CD$_3$OD): 7.70 (brs, 1H), 7.42 (brs, 1H), 7.17 (d, J=2.4 Hz, 1H), 7.08 (br s, 1H), 7.05 (dd, J=8.7, 2.5 Hz, 1H), 4.13 (t, J=6.14 Hz, 2H), 3.00-2.40 (m, 13H), 2.30 (s, 3H), 2.03-1.98 (m, 2H).

Example 20

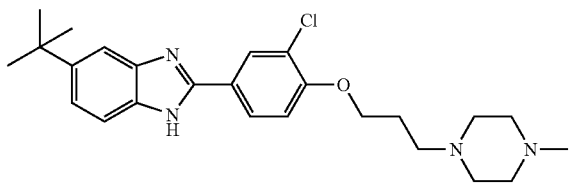

5-tert-Butyl-2-{3-chloro-4-[3-(4-methyl-piperazin-1-yl)-propoxy]-phenyl}-1H-benzoimidazole MS (electrospray): mass calculated for $C_{25}H_{33}ClN_4O$, 440.23; m/z found, 441.0 [M+H]$^+$. $^1$H NMR (400 MHz, CD$_3$OD): 8.31 (d, J=2.2 Hz, 1H), 8.17 (dd, J=8.6, 2.2 Hz, 1H), 7.78 (br s, 1H), 7.69 (br s, 1H), 7.55 (dd, J=8.6, 1.7 Hz, 1H), 7.42 (d, J=8.7 Hz, 1H), 4.40 (t, J=6.0 Hz, 2H), 3.00-2.55 (m, 10H), 2.51 (s, 3H), 2.35-2.22 (m, 2H), 1.59 (s, 9H).

Example 21

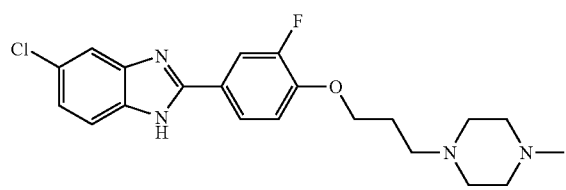

5-Chloro-2-{3-fluoro-4-[3-(4-methyl-piperazin-1-yl)-propoxy]-phenyl}-1H-benzoimidazole MS (electrospray): mass calculated for $C_{21}H_{24}ClFN_4O$, 402.16; m/z found, 403.2 [M+H]$^+$. $^1$H NMR (400 MHz, CD$_3$OD): 7.86-7.83 (m, 2H), 7.64 (d, J=1.9 Hz, 1H), 7.60 (d, J=8.7 Hz, 1H), 7.39 (dd, J=8.7, 1.9 Hz, 1H), 7.33-7.29 (m, 1H), 4.21 (t, J=5.9 Hz, 2H), 3.20-2.77 (m, 10H), 2.76 (s, 3H), 2.10-2.03 (m, 2H).

Example 22

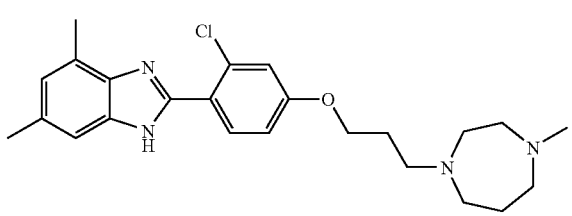

2-{2-Chloro-4-[3-(4-methyl-[1,4]diazepan-1-yl)-propoxy]-phenyl}-4,6-dimethyl-1H-benzoimidazole MS (electrospray): mass calculated for $C_{24}H_{31}ClN_4O$, 426.22; m/z found, 427.2 [M+H]$^+$. $^1$H NMR (400 MHz, CD$_3$OD): 7.58 (d, J=8.6 Hz, 1H), 7.11 (s, 1H), 7.03 (d, J=2.5 Hz, 1H), 6.91 (dd, J=8.7, 2.5 Hz, 1H), 6.80 (s, 1H), 3.99 (t, J=6.1 Hz, 2H), 2.75-2.58 (m, 10H), 2.45 (s, 3H), 2.32 (s, 3H), 2.30 (s, 3H), 1.89-1.85 (m, 2H), 1.78-1.74 (m, 2H).

Example 23

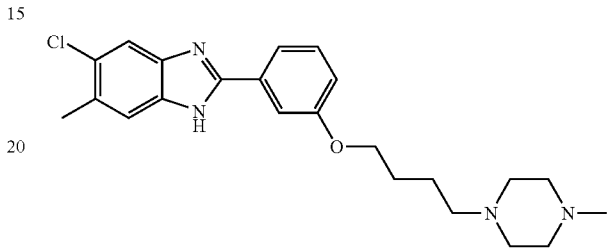

5-Chloro-6-methyl-2-{3-[4-(4-methyl-piperazin-1-yl)-butoxy]-phenyl}-1H-benzoimidazole MS (electrospray): mass calculated for $C_{23}H_{29}ClN_4O$, 412.20; m/z found, 413.1 [M+H]$^+$. $^1$H NMR (400 MHz, CD$_3$OD): 7.60-7.56 (m, 3H), 7.44-7.37 (m, 2H), 7.03-7.00 (m, 1H), 4.05 (t, J=6.1 Hz, 2H), 3.00-2.30 (m, 13H), 2.27 (s, 3H), 1.82-1.73 (m, 2H), 1.72-1.67 (m, 2H). $^{13}$C NMR (TFA salt, 100 MHz, CD$_3$OD): 161.0, 154.0, 138.5, 131.9, 131.7, 131.3, 130.2, 120.0, 118.2, 116.7, 116.2, 113.4, 68.7, 58.0, 54.2, 51.7, 44.2, 27.8, 23.5, 20.8.

Example 24

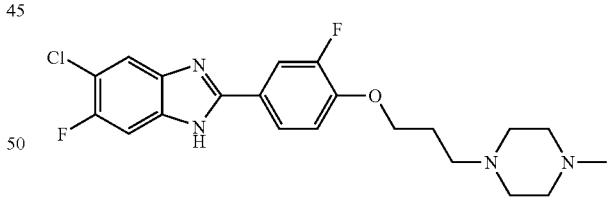

5-Chloro-6-fluoro-2-{3-fluoro-4-[3-(4-methyl-piperazin-1-yl)-propoxy]-phenyl}-1H-benzoimidazole MS (electrospray): mass calculated for $C_{21}H_{23}ClF_2N_4O$, 420.15; m/z found, 421.2 [M+H]$^+$. $^1$H NMR (400 MHz, CD$_3$OD): 7.80-7.75 (m, 2H), 7.66 (d, J=6.4 Hz, 1H), 7.45 (d, J=8.9 Hz, 1H), 7.27 (t, J=9.3 Hz, 1H), 4.21 (t, J=8.0 Hz, 2H), 3.25 (br s, 4H), 3.02 (br s, 4H), 2.90 (t, J=7.8 Hz, 2H), 2.81 (s, 3H), 2.12-2.05 (m, 2H).

Example 25

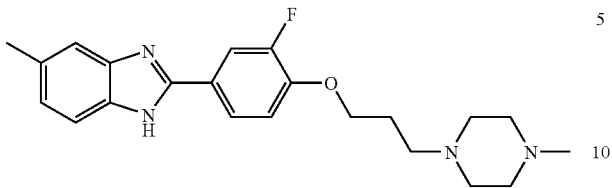

2-{3-Fluoro-4-[3-(4-methyl-piperazin-1-yl)-propoxy]-phenyl}-5-methyl-1H-benzoimidazole MS (electrospray): mass calculated for $C_{22}H_{27}FN_4O$, 382.22; m/z found, 383.3 $[M+H]^+$. $^1H$ NMR (400 MHz, $CD_3OD$): 7.85-7.80 (m, 2H), 7.57 (d, J=8.4 Hz, 1H), 7.49 (s, 1H), 7.38-7.34 (m, 2H), 4.22 (t, J=5.9 Hz, 2H), 3.24 (br s, 4H), 2.95 (br s, 4H), 2.84 (t, J=7.2 Hz, 2H), 2.77 (s, 3H), 2.46 (s, 3H), 2.12-2.05 (m, 2H).

Example 26

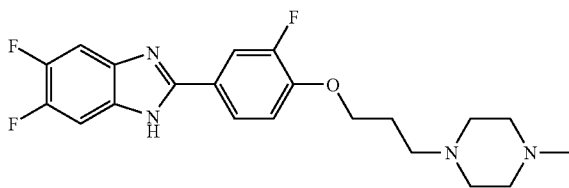

5,6-Difluoro-2-{3-fluoro-4-[3-(4-methyl-piperazin-1-yl)-propoxy]-phenyl}-1H-benzoimidazole MS (electrospray): mass calculated for $C_{21}H_{23}F_3N_4O$, 404.18; m/z found, 405.2 $[M+H]^+$. $^1H$ NMR (400 MHz, $CD_3OD$): 7.79-7.73 (m, 2H), 7.50-7.45 (m, 2H), 7.28-7.22 (m, 1H), 4.18 (t, J=5.9 Hz, 2H), 3.04-2.83 (m, 10H), 2.76 (s, 3H), 2.10-2.03 (m, 2H).

Example 27

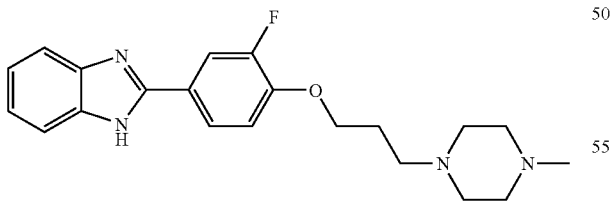

2-{3-Fluoro-4-[3-(4-methyl-piperazin-1-yl)-propoxy]-phenyl}-1H-benzoimidazole

MS (electrospray): mass calculated for $C_{21}H_{25}FN_4O$, 368.20; m/z found, 369.3 $[M+H]^+$. $^1H$ NMR (400 MHz, $CD_3OD$): 7.88-7.81 (m, 2H), 7.71-7.66 (m, 2H), 7.52-7.48 (m, 2H), 7.37 (t, J=8.8 Hz, 1H), 4.22 (t, J=6.0 Hz, 2H), 3.04-2.76 (m, 13H), 2.10-2.03 (m, 2H).

Example 28

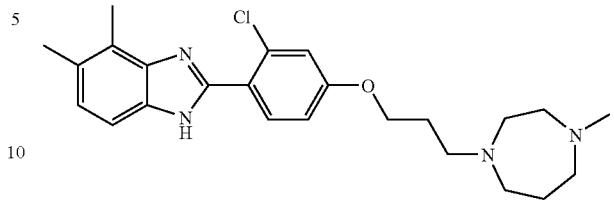

2-{2-Chloro-4-[3-(4-methyl-[1,4]diazepan-1-yl)-propoxy]-phenyl}-4,5-dimethyl-1H-benzoimidazole MS (electrospray): mass calculated for $C_{24}H_{31}ClN_4O$, 426.22; m/z found, 427.2 $[M+H]^+$. $^1H$ NMR (400 MHz, $CD_3OD$): 7.75-7.65 (m, 1H), 7.40-7.25 (m, 1H), 7.15 (d, J=2.5 Hz, 1H), 7.07 (d, J=8.2 Hz, 1H), 7.04 (dd, J=8.6, 2.5 Hz, 1H), 4.13 (t, J=6.1 Hz, 1H), 2.85-2.70 (m, 10H), 2.51 (brs, 3H), 2.42 (s, 3H), 2.40 (s, 3H), 2.02-1.96 (m, 2H), 1.88-1.86 (m, 2H). $^{13}C$ NMR (100 MHz, $CD_3OD$): 13.7, 19.4, 24.2, 26.9, 45.0, 50.9, 54.7, 55.4, 55.9, 56.6, 67.4, 112.2, 115.2, 117.7, 118.9, 123.7, 128.8, 133.6, 134.5, 134.7, 135.2, 135.5, 148.9, 163.5.

Example 29

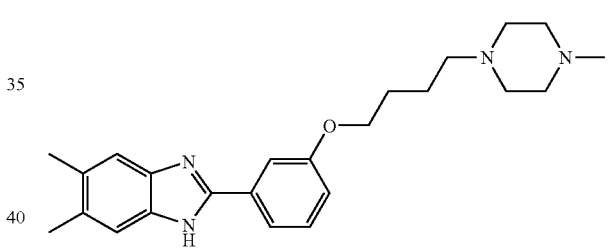

5,6-Dimethyl-2-{3-[4-(4-methyl-piperazin-1-yl)-butoxy]-phenyl}-1H-benzoimidazole HPLC: $R_t$=5.96. MS (electrospray): mass calculated for $C_{24}H_{32}N_4O$, 392.26; m/z found, 393.3 $[M+H]^+$. $^1H$ NMR (400 MHz, $CD_3OD$): 7.57-7.50 (m, 3H), 7.48 (s, 2H), 7.23-7.20 (m, 1H), 4.08 (t, J=5.8 Hz, 2H), 3.16 (br s, 4H), 3.01 (br s, 4H), 2.82-2.79 (m, 2H), 2.71 (s, 3H), 2.38 (s, 6H), 1.85-1.74 (m, 4H).

Example 30

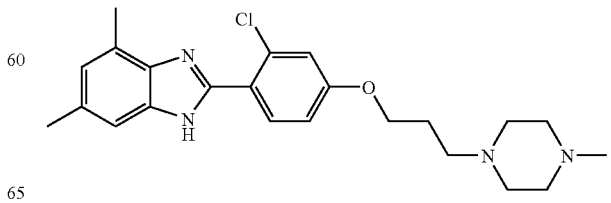

2-{2-Chloro-4-[3-(4-methyl-piperazin-1-yl)-propoxy]-phenyl}-4,6-dimethyl-1H-benzoimidazole.

MS (electrospray): mass calculated for $C_{23}H_{29}ClN_4O$, 412.20; m/z found, 413.4 [M+H]$^+$. $^1$H NMR (400 MHz, CD$_3$OD): 7.68 (d, J=8.5 Hz, 1H), 7.21 (brs, 1H), 7.15 (d, J=2.5 Hz, 1H), 7.03 (dd, J=8.7, 2.5 Hz, 1H), 6.90 (s, 1H), 4.13 (t, J=6.2 Hz, 2H), 2.70-2.40 (m, 16H), 2.96 (s, 3H), 2.06-1.98 (m, 2H).

Example 31

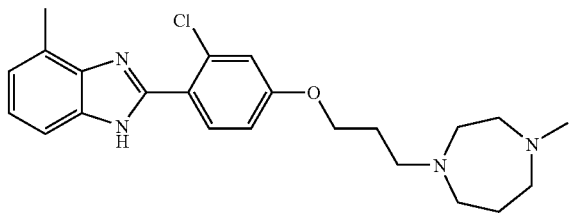

2-{2-Chloro-4-[3-(4-methyl-[1,4]diazepan-1-yl)-propoxy]-phenyl}-4-methyl-1H-benzoimidazole MS (electrospray): mass calculated for $C_{23}H_{29}ClN_4O$, 412.20; m/z found, 413.4 [M+H]$^+$. $^1$H NMR (400 MHz, CD$_3$OD): 7.72-7.69 (m, 1H), 7.50-7.35 (m, 1H), 7.18-7.13 (m, 2H), 7.06-7.03 (m, 2H), 4.14 (t, J=6.1 Hz, 2H), 2.85-2.70 (m, 10H), 2.59 (s, 3H), 2.40 (s, 3H), 2.02-1.96 (m, 2H), 1.89-1.85 (m, 2H).

Example 32

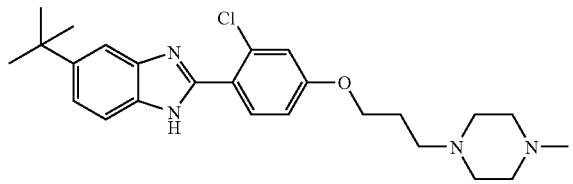

5-tert-Butyl-2-{2-chloro-4-[3-(4-methyl-piperazin-1-yl)-propoxy]-phenyl}-1H-benzoimidazole MS (electrospray): mass calculated for $C_{25}H_{33}ClN_4O$, 440.23; m/z found, 441.5 [M+H]$^+$. $^1$H NMR (400 MHz, CD$_3$OD): 7.76 (d, J=8.7 Hz, 1H), 7.62-7.53 (m, 2H), 7.38 (dd, J=8.6, 2.0 Hz, 1H), 7.15 (d, J=2.5 Hz, 1H), 7.04 (dd, J=8.7, 2.5 Hz, 1H), 4.13 (t, J=6.1 Hz, 2H), 2.80-2.20 (m, 13H), 2.06-1.96 (m, 2H), 1.40 (s, 9H).

Example 33

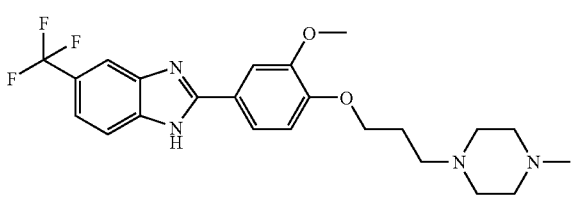

2-{3-Methoxy-4-[3-(4-methyl-piperazin-1-yl)-propoxy]-phenyl}-5-trifluoromethyl-1H-benzoimidazole HPLC: R$_t$=6.30. MS (electrospray): mass calculated for $C_{23}H_{27}F_3N_4O_2$, 448.21; m/z found, 449.2 [M+H]$^+$. $^1$H NMR (500 MHz, CD$_3$OD): 7.93 (s, 1H), 7.79 (d, J=8.6 Hz, 1H), 7.69-7.66 (m, 3H), 7.11 (d, J=9.0 Hz, 1H), 4.16 (t, J=5.6 Hz, 2H), 3.90 (s, 3H), 3.45-3.39 (m, 7H), 3.21-3.18 (m, 3H), 3.18 (s, 3H), 2.21-2.17 (m, 2H).

Example 34

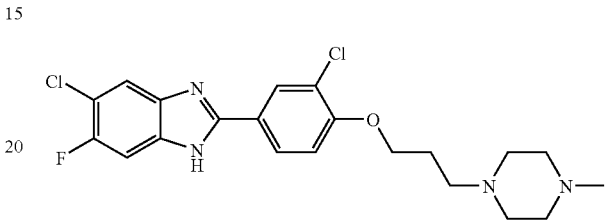

5-Chloro-2-{3-chloro-4-[3-(4-methyl-piperazin-1-yl)-propoxy]-phenyl}-6-fluoro-1H-benzoimidazole HPLC: R$_t$=6.41. MS (electrospray): mass calculated for $C_{21}H_{23}Cl_2FN_4O$, 436.12; m/z found, 437.2 [M+H]$^+$. $^1$H NMR (400 MHz, CD$_3$OD): 7.98 (d, J=2.3 Hz, 1H), 7.87 (dd, J=8.7, 2.3 Hz, 1H), 7.63 (d, J=6.4 Hz, 1H), 7.41 (d, J=8.8 Hz, 1H), 7.17 (d, J=8.7 Hz, 1H), 4.19 (t, J=5.7 Hz, 2H), 3.39 (brs, 4H), 3.25-3.20 (m, 4H), 3.09 (t, J=7.3 Hz, 2H), 2.83 (s, 3H), 2.19-2.15 (m, 2H).

Example 35

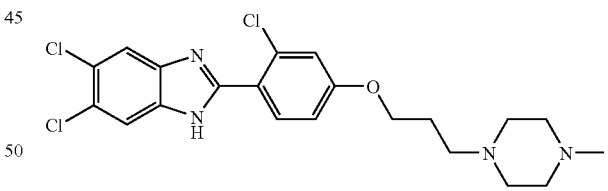

5,6-Dichloro-2-{2-chloro-4-[3-(4-methyl-piperazin-1-yl)-propoxy]-phenyl}-1H-benzoimidazole HPLC: R$_t$=6.64. MS (electrospray): mass calculated for $C_{21}H_{23}Cl_3N_4O$, 452.09; m/z found, 453.2 [M+H]$^+$. $^1$H NMR (400 MHz, CD$_3$OD): 7.74 (s, 2H), 7.60 (d, J=8.8 Hz, 1H), 7.08 (d, J=2.4 Hz, 1H), 6.94 (dd, J=8.8, 2.4 Hz, 1H), 4.00 (t, J=5.8 Hz, 2H), 3.43 (br s, 7H), 3.19 (t, J=7.7 Hz, 2H), 3.05-3.04 (m, 1H), 2.74 (s, 3H), 2.10-2.02 (m, 2H).

Example 36

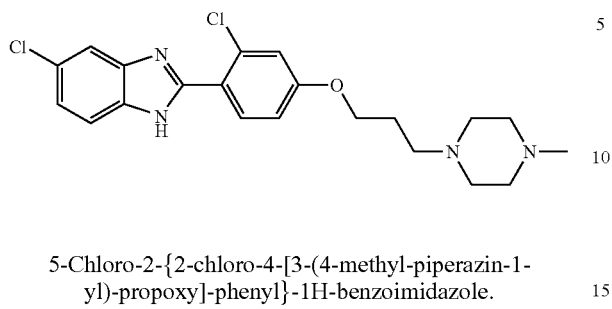

5-Chloro-2-{2-chloro-4-[3-(4-methyl-piperazin-1-yl)-propoxy]-phenyl}-1H-benzoimidazole.

HPLC: $R_t$=6.09. MS (electrospray): mass calculated for $C_{21}H_{24}Cl_2N_4O$, 418.13; m/z found, 419.2 [M+H]$^+$. $^1$H NMR (500 MHz, CD$_3$OD): 7.76 (d, J=8.8 Hz, 1H), 7.73 (dd, J=1.9, 0.4 Hz, 1H), 7.69 (dd, J=8.8, 0.4 Hz, 1H), 7.47 (dd, J=8.8, 1.9 Hz, 1H), 7.23 (d, J=2.5 Hz, 1H), 7.09 (dd, J=8.8, 2.5 Hz, 1H), 4.15 (t, J=5.9 Hz, 2H), 3.45 (br s, 4H), 3.34 (br s, 4H), 3.16-3.12 (m, 2H), 2.85 (s, 3H), 2.18-2.12 (m, 2H).

Example 37

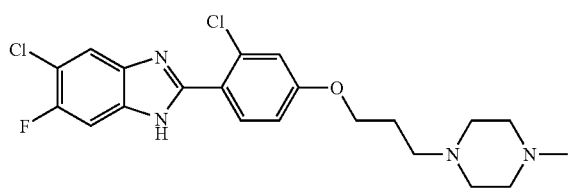

5-Chloro-2-{2-chloro-4-[3-(4-methyl-piperazin-1-yl)-propoxy]-phenyl}-6-fluoro-1H-benzoimidazole HPLC: $R_t$=6.36. MS (electrospray): mass calculated for $C_{21}H_{23}Cl_2FN_4O$, 436.12; m/z found, 437.2 [M+H]$^+$. $^1$H NMR (400 MHz, CD$_3$OD): 7.78 (d, J=6.4 Hz, 1H), 7.73 (d, J=8.8 Hz, 1H), 7.55 (d, J=8.7 Hz, 1H), 7.19 (d, J=2.5 Hz, 1H), 7.06 (dd, J=8.8, 2.5 Hz, 1H), 4.14 (t, J=5.8 Hz, 2H), 3.46 (br s, 4H), 3.37 (brs, 3H), 3.22-3.20 (m, 1H), 3.18-3.14 (m, 2H), 2.86 (s, 3H), 2.19-2.13 (m, 2H).

Example 38

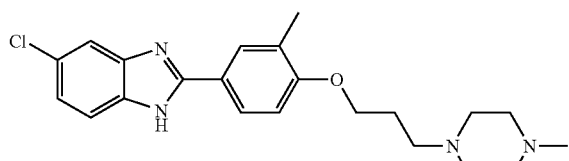

5-Chloro-2-{3-methyl-4-[3-(4-methyl-piperazin-1-yl)-propoxy]-phenyl}-1H-benzoimidazole HPLC: $R_t$=6.20. MS (electrospray): mass calculated for $C_{22}H_{27}ClN_4O$, 398.19; m/z found, 399.2 [M+H]$^+$. $^1$H NMR (500 MHz, CD$_3$OD): 7.88 (dd, J=8.7, 2.3 Hz, 1H), 7.83-7.82 (m, 1H), 7.68 (d, J=1.6 Hz, 1H), 7.63 (d, J=8.9 Hz, 1H), 7.46 (dd, J=8.7, 1.9 Hz, 1H), 7.14 (d, J=8.7 Hz, 1H), 4.16 (t, J=6.0 Hz, 2H), 3.24 (br s, 4H), 2.95 (br s, 4H), 2.88-2.85 (m, 2H), 2.77 (s, 3H), 2.26 (s, 3H), 2.11-2.05 (m, 2H).

Example 39

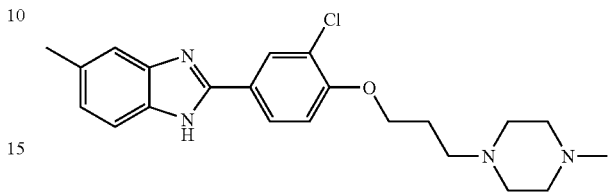

2-{3-Chloro-4-[3-(4-methyl-piperazin-1-yl)-propoxy]-phenyl}-5-methyl-1H-benzoimidazole HPLC: $R_t$=5.93. MS (electrospray): mass calculated for $C_{22}H_{27}ClN_4O$, 398.19; m/z found, 399.3 [M+H]$^+$. $^1$H NMR (500 MHz, CD$_3$OD): 8.10 (d, J=2.4 Hz, 1H), 7.97 (dd, J=8.7, 2.4 Hz, 1H), 7.56 (d, J=8.4 Hz, 1H), 7.48 (s, 1H), 7.34 (d, J=8.4 Hz, 1H), 7.31 (d, J=8.8 Hz, 1H), 4.24 (t, J=5.8 Hz, 2H), 3.34 (br s, 4H), 3.14 (br s, 4H), 3.02-2.99 (m, 2H), 2.80 (s, 3H), 2.45 (s, 3H), 2.18-2.12 (m, 2H).

Example 40

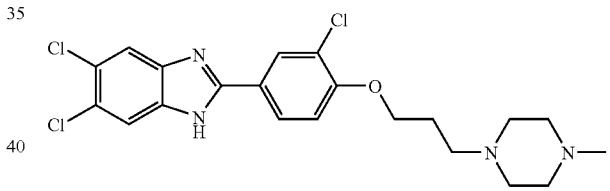

5,6-Dichloro-2-{3-chloro-4-[3-(4-methyl-piperazin-1-yl)-propoxy]-phenyl}-1H-benzoimidazole HPLC: $R_t$=6.69. MS (electrospray): mass calculated for $C_{21}H_{23}Cl_3N_4O$, 452.09; m/z found, 453.2 [M+H]$^+$. $^1$H NMR (400 MHz, CD$_3$OD): 8.08 (d, J=2.3 Hz, 1H), 7.95 (dd, J=8.7, 2.3 Hz, 1H), 7.81 (s, 2H), 7.26 (d, J=8.8 Hz, 1H), 4.25 (t, J=5.7 Hz, 2H), 3.55 (br s, 8H), 3.36-3.32 (m, 2H), 2.90 (s, 3H), 2.31-2.25 (m, 2H).

Example 41

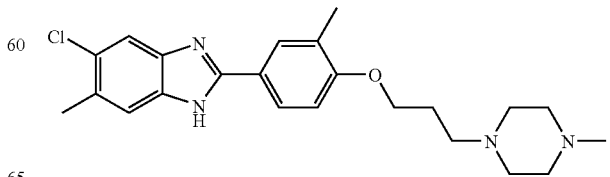

5-Chloro-6-methyl-2-{3-methyl-4-[3-(4-methyl-piperazin-1-yl)-propoxy]-phenyl}-1H-benzoimidazole HPLC: $R_t$=6.40. MS (electrospray): mass calculated for $C_{23}H_{29}ClN_4O$, 412.20; m/z found, 413.2 [M+H]$^+$. $^1$H NMR (500 MHz, CD$_3$OD): 7.87 (dd, J=8.6, 2.5 Hz, 1H), 7.82-7.81 (m, 1H), 7.69 (s, 1H), 7.58 (s, 1H), 7.14 (d, J=8.7 Hz, 1H), 4.15 (t, J=6.0 Hz, 2H), 3.20 (br s, 4H), 2.85 (br s, 4H), 2.83-2.79 (m, 2H), 2.75 (s, 3H), 2.46 (s, 3H), 2.26 (s, 3H), 2.08-2.03 (m, 2H).

Example 42

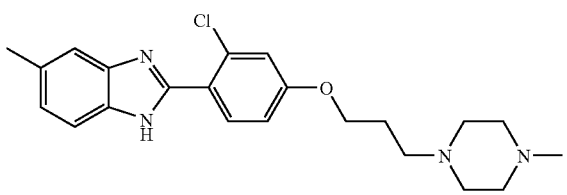

2-{2-Chloro-4-[3-(4-methyl-piperazin-1-yl)-propoxy]-phenyl}-5-methyl-1H-benzoimidazole HPLC: $R_t$=5.92. MS (electrospray): mass calculated for $C_{22}H_{27}ClN_4O$, 398.19; m/z found, 399.3 [M+H]$^+$. $^1$H NMR (500 MHz, CD$_3$OD): 7.87 (d, J=8.8 Hz, 1H), 7.72 (d, J=8.5 Hz, 1H), 7.64 (s, 1H), 7.48 (d, J=8.5 Hz, 1H), 7.36 (d, J=2.4 Hz, 1H), 7.23 (dd, J=8.8, 2.4 Hz, 1H), 4.26 (t, J=5.8 Hz, 2H), 3.60 (br s, 4H), 3.51 (br s, 4H), 3.31-3.27 (m, 2H), 2.98 (s, 3H), 2.58 (s, 3H), 2.31-2.26 (m, 2H).

Example 43

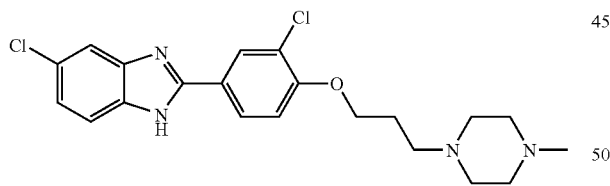

5-Chloro-2-{3-chloro-4-[3-(4-methyl-piperazin-1-yl)-propoxy]-phenyl}-1H-benzoimidazole HPLC: $R_t$=6.15. MS (electrospray): mass calculated for $C_{21}H_{24}Cl_2N_4O$, 418.13; m/z found, 419.2 [M+H]$^+$. $^1$H NMR (500 MHz, CD$_3$OD): 8.07 (d, J=2.3 Hz, 1H), 7.94 (dd, J=8.7, 2.3 Hz, 1H), 7.63 (d, J=1.7 Hz, 1H), 7.59 (d, J=8.7 Hz, 1H), 7.38 (dd, J=8.7, 1.9 Hz, 1H), 7.24 (d, J=8.8 Hz, 1H), 4.22 (t, J=5.8 Hz, 2H), 3.42 (br s, 4H), 3.29 (br s, 4H), 3.15-3.10 (m, 2H), 2.84 (s, 3H), 2.21-2.15 (m, 2H).

Example 44

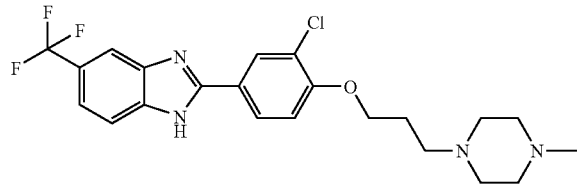

2-{3-Chloro-4-[3-(4-methyl-piperazin-1-yl)-propoxy]-phenyl}-5-trifluoromethyl-1H-benzoimidazole HPLC: $R_t$=6.53. MS (electrospray): mass calculated for $C_{22}H_{24}ClF_3N_4O$, 452.16; m/z found, 453.2 [M+H]$^+$. $^1$H NMR (500 MHz, CD$_3$OD): 8.12 (d, J=2.3 Hz, 1H), 7.99 (dd, J=8.7, 2.3 Hz, 1H), 7.90 (s, 1H), 7.75 (d, J=8.5 Hz, 1H), 7.61 (d, J=8.6 Hz, 1H), 7.26 (d, J=8.8 Hz, 1H), 4.22 (t, J=5.8 Hz, 2H), 3.37 (br s, 4H), 3.21 (br s, 4H), 3.08-3.05 (m, 2H), 2.82 (s, 3H), 2.19-2.14 (m, 2H).

Example 45

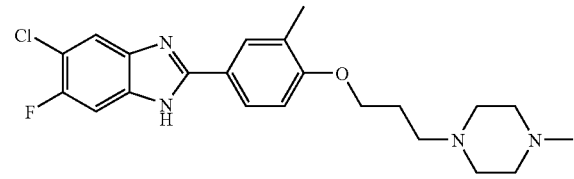

5-Chloro-6-fluoro-2-{3-methyl-4-[3-(4-methyl-piperazin-1-yl)-propoxy]-phenyl}-1H-benzoimidazole HPLC: $R_t$=6.34. MS (electrospray): mass calculated for $C_{22}H_{26}ClFN_4O$, 416.18; m/z found, 417.1 [M+H]$^+$. $^1$H NMR (500 MHz, CD$_3$OD): 7.85 (dd, J=8.6, 2.3 Hz, 1H), 7.80-7.79 (m, 1H), 7.72 (d, J=6.3 Hz, 1H), 7.51 (d, J=8.6 Hz, 1H), 7.10 (d, J=8.7 Hz, 1H), 4.14 (t, J=6.0 Hz, 2H), 3.20 (br s, 8H), 2.85-2.81 (m, 2H), 2.76 (s, 3H), 2.25 (s, 3H), 2.09-2.04 (m, 2H).

Example 46

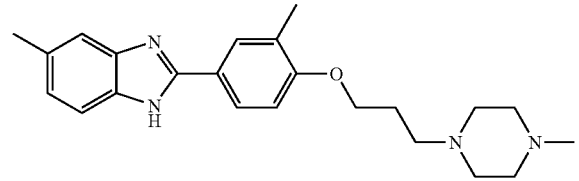

5-Methyl-2-{3-methyl-4-[3-(4-methyl-piperazin-1-yl)-propoxy]-phenyl}-1H-benzoimidazole HPLC: $R_t$=6.13. MS (electrospray): mass calculated for $C_{23}H_{30}N_4O$, 378.24; m/z found, 379.2 [M+H]$^+$. $^1$H NMR (500 MHz, CD$_3$OD): 7.87 (d, J=8.6 Hz, 1H), 7.82-7.81 (m, 1H), 7.54 (d, J=8.4 Hz, 1H), 7.46 (s, 1H), 7.32 (d, J=8.4 Hz, 1H), 7.14 (d, J=8.6 Hz, 1H), 4.16 (t, J=6.0 Hz, 2H), 3.29 (br s, 4H), 3.06 (br s, 4H), 2.96-2.93 (m, 2H), 2.79 (s, 3H), 2.46 (s, 3H), 2.26 (s, 3H), 2.14-2.08 (m, 2H).

Example 47

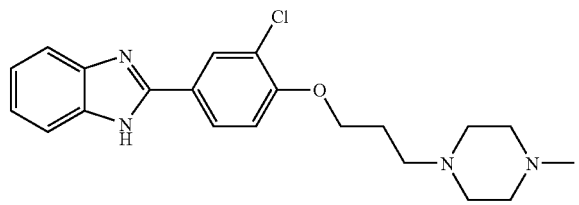

2-{3-Chloro-4-[3-(4-methyl-piperazin-1-yl)-propoxy]-phenyl}-1H-benzoimidazole

HPLC: $R_t$=5.70. MS (electrospray): mass calculated for $C_{21}H_{25}ClN_4O$, 384.17; m/z found, 385.2 [M+H]$^+$. $^1$H NMR (500 MHz, CD$_3$OD): 8.13 (d, J=2.3 Hz, 1H), 8.00 (dd, J=8.7, 2.3 Hz, 1H), 7.72-7.67 (m, 2H), 7.53-7.48 (m, 2H), 7.33 (d, J=8.8 Hz, 1H), 4.25 (t, J=5.9 Hz, 2H), 3.30 (br s, 4H), 3.06 (br s, 4H), 2.96-2.92 (m, 2H), 2.79 (s, 3H), 2.15-2.10 (m, 2H).

Example 48

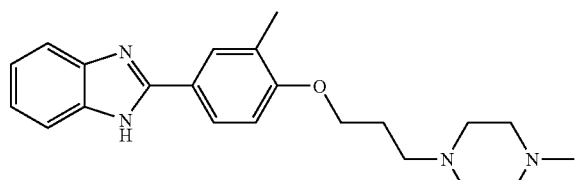

2-{3-Methyl-4-[3-(4-methyl-piperazin-1-yl)-propoxy]-phenyl}-1H-benzoimidazole

HPLC: $R_t$=5.89. MS (electrospray): mass calculated for $C_{22}H_{28}N_4O$, 364.23; m/z found, 365.2 [M+H]$^+$. $^1$H NMR (500 MHz, CD$_3$OD): 7.90 (dd, J=8.5, 2.5 Hz, 1H), 7.85-7.84 (m, 1H), 7.70-7.66 (m, 2H), 7.52-7.47 (m, 2H), 7.15 (d, J=8.6 Hz, 1H), 4.16 (t, J=6.0 Hz, 2H), 3.23 (br s, 4H), 2.96 (br s, 4H), 2.87-2.84 (m, 2H), 2.77 (s, 3H), 2.27 (s, 3H), 2.11-2.05 (m, 2H).

Example 49

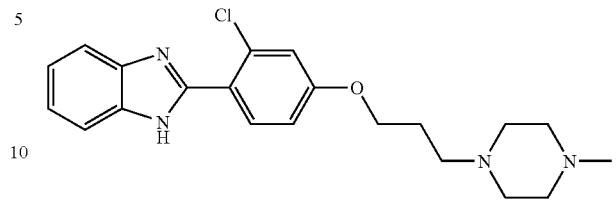

2-{2-Chloro-4-[3-(4-methyl-piperazin-1-yl)-propoxy]-phenyl}-1H-benzoimidazole.

HPLC: $R_t$=5.68. MS (electrospray): mass calculated for $C_{21}H_{25}ClN_4O$, 384.17; m/z found, 385.3 [M+H]$^+$. $^1$H NMR (500 MHz, CD$_3$OD): 7.78 (d, J=8.8 Hz, 1H), 7.77-7.74 (m, 2H), 7.56-7.53 (m, 2H), 7.27 (d, J=2.4 Hz, 1H), 7.12 (dd, J=8.8, 2.4 Hz, 1H), 4.16 (t, J=5.9 Hz, 2H), 3.44 (br s, 4H), 3.32 (br s, 4H), 3.14-3.11 (m, 2H), 2.84 (s, 3H), 2.18-2.12 (m, 2H).

Example 50

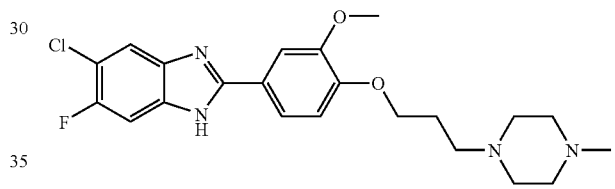

5-Chloro-6-fluoro-2-{3-methoxy-4-[3-(4-methyl-piperazin-1-yl)-propoxy]-phenyl}-1H-benzoimidazole HPLC: $R_t$=6.15. MS (electrospray): mass calculated for $C_{22}H_{26}ClFN_4O_2$, 432.17; m/z found, 433.2 [M+H]$^+$. $^1$H NMR (400 MHz, CD$_3$OD): 7.75-7.73 (m, 1H), 7.61-7.58 (m, 2H), 7.52 (d, J=8.5 Hz, 1H), 7.09-7.07 (m, 1H), 4.16 (t, J=5.6 Hz, 2H), 3.88 (s, 3H), 3.48 (br s, 8H), 3.25-3.22 (m, 2H), 2.86 (s, 3H), 2.22-2.19 (m, 2H).

Example 51

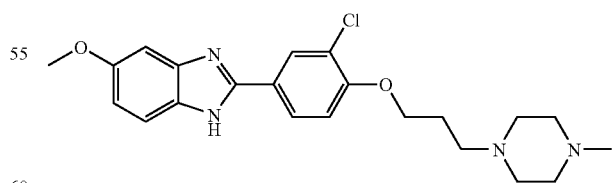

2-{3-Chloro-4-[3-(4-methyl-piperazin-1-yl)-propoxy]-phenyl}-5-methoxy-1H-benzoimidazole HPLC: $R_t$=5.85. MS (electrospray): mass calculated for $C_{22}H_{27}ClN_4O_2$, 414.18; m/z found, 415.2 [M+H]$^+$. $^1$H NMR (400 MHz, CD$_3$OD): 8.08 (d, J=2.3 Hz, 1H), 7.94 (dd, J=8.7, 2.3 Hz, 1H), 7.56 (d, J=8.9 Hz, 1H), 7.30 (d, J=8.8 Hz, 1H), 7.14 (d, J=2.0 Hz, 1H), 7.10 (dd, J=9.0, 2.3 Hz, 1H), 4.26 (t, J=5.7 Hz, 2H), 3.82 (s, 3H), 3.52 (br s, 8H), 3.30-3.26 (m, 2H), 2.88 (s, 3H), 2.29-2.22 (m, 2H).

Example 52

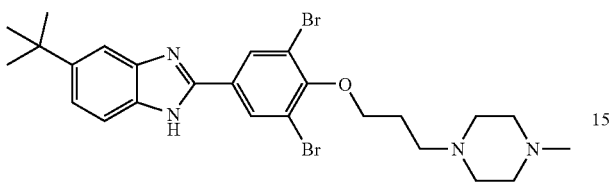

5-tert-Butyl-2-{3,5-dibromo-4-[3-(4-methyl-piperazin-1-yl)-propoxy]-phenyl}-1H-benzoimidazole HPLC: R$_t$=6.81. MS (electrospray): mass calculated for C$_{25}$H$_{32}$Br$_2$N$_4$O, 562.09; m/z found, 563.1 [M+H]$^+$. $^1$H NMR (500 MHz, CD$_3$OD): 8.31 (s, 2H), 7.70-7.62 (m, 3H), 4.17 (t, J=5.8 Hz, 2H), 3.37 (br s, 4H), 3.20 (br s, 4H), 3.18-3.15 (m, 2H), 2.82 (s, 3H), 2.22-2.16 (m, 2H), 1.34 (s, 9H).

Example 53

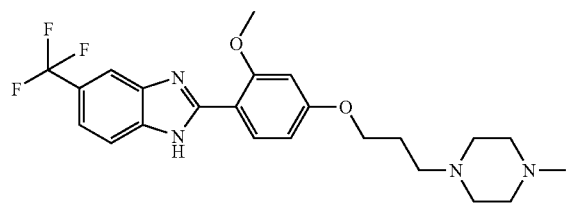

2-{2-Methoxy-4-[3-(4-methyl-piperazin-1-yl)-propoxy]-phenyl}-5-trifluoromethyl-1H-benzoimidazole HPLC: R$_t$=6.34. MS (electrospray): mass calculated for C$_{23}$H$_{27}$F$_3$N$_4$O$_2$, 448.21; m/z found, 449.3 [M+H]$^+$. $^1$H NMR (500 MHz, CD$_3$OD): 8.11-8.08 (m, 2H), 7.96 (d, J=8.6 Hz, 1H), 7.83 (d, J=8.6 Hz, 1H), 6.89-6.87 (m, 2H), 4.28 (t, J=5.8 Hz, 2H), 4.17 (s, 3H), 3.58 (br s, 4H), 3.49 (br s, 4H), 3.30-3.27 (m, 2H), 2.97 (s, 3H), 2.31-2.25 (m, 2H).

Example 54

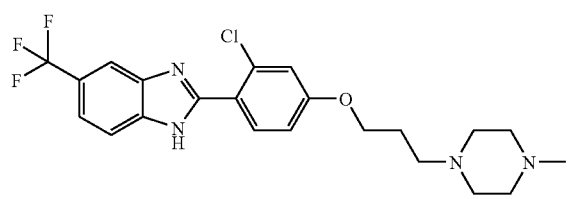

2-{2-Chloro-4-[3-(4-methyl-piperazin-1-yl)-propoxy]-phenyl}-5-trifluoromethyl-1H-benzoimidazole HPLC: R$_t$=6.47. MS (electrospray): mass calculated for C$_{22}$H$_{24}$ClF$_3$N$_4$O, 452.16; m/z found, 453.2 [M+H]$^+$. $^1$H NMR (400 MHz, CD$_3$OD): 8.09 (s, 1H), 7.93 (d, J=8.7 Hz, 1H), 7.85-7.80 (m, 2H), 7.29 (d, J=2.3 Hz, 1H), 7.15 (dd, J=8.8, 2.5 Hz, 1H), 4.20 (t, J=5.8 Hz, 2H), 3.62 (br s, 8H), 3.40-3.36 (m, 2H), 2.93 (s, 3H), 2.29-2.20 (m, 2H).

Example 55

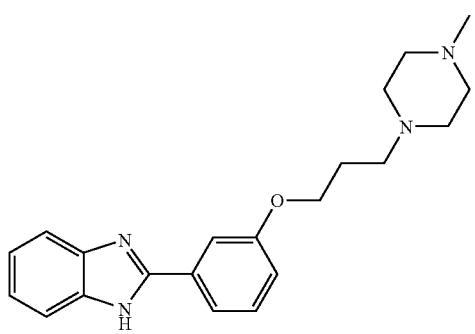

2-{3-[3-(4-Methyl-piperazin-1-yl)-propoxy]-phenyl}-1H-benzoimidazole

HPLC: R$_t$=5.51. MS (electrospray): mass calculated for C$_{21}$H$_{26}$N$_4$O, 350.21; m/z found, 351.2 [M+H]$^+$. $^1$H NMR (400 MHz, CD$_3$OD): 7.75-7.72 (m, 2H), 7.70-7.60 (m, 2H), 7.54-7.51 (m, 3H), 7.26-7.24 (m, 1H), 4.16 (t, J=6.0 Hz, 2H), 3.35 (br s, 4H), 3.19 (br s, 4H), 3.05-3.01 (m, 2H), 2.81 (s, 3H), 2.14-2.10 (m, 2H).

Example 56

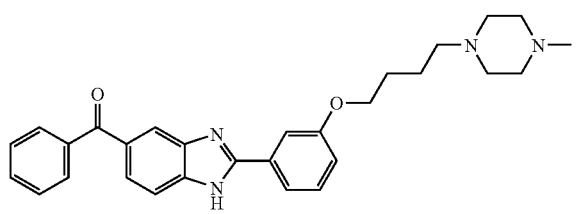

(2-{3-[4-(4-Methyl-piperazin-1-yl)-butoxy]-phenyl}-1H-benzoimidazol-5-yl)-phenyl-methanone HPLC: R$_t$=6.36. MS (electrospray): mass calculated for C$_{29}$H$_{32}$N$_4$O$_2$, 468.25; m/z found, 469.3 [M+H]$^+$. $^1$H NMR (400 MHz, CD$_3$OD): 8.11 (s, 1H), 7.90-7.77 (m, 4H), 7.72-7.65 (m, 3H), 7.58-7.52 (m, 3H), 7.23-7.20 (m, 1H), 4.15 (t, J=5.7 Hz, 2H), 3.57 (br s, 8H), 3.26-3.21 (m, 2H), 2.95 (s, 3H), 1.96-1.93 (m, 4H).

The following compounds in Examples 57-71 were prepared according to the procedures described in Example 2.

Example 57

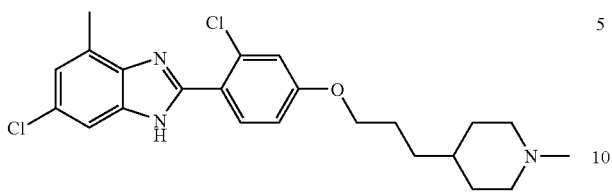

6-Chloro-2-{2-chloro-4-[3-(1-methyl-piperidin-4-yl)-propoxy]-phenyl}-4-methyl-1H-benzoimidazole MS (electrospray): mass calculated for $C_{23}H_{27}Cl_2N_3O$, 431.15; m/z found, 432.1 [M+H]$^+$. $^1$H NMR (400 MHz, CD$_3$OD): 7.69 (d, J=8.0 Hz, 1H), 7.42 (br s, 1H), 7.14 (d, J=4.0 Hz, 1H), 7.07-7.05 (m, 1H), 7.02 (dd, J=8.0, 4.0 Hz, 1H), 4.04 (t, J=8.0 Hz, 2H), 2.95-2.85 (m, 2H), 2.58 (s, 3H), 2.28 (s, 3H), 2.10-2.00 (m, 2H), 1.84-1.75 (m, 4H), 1.46-1.41 (m, 2H), 1.22-1.35 (m, 3H).

Example 58

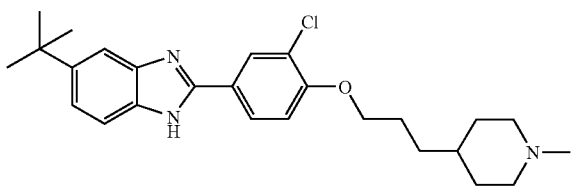

5-tert-Butyl-2-{3-chloro-4-[3-(1-methyl-piperidin-4-yl)-propoxy]-phenyl}-1H-benzoimidazole MS (electrospray): mass calculated for $C_{26}H_{34}ClN_3O$, 439.24; m/z found, 440.2 [M+H]$^+$. $^1$H NMR (400 MHz, CD$_3$OD): 8.10 (d, J=2.2 Hz, 1H), 7.97 (dd, J=8.6, 2.2 Hz, 1H), 7.58 (br s, 1H), 7.52-7.45 (m, 1H), 7.36 (dd, J=8.6, 1.7 Hz, 1H), 7.21 (d, J=8.7 Hz, 1H), 4.14 (t, J=6.2 Hz, 2H), 2.93-2.85 (m, 2H), 2.28 (s, 3H), 2.11-2.00 (m, 2H), 1.92-1.83 (m, 2H), 1.82-1.74 (m, 2H), 1.52-1.45 (m, 2H), 1.42-1.20 (m, 12H).

Example 59

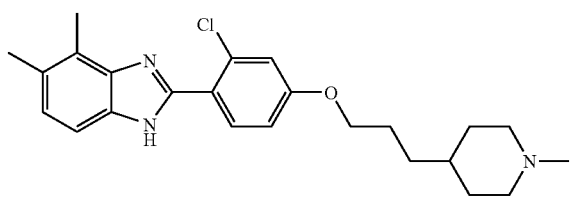

2-{2-Chloro-4-[3-(1-methyl-piperidin-4-yl)-propoxy]-phenyl}-4,5-dimethyl-1H-benzoimidazole MS (electrospray): mass calculated for $C_{24}H_{30}ClN_3O$, 411.21; m/z found, 412.4 [M+H]$^+$. $^1$H NMR (400 MHz, CD$_3$OD): 7.73-7.63 (m, 1H), 7.31 (br s, 1H), 7.13 (d, J=2.5 Hz, 1H), 7.07 (d, J=8.2 Hz, 1H), 7.02 (dd, J=8.7, 2.5 Hz, 1H), 4.06 (t, J=6.3 Hz, 2H), 2.93-2.89 (m, 2H), 2.51 (s, 3H), 2.40 (s, 3H), 2.29 (s, 3H), 2.00-2.15 (m, 2H), 1.86-1.77 (m, 4H), 1.48-1.42 (m, 2H), 1.35-1.24 (m, 3H).

Example 60

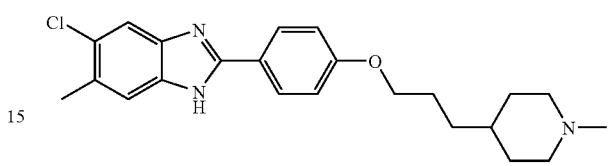

5-Chloro-6-methyl-2-{4-[3-(1-methyl-piperidin-4-yl)-propoxy]-phenyl}-1H-benzoimidazole.

HPLC: R$_t$=6.84. MS (electrospray): mass calculated for $C_{23}H_{28}ClN_3O$, 397.19; m/z found, 398.5 [M+H]$^+$. $^1$H NMR (500 MHz, CD$_3$OD): 7.95 (d, J=9.0 Hz, 2H), 7.67 (s, 1H), 7.57 (s, 1H), 7.12 (d, J=9.0 Hz, 2H), 4.05 (t, J=6.3 Hz, 2H), 3.42 (d, J=10.4 Hz, 2H), 2.92-2.86 (m, 2H), 2.89 (s, 3H), 2.45 (s, 3H), 1.96-1.93 (m, 2H), 1.82-1.77 (m, 2H), 1.60-1.52 (m, 1H), 1.45-1.30 (m, 4H).

Example 61

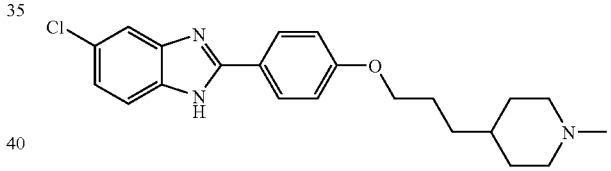

5-Chloro-2-{4-[3-(1-methyl-piperidin-4-yl)-propoxy]-phenyl}-1H-benzoimidazole.

HPLC: R$_t$=6.62. MS (electrospray): mass calculated for $C_{22}H_{26}ClN_3O$, 383.18; m/z found, 384.5 [M+H]$^+$. $^1$H NMR (500 MHz, CD$_3$OD): 7.96 (d, J=9.0 Hz, 2H), 7.66 (d, J=2.0 Hz, 1H), 7.61 (d, J=8.7 Hz, 1H), 7.42 (dd, J=8.7, 1.9 Hz, 1H), 7.12 (d, J=9.0 Hz, 2H), 4.05 (t, J=6.3 Hz, 2H), 3.43-3.40 (m, 2H), 2.92-2.86 (m, 2H), 2.76 (s, 3H), 1.96-1.93 (m, 2H), 1.82-1.76 (m, 2H), 1.60-1.51 (m, 1H), 1.46-1.30 (m, 4H).

Example 62

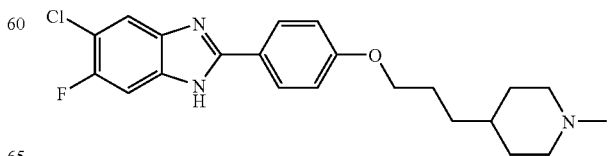

5-Chloro-6-fluoro-2-{4-[3-(1-methyl-piperidin-4-yl)-propoxy]-phenyl}-1H-benzoimidazole HPLC: $R_t$=6.80. MS (electrospray): mass calculated for $C_{22}H_{25}ClFN_3O$, 401.17; m/z found, 402.5 [M+H]$^+$. $^1$H NMR (500 MHz, CD$_3$OD): 7.93 (d, J=9.0 Hz, 2H), 7.71 (d, J=6.3 Hz, 1H), 7.49 (d, J=8.6 Hz, 1H), 7.08 (d, J=9.0 Hz, 2H), 4.03 (t, J=6.3 Hz, 2H), 3.44-3.40 (m, 2H), 2.92-2.86 (m, 2H), 2.76 (s, 3H), 1.96-1.93 (m, 2H), 1.82-1.76 (m, 2H), 1.60-1.51 (m, 1H), 1.43-1.29 (m, 4H).

Example 63

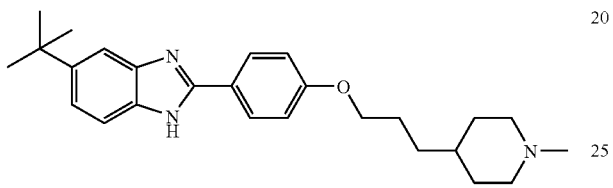

5-tert-Butyl-2-{4-[3-(1-methyl-piperidin-4-yl)-propoxy]-phenyl}-1H-benzoimidazole HPLC: $R_t$=7.16. MS (electrospray): mass calculated for $C_{26}H_{35}N_3O$, 405.28; m/z found, 406.6 [M+H]$^+$. $^1$H NMR (500 MHz, CD$_3$OD): 8.09 (d, J=9.0 Hz, 2H), 7.70 (s, 1H), 7.71 (s, 2H), 7.25 (d, J=9.0 Hz, 2H), 4.16 (t, J=6.3 Hz, 2H), 3.58-3.52 (m, 2H), 3.03-2.97 (m, 2H), 2.87 (s, 3H), 2.06-2.03 (m, 2H), 1.93-1.87 (m, 2H), 1.71-1.63 (m, 1H), 1.57-1.49 (m, 4H), 1.44 (s, 9H).

Example 64

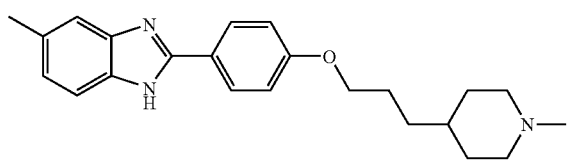

5-Methyl-2-{4-[3-(1-methyl-piperidin-4-yl)-propoxy]-phenyl}-1H-benzoimidazole

HPLC: $R_t$=6.53. MS (electrospray): mass calculated for $C_{23}H_{29}N_3O$, 363.23; m/z found, 364.5 [M+H]$^+$. $^1$H NMR (500 MHz, CD$_3$OD): 7.96 (d, J=9.0 Hz, 2H), 7.53 (d, J=8.4 Hz, 1H), 7.47 (s, 1H), 7.33 (d, J=8.4 Hz, 1H), 7.14 (d, J=9.0 Hz, 2H), 4.05 (t, J=6.2 Hz, 2H), 3.44-3.41 (m, 2H), 2.92-2.86 (m, 2H), 2.76 (s, 3H), 2.45 (s, 3H), 1.96-1.92 (m, 2H), 1.82-1.76 (m, 2H), 1.60-1.50 (m, 1H), 1.45-1.33 (m, 4H).

Example 65

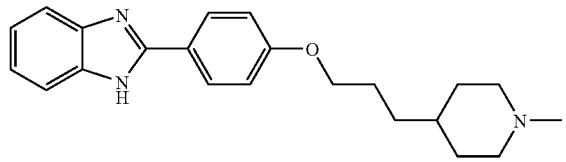

2-{4-[3-(1-Methyl-piperidin-4-yl)-propoxy]-phenyl}-1H-benzoimidazole

HPLC: $R_t$=6.28. MS (electrospray): mass calculated for $C_{22}H_{27}N_3O$, 349.22; m/z found, 350.5 [M+H]$^+$. $^1$H NMR (500 MHz, CD$_3$OD): 8.00 (d, J=8.9 Hz, 2H), 7.70-7.66 (m, 2H), 7.51-7.47 (m, 2H), 7.15 (d, J=8.9 Hz, 2H), 4.06 (t, J=6.2 Hz, 2H), 3.43-3.40 (m, 2H), 2.92-2.85 (m, 2H), 2.76 (s, 3H), 1.96-1.93 (m, 2H), 1.82-1.77 (m, 2H), 1.60-1.50 (m, 1H), 1.45-1.33 (m, 4H).

Example 66

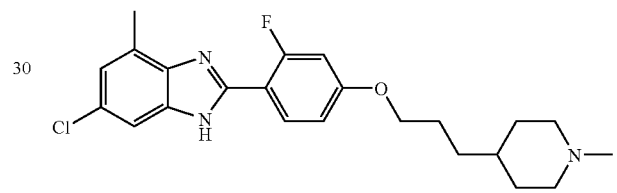

6-Chloro-2-{2-fluoro-4-[3-(1-methyl-piperidin-4-yl)-propoxy]-phenyl}-4-methyl-1H-benzoimidazole MS (electrospray): mass calculated for $C_{23}H_{27}ClFN_3O$, 415.18; m/z found, 416.3 [M+H]$^+$. $^1$H NMR (400 MHz, CD$_3$OD): 8.02 (s, 1H), 7.41 (s, 1H), 7.07-7.02 (m, 1H), 6.96-6.85 (m, 2H), 4.06 (t, J=6.3 Hz, 2H), 2.93-2.83 (m, 2H), 2.60 (s, 3H), 2.26 (s, 3H), 2.07-1.97 (m, 2H), 1.89-1.71 (m, 4H), 1.49-1.40 (m, 2H), 1.38-1.22 (m, 3H).

Example 67

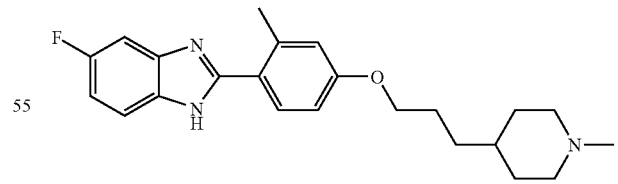

5-Fluoro-2-{2-methyl-4-[3-(1-methyl-piperidin-4-yl)-propoxy]-phenyl}-1H-benzoimidazole MS (electrospray): mass calculated for $C_{23}H_{28}FN_3O$, 381.22; m/z found, 382.3 [M+H]$^+$. $^1$H NMR (400 MHz, CD$_3$OD): 7.61-7.52 (m, 2H), 7.29 (dd, J=9.1, 2.3 Hz, 1H), 7.09-7.01 (m, 1H), 6.96-6.86 (m, 2H), 4.04 (t, J=6.4 Hz, 2H), 2.95-2.82 (m, 2H), 2.52 (s, 3H), 2.28 (s, 3H), 2.08-1.96 (m, 2H), 1.88-1.72 (m, 4H), 1.51-1.40 (m, 2H), 1.38-1.19 (m, 3H).

Example 68

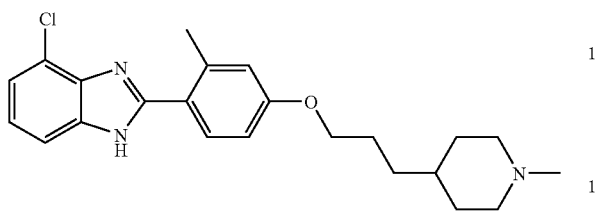

4-Chloro-2-{2-methyl-4-[3-(1-methyl-piperidin-4-yl)-propoxy]-phenyl}-1H-benzoimidazole MS (electrospray): mass calculated for $C_{23}H_{28}ClN_3O$, 397.19; m/z found, 398.3 [M+H]$^+$. $^1$H NMR (400 MHz, CD$_3$OD): 7.56 (d, J=8.5 Hz, 1H), 7.54 (d, J=7.7 Hz, 1H), 7.31-7.20 (m, 2H), 6.93 (d, J=2.3 Hz, 1H), 7.90 (dd, J=8.5, 2.5 Hz, 1H), 4.04 (t, J=6.3 Hz, 2H), 2.94-2.84 (m, 2H), 2.51 (s, 3H), 2.28 (s, 3H), 2.09-1.97 (m, 2H), 1.89-1.72 (m, 4H), 1.52-1.40 (m, 2H), 1.37-1.21 (m, 3H).

Example 69

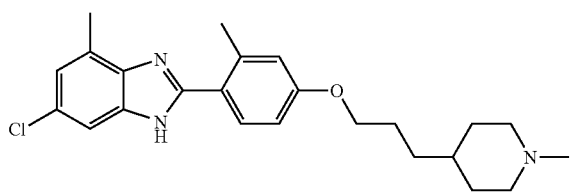

6-Chloro-4-methyl-2-{2-methyl-4-[3-(1-methyl-piperidin-4-yl)-propoxy]-phenyl}-1H-benzoimidazole MS (electrospray): mass calculated for $C_{24}H_{30}ClN_3O$, 411.21; m/z found, 412.4 [M+H]$^+$. $^1$H NMR (400 MHz, CD$_3$OD): 7.54 (d, J=8.4 Hz, 1H), 7.42 (br s, 1H), 7.09-7.05 (m, 1H), 6.94 (d, J=2.3 Hz, 1H), 6.90 (dd, J=8.4, 2.4 Hz, 1H), 4.06 (t, J=6.3 Hz, 2H), 2.96-2.86 (m, 2H), 2.59 (s, 3H), 2.49 (s, 3H), 2.29 (s, 3H), 2.10-2.00 (m, 2H), 1.90-1.75 (m, 4H), 1.52-1.43 (m, 2H), 1.38-1.23 (m, 3H).

Example 70

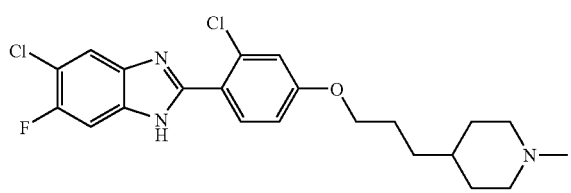

5-Chloro-2-{2-chloro-4-[3-(1-methyl-piperidin-4-yl)-propoxy]-phenyl}-6-fluoro-1H-benzoimidazole MS (electrospray): mass calculated for $C_{22}H_{24}Cl_2FN_3O$, 435.13; m/z found, 436.3 [M+H]$^+$. $^1$H NMR (400 MHz, CD$_3$OD): 7.78 (d, J=8.7 Hz, 1H), 7.70 (d, J=6.6 Hz, 1H), 7.46 (d, J=9.3 Hz, 1H), 7.14 (d, J=2.4 Hz, 1H), 7.04 (dd, J=8.7, 2.5 Hz, 1H), 4.06 (t, J=6.4 Hz, 2H), 2.93-2.84 (m, 2H), 2.28 (s, 3H), 2.09-1.96 (m, 2H), 1.87-1.71 (m, 4H), 1.49-1.39 (m, 2H), 1.35-1.22 (m, 3H).

Example 71

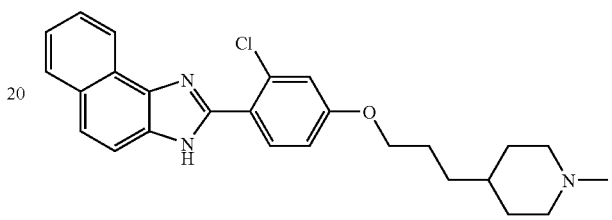

2-{2-Chloro-4-[3-(1-methyl-piperidin-4-yl)-propoxy]-phenyl}-3H-naphtho[1,2-d]imidazole MS (electrospray): mass calculated for $C_{26}H_{28}ClN_3O$, 433.19; m/z found, 434.3 [M+H]$^+$. $^1$H NMR (400 MHz, CD$_3$OD): 8.52-8.44 (m, 1H), 7.97 (d, J=8.2 Hz, 1H), 7.78 (d, J=8.6 Hz, 1H), 7.74 (s, 2H), 7.64-7.57 (m, 1H), 7.53-7.47 (m, 1H), 7.15 (d, J=2.5 Hz, 1H), 7.02 (dd, J=8.6, 2.5 Hz, 1H), 4.01 (t, J=6.3 Hz, 2H), 2.89-2.78 (m, 2H), 2.25 (s, 3H), 2.03-1.90 (m, 2H), 1.83-1.64 (m, 4H), 1.43-1.33 (m, 2H), 1.33-1.18 (m, 3H).

The following compounds in Examples 72-81 were prepared according to the procedures described in Example 1.

Example 72

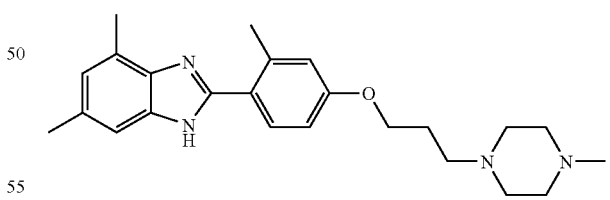

4,6-Dimethyl-2-{2-methyl-4-[3-(4-methyl-piperazin-1-yl)-propoxy]-phenyl}-1H-benzoimidazole MS (electrospray): mass calculated for $C_{24}H_{32}N_4O$, 392.26; m/z found, 393.3 [M+H]$^+$. $^1$H NMR (400 MHz, CD$_3$OD): 7.51 (d, J=8.5 Hz, 1H), 7.20 (s, 1H), 6.92-6.70 (m, 3H), 4.07 (t, J=6.1 Hz, 2H), 2.72-2.40 (m, 19H), 2.30 (s, 3H), 2.02-1.98 (m, 2H).

Example 73

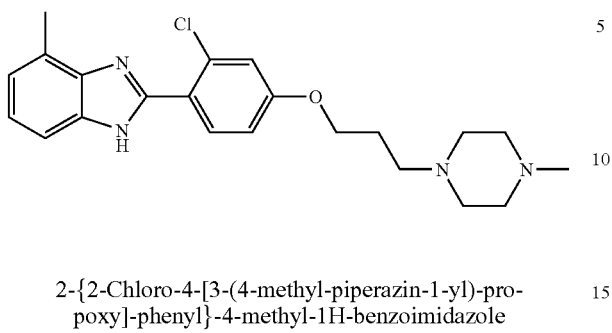

2-{2-Chloro-4-[3-(4-methyl-piperazin-1-yl)-propoxy]-phenyl}-4-methyl-1H-benzoimidazole MS (electrospray): mass calculated for $C_{22}H_{27}ClN_4O$, 398.19; m/z found, 399.4 [M+H]$^+$. $^1$H NMR (400 MHz, CD$_3$OD): 7.72-7.67 (m, 1H), 7.41 (s, 1H), 7.18-7.13 (m, 2H), 7.07-7.02 (m, 2H), 4.13 (t, J=6.1 Hz, 2H), 2.80-2.40 (m, 13H), 2.30 (s, 3H), 2.05-1.98 (m, 2H).

Example 74

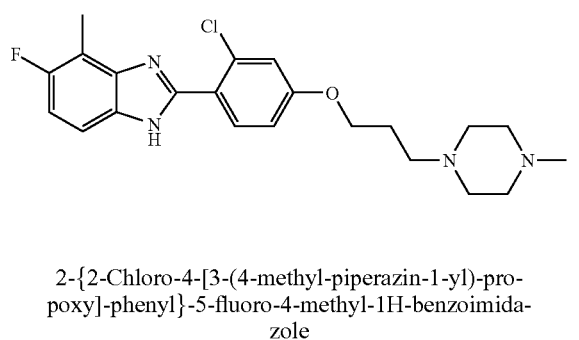

2-{2-Chloro-4-[3-(4-methyl-piperazin-1-yl)-propoxy]-phenyl}-5-fluoro-4-methyl-1H-benzoimidazole MS (electrospray): mass calculated for $C_{22}H_{26}ClFN_4O$, 416.18; m/z found, 417.1 [M+H]$^+$. $^1$H NMR (400 MHz, CD$_3$OD): 7.76-7.65 (br s, 1H), 7.47-7.33 (br s, 1H), 7.17 (d, J=2.5 Hz, 1H), 7.07-7.00 (m, 2H), 4.13 (t, J=6.1 Hz, 2H), 2.68-2.40 (m, 13H), 2.32 (s, 3H), 2.08-1.97 (m, 2H).

Example 75

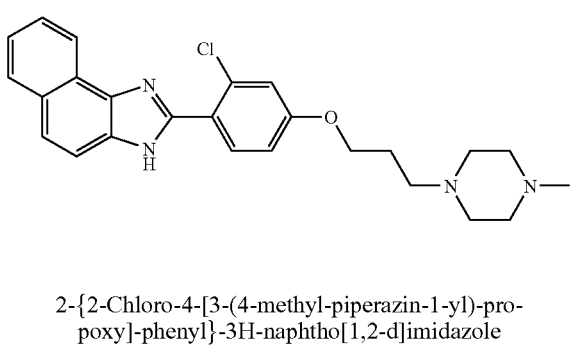

2-{2-Chloro-4-[3-(4-methyl-piperazin-1-yl)-propoxy]-phenyl}-3H-naphtho[1,2-d]imidazole MS (electrospray): mass calculated for $C_{25}H_{27}ClN_4O$, 434.19; m/z found, 435.2 [M+H]$^+$. $^1$H NMR (400 MHz, CD$_3$OD): 8.49 (s, 1H), 7.93 (d, J=8.1 Hz, 1H), 7.74-7.68 (m, 3H), 7.60-7.55 (m, 1H), 7.48-7.43 (m, 1H), 7.07 (d, J=2.5 Hz, 1H), 6.90 (dd, J=8.7, 2.5 Hz, 1H), 3.92 (t, J=6.1 Hz, 2H), 2.62-2.30 (m, 10H), 2.22 (s, 3H), 1.89-1.81 (m, 2H).

Example 76

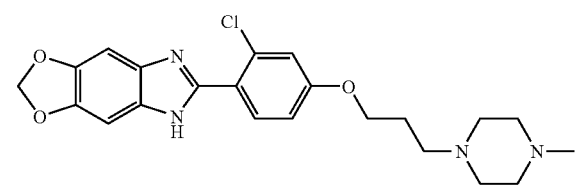

6-{2-Chloro-4-[3-(4-methyl-piperazin-1-yl)-propoxy]-phenyl}-5H-[1,3]dioxolo[4',5':4,5]benzo[1,2-d]imidazole MS (electrospray): mass calculated for $C_{22}H_{25}ClN_4O_3$, 428.16; m/z found, 429.2 [M+H]$^+$. $^1$H NMR (400 MHz, CD$_3$OD): 7.74 (d, J=8.7 Hz, 1H), 7.13 (d, J=2.5 Hz, 1H), 7.07-6.97 (m, 3H), 5.98 (s, 2H), 4.11 (t, J=6.2 Hz, 2H), 2.74-2.36 (m, 10H), 2.31 (s, 3H), 2.07-1.96 (m, 2H).

Example 77

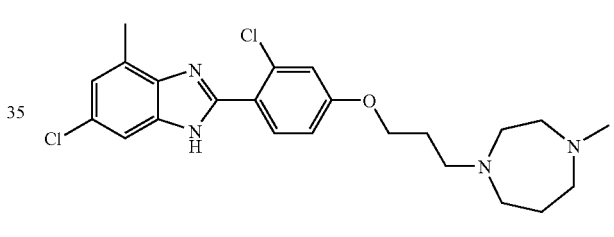

6-Chloro-2-{2-chloro-4-[3-(4-methyl-[1,4]diazepan-1-yl)-propoxy]-phenyl}-4-methyl-1H-benzoimidazole MS (electrospray): mass calculated for $C_{23}H_{28}Cl_2N_4O$, 446.16; m/z found, 447.1 [M+H]$^+$. $^1$H NMR (400 MHz, CD$_3$OD): 7.72 (d, J=8.6 Hz, 1H), 7.44 (br s, 1H), 7.18 (d, J=2.5 Hz, 1H), 7.10-7.08 (m, 1H), 7.05 (dd, J=8.7, 2.5 Hz, 1H), 4.14 (t, J=6.1 Hz, 2H), 2.83-2.78 (m, 4H), 2.75-2.69 (m, 6H), 2.60 (s, 3H), 2.39 (s, 3H), 2.04-1.96 (m, 2H), 1.90-1.84 (m, 2H).

Example 78

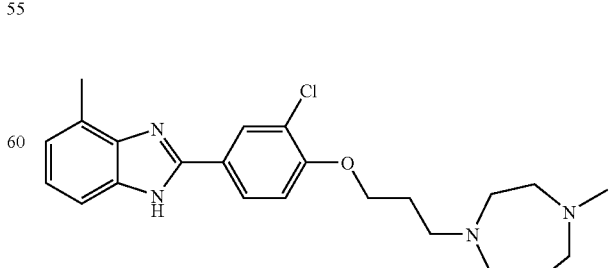

2-{3-Chloro-4-[3-(4-methyl-[1,4]diazepan-1-yl)-propoxy]-phenyl}-4-methyl-1H-benzoimidazole.

MS (electrospray): mass calculated for C$_{23}$H$_{29}$ClN$_4$O, 412.20; m/z found, 413.2 [M+H]$^+$. $^1$H NMR (400 MHz, CD$_3$OD): 8.19 (d, J=2.2 Hz, 1H), 8.04 (dd, J=8.6, 2.2 Hz, 1H), 7.42 (d, J=7.9 Hz, 1H), 7.22 (d, J=8.7 Hz, 1H), 7.18-7.11 (m, 1H), 7.04 (d, J=7.2 Hz, 1H), 4.19 (t, J=6.0 Hz, 2H), 2.84-2.66 (m, 10H), 2.62 (s, 3H), 2.36 (s, 3H), 2.08-1.98 (m, 2H), 1.89-1.82 (m, 2H).

Example 79

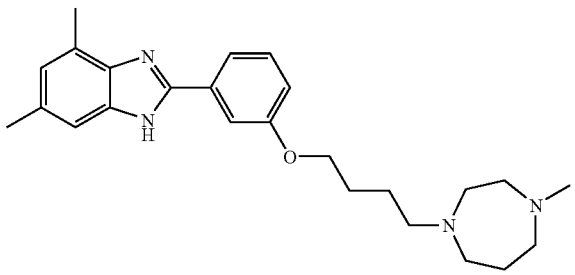

4,6-Dimethyl-2-{3-[4-(4-methyl-[1,4]diazepan-1-yl)-butoxy]-phenyl}-1H-benzoimidazole MS (electrospray): mass calculated for C$_{25}$H$_{34}$N$_4$O, 406.27; m/z found, 407.2 [M+H]$^+$. $^1$H NMR (400 MHz, CD$_3$OD): 7.75-7.70 (m, 1H), 7.69-7.64 (d, J=7.7 Hz, 1H), 7.46-7.40 (m, 1H), 7.23 (br s, 1H), 7.04 (m, 1H), 6.90 (br s, 1H), 4.12 (t, J=6.2 Hz, 2H), 2.83-2.75 (m, 4H), 2.73-2.65 (m, 4H), 2.63-2.54 (m, 5H), 2.44 (s, 3H), 2.35 (s, 3H), 1.89-1.79 (m, 4H), 1.76-1.68 (m, 2H).

Example 80

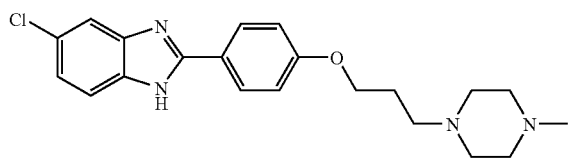

5-Chloro-2-{4-[3-(4-methyl-piperazin-1-yl)-propoxy]-phenyl}-1H-benzoimidazole.

Example 81

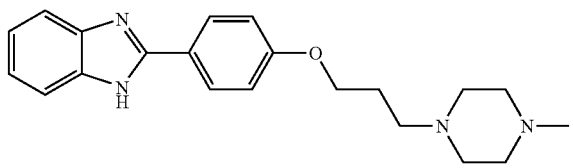

2-{4-[3-(4-Methyl-piperazin-1-yl)-propoxy]-phenyl}-1H-benzoimidazole

Example 82

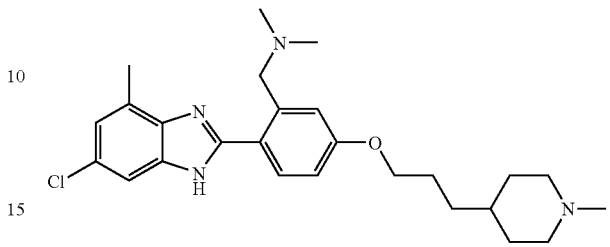

{2-(6-Chloro-4-methyl-1H-benzoimidazol-2-yl)-5-[3-(1-methyl-piperidin-4-yl)-propoxy]-benzyl}-dimethyl-amine A. 4-Bromo-3-dimethylaminomethyl-phenol. 2-Bromo-5-hydroxy-benzaldehyde (5.0 g, 24.9 mmol, 1.0 equiv) and 2.0 M dimethylamine in THF (31 mL, 62 mmol, 2.5 equiv) were stirred in dichloroethane (50 mL) at rt for 1.0 h. Sodium triacetoxyborohydride (15.8 g, 75 mmol, 3.0 equiv) was added, and the mixture was stirred for 3.0 h then poured into satd. aq. NaHCO$_3$. The aqueous mixture was extracted three times with chloroform and the combined extracts were dried (Na$_2$SO$_4$), filtered, and concentrated under reduced pressure. The residue was purified by Method 2 to afford 2.12 g (38%) of the title compound. $^1$H NMR (400 MHz, CD$_3$OD): 7.36 (dd, J=8.6, 1.8 Hz, 1H), 6.91-6.90 (m, 1H), 6.67-6.62 (m, 1H), 3.53 (d, J=1.3 Hz, 1H), 2.30 (m, 6H).

B. {2-Bromo-5-[3-(1-methyl-piperidin-4-yl)-propoxy]-benzyl}-dimethyl-amine. To a solution of 3-(1-methyl-piperidin-4-yl)-propan-1-ol (989 mg, 6.3 mmol, 1.0 equiv) and methanesulfonyl chloride (683 µL, 8.8 mmol, 1.4 equiv) in dichloromethane (12 mL) at 0° C. was added triethylamine (1.57 mL, 11.3 mmol, 1.8 equiv). The reaction mixture, which was allowed to warm to rt, was stirred for 12 h and then poured into satd. aq. NaHCO$_3$. The aqueous mixture was extracted three times with 10% 2-propanol in chloroform and the extract was dried (Na$_2$SO$_4$), filtered, and concentrated under reduced pressure. The residue was dissolved in acetonitrile (21 mL) and 4-bromo-3-dimethylaminomethyl-phenol (1.44 g, 6.3 mmol, 1.0 equiv) and cesium carbonate (4.1 g, 12.6 mmol, 2.0 equiv) were added. The mixture was stirred at rt for 12 h, then warmed to 40° C. for 2.0 h, then 50° C. for 1.0 h, and finally 65° C. for 1.5 h. The mixture was poured into satd. aq. NaHCO$_3$ and extracted two times with ethyl acetate and one time with chloroform. The combined extracts were dried (Na$_2$SO$_4$), filtered, and concentrated under reduced pressure. Purification by Method 2 afforded 814 mg (40%) of the title compound. $^1$H NMR (400 MHz, CD$_3$OD): 7.45 (d, J=8.8 Hz, 1H), 7.05 (d, J=3.1 Hz, 1H), 6.78 (dd, J=8.8, 3.1 Hz, 1H), 3.98 (t, J=6.4 Hz, 2H), 3.58 (s, 2H), 2.93-2.86 (m, 2H), 2.31 (s, 6H), 2.29 (s, 3H), 2.10-1.98 (m, 2H), 1.86-1.73 (m, 4H), 1.49-1.22 (m, 5H).

C. {2-(6-Chloro-4-methyl-1H-benzoimidazol-2-yl)-5-[3-(1-methyl-piperidin-4-yl)-propoxy]-benzyl}-dimethyl-amine. To a solution of {2-bromo-5-[3-(1-methyl-piperidin-4-yl)-propoxy]-benzyl}-dimethyl-amine (801 mg, 2.2 mmol, 1.0 equiv) in THF (10 mL) at −78° C., 1.7 M tert-butyllithium in pentane (3.83 mL, 6.5 mmol, 3.0 equiv) was added and the solution was stirred for 15 min. The solution was then warmed to 0° C., stirred for 5 min, and then re-cooled to −78° C. DMF (1.68 mL, 21.7 mmol, 10.0 equiv) was added and the mixture was stirred for 30 min. Water (1.0 mL) was added and the mixture was poured into satd. aq. NaHCO$_3$. The aqueous mixture was extracted three times with ethyl acetate and the combined extracts were dried (Na$_2$SO$_4$), filtered, and concentrated under reduced pressure. The residue was partially purified by Method 2 to afford 221 mg of a mixture of 2-dimethylaminomethyl-4-[3-(1-methyl-piperidin-4-yl)-propoxy]-benzaldehyde and several other unidentified products. The crude dimethylaminomethyl-4-[3-(methyl-piperidin-4-yl)-propoxy]-benzaldehyde (110 mg) was dissolved in DMF and 5-chloro-3-methyl-benzene-1,2-diamine (54 mg, 0.34 mmol) and Na$_2$S$_2$O$_5$ (85 mg, 0.45 mmol) were added. The mixture was warmed to 90° C. and stirred for 3 h. The reaction mixture was purified by Method 2 to afford 15.2 mg of the title compound. MS (electrospray): mass calculated for C$_{26}$H$_{35}$ClN$_4$O, 454.25; m/z found, 455.5 [M+H]$^+$. $^1$H NMR (400 MHz, CD$_3$OD): 8.07 (d, J=8.6 Hz, 1H), 7.47-7.42 (m, 1H), 7.07-6.97 (m, 3H), 4.04 (t, J=6.4 Hz, 2H), 3.58 (s, 2H), 2.93-2.82 (m, 2H), 2.56 (s, 3H), 2.43 (s, 6H), 2.27 (s, 3H), 2.06-1.93 (m, 2H), 1.87-1.70 (m, 4H), 1.49-1.40 (m, 2H), 1.36-1.21 (m, 3H).

Example 83

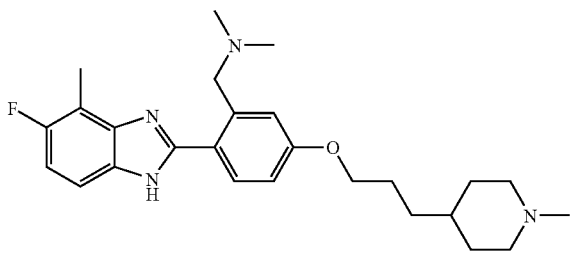

{2-(5-Fluoro-4-methyl-1H-benzoimidazol-2-yl)-5-[3-(1-methyl-piperidin-4-yl)-propoxy]-benzyl}-dimethyl-amine The title compound was prepared as described in Example 77. MS (electrospray): mass calculated for C$_{26}$H$_{35}$FN$_4$O, 438.28; m/z found, 439.5 [M+H]$^+$. $^1$H NMR (400 MHz, CD$_3$OD): 8.06 (d, J=8.6 Hz, 1H), 7.43-7.40 (m, 1H), 7.06 (dd, J=8.6, 2.6 Hz, 1H), 7.03-6.95 (m, 2H), 4.06 (t, J=6.4 Hz, 2H), 3.59 (s, 2H), 2.89-2.86 (m, 2H), 2.49 (s, 3H), 2.44 (s, 6H), 2.27 (s, 3H), 2.07-1.96 (m, 2H), 1.89-1.72 (m, 4H), 1.51-1.41 (m, 2H), 1.39-1.22 (m, 3H).

Example 84

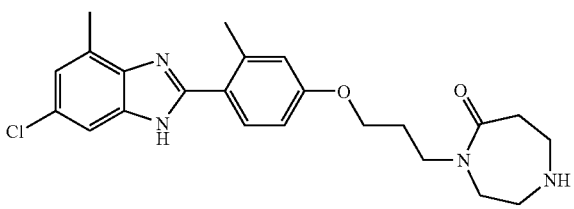

4-{3-[4-(6-Chloro-4-methyl-1H-benzoimidazol-2-yl)-3-methyl-phenoxy]-propyl}-[1,4]diazepan-5-one A. 4-(3-Iodo-propoxy)-2-methyl-benzaldehyde. 1-Bromo-3-chloropropane (5.03 g, 32.0 mmol, 1.0 equiv) was added to a solution of 2-methyl-4-hydroxybenzaldehyde (4.35 g, 32.0 mmol, 1.0 equiv) and K$_2$CO$_3$ (8.8 g, 64.0 mmol, 2.0 equiv) in acetonitrile (75 mL). The mixture was heated at 65° C. for 16 h, then cooled to rt and filtered through diatomaceous earth. The filtrate was concentrated and the residue was purified by column chromatography (silica gel, 10% ethyl acetate in hexanes) to afford 5.58 g (82%) of 4-(3-chloro-propoxy)-2-methyl-benzaldehyde. To a refluxing solution of 4-(3-chloro-propoxy)-2-methyl-benzaldehyde in acetone (100 mL), KI (58 g) was added portion wise over 3 d. The mixture was cooled to rt and water was added. The aqueous mixture was extracted three times with ethyl acetate and the combined extracts were dried (Na$_2$SO$_4$), filtered, and concentrated. The residue was purified by column chromatography (silica gel, 5% ethyl acetate in hexanes) to afford 6.13 g (77%) of the title compound. $^1$H NMR (400 MHz, CD$_3$OD): 10.1 (s, 1H), 7.75 (d, J=8.6 Hz, 1H), 6.84 (dd, J=8.6, 2.5 Hz, 1H), 6.74 (d, J=2.2 Hz, 1H), 4.11 (t, J=5.8 Hz, 2H), 3.36 (t, J=6.7 Hz, 2H), 2.65 (s, 3H), 2.29 (m, 2H).

B. 4-{3-[4-(6-Chloro-4-methyl-1H-benzoimidazol-2-yl)-3-methyl-phenoxy]-propyl}-[1,4]diazepan-5-one. To a stirred solution of 5-oxo-[1,4]diazepane-1-carboxylic acid tert-butyl ester (3.0 g, 14.0 mmol, 1.0 equiv) in DMF (45 mL) at rt was added 60% sodium hydride (560 mg, 14.0 mmol, 1.0 equiv). After stirring for 30 min, 4-(3-iodo-propoxy)-2-methyl-benzaldehyde (4.26 g, 14.0 mmol, 1.0 equiv) was added as a solution in DMF (5 mL). The mixture was stirred for 16 h and then poured into water and extracted with ethyl acetate. The combined extracts were dried (Na$_2$SO$_4$), filtered, and concentrated. The residue was partially purified by column chromatography (silica gel, 5-50% ethyl acetate in hexanes) to afford 4-[3-(4-formyl-3-methyl-phenoxy)-propyl]-5-oxo-[1,4]diazepane-1-carboxylic acid tert-butyl ester as a mixture with several unidentified products. This impure mixture (200 mg), 5-chloro-3-methyl-benzene-1,2-diamine (80.1 mg), and Na$_2$S$_2$O$_5$ (97 mg) were stirred in DMF (1.0 mL) at 90° C. for 3 h. After cooling to rt, the reaction mixture was loaded on silica gel and was purified by Method 2 to afford 4-{3-[4-(6-chloro-4-methyl-1H-benzoimidazol-2-yl)-3-methyl-phenoxy]-propyl}-5-oxo-[1,4]diazepane-1-carboxylic acid tert-butyl ester as a mixture with several unidentified products. This mixture was dissolved in dichloromethane (1.0 mL) and TFA (1.0 mL) and stirred at rt for 1 h. The reaction mixture was loaded on silica gel and purified by Method 2 to afford 91.0 mg (42%) of the title compound. MS (electrospray): mass calculated for C$_{23}$H$_{27}$ClN$_4$O$_2$, 426.18; m/z found, 427.4 [M+H]$^+$. $^1$H NMR (400 MHz, CD$_3$OD): 7.55 (d, J=8.5 Hz, 1H), 7.42 (br s, 1H), 7.09-7.06 (m, 1H), 6.97 (d, J=2.4 Hz, 1H), 6.93 (dd, J=8.5, 2.5 Hz, 1H), 4.10 (t, J=6.1 Hz, 2H), 3.67-3.56 (m, 4H), 2.98-2.89 (m, 4H), 2.72-2.66 (m, 2H), 2.59 (s, 3H), 2.50 (s, 3H), 2.12-2.01 (m, 2H).

Example 85

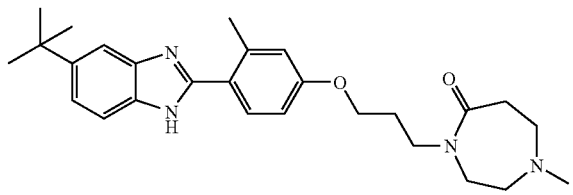

4-{3-[4-(5-tert-Butyl-1H-benzoimidazol-2-yl)-3-methyl-phenoxy]-propyl}-1-methyl-[1,4]diazepan-5-one 4-{3-[4-(6-Chloro-4-methyl-1H-benzoimidazol-2-yl)-3-methyl-phenoxy]-propyl}-[1,4]diazepan-5-one (95 mg, 0.22 mmol, 1.0 equiv) and 37% aq. formaldehyde (35 μL, 0.44 mmol, 2.0 equiv) were stirred in dichloroethane at rt for 1.0 h. Sodium triacetoxyborohydride (139 mg, 0.66 mmol, 3.0 equiv) was added, and the mixture was stirred for 1.0 h then poured into satd. aq. NaHCO$_3$. The aqueous mixture was extracted three times with ethyl acetate and the combined extracts were dried (Na$_2$SO$_4$), filtered, and concentrated. The residue was purified by Method 2 to afford 34 mg (35%) of the title compound. MS (electrospray): mass calculated for C$_{27}$H$_{36}$N$_4$O$_2$, 448.28; m/z found, 449.4 [M+H]$^+$. $^1$H NMR (400 MHz, CD$_3$OD): 7.62 (br s, 1H), 7.56 (d, J=8.4 Hz, 1H), 7.53 (d, J=8.5 Hz, 1H), 7.38 (dd, J=8.6, 1.7 Hz, 1H), 6.95 (d, J=2.3 Hz, 1H), 6.92 (dd, J=8.5, 2.5 Hz, 1H), 4.09 (t, J=6.0 Hz, 2H), 3.65-3.59 (m, 4H), 2.73-2.59 (m, 6H), 2.52 (s, 3H), 2.38 (s, 3H), 2.11-2.02 (m, 2H). 1.43 (s, 9H).

Example 86

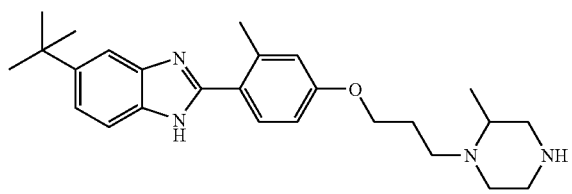

5-tert-Butyl-2-{2-methyl-4-[3-(2-methyl-piperazin-1-yl)-propoxy]-phenyl}-1H-benzoimidazole The title compound was prepared as described in Example 84, substituting 3-methyl-piperazine-1-carboxylic acid tert-butyl ester for 5-oxo-[1,4]diazepane-1-carboxylic acid tert-butyl ester. MS (electrospray): mass calculated for C$_{26}$H$_{36}$N$_4$O, 420.29; m/z found, 421.5 [M+H]$^+$. $^1$H NMR (400 MHz, CD$_3$OD): 7.66-7.49 (m, 3H), 7.38 (dd, J=8.6, 1.8 Hz, 1H), 6.95 (d, J=2.2 Hz, 1H), 6.91 (dd, J=8.4, 2.5 Hz, 1H), 4.12 (t, J=6.2 Hz, 2H), 3.10-2.82 (m, 5H), 2.60-2.32 (m, 7H), 2.09-1.89 (m, 2H), 1.43 (s, 9H), 1.10 (d, J=6.0 Hz, 3H).

Example 87

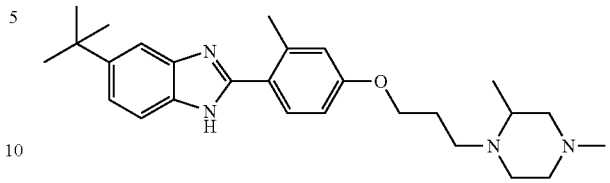

5-tert-Butyl-2-{2-methyl-4-[3-(2-methyl-piperazin-1-yl)-propoxy]-phenyl}-1H-benzoimidazole The title compound was prepared from 5-tert-butyl-2-{2-methyl-4-[3-(2-methyl-piperazin-1-yl)-propoxy]-phenyl}-1H-benzoimidazole according to the method described in Example 85. MS (electrospray): mass calculated for C$_{27}$H$_{38}$N$_4$O, 434.30; m/z found, 435.5 [M+H]$^+$. $^1$H NMR (400 MHz, CD$_3$OD): 7.69-7.47 (m, 3H), 7.38 (dd, J=8.6, 1.9 Hz, 1H), 6.95 (d, J=2.3 Hz, 1H), 6.91 (dd, J=8.5, 2.4 Hz, 1H), 4.11 (t, J=6.2 Hz, 2H), 3.10-2.94 (m, 2H), 2.84-2.70 (m, 2H), 2.56-2.39 (m, 6H), 2.31-2.19 (m, 4H), 2.09-1.88 (m, 3H), 1.43 (s, 9H), 1.12 (d, J=6.3 Hz, 3H).

Example 88

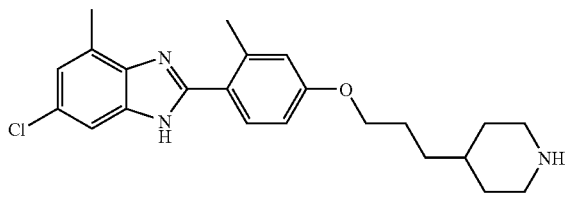

6-Chloro-4-methyl-2-[2-methyl-4-(3-piperidin-4-yl-propoxy)-phenyl]-1H-benzoimidazole To a solution of (3-hydroxy-propyl)-piperidine-1-carboxylic acid tert-butyl ester (4.00 g, 16.4 mmol, 1.0 equiv) and triethylamine (3.40 mL, 24.6 mmol, 1.5 equiv) in dichloromethane at 0° C. was added methanesulfonyl chloride (1.53 mL, 19.7 mmol, 1.2 equiv). The solution was warmed to rt and stirred for 1.0 h then poured into satd. aq. NaHCO$_3$. The aqueous mixture was extracted three times with chloroform and the combined extracts were dried (Na$_2$SO$_4$), filtered, and concentrated. The residue was subjected to column chromatography (silica gel, 10% methanol in dichloromethane). The partially purified 4-(3-methanesulfonyloxy-propyl)-piperidine-1-carboxylic acid tert-butyl ester (500 mg, 1.56 mmol, 1.0 equiv) was stirred with 4-hydroxy-2-methyl-benzaldehyde (212 mg, 1.56 mmol, 1.0 equiv) and cesium carbonate (1.01 g, 3.12 mmol, 2.0 equiv) in acetonitrile at rt for 4 d. The mixture was filtered through diatomaceous earth and the filtrate was concentrated. The crude material was partially purified by column chromatography (silica gel, 25% ethyl acetate in hexanes). 4-[3-(4-Formyl-3-methyl-phenoxy)-propyl]-piperidine-1-carboxylic acid tert-butyl ester (146 mg, 0.41 mmol, 1.0 equiv), 5-chloro-3-methyl-benzene-1,2-diamine (63 mg, 0.41 mmol, 1.0 equiv), and Na$_2$S$_2$O$_5$ (100 mg, 0.53 mmol, 1.3 equiv) were stirred at 90° C. in DMF for 2.5 h. The mixture was cooled to rt and water (75 mL) was added causing a light brown precipitate to form. The solid 4-{3-[4-(6-chloro-4-methyl-1H-benzoimidazol-2-yl)-3-methyl-phenoxy]-propyl}-piperidine-1-carboxylic acid tert-butyl ester was collected by filtration, dissolved in a solution of dichloromethane (2.0 mL) and trifluroacetic acid (1.0 mL), and stirred at rt for 1.5 h. The reaction mixture was loaded directly on silica gel and purified according to Method 2, which afforded 52.1 mg of the title compound. MS (electrospray): mass calculated for $C_{23}H_{28}ClN_3O$, 397.19; m/z found, 398.3 [M+H]$^+$. $^1$H NMR (400 MHz, $CD_3OD$): 7.55 (d, J=8.4 Hz, 1H), 7.42 (br s, 1H), 7.10-7.07 (m, 1H), 6.96-6.95 (m, 1H), 6.91 (dd, J=8.5, 2.4 Hz, 1H), 4.09 (t, J=6.2 Hz, 2H), 3.45-3.39 (m, 2H), 3.06-2.96 (m, 2H), 2.59 (s, 3H), 2.50 (s, 3H), 2.07-1.99 (m, 2H), 1.93-1.84 (m, 2H), 1.76-1.64 (m, 1H), 1.59-1.50 (m, 2H), 1.48-1.36 (m, 2H).

Example 89

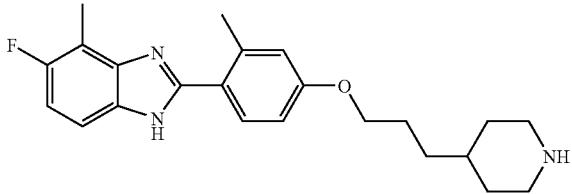

5-Fluoro-4-methyl-2-[2-methyl-4-(3-piperidin-4-yl-propoxy)-phenyl]-1H-benzoimidazole The title compound was prepared as described in Example 88. MS (electrospray): mass calculated for $C_{23}H_{28}FN_3O$, 381.22; m/z found, 382.4 [M+H]$^+$. $^1$H NMR (400 MHz, $CD_3OD$): 7.56 (d, J=8.5 Hz, 1H), 7.44-7.38 (m, 1H), 7.09-7.02 (m, 1H), 6.96 (d, J=2.3 Hz, 1H), 6.91 (dd, J=8.4, 2.5 Hz, 1H), 4.09 (t, J=6.2 Hz, 2H), 3.44-3.36 (m, 2H), 3.06-2.95 (m, 2H), 2.52 (d, J=1.6 Hz, 3H), 2.50 (s, 3H), 2.08-1.98 (m, 2H), 1.94-1.83 (m, 2H), 1.77-1.65 (m, 1H), 1.59-1.50 (m, 2H), 1.48-1.35 (m, 2H).

Example 90

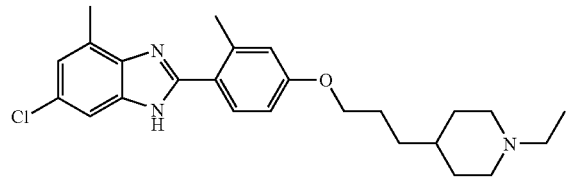

6-Chloro-2-{4-[3-(1-ethyl-piperidin-4-yl)-propoxy]-2-methyl-phenyl}-4-methyl-1H-benzoimidazole.

The title compound was prepared as described in Example 85, substituting acetaldehyde for aq. formaldehyde. MS (electrospray): mass calculated for $C_{25}H_{32}ClN_3O$, 425.22; m/z found, 426.4 [M+H]$^+$. $^1$H NMR (400 MHz, $CD_3OD$): 7.53 (d, J=8.5 Hz, 1H), 7.41 (br s, 1H), 7.09-7.04 (m, 1H), 6.93 (d, J=2.2 Hz, 1H), 6.89 (dd, J=8.4, 2.4 Hz, 1H), 4.04 (t, J=6.3 Hz, 2H), 3.05-2.94 (m, 2H), 2.59 (s, 3H), 2.49 (s, 3H), 2.45 (q, J=7.2 Hz, 2H), 2.05-1.94 (m, 2H), 1.89-1.74 (m, 4H), 1.50-1.21 (m, 5H), 1.13 (t, J=7.2 Hz, 3H).

Example 91

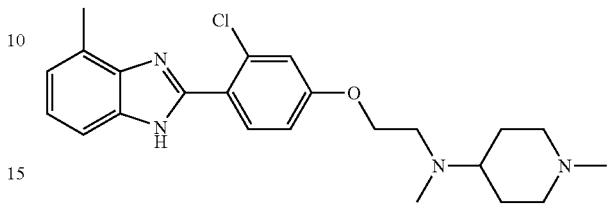

{2-[3-Chloro-4-(4-methyl-1H-benzoimidazol-2-yl)-phenoxy]-ethyl}-methyl-(1-methyl-piperidin-4-yl)-amine A. 4-(2-Bromo-ethoxy)-2-chloro-benzaldehyde. 1,2-Dibromoethane (5.5 mL, 64.0 mmol, 5.0 equiv) was added to a mixture of 2-chloro-4-hydroxy-benzaldehyde (2.0 g, 12.8 mmol, 1.0 equiv) and $K_2CO_3$ (4.0 g, 29.0 mmol, 2.25 equiv) in acetonitrile (13 mL). The mixture was heated at reflux for 16 h, cooled to rt, and filtered through diatomaceous earth. The filtrate was concentrated to yield crude product, which was purified by column chromatography (silica gel, 5% ethyl acetate in hexanes) to afford 2.28 g (72%) of the title compound. $^1$H NMR (400 MHz, $CD_3OD$): 10.3 (d, J=0.7 Hz, 1H), 7.90 (d, J=8.8 Hz, 1H), 7.13 (d, J=2.4 Hz, 1H), 7.06 (ddd, J=8.8, 2.5, 0.7 Hz, 1H), 4.48-4.42 (m, 2H), 3.78-3.74 (m, 2H).

B. 2-Chloro-4-{2-[methyl-(1-methyl-piperidin-4-yl)-amino]-ethoxy}-benzaldehyde. To a solution of 4-(2-bromo-ethoxy)-2-chloro-benzaldehyde (1.24 g, 5.0 mmol, 1.0 equiv) and methyl-(1-methyl-piperidin-4-yl)-amine (1.28 g, 10.0 mmol, 2.0 equiv) in 1-butanol was added $K_2CO_3$ (2.10 g, 15 mmol, 3.0 equiv) and the solution was warmed to 90° C. After stirring for 16 h, the mixture was poured into water and extracted two times with ethyl acetate. The combined extracts were dried ($Na_2SO_4$), filtered, and concentrated. The residue was purified by Method 2 to afford 467 mg (30%) of the title compound. $^1$H NMR (400 MHz, $CD_3OD$): 10.3 (s, 1H), 7.89 (d, J=8.8 Hz, 1H), 7.13 (d, J=2.4 Hz, 1H), 7.05 (dd, J=8.8, 2.4 Hz, 1H), 4.21 (t, J=5.5 Hz, 2H), 3.00-2.88 (m, 4H), 2.57-2.47 (m, 1H), 2.41 (s, 3H), 2.29 (s, 3H), 2.11-2.01 (m, 2H), 1.91-1.82 (m, 2H), 1.68-1.58 (m, 2H).

C. {2-[3-Chloro-4-(4-methyl-1H-benzoimidazol-2-yl)-phenoxy]-ethyl}-methyl-(1-methyl-piperidin-4-yl)-amine. This compound was prepared by the method described in General Procedure 3 using 2-chloro-4-{2-[methyl-(1-methyl-piperidin-4-yl)-amino]-ethoxy}-benzaldehyde (62.2 mg, 0.20 mmol, 1.0 equiv), 3-methyl-benzene-1,2-diamine (26 mg, 0.20 mmol, 1.0 equiv), and $Na_2S_2O_5$ (50 mg, 0.26 mmol, 1.3 equiv). Purification by Method 2 afforded 29 mg (35%) of the title compound. MS (electrospray): mass calculated for $C_{23}H_{29}ClN_4O$, 412.20; m/z found, 413.4 [M+H]$^+$. $^1$H NMR (400 MHz, $CD_3OD$): 7.73 (d, J=8.6 Hz, 1H), 7.49-7.40 (m, 1H), 7.22-7.14 (m, 2H), 7.11-7.04 (m, 2H), 4.18 (t, J=5.5 Hz, 2H), 3.00-2.92 (m, 4H), 2.62 (s, 3H), 2.56-2.48 (m, 1H), 2.41 (s, 3H), 2.28 (s, 3H), 2.11-1.99 (m, 2H), 1.92-1.81 (m, 2H), 1.70-1.55 (m, 2H).

Example 92

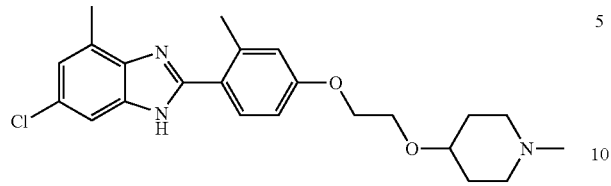

6-Chloro-4-methyl-2-{2-methyl-4-[2-(1-methyl-piperidin-4-yloxy)-ethoxy]-phenyl}-1H-benzoimidazole A. 4-[2-(4-Formyl-3-methyl-phenoxy)-ethoxy]-1-methyl-piperidinium toluene-4-sulfonate. To a solution of 1,4-dioxa-8-aza-spiro[4.5]decane (1.0 g, 7.0 mmol, 1.0 equiv) in toluene (20 mL) at 0° C. was added 1.0 M diisobutylaluminum hydride in hexane (20 mL, 20 mmol, 2.9 equiv). The solution was warmed to 80° C. and stirred for 12 h. Methanol (20 mL), satd. aq. sodium potassiuim tartrate (20 mL), and 10% 2-propanol in chloroform (100 mL) were added and the mixture was stirred for 30 min. The chloroform layer was separated and the aqueous mixture was extracted five times with 10% 2-propanol in chloroform (25 mL). The combined extracts were dried ($Na_2SO_4$), filtered, and concentrated to provide crude 2-(piperidin-4-yloxy)-ethanol as a white solid. The solid was dissolved in dichloroethane (20 mL) and 37% aq. formaldehyde (0.60 mL, 6.9 mmol) was added. After stirring for 30 min, sodium triacetoxyborohydride (2.04 g, 9.6 mmol) was added and the mixture was stirred for 1.5 h. The reaction mixture was diluted with satd. aq. $NaHCO_3$ (20 mL) and extracted six times with 10% 2-propanol in chloroform (80 mL). The combined extracts were dried ($Na_2SO_4$), filtered, and concentrated to give 2-(1-methyl-piperidin-4-yloxy)-ethanol. The residue was dissolved in dichloromethane, cooled to 0° C., and pyridine (463 μL, 5.7 mmol) and p-toluenesulfonyl chloride (1.1 g, 5.7 mmol) were added. The solution was warmed to rt and stirred for 16 h. The reaction mixture was concentrated under reduced pressure and the residue was partially purified by Method 2. The resulting material, toluene-4-sulfonic acid 2-(1-methyl-piperidin-4-yloxy)-ethyl ester, was added to a mixture of 4-hydroxy-2-methyl-benzaldehyde (275 mg, 2.0 mmol) and $K_2CO_3$ (699 mg, 5.1 mmol) in DMF. The mixture was heated to 100° C. and stirred for 16 h. After cooling to rt, the mixture was poured into water and extracted three times with ethyl acetate. The combined extracts were dried ($Na_2SO_4$), filtered, and concentrated. The crude product was purified by Method 2 to afford 409 mg of the title compound. $^1$H NMR (400 MHz, $CD_3OD$): 10.10 (s, 1H), 7.80 (d, J=8.6 Hz, 1H), 7.72 (d, J=8.2 Hz, 2H), 7.26 (d, J=7.9 Hz, 2H), 6.96 (dd, J=8.6, 2.4 Hz, 1H), 6.88 (d, J=2.1 Hz, 1H), 4.27-4.22 (m, 2H), 3.90-3.85 (m, 2H), 3.75-3.65 (m, 1H), 3.19-3.07 (m, 2H), 3.03-2.86 (m, 2H), 2.67 (s, 3H), 2.65 (s, 3H), 2.39 (s, 3H), 2.07-1.83 (m, 4H).

B. 6-Chloro-4-methyl-2-{2-methyl-4-[2-(1-methyl-piperidin-4-yloxy)-ethoxy]-phenyl}-1H-benzoimidazole. This compound was prepared by the method described in General Procedure 3 using 4-[2-(4-formyl-3-methyl-phenoxy)-ethoxy]-1-methyl-piperidinium toluene-4-sulfonate (47.5 mg, 0.11 mmol, 1.0 equiv), 5-chloro-3-methyl-benzene-1,2-diamine (27 mg, 0.17 mmol, 1.6 equiv), and $Na_2S_2O_5$ (42 mg, 0.22 mmol, 2.1 equiv). Purification by Method 2 afforded 20 mg (46%) of the title compound. MS (electrospray): mass calculated for $C_{23}H_{28}ClN_3O_2$, 413.19; m/z found, 414.3 [M+H]$^+$. $^1$H NMR (400 MHz, $CD_3OD$): 7.55 (d, J=8.5 Hz, 1H), 7.42 (br s, 1H), 7.08-7.05 (m, 1H), 6.98 (d, J=2.3 Hz, 1H), 6.93 (dd, J=8.5, 2.5 Hz, 1H), 4.21-4.17 (m, 2H), 3.88-3.83 (m, 2H), 3.57-3.47 (m, 1H), 2.81-2.67 (m, 2H), 2.59 (s, 3H), 2.50 (s, 3H), 2.33-2.20 (m, 5H), 2.02-1.90 (m, 2H), 1.76-1.60 (m, 2H).

Example 93

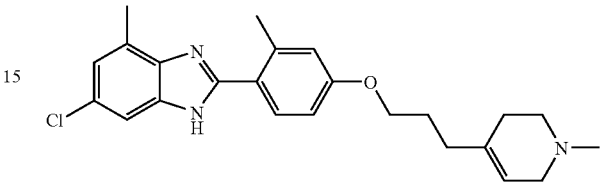

6-Chloro-4-methyl-2-{2-methyl-4-[3-(1-methyl-1,2,3,6-tetrahydro-pyridin-4-yl)-propoxy]-phenyl}-1H-benzoimidazole A. 3-(1-Methyl-1,2,3,6-tetrahydro-pyridin-4-yl)-propan-1-ol. To a solution of 4-(3-hydroxy-propyl)-1-methyl-pyridinium iodide (28 g, 100.4 mmol, 1.0 equiv) in ethanol (200 mL) at 0° C. was added sodium borohydride (5.7 g, 151 mmol, 1.5 equiv). The reaction mixture, which was allowed to warm to rt, was stirred for 30 min and then poured into water. The aqueous solution was extracted with ethyl acetate and the extract was dried ($Na_2SO_4$), filtered, and concentrated to afford 15.2 g (97%) of the title compound. $^1$H NMR (400 MHz, $CD_3OD$): 5.46-5.41 (m, 1H), 3.56 (t, J=6.6 Hz, 2H), 2.98-2.91 (m, 2H), 2.60 (t, J=5.9 Hz, 2H), 2.35 (s, 3H), 2.21-2.14 (m, 2H), 2.12-2.04 (m, 2H), 1.71-1.62 (m, 2H).

B. 2-Methyl-4-[3-(1-methyl-1,2,3,6-tetrahydro-pyridin-4-yl)-propoxy]-benzaldehyde. To a solution of 3-(1-methyl-1,2,3,6-tetrahydro-pyridin-4-yl)-propan-1-ol (2.24 g, 14.5 mmol, 1.0 equiv) and pyridine (1.64 mL, 20.2 mmol, 1.4 equiv) in dichloromethane (50 mL) at 0° C. was added p-toluenesulfonyl chloride (3.85 g, 20.2 mmol, 1.4 equiv). The reaction mixture, which was allowed to warm to rt, was stirred for 12 h and then poured into water. The aqueous mixture was extracted with dichloromethane and the extract was dried ($Na_2SO_4$), filtered, and concentrated. The residue was subjected to column chromatography on silica gel (10% methanol in dichloromethane) and the resulting oil was added to a mixture of 4-hydroxy-2-methyl-benzaldehyde (639 mg, 4.69 mmol) and $K_2CO_3$ (1.62 g, 11.7 mmol) in DMF and warmed to 100° C. After stirring for 16 h, the mixture was allowed to cool to rt and filtered through a pad of diatomaceous earth. The diatomaceous earth was rinsed with ethyl acetate, and the filtrate was concentrated. The residue was purified by Method 2 to afford 356 mg (9%) of the title compound. $^1$H NMR (400 MHz, $CD_3OD$): 10.1 (s, 1H), 7.78 (d, J=8.6 Hz, 1H), 6.92 (dd, J=8.6, 2.4 Hz, 1H), 6.84 (d, J=2.1 Hz, 1H), 5.49-5.43 (m, 1H), 4.09 (t, J=6.3 Hz, 2H), 2.97-2.91 (m, 2H), 2.65-2.57 (m, 5H), 2.35 (s, 3H), 2.25-2.16 (m, 4H), 1.99-1.88 (m, 2H).

C. 6-Chloro-4-methyl-2-{2-methyl-4-[3-(1-methyl-1,2,3,6-tetrahydro-pyridin-4-yl)-propoxy]-phenyl}-1H-benzoimidazole. This compound was prepared by the method described in General Procedure 3 using 2-methyl-4-[3-(1-methyl-1,2,3,6-tetrahydro-pyridin-4-yl)-propoxy]-benzaldehyde (50 mg, 0.18 mmol, 1.0 equiv), 5-chloro-3-methyl-benzene-1,2-diamine (29 mg, 0.18 mmol, 1.0 equiv), and Na₂S₂O₅ (45.2 mg, 0.24 mmol, 1.3 equiv). Purification by Method 2 afforded 15.7 mg (21%) of the title compound. MS (electrospray): mass calculated for $C_{24}H_{28}ClN_3O$, 409.19; m/z found, 410.4 [M+H]⁺. ¹H NMR (400 MHz, CD₃OD): 7.53 (d, J=8.5 Hz, 1H), 7.41 (br s, 1H), 7.08-7.04 (m, 1H), 6.93 (d, J=2.3 Hz, 1H), 6.89 (dd, J=8.5, 2.5 Hz, 1H), 5.49-5.44 (m, 1H), 4.04 (t, J=6.3 Hz, 2H), 2.96-2.91 (m, 2H), 2.64-2.56 (m, 5H), 2.49 (s, 3H), 2.35 (s, 3H), 2.28-2.16 (m, 4H), 1.96-1.88 (m, 2H).

Example 94

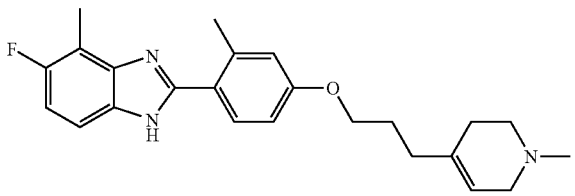

5-Fluoro-4-methyl-2-{2-methyl-4-[3-(1-methyl-1,2,3,6-tetrahydro-pyridin-4-yl)-propoxy]-phenyl}-1H-benzoimidazole The title compound was prepared as described in Example 93. MS (electrospray): mass calculated for $C_{24}H_{28}FN_3O$, 393.22; m/z found, 394.4 [M+H]⁺. ¹H NMR (400 MHz, CD₃OD): 7.54 (d, J=8.5 Hz, 1H), 7.39 (br s, 1H), 7.05-6.95 (m, 1H), 6.94 (d, J=2.4 Hz, 1H), 6.90 (dd, J=8.5, 2.5 Hz, 1H), 5.50-5.46 (m, 1H), 4.06 (t, J=6.3 Hz, 2H), 2.99-2.94 (m, 2H), 2.65-2.59 (m, 2H), 2.53-2.47 (m, 6H), 2.36 (s, 3H), 2.27-2.18 (m, 4H), 1.98-1.90 (m, 2H).

Example 95

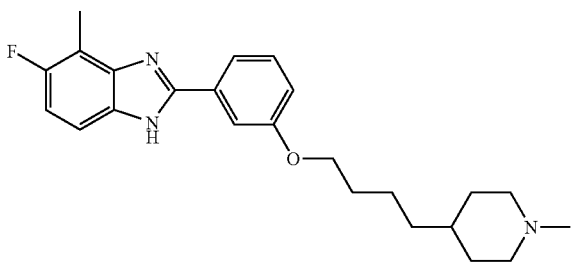

6-Fluoro-7-methyl-2-{3-[4-(1-methyl-piperidin-4-yl)-butoxy]-phenyl}-1H-benzoimidazole A. 3-[4-(1-Methyl-piperidin-4-yl)-butoxy]-benzonitrile. 4-(1-Methyl-piperidin-4-yl)-butan-1-ol (0.747 g, 4.37 mmol, 1.0 equiv), 3-hydroxy-benzonitrile (0.52 g, 4.37 mmol, 1.0 equiv), and polymer-supported triphenylphosphine (2.3 g, 8.73 mmol, 2.0 equiv) were suspended in THF (40 mL). The mixture was stirred under N₂ and cooled to 0° C. Diisopropyl azodicarboxylate (1.72 mL, 8.73 mmol, 2.0 equiv) was added dropwise via syringe. After 6 h, the mixture was filtered and concentrated. The resulting crude oil was purified by Method 2 to afford 0.84 g (71%) of the title compound. MS (electrospray): mass calculated for $C_{17}H_{24}N_2O$, 272.19; m/z found, 273.4 [M+H]⁺. ¹H NMR (400 MHz, CDCl₃): 7.38-7.33 (m, 1H), 7.24-7.20 (m, 1H), 7.14-7.09 (m, 2H), 3.96 (t, J=6.4 Hz, 2H), 2.88-2.80 (m, 2H), 2.26 (s, 3H), 1.94-1.84 (m, 2H), 1.82-1.73 (m, 2H), 1.72-1.64 (m, 2H), 1.52-1.42 (m, 2H), 1.34-1.17 (m, 5H).

B. 3-[4-(1-Methyl-piperidin-4-yl)-butoxy]-benzaldehyde. To a stirred solution of 3-[4-(1-methyl-piperidin-4-yl)-butoxy]-benzonitrile (0.84 g, 3.09 mmol, 1.0 equiv) in toluene (5.0 mL) at 0° C. was added 1.5 M diisobutylaluminum hydride in toluene (4.63 mL, 4.63 mmol, 1.5 equiv). After 3 h, methanol (9.0 mL) and 1.0 M H₂SO₄ (10 mL) were added dropwise. After stirring for 30 min, 1.0 M NaOH (10 mL) was added, followed by satd. aq. sodium potassium tartrate (40 mL) and dichloromethane (100 mL). The solution was extracted three times with chloroform (50 mL) and the combined extracts were washed with brine, dried (Na₂SO₄), filtered, and concentrated. The crude oil was purified by Method 2 to afford 0.56 g (66%) of the title compound. ¹H NMR (400 MHz, CDCl₃): 9.97 (s, 1H), 7.46-7.43 (m, 2H), 7.39-7.37 (m, 1H), 7.19-7.15 (m, 1H), 4.02 (t, J=6.6 Hz, 2H), 2.86-2.80 (m, 2H), 2.25 (s, 3H), 1.92-1.83 (m, 2H), 1.83-1.75 (m, 2H), 1.73-1.63 (m, 2H), 1.54-1.44 (m, 2H), 1.34-1.18 (m, 5H).

C. 6-Fluoro-7-methyl-2-{3-[4-(1-methyl-piperidin-4-yl)-butoxy]-phenyl}-1H-benzoimidazole. This compound was prepared by the method described in General Procedure 3 using 3-[4-(1-methyl-piperidin-4-yl)-butoxy]-benzaldehyde (20 mg, 0.07 mmol, 1.0 equiv), 4-fluoro-3-methyl-benzene-1,2-diamine (12 mg, 0.09 mmol, 1.0 equiv) and Na₂S₂O₅ (18 mg, 0.10 mmol, 1.3 equiv). Purification by Method 2 afforded 28.7 mg (54%) of the title compound. MS (electrospray): mass calculated for $C_{24}H_{30}FN_3O$, 395.24; m/z found, 396.4 [M+H]⁺. ¹H NMR (400 MHz, CD₃OD): 7.72-7.62 (m, 2H), 7.47-7.32 (m, 2H), 7.08-6.94 (m, 2H), 4.07 (t, J=6.3 Hz, 2H), 2.90-2.80 (m, 2H), 2.53 (s, 3H), 2.24 (s, 3H), 2.04-1.92 (m, 2H), 1.85-1.66 (m, 4H), 1.59-1.47 (m, 2H), 1.39-1.17 (m, 5H).

The following compounds in Examples 96-101 were prepared according to the procedures described in Example 95.

Example 96

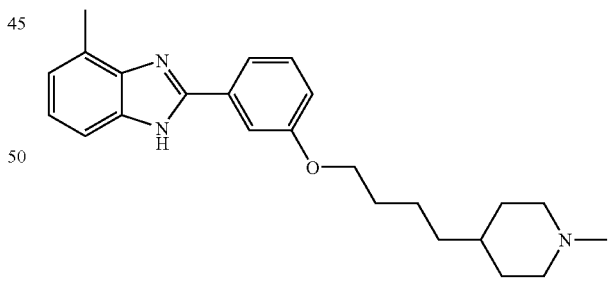

7-Methyl-2-{3-[4-(1-methyl-piperidin-4-yl)-butoxy]-phenyl}-1H-benzoimidazole

MS (electrospray): mass calculated for $C_{24}H_{31}N_3O$, 377.25; m/z found, 378.4 [M+H]⁺. ¹H NMR (400 MHz, CD₃OD): 7.86-7.71 (m, 2H), 7.44 (br s, 1H), 7.29-7.22 (m, 1H), 7.26-7.09 (m, 1H), 7.02 (d, J=7.3 Hz, 1H), 6.89 (dd, J=8.2, 1.8 Hz, 1H), 3.59 (t, J=6.4 Hz, 2H), 2.82 (m, 2H), 2.52 (br s, 3H), 2.25 (s, 3H), 1.89 (m, 2H), 1.63-1.47 (m, 4H), 1.28-1.07 (m, 7H).

Example 97

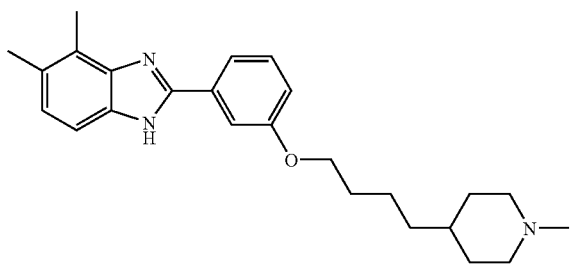

6,7-Dimethyl-2-{3-[4-(1-methyl-piperidin-4-yl)-butoxy]-phenyl}-1H-benzoimidazole MS (electrospray): mass calculated for $C_{25}H_{33}N_3O$, 391.56; m/z found, 392.5 [M+H]$^+$. $^1$H NMR (400 MHz, CD$_3$OD): 7.73-7.61 (m, 2H), 7.46-7.36 (m, 1H), 7.36-7.25 (m, 1H), 7.09-6.98 (m, 2H), 4.08 (t, J=6.3 Hz, 2H), 2.93-2.82 (m, 2H), 2.53 (s, 3H), 2.38 (s, 3H), 2.26 (s, 3H), 2.08-1.97 (m, 2H), 1.86-1.68 (m, 4H), 1.60-1.47 (m, 2H), 1.39-1.17 (m, 5H).

Example 98

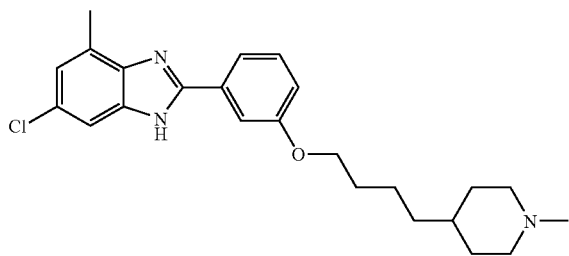

5-Chloro-7-methyl-2-{3-[4-(1-methyl-piperidin-4-yl)-butoxy]-phenyl}-1H-benzoimidazole MS (electrospray): mass calculated for $C_{24}H_{30}ClN_3O$, 411.21; m/z found, 412.4 [M+H]$^+$. $^1$H NMR (400 MHz, CD$_3$OD): 7.73-7.62 (m, 2H), 7.47-7.38 (m, 2H), 7.09-7.02 (m, 2H), 4.09 (t, J=6.3 Hz, 2H), 2.91-2.81 (m, 2H), 2.68 (s, 3H), 2.24 (s, 3H), 2.05-1.93 (m, 2H), 1.87-1.67 (m, 4H), 1.60-1.48 (m, 2H), 1.39-1.18 (m, 5H).

Example 99

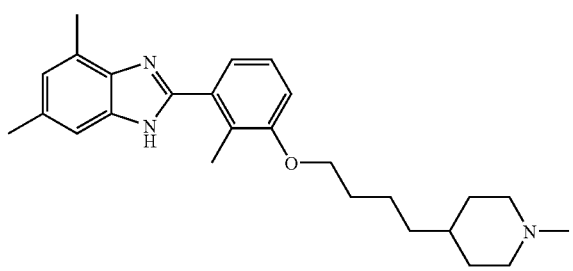

5,7-Dimethyl-2-{2-methyl-3-[4-(1-methyl-piperidin-4-yl)-butoxy]-phenyl}-1H-benzoimidazole MS (electrospray): mass calculated for $C_{26}H_{35}N_3O$, 405.28; m/z found, 406.4 [M+H]$^+$. $^1$H NMR (400 MHz, CD$_3$OD): 7.30-7.23 (m, 1H), 7.19 (s, 1H), 7.16-7.11 (m, 1H), 7.07-7.01 (m, 1H), 6.89 (s, 1H), 4.04 (t, J=6.4 Hz, 2H), 2.89-2.80 (m, 2H), 2.54 (s, 3H), 2.43 (s, 3H), 2.29 (s, 3H), 2.23 (s, 3H), 2.04-1.91 (m, 2H), 1.88-1.77 (m, 2H), 1.77-1.68 (m, 2H), 1.61-1.49 (m, 2H), 1.40-1.17 (m, 5H).

Example 100

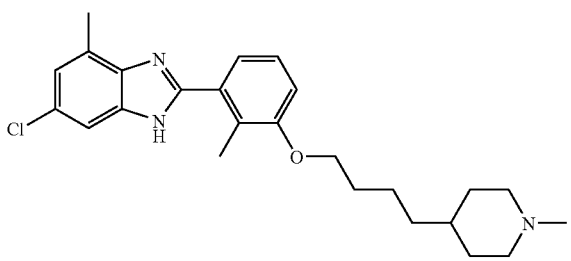

5-Chloro-7-methyl-2-{2-methyl-3-[4-(1-methyl-piperidin-4-yl)-butoxy]-phenyl}-1H-benzoimidazole MS (electrospray): mass calculated for $C_{25}H_{32}ClN_3O$, 425.22; m/z found, 426.4 [M+H]$^+$. $^1$H NMR (400 MHz, CD$_3$OD): 7.40 (s, 1H), 7.33-7.24 (m, 1H), 7.17-7.10 (m, 1H), 7.10-7.02 (m, 2H), 4.04 (t, J=5.6 Hz, 2H), 2.91-2.80 (m, 2H), 2.56 (s, 3H), 2.28 (s, 3H), 2.24 (s, 3H), 2.04-1.92 (m, 2H), 1.89-1.65 (m, 4H), 1.63-1.48 (m, 2H), 1.41-1.16 (m, 5H).

Example 101

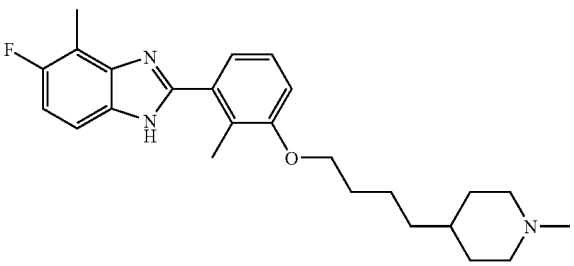

6-Fluoro-7-methyl-2-{2-methyl-3-[4-(1-methyl-piperidin-4-yl)-butoxy]-phenyl}-1H-benzoimidazole MS (electrospray): mass calculated for $C_{25}H_{32}FN_3O$, 409.25; m/z found, 410.4 [M+H]$^+$. $^1$H NMR (400 MHz, CD$_3$OD): 7.43-7.33 (s, 1H), 7.30 (t, J=7.8 Hz, 1H), 7.16-7.10 (s, 1H), 7.10-6.96 (m, 2H), 4.05 (t, J=5.4 Hz, 2H), 2.91-2.81 (m, 2H), 2.49 (s, 3H), 2.29 (s, 3H), 2.25 (s, 3H), 2.07-1.94 (m, 2H), 1.89-1.67 (m, 4H), 1.63-1.49 (m, 2H), 1.41-1.16 (m, 5H).

Example 102

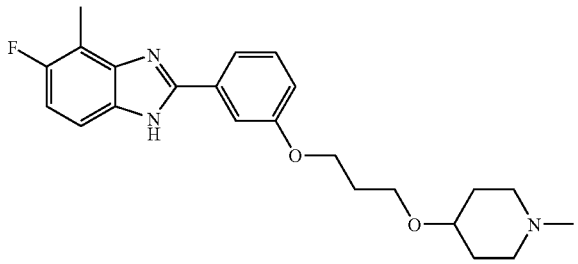

6-Fluoro-7-methyl-2-{3-[3-(1-methyl-piperidin-4-yloxy)-propoxy]-phenyl}-1H-benzoimidazole A. 3-[3-(1-Methyl-piperidin-4-yloxy)-propoxy]-benzonitrile. To a mixture of 3-(1-methyl-piperidin-4-yloxy)-propan-1-ol (295 mg, 1.7 mmol, 1.0 equiv) and polymer-supported triphenylphosphine (1.14 g, 3.41 mmol, 2.0 equiv) in THF (40 mL) at 0° C. was added diisopropyl azodicarboxylate (0.67 mL, 3.41 mmol, 2.0 equiv) dropwise via syringe. After 6 h, the mixture was filtered through a glass frit and the filtrate was concentrated. The crude oil was purified by Method 2 to afford 187 mg (40%) of the title compound. MS (electrospray): mass calculated for $C_{16}H_{22}N_2O_2$, 274.17; m/z found, 275.4 $[M+H]^+$. $^1$H NMR (400 MHz, $CDCl_3$): 7.40-7.33 (m, 1H), 7.25-7.21 (m, 1H), 7.17-7.10 (m, 2H), 4.09 (t, J=6.2 Hz, 2H), 3.61 (t, J=6.2 Hz, 2H), 3.34-3.25 (m, 1H), 2.73-2.61 (m, 2H), 2.26 (s, 3H), 2.17-2.00 (m, 4H), 1.94-1.84 (m, 2H), 1.68-1.55 (m, 2H).

B. 6-Fluoro-7-methyl-2-{3-[3-(1-methyl-piperidin-4-yloxy)-propoxy]-phenyl}-1H-benzoimidazole. To a stirred solution of 3-[3-(1-methyl-piperidin-4-yloxy)-propoxy]-benzonitrile (0187 g, 0.68 mmol, 1.0 equiv) in toluene (5.0 mL) at 0° C. was added 1.5 M diisobutylaluminum hydride in toluene (1.02 mL, 1.02 mmol, 1.5 equiv). After 3 h, methanol (9 mL) and 1 M $H_2SO_4$ (10 mL) were added. The mixture was stirred for 30 min, then 1.0 M NaOH (10 mL) was added, followed by satd. aq. sodium potassium tartrate (40 mL) and dichloromethane (100 mL). After stirring for 30 min, the mixture was extracted three times with chloroform (50 mL) and the combined extracts were washed with brine, dried ($Na_2SO_4$), filtered, and concentrated. The residue was partially purified by Method 2 to afford 106 mg of a mixture of 3-[3-(1-methyl-piperidin-4-yloxy)-propoxy]-benzaldehyde and several other unidentified products. A solution of the crude 3-[3-(1-methyl-piperidin-4-yloxy)-propoxy]-benzaldehyde (53 mg), 4-fluoro-3-methyl-benzene-1,2-diamine (27 mg), and $Na_2S_2O_5$ in DMF was stirred at 90° C. for 18 h. The reaction mixture was loaded directly on silica gel and purified according to Method 2, which afforded 28.7 mg of the title compound. MS (electrospray): mass calculated for $C_{23}H_{28}FN_3O_2$, 397.22; m/z found, 398.4 $[M+H]^+$. $^1$H NMR (400 MHz, $CD_3OD$): 7.64-7.53 (m, 2H), 7.38-7.25 (m, 2H), 7.00-6.85 (m, 2H), 4.06 (t, J=6.1 Hz, 2H), 3.60-3.52 (m, 2H), 3.33-3.19 (br s, 1H), 2.58 (br s, 2H), 2.42 (s, 3H), 2.17-2.03 (m, 5H), 2.01-1.90 (m, 2H), 1.86-1.72 (m, 2H), 1.60-1.42 (m, 2H).

Example 103

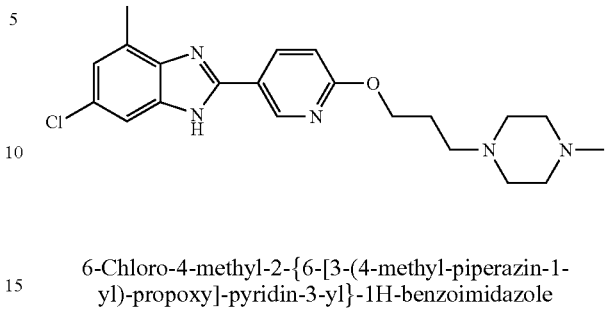

6-Chloro-4-methyl-2-{6-[3-(4-methyl-piperazin-1-yl)-propoxy]-pyridin-3-yl}-1H-benzoimidazole A. 6-[3-(4-Methyl-piperazin-1-yl)-propoxy]-nicotinonitrile. To a stirred solution of 3-(4-methyl-piperazin-1-yl)-propan-1-ol (1.0 g, 6.32 mmol, 1.0 equiv) in DMF (60 mL) under an atmosphere of nitrogen, was added 60% sodium hydride (379 mg, 9.48 mmol, 1.5 equiv) portion wise. Once the initial effervescence had subsided, the mixture was heated at 60° C. for 1 h then cooled to rt. A solution of 6-chloronicotinonitrile (876 mg, 6.32 mmol, 1.0 equiv) in DMF (5 mL) was then added and the mixture stirred for 16 h. The reaction mixture was partitioned between satd. aq. $NaHCO_3$ (30 mL) and chloroform (60 mL). The organic layer was dried ($Na_2SO_4$), filtered, and concentrated to give a crude mixture, which was purified by column chromatography (silica gel, 0-10% (2.0 M ammonia in methanol) in dichloromethane) to afford 776 mg (47%) of a beige solid. MS (electrospray): mass calculated for $C_{14}H_{20}N_4O$, 260.16; m/z found, 261.3 $[M+H]^+$. $^1$H NMR (400 MHz, $CDCl_3$): 8.47 (dd, J=2.3, 0.8 Hz, 1H), 7.77 (dd, J=8.6, 2.3 Hz, 1H), 6.80 (dd, J=8.6, 0.8 Hz, 1H), 4.41 (t, J=6.6 Hz, 2H), 2.76-2.35 (m, 10H), 2.29 (s, 3H), 2.01-1.95 (m, 2H).

B. 6-[3-(4-Methyl-piperazin-1-yl)-propoxy]-pyridine-3-carbaldehyde. To a cooled (0° C.) solution of 6-[3-(4-methyl-piperazin-1-yl)-propoxy]-nicotinonitrile (486 mg, 1.86 mmol, 1.0 equiv) in toluene (20 mL), under an atmosphere of nitrogen, was added 1 M diisobutylaluminum hydride in hexanes (2.79 mL, 2.79 mmol, 1.5 equiv) dropwise. The mixture was warmed to rt and stirred for 2 h. Methanol was added (5 mL), followed by 1 M $H_2SO_4$ (10 mL). After stirring for 30 min, the solution was neutralized with satd. aq. $NaHCO_3$, diluted with satd. aq. sodium potassium tartrate (10 mL), and stirred an additional 30 min or until clear. The mixture was extracted with chloroform (3×50 mL) and the combined extracts were dried ($Na_2SO_4$), and concentrated, yielding the crude product, which was purified by column chromatography (silica gel, 0-10% (2 M ammonia in methanol) in dichloromethane) to afford 225 mg (46%) of a colorless residue. MS (electrospray): mass calculated for $C_{14}H_{21}N_3O_2$, 263.16; m/z found, 264.2 $[M+H]^+$. $^1$H NMR (400 MHz, $CDCl_3$): $^1$H NMR (400 MHz, $CDCl_3$): 9.94 (1H, s), 8.61 (d, J=2.3 Hz, 1H), 8.06 (dd, J=8.6, 2.3 Hz, 1H), 6.82 (d, J=8.6 Hz, 1H), 4.46 (t, J=6.6 Hz, 2H), 2.64-2.33 (m, 10H), 2.29 (s, 3H), 2.03-1.96 (m, 2H).

C. 6-Chloro-4-methyl-2-{6-[3-(4-methyl-piperazin-1-yl)-propoxy]-pyridin-3-yl}-1H-benzoimidazole. This compound was prepared by the method described in General Procedure 3 using 6-[3-(4-methyl-piperazin-1-yl)-propoxy]-pyridine-3-carbaldehyde (49 mg, 0.17 mmol, 1.0 equiv), 5-chloro-3-methyl-benzene-1,2-diamine (27 mg, 0.17 mmol, 1.0 equiv), and $Na_2S_2O_5$ (42 mg, 0.22 mmol, 1.3 equiv). Purification by Method 2 afforded 54 mg (79%) of the title compound. MS (electrospray): mass calculated for C$_{21}$H$_{26}$ClN$_5$O, 399.18; m/z found, 400.3 [M+H]$^+$. $^1$H NMR (400 MHz, CDCl$_3$): 8.75 (s, 1H), 8.25 (dd, J=8.2, 2.4 Hz, 1H), 7.49-7.32 (m, 1H), 6.91 (s, 1H), 6.71 (d, J=8.7 Hz, 1H), 4.28 (t, J=6.7 Hz, 2H), 2.67-2.31 (m, 13H), 2.26 (s, 3H), 1.98-1.87 (m, 2H).

The following compounds in Examples 104-105 were prepared according to the procedures described in Example 103.

Example 104

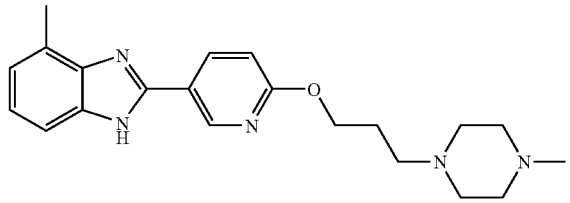

4-Methyl-2-{6-[3-(4-methyl-piperazin-1-yl)-propoxy]-pyridin-3-yl}-1H-benzoimidazole MS (electrospray): mass calculated for C$_{21}$H$_{27}$N$_5$O, 365.47; m/z found, 366.2 [M+H]$^+$.

Example 105

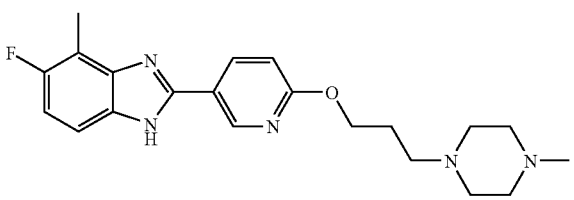

5-Fluoro-4-methyl-2-{6-[3-(4-methyl-piperazin-1-yl)-propoxy]-pyridin-3-yl}-1H-benzoimidazole MS (electrospray): mass calculated for C$_{21}$H$_{26}$FN$_5$O, 383.46; m/z found, 384.2 [M+H]$^+$.

Example 106

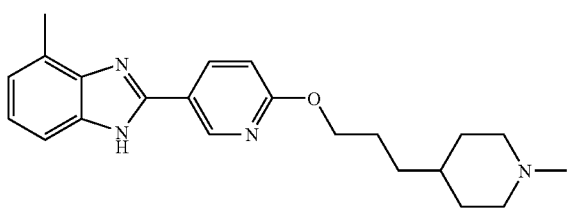

4-Methyl-2-{6-[3-(1-methyl-piperidin-4-yl)-propoxy]-pyridin-3-yl}-1H-benzoimidazole A. 6-[3-(1-Methyl-piperidin-4-yl)-propoxy]-nicotinonitrile. To a stirred solution of 3-(1-methyl-piperidin-4-yl)-propan-1-ol (5.0 g, 31.7 mmol, 1.1 equiv) in DMF (200 mL) under an atmosphere of nitrogen, was added 60% sodium hydride (1.73 g, 43.3 mmol, 1.5 equiv) portion wise. Once the initial effervescence had subsided, the mixture was heated at 60° C. for 1 h then cooled to rt. A solution of 6-chloronicotinonitrile (4.0 g, 28.9 mmol, 1.0 equiv) in DMF (20 mL) was then added and the mixture stirred for 16 h. The reaction was quenched with satd. aq. NaHCO$_3$ (50 mL) and brine (50 mL). A precipitate was formed and was collected by vacuum filtration to afford 3.67 g of the desired product. The filtrate was concentrated to half the volume and a second crop of precipitate was collected and combined to give 5.64 g (76%) of an orange solid, which was used without further purification. MS (electrospray): mass calculated for C$_{15}$H$_{21}$N$_3$O, 259.17; m/z found, 260.4 [M+H]$^+$. $^1$H NMR (400 MHz, CDCl$_3$): 8.46 (dd, J=2.3, 0.8 Hz, 1H), 7.77 (dd, J=8.6, 2.3 Hz, 1H), 6.80 (dd, J=8.6, 0.8 Hz, 1H), 4.34 (t, J=6.6 Hz, 2H), 2.96-2.82 (m, 2H), 2.25 (s, 3H), 1.92-1.68 (m, 7H), 1.37-1.34 (m, 2H), 0.89-0.81 (m, 2H).

B. 6-[3-(1-Methyl-piperidin-4-yl)-propoxy]-pyridine-3-carbaldehyde. To a cooled (0° C.) solution of 6-[3-(1-methyl-piperidin-4-yl)-propoxy]-nicotinonitrile (640 mg, 2.47 mmol, 1.0 equiv) in toluene (20 mL), under an atmosphere of nitrogen, was added 1 M diisobutylaluminum hydride in hexanes (3.70 mL, 3.70 mmol, 1.5 equiv) dropwise. The mixture was warmed to rt and stirred for 2 h. Methanol was added (5 mL), followed by 1 M H$_2$SO$_4$ (10 mL). After stirring for 30 min the solution was neutralized with satd. aq. NaHCO$_3$, diluted with satd. aq. sodium potassium tartrate (10 mL), and stirred an additional 30 min or until clear. The mixture was extracted with chloroform (3×50 mL) and the combined extracts were dried (Na$_2$SO$_4$), filtered and concentrated. The crude product was purified by column chromatography (silica gel, 0-10% (2 M ammonia in methanol) in dichlromethane) to afford 598 mg (92%) of a colorless oil. MS (electrospray): mass calculated for C$_{15}$H$_{22}$N$_2$O$_2$, 262.17; m/z found, 263.1 [M+H]$^+$. $^1$H NMR (400 MHz, CDCl$_3$): $^1$H NMR (400 MHz, CDCl$_3$): 9.87 (br s, 1H), 8.53 (d, J=2.3 Hz, 1H), 7.98 (dd, J=8.6, 2.3 Hz, 1H), 6.74 (d, J=8.6 Hz, 1H), 4.34 (t, J=6.6 Hz, 2H), 2.78-2.26 (m, 2H), 2.19 (s, 3H), 1.85-1.62 (m, 7H), 1.35-1.16 (m, 4H).

C. 4-Methyl-2-{6-[3-(1-methyl-piperidin-4-yl)-propoxy]-pyridin-3-yl}-1H-benzoimidazole. This compound was prepared by the method described in General Procedure 3 using 6-[3-(1-methyl-piperidin-4-yl)-propoxy]-pyridine-3-carbaldehyde (100 mg, 0.38 mmol, 1.0 equiv), 3-methyl-benzene-1,2-diamine (46 mg, 0.38 mmol, 1.0 equiv) and Na$_2$S$_2$O$_5$ (94 mg, 0.50 mmol, 1.3 equiv). Purification by Method 2 afforded 35 mg (25%) of the title compound. MS (electrospray): mass calculated for C$_{22}$H$_{28}$N$_4$O, 364.23; m/z found, 365.4 [M+H]$^+$. $^1$H NMR (400 MHz, CD$_3$OD): 8.77 (s, 1H), 8.23 (dd, J=8.7, 2.3 Hz, 1H), 7.25 (m, 1H), 7.12 (t, J=7.5 Hz, 1H), 7.04-6.98 (m, 1H), 6.74 (d, J=8.7 Hz, 1H), 4.34 (t, J=6.6 Hz, 2H), 2.84-2.76 (m, 2H), 2.73-2.34 (br s, 3H), 2.23 (s, 3H), 1.92-1.83 (m, 2H), 1.81-1.62 (m, 4H), 1.39-1.17 (m, 5H).

The following compounds in Examples 107-108 were prepared according to the procedures described in Example 106.

Example 107

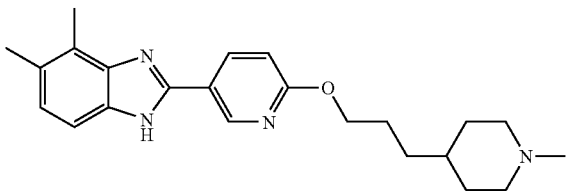

4,5-Dimethyl-2-{6-[3-(1-methyl-piperidin-4-yl)-propoxy]-pyridin-3-yl}-1H-benzoimidazole MS (electrospray): mass calculated for $C_{23}H_{30}N_4O$, 378.24; m/z found, 379.4 $[M+H]^+$.

Example 108

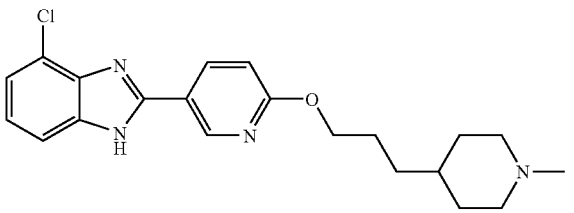

4-Chloro-2-{6-[3-(1-methyl-piperidin-4-yl)-propoxy]-pyridin-3-yl}-1H-benzoimidazole MS (electrospray): mass calculated for $C_{21}H_{25}ClN_4O$, 384.17; m/z found, 385.3 $[M+H]^+$.

Example 109

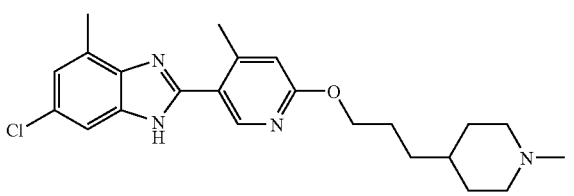

6-Chloro-4-methyl-2-{4-methyl-6-[3-(1-methyl-piperidin-4-yl)-propoxy]-pyridin-3-yl}-1H-benzoimidazole A. 4-Methyl-6-[3-(1-methyl-piperidin-4-yl)-propoxy]-nicotinonitrile. To a stirred solution of 2,2,6,6-tetramethyl-piperidine (0.20 mL, 1.16 mmol, 1.5 equiv) in THF (3 mL) at −78° C. was added 2.5 M n-butyllithium in hexanes (0.46 mL, 1.16 mmol, 1.5 equiv). After 10 min, the reaction mixture was warmed to 0° C. for 45 min before re-cooling to −78° C. A solution of 6-[3-(1-methyl-piperidin-4-yl)-propoxy]-nicotinonitrile (200 mg, 0.77 mmol, 1.0 equiv) in THF (3 mL) was then added. After stirring for 1 h at −78° C., the mixture was treated with methyl iodide (0.05 mL, 0.84 mmol, 1.1 equiv) and stirring was continued for 1.5 h before quenching at −78° C. with satd. aq. NaHCO₃ (5 mL). The mixture was warmed to rt and extracted with chloroform (2×10 mL). The combined extracts were dried (Na₂SO₄), filtered, and concentrated to give a crude residue, which was purified by Method 2 to give 120 mg (57%) of the title compound. MS (electrospray): mass calculated for $C_{16}H_{23}N_3O$, 273.18; m/z found, 274.4 $[M+H]^+$. ¹H NMR (400 MHz, CDCl₃): 8.39 (s, 1H), 6.67 (s, 1H), 4.31 (t, J=6.7 Hz, 2H), 2.90-2.79 (m, 2H), 2.48 (s, 3H), 2.28 (s, 3H), 1.95-1.63 (m, 6H), 1.40-1.20 (m, 5H).

B. 4-Methyl-6-[3-(1-methyl-piperidin-4-yl)-propoxy]-pyridine-3-carbaldehyde. To a solution of 4-methyl-6-[3-(1-methyl-piperidin-4-yl)-propoxy]-nicotinonitrile (260 mg, 0.95 mmol, 1.0 equiv) in toluene (10 mL) at 0° C. was added 1.5 M diisobutylaluminum hydride in toluene (1.26 mL, 1.90 mmol, 2.0 equiv). The mixture was warmed to rt and stirred for 2 h. Methanol (2 mL) was added, followed by 1.0 M H₂SO₄ (3 mL). After stirring for 30 min, the solution was neutralized with satd. aq. NaHCO₃, diluted with satd. aq. sodium potassium tartrate (10 mL), and stirred an additional 30 min or until clear. The mixture was extracted with chloroform (3×15 mL) and the combined extracts were dried (Na₂SO₄), filtered, and concentrated to afford 200 mg of the crude product, which was used without purification. ¹H NMR (400 MHz, CDCl₃): 10.0 (s, 1H), 8.47 (s, 1H), 6.57 (s, 1H), 4.35 (t, J=6.7 Hz, 2H), 2.86-2.80 (m, 2H), 2.59 (s, 3H), 2.25 (s, 3H), 1.92-1.66 (m, 6H), 1.43-1.22 (m, 5H).

C. 4-Methyl-2-{6-[3-(1-methyl-piperidin-4-yl)-propoxy]-pyridin-3-yl}-1H-benzoimidazole. This compound was prepared by the method described in General Procedure 3 using 4-methyl-6-[3-(1-methyl-piperidin-4-yl)-propoxy]-pyridine-3-carbaldehyde (60 mg, 0.22 mmol, 1.0 equiv), 5-chloro-3-methyl-benzene-1,2-diamine (34 mg, 0.22 mmol, 1.0 equiv) and Na₂S₂O₅ (54 mg, 0.29 mmol, 1.3 equiv). Purification by Method 2 afforded 27 mg (30%) of the title compound. MS (electrospray): mass calculated for $C_{23}H_{29}ClN_4O$, 412.20; m/z found, 413.4 $[M+H]^+$. ¹H NMR (400 MHz, CD₃OD): 8.77 (s, 1H), 8.23 (dd, J=8.7, 2.3 Hz, 1H), 7.25 (m, 1H), 7.12 (t, J=7.5 Hz, 1H), 7.04-6.98 (m, 1H), 6.74 (d, J=8.7 Hz, 1H), 4.34 (t, J=6.6 Hz, 2H), 2.84-2.76 (m, 2H), 2.73-2.34 (br s, 3H), 2.23 (s, 3H), 1.92-1.83 (m, 2H), 1.81-1.62 (m, 4H), 1.39-1.17 (m, 4H).

The following compounds in Examples 110-114 were prepared according to the procedures described in Example 109.

Example 110

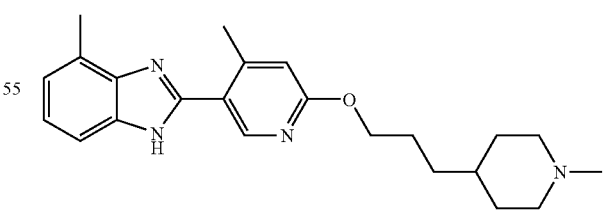

4-Methyl-2-{4-methyl-6-[3-(1-methyl-piperidin-4-yl)-propoxy]-pyridin-3-yl}-1H-benzoimidazole MS (electrospray): mass calculated for $C_{23}H_{30}N_4O$, 378.24; m/z found, 379.5 $[M+H]^+$.

Example 111

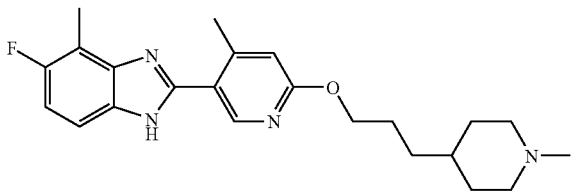

5-Fluoro-4-methyl-2-{4-methyl-6-[3-(1-methyl-piperidin-4-yl)-propoxy]-pyridin-3-yl}-1H-benzoimidazole MS (electrospray): mass calculated for $C_{23}H_{29}FN_4O$, 396.23; m/z found, 397.4 $[M+H]^+$.

Example 112

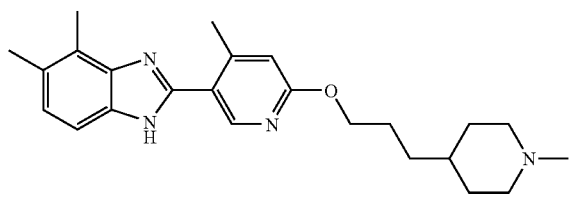

4,5-Dimethyl-2-{4-methyl-6-[3-(1-methyl-piperidin-4-yl)-propoxy]-pyridin-3-yl}-1H-benzoimidazole MS (electrospray): mass calculated for $C_{24}H_{32}N_4O$, 392.26; m/z found, 393.5 $[M+H]^+$.

Example 113

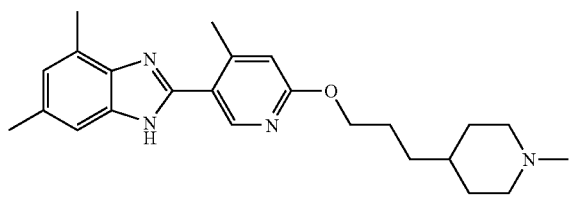

4,6-Dimethyl-2-{4-methyl-6-[3-(1-methyl-piperidin-4-yl)-propoxy]-pyridin-3-yl}-1H-benzoimidazole MS (electrospray): mass calculated for $C_{24}H_{32}N_4O$, 392.26; m/z found, 393.5 $[M+H]^+$.

Example 114

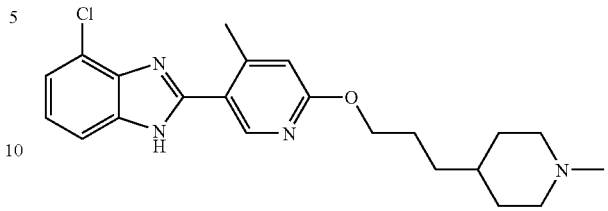

4-Chloro-2-{4-methyl-6-[3-(1-methyl-piperidin-4-yl)-propoxy]-pyridin-3-yl}-1H-benzoimidazole MS (electrospray): mass calculated for $C_{22}H_{27}ClN_4O$, 398.19; m/z found, 399.3 $[M+H]^+$.

Example 115

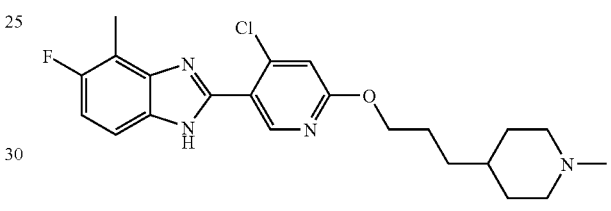

2-{4-Chloro-6-[3-(1-methyl-piperidin-4-yl)-propoxy]-pyridin-3-yl}-5-fluoro-4-methyl-1H-benzoimidazole A. 4-Chloro-6-[3-(1-methyl-piperidin-4-yl)-propoxy]-nicotinonitrile. To a stirred solution of 2,2,6,6-tetramethyl-piperidine (0.31 mL, 2.32 mmol, 1.2 equiv) in THF (10 mL) at −78° C. was added 1.6 M n-butyllithium in hexanes (1.45 mL, 2.32 mmol, 1.2 equiv). After 10 min the reaction mixture was warmed to 0° C. for 45 min before re-cooling to −78° C. A solution of 6-[3-(1-methyl-piperidin-4-yl)-propoxy]-nicotinonitrile (500 mg, 1.93 mmol, 1.0 equiv) in THF (10 mL) was then added. After stirring for 1 h at −78° C., the mixture was treated with hexachloroethane (0.05 mL, 0.84 mmol, 1.1 equiv) in THF (2 mL) and allowed to warm to 0° C. Stirring was continued for 1.5 h before quenching at 0° C. with sodium hydrogen carbonate (10 mL). The mixture was warmed to rt and extracted with chloroform (2×20 mL). The combined extracts were dried ($Na_2SO_4$), filtered, and concentrated to give a crude residue, which was purified by Method 2 to give 380 mg (67%) of the title compound. MS (electrospray): mass calculated for $C_{15}H_{20}ClN_3O$, 293.13; m/z found, 294.5 $[M+H]^+$. $^1H$ NMR (400 MHz, $CDCl_3$): 8.43 (s, 1H), 6.87 (s, 1H), 4.35 (t, J=6.7 Hz, 2H), 2.97-2.88 (m, 2H), 2.33 (s, 3H), 2.05-1.94 (m, 2H), 1.83-1.67 (m, 5H), 1.43-1.23 (m, 4H).

B. 2-{4-Chloro-6-[3-(1-methyl-piperidin-4-yl)-propoxy]-pyridin-3-yl}-5-fluoro-4-methyl-1H-benzoimidazole. To a solution of 4-chloro-6-[3-(1-methyl-piperidin-4-yl)-propoxy]-nicotinonitrile (380 mg, 1.30 mmol, 1.0 equiv) in toluene (10 mL) at 0° C. was added 1.5 M diisobutylaluminum hydride in toluene (1.72 mL, 2.60 mmol, 2.0 equiv). The mixture was warmed to rt and stirred for 2 h. Methanol was added (5 mL), followed by 1.0 M H₂SO₄ (5 mL). After stirring for 30 min, the solution was neutralized with satd. aq. NaHCO₃, diluted with satd. aq. sodium potassium tartrate (10 mL), and stirred an additional 30 min or until clear. The mixture was extracted with chloroform (3×15 mL) and the combined extracts were dried (Na₂SO₄), filtered, and concentrated to afford 132 mg of the crude product which was used without purification. This crude mixture (33 mg, 0.11 mmol, 1.0 equiv) was used as described in General Procedure 3 with 4-fluoro-3-methyl-benzene-1,2-diamine (16 mg, 0.11 mmol, 1.0 equiv) and Na₂S₂O₅ (27 mg, 0.14 mmol, 1.3 equiv). Purification by Method 2 afforded 12 mg (26%) of an oily residue. MS (electrospray): mass calculated for $C_{22}H_{26}ClFN_4O$, 416.18; m/z found, 417.3 [M+H]⁺. ¹H NMR (400 MHz, CD₃OD): 8.48 (s, 1H), 7.41 (dd, J=8.7, 4.3 Hz, 1H), 7.46-6.99 (m, 2H), 4.36 (t, J=6.6 Hz, 2H), 2.91-2.82 (m, 2H), 2.50 (s, 3H), 2.25 (s, 3H), 2.06-1.95 (m, 2H), 1.88-1.69 (m, 4H), 1.47-1.18 (m, 5H).

The following compounds in Examples 116-118 were prepared according to the procedures described in Example 115.

Example 116

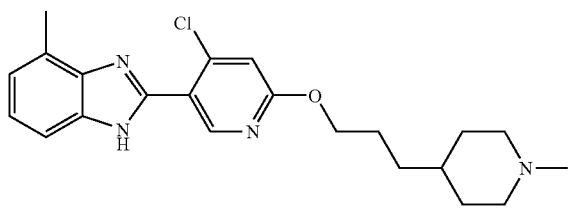

2-{4-Chloro-6-[3-(1-methyl-piperidin-4-yl)-propoxy]-pyridin-3-yl}-4-methyl-1H-benzoimidazole MS (electrospray): mass calculated for $C_{22}H_{27}ClN_4O$, 398.19; m/z found, 399.3 [M+H]⁺.

Example 117

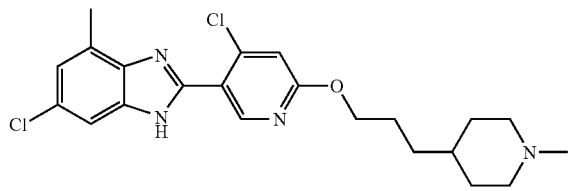

6-Chloro-2-{4-chloro-6-[3-(1-methyl-piperidin-4-yl)-propoxy]-pyridin-3-yl}-4-methyl-1H-benzoimidazole MS (electrospray): mass calculated for $C_{22}H_{26}Cl_2N_4O$, 432.15; m/z found, 433.3 [M+H].

Example 118

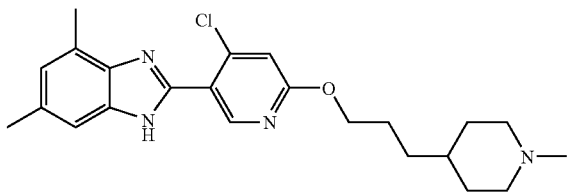

2-{4-Chloro-6-[3-(1-methyl-piperidin-4-yl)-propoxy]-pyridin-3-yl}-4,6-dimethyl-1H-benzoimidazole MS (electrospray): mass calculated for $C_{23}H_{29}ClN_4O$, 412.20; m/z found, 413.4 [M+H]⁺.

Example 119

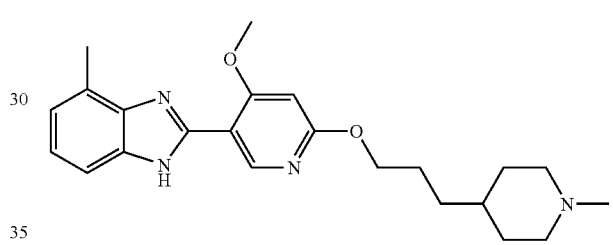

2-{4-Methoxy-6-[3-(1-methyl-piperidin-4-yl)-propoxy]-pyridin-3-yl}-4-methyl-1H-benzoimidazole A solution of 4-chloro-6-[3-(1-methyl-piperidin-4-yl)-propoxy]-nicotinonitrile (Example 115) in methanol (0.2 M) was treated with sodium methoxide (4 equiv) at reflux temperature for 4 h. The mixture was cooled to rt, diluted with satd. aq. NaHCO₃, and extracted with chloroform. The organic extract was dried (Na₂SO₄), filtered, and concentrated to yield 4-methoxy-6-[3-(1-methyl-piperidin-4-yl)-propoxy]-nicotinonitrile (100%). This intermediate was converted to the title compound according to Example 115. MS (electrospray): mass calculated for $C_{23}H_{30}ClN_4O_2$, 394.24; m/z found, 395.4 [M+H]⁺.

Example 120

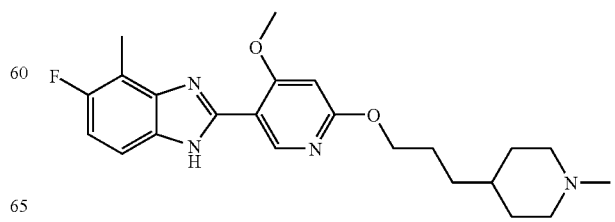

5-Fluoro-2-{4-methoxy-6-[3-(1-methyl-piperidin-4-yl)-propoxy]-pyridin-3-yl}-4-methyl-1H-benzoimidazole The title compound was prepared according to the procedures described in Example 119. MS (electrospray): mass calculated for $C_{23}H_{29}FN_4O_2$, 412.23; m/z found, 413.4 $[M+H]^+$.

Example 121

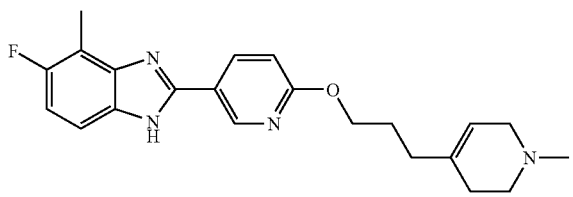

5-Fluoro-4-methyl-2-{6-[3-(1-methyl-1,2,3,6-tetrahydro-pyridin-4-yl)-propoxy]-pyridin-3-yl}-1H-benzoimidazole A. 6-[3-(1-Methyl-1,2,3,6-tetrahydro-pyridin-4-yl)-propoxy]-nicotinonitrile. To a stirred solution of 3-(1-methyl-1,2,3,6-tetrahydro-pyridin-4-yl)-propan-1-ol (1.23 g, 7.94 mmol, 1.1 equiv) in DMF (50 mL), under an atmosphere of nitrogen, was added 60% sodium hydride (433 mg, 10.8 mmol, 1.5 equiv) portion wise. Once the initial effervescence had subsided, the mixture was heated at 60° C. for 1 h then cooled to rt. A solution of 6-chloronicotinonitrile (1.0 g, 7.21 mmol, 1.0 equiv) in DMF (5 mL) was then added and the mixture was stirred for 16 h. The reaction was quenched with satd. aq. NaHCO$_3$ (10 mL) and brine (10 mL). The mixture was extracted with chloroform (2×50 mL). The combined extracts were dried (Na$_2$SO$_4$), filtered, and concentrated to give a crude residue, which was purified by Method 2 affording 1.43 g (77%) of the title compound. MS (electrospray): mass calculated for $C_{15}H_{19}N_3O$, 257.15; m/z found, 258.3 $[M+H]^+$. $^1$H NMR (400 MHz, CDCl$_3$): 8.46 (dd, J=2.4, 0.6 Hz, 1H), 7.76 (dd, J=8.7, 2.4 Hz, 1H), 6.80 (dd, J=8.7, 0.6 Hz, 1H), 5.44-5.39 (m, 1H), 4.35 (t, J=6.6 Hz, 2H), 2.92-2.87 (m, 2H), 2.51 (t, J=5.8 Hz, 2H), 2.34 (s, 3H), 2.18-2.08 (m, 4H), 1.96-1.83 (m, 2H).

B. 6-[3-(1-Methyl-1,2,3,6-tetrahydro-pyridin-4-yl)-propoxy]-Pyridine-3-carbaldehyde. To a cooled (0° C.) solution of 6-[3-(1-methyl-1,2,3,6-tetrahydro-pyridin-4-yl)-propoxy]-nicotinonitrile (1.42 mg, 5.56 mmol, 1.0 equiv) in toluene (40 mL), under an atmosphere of nitrogen, was added 1.0 M diisobutylaluminum hydride in hexanes (8.34 mL, 8.34 mmol, 1.5 equiv). dropwise. The mixture was warmed to rt and stirred for 2 h. Methanol was added (5 mL), followed by 1.0 M H$_2$SO$_4$ (10 mL). After stirring for 30 min, the solution was neutralized with satd. aq. NaHCO$_3$, diluted with satd. aq. sodium potassium tartrate (25 mL), and stirred an additional 30 min or until clear. The mixture was extracted with chloroform (3×50 mL) and the combined extracts were dried (Na$_2$SO$_4$), filtered, and concentrated to afford 1.29 g of the product which was used without purification. $^1$H NMR (400 MHz, CDCl$_3$): 9.93 (s, 1H), 8.60 (d, J=2.3 Hz, 1H), 8.05 (dd, J=8.7, 2.3 Hz, 1H), 6.81 (d, J=8.7 Hz, 1H), 5.45-5.39 (m, 1H), 4.40 (t, J=6.6 Hz, 2H), 2.92-2.86 (m, 2H), 2.54-2.48 (m, 2H), 2.30 (s, 3H), 2.18-2.09 (m, 4H), 2.98-1.84 (m, 2H).

C. 5-Fluoro-4-methyl-2-{6-[3-(1-methyl-1,2,3,6-tetrahydro-pyridin-4-yl)-propoxy]-pyridin-3-yl}-1H-benzoimidazole. This compound was prepared by the method described in General Procedure 3 using 6-[3-(1-methyl-1,2,3,6-tetrahydro-pyridin-4-yl)-propoxy]-pyridine-3-carbaldehyde (100 mg, 0.39 mmol, 1.0 equiv), 4-fluoro-3-methyl-benzene-1,2-diamine (66 mg, 0.39 mmol, 1.0 equiv) and Na$_2$S$_2$O$_5$ (96 mg, 0.51 mmol, 1.3 equiv). Purification by Method 2 afforded 24 mg (16%) of the title compound. MS (electrospray): mass calculated for $C_{22}H_{25}FN_4O$, 380.20; m/z found, 381.4 $[M+H]^+$. $^1$H NMR (400 MHz, CDCl$_3$): 11.8-10.8 (br s, 1H), 8.86-8.58 (m, 1H), 8.24 (dd, J=8.7, 2.5 Hz, 1H), 7.58-7.36 (m, 0.5H), 7.21-7.03 (m, 0.5H), 6.93 (t, J=9.9 Hz, 1H), 6.73 (d, J=8.7 Hz, 1H), 5.42-5.33 (m, 1H), 4.29 (t, J=6.7 Hz, 2H), 2.92-2.81 (m, 2H), 2.58-2.44 (m, 4H), 2.36-2.26 (m, 4H), 2.18-2.02 (m, 4H), 1.93-1.82 (m, 2H).

The following compounds in Examples 122-126 were prepared according to the procedures described in Example 121.

Example 122

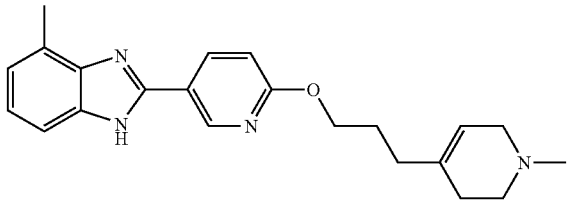

4-Methyl-2-{6-[3-(1-methyl-1,2,3,6-tetrahydro-pyridin-4-yl)-propoxy]-pyridin-3-yl}-1H-benzoimidazole MS (electrospray): mass calculated for $C_{22}H_{26}N_4O$, 362.21; m/z found, 363.4 $[M+H]^+$.

Example 123

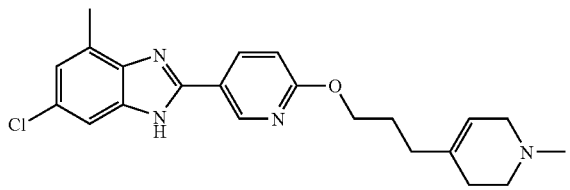

6-Chloro-4-methyl-2-{6-[3-(1-methyl-1,2,3,6-tetrahydro-pyridin-4-yl)-propoxy]-pyridin-3-yl}-1H-benzoimidazole MS (electrospray): mass calculated for $C_{22}H_{25}ClN_4O$, 396.17; m/z found, 397.4 $[M+H]^+$.

Example 124

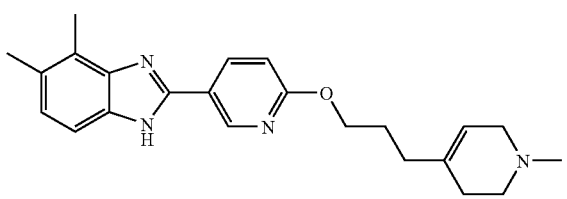

4,5-Dimethyl-2-{6-[3-(1-methyl-1,2,3,6-tetrahydro-pyridin-4-yl)-propoxy]-pyridin-3-yl}-1H-benzoimidazole MS (electrospray): mass calculated for $C_{23}H_{28}N_4O$, 376.23; m/z found, 377.4 $[M+H]^+$.

Example 125

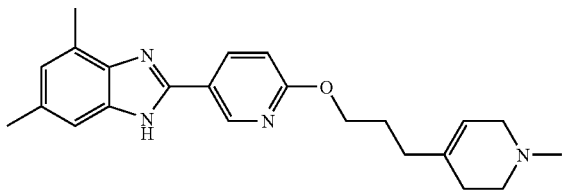

4,6-Dimethyl-2-{6-[3-(1-methyl-1,2,3,6-tetrahydro-pyridin-4-yl)-propoxy]-pyridin-3-yl}-1H-benzoimidazole MS (electrospray): mass calculated for $C_{23}H_{28}N_4O$, 376.23; m/z found, 377.4 $[M+H]^+$.

Example 126

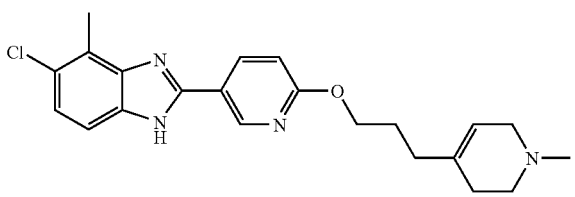

5-Chloro-4-methyl-2-{6-[3-(1-methyl-1,2,3,6-tetrahydro-pyridin-4-yl)-propoxy]-pyridin-3-yl}-1H-benzoimidazole MS (electrospray): mass calculated for $C_{22}H_{25}ClN_4O$, 396.17; m/z found, 397.4 $[M+H]^+$.

Example 127

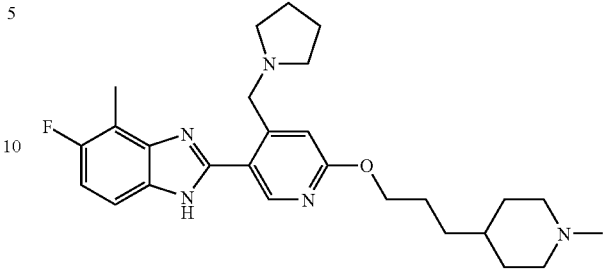

5-Fluoro-4-methyl-2-{6-[3-(1-methyl-piperidin-4-yl)-propoxy]-4-pyrrolidin-1-ylmethyl-pyridin-3-yl}-1H-benzoimidazole A. 5-Bromo-2-[3-(1-methyl-piperidin-4-yl)-propoxy]-pyridine. To a stirred solution of 3-(1-methyl-piperidin-4-yl)-propan-1-ol (2.0 g, 12.7 mmol, 1.0 equiv), in DMF (100 mL) under an atmosphere of nitrogen, was added 60% sodium hydride (764 mg, 19.1 mmol, 1.5 equiv) portion wise. Once the initial effervescence had subsided, the mixture was heated at 60° C. for 1 h, then was cooled to rt. A solution of 2,5-dibromopyridine (3.0 g, 12.7 mmol, 1.0 equiv) in DMF (7 mL) was then added and the mixture was stirred for 16 h. The reaction was quenched with satd. aq. NaHCO$_3$ (25 mL) and brine (25 mL). The mixture was extracted with chloroform (2×30 mL). The organic extracts were dried (Na$_2$SO$_4$), filtered, and concentrated to give a crude residue, which was purified by Method 2 affording 3.31 g (88%) of the title compound. $^1$H NMR (400 MHz, CDCl$_3$): 8.18-8.13 (m, 1H), 7.65-7.58 (m, 1H), 6.65-6.60 (m, 1H), 4.21 (t, J=6.7 Hz, 2H), 2.87-2.80 (m, 2H), 2.26 (s, 3H), 1.94-1.62 (m, 6H), 1.43-1.17 (m, 5H).

B. 5-Bromo-2-[3-(1-methyl-piperidin-4-yl)-propoxy]-pyridine-4-carbaldehyde. To a cooled solution (−78° C.) of 2.0 M LDA in heptane/THF (4.05 mL, 8.07 mmol, 2.0 equiv) in THF (20 mL), was added a solution of 5-bromo-2-[3-(1-methyl-piperidin-4-yl)-propoxy]-pyridine (1.2 g, 3.85 mmol, 1.0 equiv) in THF (15 mL) dropwise. After 30 min, DMF (1.49 mL, 19.2 mmol, 5.0 equiv) was added dropwise and the mixture stirred for an additional 20 min at −78° C. then warmed to 0° C. and quenched with satd. aq. NaHCO$_3$ (5 mL). The mixture was warmed to rt and extracted with chloroform (2×30 mL). The combined extracts were dried (Na$_2$SO$_4$), filtered, and concentrated to afford 1.10 g of a crude oil, which was used without purification. $^1$H NMR (400 MHz, CDCl$_3$): 10.3 (s, 1H), 8.39 (s, 1H), 7.15 (s, 1H), 4.31 (t, J=6.7 Hz, 2H), 2.87-2.75 (m, 2H), 2.28 (s, 3H), 1.97-1.60 (m, 6H), 1.43-1.15 (m, 5H).

C. 5-Bromo-2-[3-(1-methyl-piperidin-4-yl)-propoxy]-4-pyrrolidin-1-ylmethyl-pyridine. To a mixture of 5-bromo-2-[3-(1-methyl-piperidin-4-yl)-propoxy]-pyridine-4-carbaldehyde (85 mg, 0.25 mmol, 1.0 equiv) and pyrrolidine (0.05 mL, 0.62 mmol, 2.5 equiv) in dichloroethane (5 mL), was added sodium triacetoxyborohydride (156 mg, 0.74 mmol, 3.0 equiv). After 24 h, the mixture was neutralized with satd. aq. NaHCO$_3$ and extracted with chloroform (2×15 mL). The combined extracts were dried (Na$_2$SO$_4$), filtered, and concentrated to give a crude oil product, which was purified by Method 2 to give 38 mg of a white solid. $^1$H NMR (400 MHz, CDCl$_3$): 8.15 (s, 1H), 6.90 (s, 1H), 4.24 (t, J=6.7 Hz, 2H), 3.65 (s, 2H), 2.87-2.77 (m, 2H), 2.64-2.53 (m, 4H), 2.25 (s, 3H), 1.95-1.62 (m, 10H), 1.42-1.20 (m, 5H).

D. 5-Fluoro-4-methyl-2-[6-[3-(1-methyl-piperidin-4-yl)-propoxy]-4-pyrrolidin-1-ylmethyl-pyridin-3-yl]-1H-benzoimidazole. To a cooled solution (−78° C.) of 5-bromo-2-[3-(1-methyl-piperidin-4-yl)-propoxy]-4-pyrrolidin-1-ylmethyl-pyridine (38 mg, 0.10 mmol, 1.0 equiv) in dry THF (2 mL), under an atmosphere of nitrogen, was added n-butyl-lithium (2.75 M in hexanes, 0.04 mL, 0.11 mmol, 1.1 equiv) dropwise. After 10 min, DMF (0.07 mL, 1.00 mmol, 10.0 equiv) was added. The solution was warmed to 0° C., quenched with satd. aq. NaHCO$_3$ (2 mL), and extracted with chloroform (2×10 mL). The combined extracts were dried (Na$_2$SO$_4$), filtered, and concentrated to obtain a crude residue. This residue was immediately dissolved in DMF (2 mL) and treated with 4-fluoro-4-fluoro-3-methyl-benzene-1,2-diamine (15 mg, 0.11 mmol, 1.1 equiv) and Na$_2$S$_2$O$_5$(25 mg, 0.13 mmol, 1.3 equiv) according to General Procedure 3. Purification by Method 2 afforded 10 mg (22%) of the title compound. MS (electrospray): mass calculated for C$_{27}$H$_{36}$FN$_5$O, 465.26; m/z found, 466.5 [M+H]$^+$. $^1$H NMR (400 MHz, CD$_3$OD): 8.81 (s, 1H), 7.42 (dd, J=8.7, 4.3 Hz, 1H), 7.01 (dd, J=10.3, 8.8 Hz, 1H), 6.95 (s, 1H), 4.40 (t, J=6.6 Hz, 2H), 3.79 (s, 3H), 2.94-2.81 (m, 2H), 2.77-2.66 (m, 4H), 2.51 (s, 3H), 2.25 (s, 3H), 2.00-1.92 (m, 6H), 1.89-1.70 (m, 4H), 1.46-1.19 (m, 5H).

Example 128

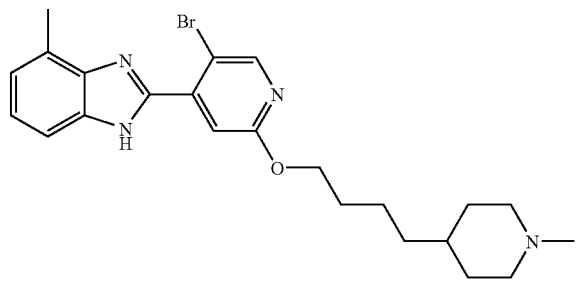

2-{5-Bromo-2-[4-(1-methyl-piperidin-4-yl)-butoxy]-pyridin-4-yl}-4-methyl-1H-benzoimidazole A. 5-Bromo-2-[4-(1-methyl-piperidin-4-yl)-butoxy]-pyridine. To a stirred solution of 4-(1-methyl-piperidin-4-yl)-butan-1-ol (3.98 g, 623 mmol, 1.1 equiv) in DMF (100 mL), under an atmosphere of nitrogen, was added 60% sodium hydride (1.26 mg, 6.81 mmol, 1.5 equiv) portion wise. Once the initial effervescence had subsided, the mixture was heated at 60° C. for 1 h, then was cooled to rt. A solution of 2,5-dibromopyridine (5 mg, 21.1 mmol, 1.0 equiv) in DMF (50 mL) was then added and the mixture was stirred for 16 h. The mixture was partitioned between satd. aq. NaHCO$_3$ (100 mL) and chloroform (200 mL). The chloroform layer was dried (Na$_2$SO$_4$), filtered, and concentrated to give a crude mixture, which was purified by column chromatography (silica gel, 0-10% (2 M ammonia in methanol) in dichloromethane) to afford 2.73 g (40%) of a white solid. MS (electrospray): mass calculated for C$_{15}$H$_{23}$BrN$_2$O, 326.1; m/z found, 327.3 [M+H]$^+$. $^1$H NMR (400 MHz, CDCl$_3$): 8.17 (d, J=2.5 Hz, 1H), 7.63 (dd, J=7.6, 2.5 Hz, 1H), 6.63 (d, J=8.8 Hz, 1H), 4.24 (t, J=6.6 Hz, 2H), 2.91-2.80 (m, 2H), 2.27 (s, 3H), 1.98-1.88 (m, 2H), 1.79-1.63 (m, 4H), 1.49-1.38 (m, 2H), 1.34-1.20 (m; 5H).

B. 5-Bromo-2-[4-(1-methyl-piperidin-4-yl)-butoxy]-pyridine-4-carbaldehyde. To a cooled solution (−78° C.) of 2.0 M LDA in heptane/THF (3.47 mL, 6.94 mmol, 2.0 equiv) in THF (10 ML), was added a solution of 5-bromo-2-[4-(1-methyl-piperidin-4-yl)-butoxy]-pyridine (1.13 g, 3.47 mmol, 1.0 equiv) in THF (15 mL) dropwise. After 30 min, DMF (1.07 mL, 13.9 mmol, 4.0 equiv) was added dropwise and the mixture stirred for an additional 20 min at −78° C. The mixture was warmed to 0° C. and satd. aq. NaHCO$_3$ (5 mL) was added. After warming to rt, the mixture was extracted with chloroform (2×20 mL). The combined extracts were dried (Na$_2$SO$_4$), filtered, and concentrated to give 1.34 g of a crude orange oil which was used without purification. $^1$H NMR (400 MHz, CDCl$_3$): 10.3 (s, 1H), 8.39 (s, 1H), 7.14 (s, 1H), 4.31 (t, J=6.7 Hz, 2H), 2.89-2.79 (m, 2H), 2.28 (s, 3H), 1.96-1.63 (m, 9H), 1.43-1.20 (m, 4H).

C. 2-{5-Bromo-2-[4-(1-methyl-piperidin-4-yl)-butoxy]-pyridin-4-yl}-4-methyl-1H-benzoimidazole. This compound was prepared by the method described in General Procedure 3 using 5-bromo-2-[4-(1-methyl-piperidin-4-yl)-butoxy]-pyridine-4-carbaldehyde (100 mg, 0.28 mmol, 1.0 equiv), 3-methyl-benzene-1,2-diamine (38 mg, 0.31 mmol, 1.1 equiv) and Na$_2$S$_2$O$_5$(70 mg, 0.37 mmol, 1.3 equiv). Purification by Method 2 afforded 25 mg (20%) of the title compound. MS (electrospray): mass calculated for C$_{23}$H$_{29}$BrN$_4$O, 456.15; m/z found, 466.5 [M+H]$^+$. $^1$H NMR (400 MHz, CDCl$_3$): 10.6-10.3 (br s, 1H), 8.45-8.28 (m, 1H), 7.76-7.62 (m, 2H), 7.25-7.21 (m, 1H), 7.19-7.07 (m, 1H), 4.29 (t, J=6.7 Hz, 2H), 2.87-2.77 (m, 2H), 2.76-2.63 (m, 3H), 2.25 (s, 3H), 1.95-1.61 (m, 7H), 1.53-1.39 (m, 2H), 1.35-1.15 (m, 4H).

The following compounds in Examples 129-135 were prepared according to the procedures described in Example 128.

Example 129

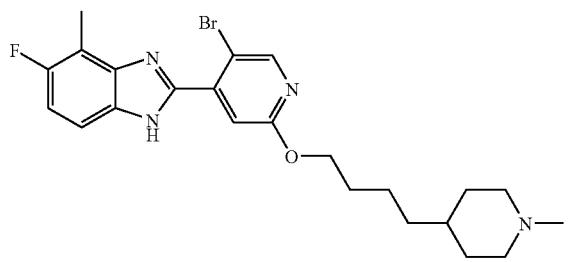

2-{5-Bromo-2-[4-(1-methyl-piperidin-4-yl)-butoxy]-pyridin-4-yl}-5-fluoro-4-methyl-1H-benzoimidazole MS (electrospray): mass calculated for C$_{23}$H$_{28}$BrFN$_5$O, 474.14; m/z found, 477.4 [M+H]$^+$.

Example 130

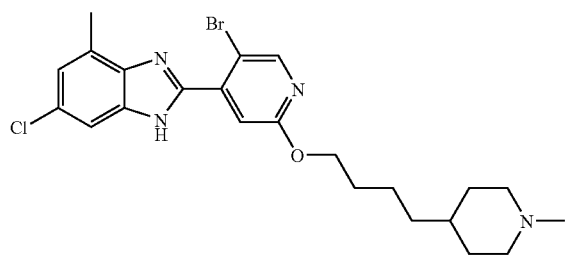

2-{5-Bromo-2-[4-(1-methyl-piperidin-4-yl)-butoxy]-pyridin-4-yl}-6-chloro-4-methyl-1H-benzoimidazole MS (electrospray): mass calculated for $C_{23}H_{28}BrClN_5O$, 490.1; m/z found, 493.4 [M+H]$^+$.

Example 131

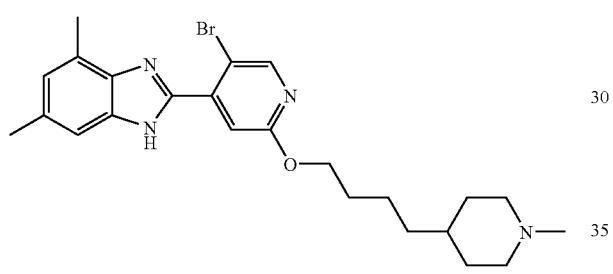

2-{5-Bromo-2-[4-(1-methyl-piperidin-4-yl)-butoxy]-pyridin-4-yl}-4,6-dimethyl-1H-benzoimidazole MS (electrospray): mass calculated for $C_{24}H_{31}BrN_4O$, 470.17; m/z found, 471.4 [M+H]$^+$.

Example 132

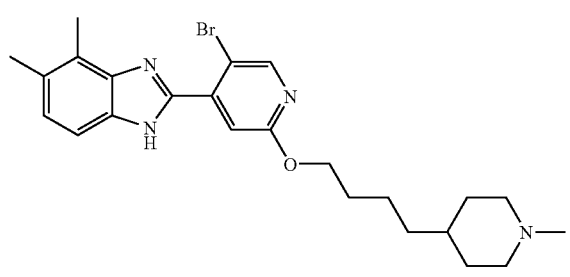

2-{5-Bromo-2-[4-(1-methyl-piperidin-4-yl)-butoxy]-pyridin-4-yl}-4,5-dimethyl-1H-benzoimidazole MS (electrospray): mass calculated for $C_{24}H_{31}BrN_4O$, 470.17; m/z found, 471.4 [M+H]$^+$.

Example 133

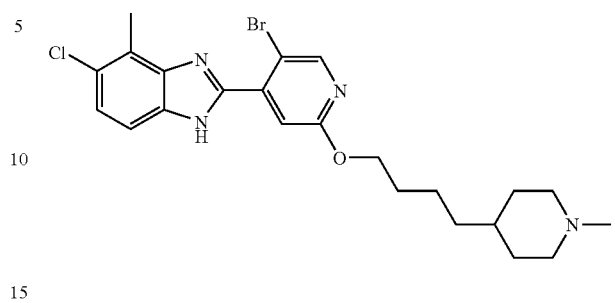

2-{5-Bromo-2-[4-(1-methyl-piperidin-4-yl)-butoxy]-pyridin-4-yl}-5-chloro-4-methyl-1H-benzoimidazole MS (electrospray): mass calculated for $C_{24}H_{31}BrN_4O$, 470.17 m/z found, 471.4 [M+H]$^+$. MS (electrospray): mass calculated for $C_{23}H_{28}BrClN_4O$, 490.11; m/z found, 493.4 [M+H]$^+$.

Example 134

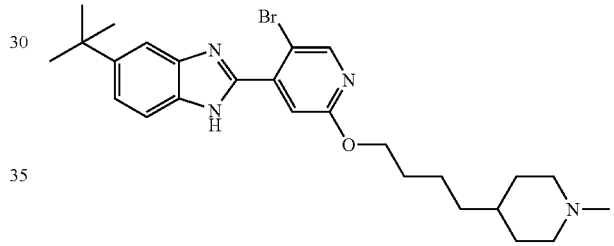

2-{5-Bromo-2-[4-(1-methyl-piperidin-4-yl)-butoxy]-pyridin-4-yl}-5-tert-butyl-1H-benzoimidazole MS (electrospray): mass calculated for $C_{26}H_{35}BrN_4O$, 498.20; m/z found, 501.4 [M+H]$^+$.

Example 135

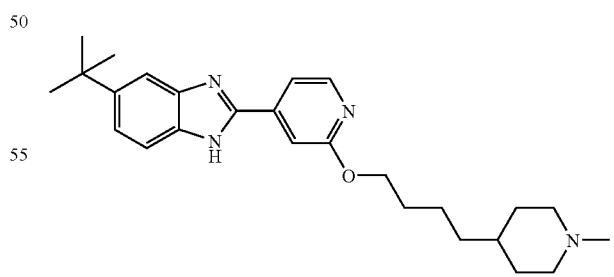

5-tert-Butyl-2-{2-[4-(1-methyl-piperidin-4-yl)-butoxy]-pyridin-4-yl}-1H-benzoimidazole MS (electrospray): mass calculated for $C_{26}H_{36}N_4O$, 420.29; m/z found, 421.5 [M+H]$^+$.

Example 136

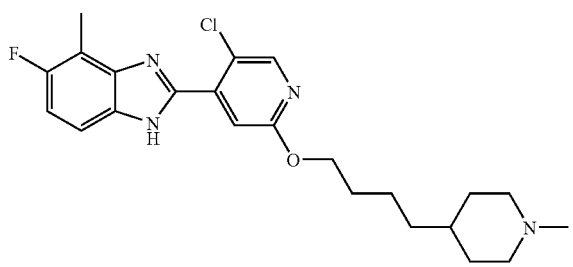

2-{5-Chloro-2-[4-(1-methyl-piperidin-4-yl)-butoxy]-pyridin-4-yl}-5-fluoro-4-methyl-1H-benzoimidazole A. 5-Chloro-2-[4-(1-methyl-piperidin-4-yl)-butoxy]-pyridine. To a stirred solution of 4-(1-methyl-piperidin-4-yl)-butan-1-ol (1.5 g, 8.77 mmol, 1.0 equiv) in DMF (10 mL) under an atmosphere of nitrogen, was added 60% sodium hydride (573 mg, 14.3 mmol, 1.5 equiv) portion wise. Once the initial effervescence had subsided, the mixture was heated at 60° C. for 1 h, then was cooled to rt. A solution of 2,5-dichloropyridine (1.42 mg, 9.55 mmol, 1.1 equiv) in DMF (10 mL) was then added and the mixture was stirred for 4 h. The mixture was partitioned between satd. aq. NaHCO$_3$ (20 mL) and chloroform (40 mL). The chloroform layer was dried (Na$_2$SO$_4$), filtered, and concentrated to give a crude mixture, which was purified by column chromatography (silica gel, 0-10% (2 M ammonia in methanol) in dichloromethane) to afford 1.62 g (65%) of a white solid. $^1$H NMR (400 MHz, CDCl$_3$): 8.07 (dd, J=2.5, 0.4 Hz, 1H), 7.51 (dd, J=8.8, 2.7 Hz, 1H), 6.67 (dd, J=8.8, 0.4 Hz, 1H), 4.27 (t, J=6.6 Hz, 2H), 2.86-2.78 (m, 2H), 2.26 (s, 3H), 1.94-1.60 (m, 7H), 1.52-1.37 (m, 2H), 1.35-1.14 (m, 4H).

B. 5-Chloro-2-[4-(1-methyl-piperidin-4-yl)-butoxy]-pyridine-4-carbaldehyde. To a cooled solution (−78° C.) of 2.0 M LDA in heptane/THF (5.74 mL, 11.5 mmol, 2.0 equiv) in THF (10 ML), was added a solution of 5-chloro-2-[4-(1-methyl-piperidin-4-yl)-butoxy]-pyridine (1.62 g, 5.74 mmol, 1.0 equiv) in THF (15 mL) dropwise. After 30 min, DMF (2.22 mL, 28.7 mmol, 5.0 equiv) was added dropwise and the mixture was stirred for an additional 20 min at −78° C. The mixture was warmed to 0° C. and quenched with satd. aq. NaHCO$_3$ (5 mL). The mixture was warmed to rt and extracted with chloroform (2×20 mL). The combined extracts were dried (Na$_2$SO$_4$), filtered, and concentrated to give 968 mg of a crude residue, which was used without purification. $^1$H NMR (400 MHz, CDCl$_3$): 10.4 (s, 1H), 8.26 (s, 1H), 7.13 (s, 1H), 4.31 (t, J=6.6 Hz, 2H), 2.87-2.80 (m, 2H), 2.25 (s, 3H), 1.99-1.60 (m, 7H), 1.51-1.38 (m, 2H), 1.43-1.20 (m, 4H).

C. 2-{5-Chloro-2-[4-(1-methyl-piperidin-4-yl)-butoxy]-pyridin-4-yl}-5-fluoro-4-methyl-1H-benzoimidazole. This compound was prepared by the method described in General Procedure 3 using 5-chloro-2-[4-(1-methyl-piperidin-4-yl)-butoxy]-pyridine-4-carbaldehyde (45 mg, 0.15 mmol, 1.0 equiv), 4-fluoro-3-methyl-benzene-1,2-diamine (23 mg, 0.17 mmol, 1.1 equiv) and Na$_2$S$_2$O$_5$ (37 mg, 0.20 mmol, 1.3 equiv). Purification by Method 2 afforded 12 mg (18%) of the title compound. MS (electrospray): mass calculated for C$_{23}$H$_{28}$ClFN$_4$O, 430.19; m/z found, 431.4 [M+H]$^+$. $^1$H NMR (400 MHz, CD$_3$OD): 8.30 (s, 1H), 7.45 (dd, J=8.9, 4.5 Hz, 1H), 7.22-7.19 (m, 1H), 7.07 (dd, J=10.2, 8.9 Hz 1H), 4.31 (t, J=6.6 Hz, 2H), 2.88-2.81 (m, 2H), 2.53 (s, 3H), 2.24 (s, 3H), 2.05-1.90 (m, 2H), 1.84-1.66 (m, 4H), 1.55-1.42 (m, 2H), 1.37-1.15 (m, 5H).

Example 137

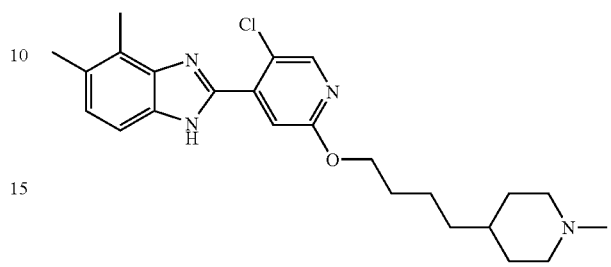

2-{5-Chloro-2-[4-(1-methyl-piperidin-4-yl)-butoxy]-pyridin-4-yl}-4,5-dimethyl-1H-benzoimidazole The title compound was prepared according to the methods described in Example 136. MS (electrospray): mass calculated for C$_{24}$H$_{31}$ClN$_4$O, 426.22; m/z found, 427.4 [M+H]$^+$.

Example 138

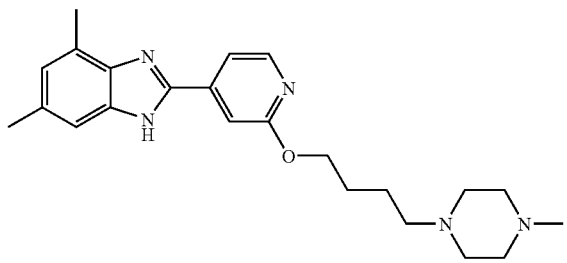

4,6-Dimethyl-2-{2-[4-(4-methyl-piperazin-1-yl)-butoxy]-pyridin-4-yl}-1H-benzoimidazole A. 2-[4-(4-Methyl-piperazin-1-yl)-butoxy]-isonicotinonitrile. To a solution of 4-(4-methyl-piperazin-1-yl)-butan-1-ol (2.5 g, 14.5 mmol, 1.0 equiv) in DMF (25 mL) at 0° C. was added sodium hydride (60% dispersion in oil, 0.70 g, 17.4 mmol, 1.2 equiv). The mixture was warmed to rt and stirred for 1 h before re-cooling to 0° C. A solution of 2-chloro-isonicotinonitrile (2.01 g, 14.5 mmol, 1.0 equiv) in DMF (12 mL) was added dropwise. The mixture was stirred at rt for 18 h. The reaction was diluted with water (5 mL) and satd. aq. NaHCO$_3$ (25 mL) was added. The mixture was extracted with chloroform (3×25 mL), and the combined extracts were concentrated. Purification by Method 2 afforded 1.07 g of impure compound. Mass calculated for C$_{15}$H$_{22}$N$_4$O, 274.18; m/z found, 275.4 [M+H]$^+$.

B. 4.6-Dimethyl-2-{2-[4-(4-methyl-piperazin-1-yl)-butoxy]-pyridin-4-yl}-1H-benzoimidazole. To a stirred solution of 2-[4-(4-methyl-piperazin-1-yl)-butoxy]-isonicotinonitrile) in toluene (5.0 mL) at 0° C. was added 1.5 M diisobutylaluminum hydride in toluene (3.9 mL, 5.86 mmol, 1.5 equiv). After 3 h, methanol (9 mL) and 1.0 M H$_2$SO$_4$ (10 mL) were added. The mixture was stirred for 30 min, and then 1.0 M NaOH (10 mL) was added, followed by satd. aq. sodium potassium tartrate (40 mL) and dichloromethane (100 mL). After stirring for 30 min, the mixture was extracted with chloroform (3×50 mL) and the combined extracts were washed with brine, dried (Na$_2$SO$_4$), filtered, and concentrated. The residue was partially purified by Method 2 to afford 240 mg of a mixture of 3-[3-(1-methyl-piperidin-4-yloxy)-propoxy]-benzaldehyde and several other unidentified products. A portion of the the crude 3-[3-(1-methyl-piperidin-4-yloxy)-propoxy]-benzaldehyde (40 mg), 3,5-dimethyl-benzene-1,2-diamine (17.6 mg), and Na$_2$S$_2$O$_5$ (32 mg) were stirred in DMF (4 mL) at 90° C. for 18 h. The reaction mixture was loaded directly on silica gel and purified by Method 2, which afforded 19 mg of the title compound. MS (electrospray): mass calculated for C$_{23}$H$_{31}$N$_5$O, 393.25; m/z found, 394.5 [M+H]$^+$. $^1$H NMR (400 MHz, CD$_3$OD): 8.26 (d, J=5.4 Hz, 1H), 7.63 (d, J=5.5 Hz, 1H), 7.49 (s, 1H), 7.25 (br s, 1H), 6.95 (s, 1H), 4.38 (t, J=6.3 Hz, 2H), 2.76-2.33 (m, 16H), 2.32-2.24 (s, 3H), 1.92-1.79 (m, 2H), 1.79-1.66 (m, 2H).

The following compounds in Examples 139-142 were prepared according to the procedures described in Example 138.

Example 139

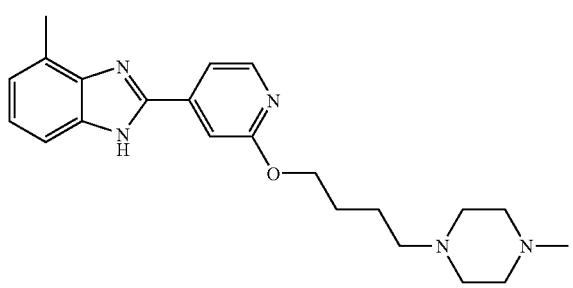

4-Methyl-2-{2-[4-(4-methyl-piperazin-1-yl)-butoxy]-pyridin-4-yl}-1H-benzoimidazole MS (electrospray): mass calculated for C$_{22}$H$_{29}$N$_5$O, 379.24; m/z found, 380.4 [M+H].

Example 140

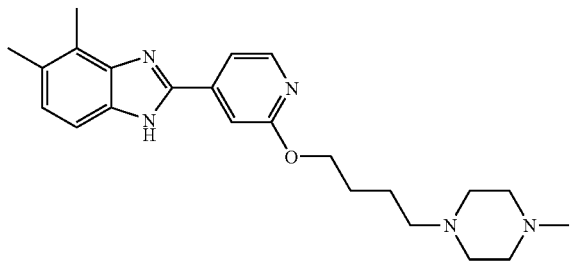

4,5-Dimethyl-2-{2-[4-(4-methyl-piperazin-1-yl)-butoxy]-pyridin-4-yl}-1H-benzoimidazole MS (electrospray): mass calculated for C$_{23}$H$_{31}$N$_5$O, 393.25; m/z found, 394.5 [M+H]$^+$.

Example 141

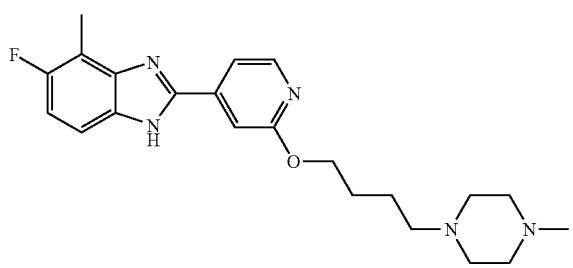

5-Fluoro-4-methyl-2-{2-[4-(4-methyl-piperazin-1-yl)-butoxy]-pyridin-4-yl}-1H-benzoimidazole MS (electrospray): mass calculated for C$_{22}$H$_{28}$FN$_5$O, 397.23; m/z found, 398.4 [M+H]$^+$.

Example 142

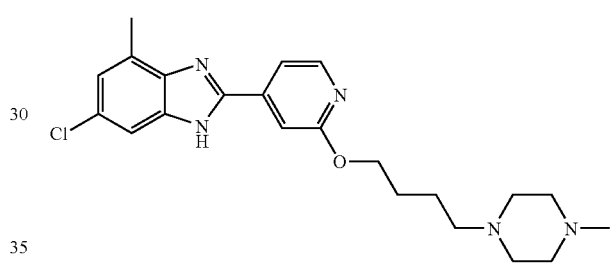

6-Chloro-4-methyl-2-{2-[4-(4-methyl-piperazin-1-yl)-butoxy]-pyridin-4-yl}-1H-benzoimidazole MS (electrospray): mass calculated for C$_{22}$H$_{28}$ClN$_5$O, 413.20; m/z found, 414.4 [M+H]$^+$.

Example 143

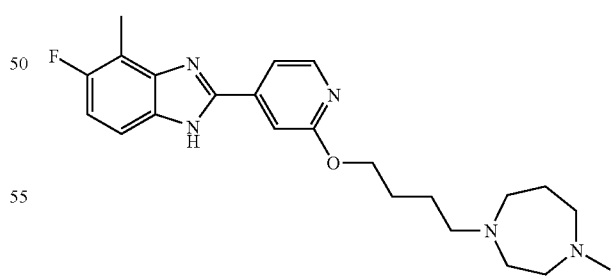

5-Fluoro-4-methyl-2-{2-[4-(4-methyl-[1,4]diazepan-1-yl)-butoxy]-pyridin-4-yl}-1H-benzoimidazole A. 2-[4-(4-Methyl-[1,4]diazepan-1-yl)-butoxy]-isonicotinonitrile. To a solution of 1-methyl-[1,4]diazepane (21.3 g, 185 mmol, 2.0 equiv) and 4-chloro-butan-1-ol (10.0 g, 92.6 mmol, 1.0 equiv) in 1-butanol (200 mL) were added K$_2$CO$_3$ (38.0 g, 278 mmol, 3.0 equiv) and NaI (13.9 g, 92.6 mmol, 1.0 equiv). The mixture was warmed to 95° C. and stirred for 36 h. The mixture was then cooled to rt, diluted with water, and extracted with chloroform (3×100 mL). The combined extracts were washed with brine, dried (MgSO$_4$), filtered, and concentrated. Purification by Method 2 afforded 9.3 g of 4-(4-methyl-[1,4]diazepan-1-yl)-butan-1-ol with a small unidentified impurity. A portion of the impure alcohol (5.0 g) was dissolved in DMF (50 mL) and cooled to 0° C. Sodium hydride (60% dispersion in oil, 1.29 g, 32.2 mmol, 1.2 equiv) was added. The mixture was warmed to rt, stirred for 1 h, and then re-cooled to 0° C. A solution of 2-chloro-isonicotinonitrile (3.72 g, 26.8 mmol, 1.0 equiv) in DMF (25 mL) was added dropwise. The mixture was stirred at rt for 18 h, then was diluted with water (25 mL) and satd. aq. NaHCO$_3$ (100 mL), and was extracted with chloroform (3×100 mL). The combined extracts were washed with brine, dried (Na$_2$SO$_4$), filtered and concentrated. Purification by Method 2 afforded the title compound (1.0 g). MS (electrospray): mass calculated for C$_{16}$H$_{24}$N$_4$O, 288.20; m/z found, 289.4 [M+H]$^+$. $^1$H NMR (400 MHz, CDCl$_3$): 8.28 (dd, J=4.4 Hz, 0.8 Hz, 1H), 7.05 (dd, J=3.9, 1.1 Hz, 1H) 6.96 (s, 1H), 4.33 (t, J=6.6 Hz, 2H), 2.75-2.68 (m, 4H), 2.65-2.57 (m, 4H), 2.56-2.49 (m, 2H), 2.35 (s, 3H), 1.84-1.74 (m, 4H), 1.66-1.55 (m, 2H).

B. 5-Fluoro-4-methyl-2-{2-[4-(4-methyl-[1,4]diazepan-1-yl)-butoxy]-pyridin-4-yl}-1H-benzoimidazole. To a stirred solution of 2-[4-(4-methyl-[1,4]diazepan-1-yl)-butoxy]-isonicotinonitrile (1.0 g, 3.47 mmol, 1.0 equiv) in toluene (5.0 mL) at 0° C. was added 1.0 M diisobutylaluminum hydride in toluene (5.2 mL, 5.2 mmol, 1.5 equiv). After 3 h, methanol (9 mL) and 1.0 M H$_2$SO$_4$ (10 mL) were added. The mixture was stirred for 30 min, and then 1.0 M NaOH (10 mL) was added, followed by satd. aq. sodium potassium tartrate (40 mL) and dichloromethane (100 mL). After stirring for 30 min, the mixture was extracted with chloroform (3×50 mL) and the combined extracts were washed with brine, dried (Na$_2$SO$_4$), filtered, and concentrated. The residue was partially purified by Method 2 to afford 268 mg of a mixture of 2-[4-(4-methyl-[1,4]diazepan-1-yl)-butoxy]-pyridine-4-carbaldehyde and several other unidentified products. A portion of the impure 2-[4-(4-methyl-[1,4]diazepan-1-yl)-butoxy]-pyridine-4-carbaldehyde (63 mg), 4-fluoro-3-methyl-benzene-1,2-diamine (30.3 mg), and Na$_2$S$_2$O$_5$ (53.4 mg) were stirred in DMF (3 mL) at 90° C. for 18 h. The reaction mixture was loaded directly on silica gel and purified by Method 2, which afforded 5.0 mg of the title compound. MS (electrospray): mass calculated for C$_{23}$H$_{30}$FN$_5$O, 411.24; m/z found, 412.5 [M+H]$^+$. $^1$H NMR (400 MHz, CD$_3$OD): 8.27 (dd, J=4.8, 0.5 Hz, 1H), 7.63 (dd, J=4.0, 1.4 Hz, 1H), 7.52-7.40 (m, 2H), 7.10-7.01 (m, 1H), 4.27 (t, J=6.3 Hz, 2H), 2.86-2.77 (m, 4H), 2.77-2.68 (m, 4H), 2.65-2.57 (m, 2H), 2.53 (s, 3H), 2.37 (s, 3H), 1.90-1.66 (m, 6H).

Example 144

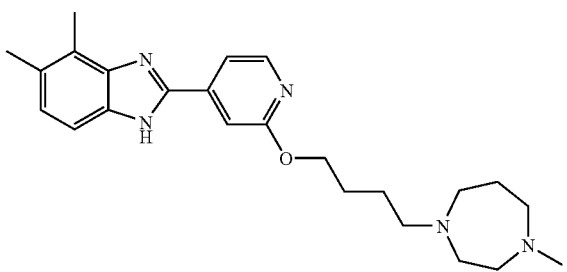

4,5-Dimethyl-2-{2-[4-(4-methyl-[1,4]diazepan-1-yl)-butoxy]-pyridin-4-yl}-1H-benzoimidazole This compound was prepared according to the methods described in Example 143. MS (electrospray): mass calculated for C$_{24}$H$_{33}$N$_5$O, 407.27; m/z found, 408.5 [M+H]$^+$.

Example 145

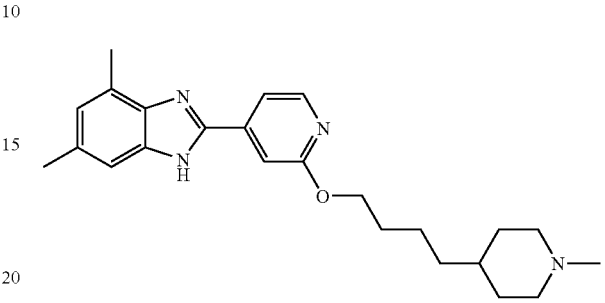

4,6-Dimethyl-2-{2-[4-(1-methyl-piperidin-4-yl)-butoxy]-pyridin-4-yl}-1H-benzoimidazole A. 2-[4-(1-Methyl-piperidin-4-yl)-butoxy]-isonicotinonitrile. To a solution of 4-(1-methyl-piperidin-4-yl)-butan-1-ol (1.0 g, 5.85 mmol, 1.0 equiv) in DMF (25 mL) at 0° C. was added sodium hydride (60% dispersion in oil, 0.28 g, 7.02 mmol, 1.2 equiv). The mixture was warmed to rt and stirred for 1 h. The mixture was then re-cooled to 0° C. and a solution of 2-chloro-isonicotinonitrile (0.81 g, 5.85 mmol, 1.0 equiv) in DMF (10 mL) was added dropwise. The mixture was stirred at rt for 18 h, then was diluted with water (25 mL) and satd. aq. NaHCO$_3$ (100 mL). The mixture was extracted with chloroform (3×100 mL), and the combined extracts were concentrated. Purification by Method 2 afforded 0.44 g (28%) of title compound. MS (electrospray): mass calculated for C$_{16}$H$_{23}$N$_3$O, 273.18; m/z found, 274.4 [M+H]$^+$. $^1$H NMR (400 MHz, CD$_3$OD): 8.28 (dd, J=5.2, 0.7 Hz, 1H), 7.05 (dd, J=5.2, 1.3 Hz, 1H), 6.99-6.95 (m, 1H), 4.21 (t, J=6.6 Hz, 2H), 2.88-2.79 (m, 2H), 2.26 (s, 3H), 1.95-1.83 (m, 2H), 1.81-1.59 (m, 4H), 1.51-1.38 (m, 2H), 1.34-1.16 (m, 5H).

B. 4,6-Dimethyl-2-{2-[4-(1-methyl-piperidin-4-yl)-butoxy]-pyridin-4-yl}-1H-benzoimidazole. To a stirred solution of 2-[4-(1-methyl-piperidin-4-yl)-butoxy]-isonicotinonitrile (440 mg, 1.61 mmol, 1.0 equiv) in toluene (5.0 mL) at 0° C. was added 1.0 M diisobutylaluminum hydride in toluene (2.41 mL, 2.41 mmol, 1.5 equiv). After 3 h, methanol (8 mL) and 1.0 M H$_2$SO$_4$ (5 mL) were added. The mixture was stirred for 30 min, and then 1.0 M NaOH (10 mL) was added, followed by satd. aq. sodium potassium tartrate (40 mL) and dichloromethane (100 mL). After stirring for 30 min, the mixture was extracted with chloroform (3×50 mL) and the combined extracts were washed with brine, dried (Na$_2$SO$_4$), filtered, and concentrated. The residue was partially purified by Method 2 to afford 318 mg of a mixture of 2-(4-piperidin-4-yl-butoxy)-pyridine-4-carbaldehyde and several other unidentified products. A portion of the crude of 2-(4-piperidin-4-yl-butoxy)-pyridine-4-carbaldehyde (100 mg), 3,5-dimethyl-benzene-1,2-diamine (70 mg), and Na$_2$S$_2$O$_5$ (93 mg) were stirred in DMF (3 mL) at 90° C. for 18 h. The reaction mixture was loaded directly on silica gel and purified according to Method 2, which afforded 38 mg of the title compound. MS (electrospray): mass calculated for C$_{24}$H$_{32}$N$_4$O, 392.26; m/z found 393.4 [M+H]$^+$. $^1$H NMR (400 MHz, CD$_3$OD): 8.25 (d, J=5.3 Hz, 1H), 7.62 (dd, J=4.5, 1.0 Hz, 1H), 7.48 (s, 1H), 7.24 (s, 1H), 6.95 (s, 1H), 4.34 (t, J=6.6 Hz, 2H), 2.91-2.83 (m, 2H), 2.58 (s, 3H), 2.43 (s, 3H), 2.25 (s, 3H), 2.07-1.95 (m, 2H), 1.86-1.69 (m, 5H), 1.57-1.18 (m, 6H). The following compounds in Examples 146-151 were prepared according to the methods described for Example 145.

Example 146

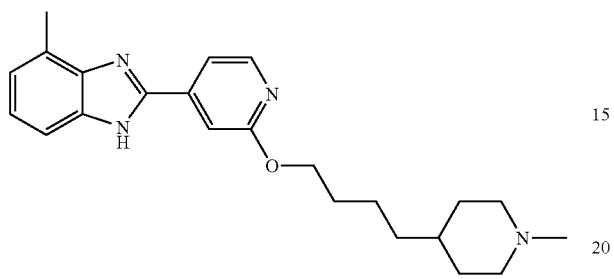

4-Methyl-2-{2-[4-(1-methyl-piperidin-4-yl)-butoxy]-pyridin-4-yl}-1H-benzoimidazole MS (electrospray): mass calculated for C$_{23}$H$_{30}$N$_4$O, 378.24; m/z found, 379.4 [M+H]$^+$.

Example 147

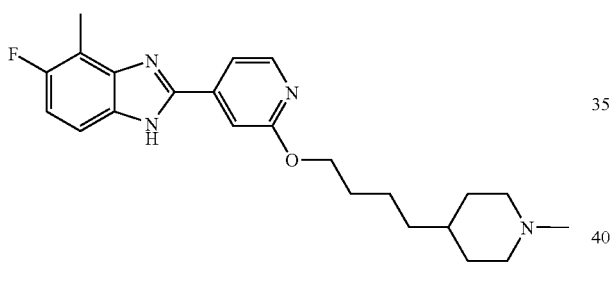

5-Fluoro-4-methyl-2-{2-[4-(1-methyl-piperidin-4-yl)-butoxy]-pyridin-4-yl}-1H-benzoimidazole MS (electrospray): mass calculated for C$_{23}$H$_{29}$FN$_4$O, 396.23; m/z found, 387.4 [M+H]$^+$.

Example 148

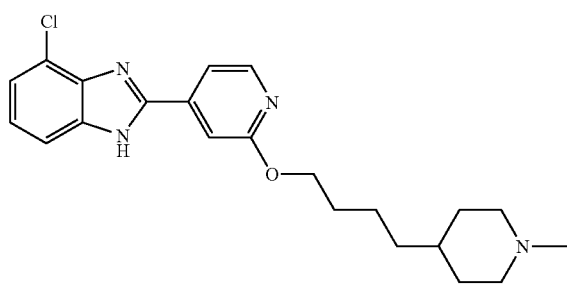

4-Chloro-2-{2-[4-(1-methyl-piperidin-4-yl)-butoxy]-pyridin-4-yl}-1H-benzoimidazole MS (electrospray): mass calculated for C$_{22}$H$_{27}$ClN$_4$O, 398.19; m/z found, 398.4 [M+H]$^+$.

Example 149

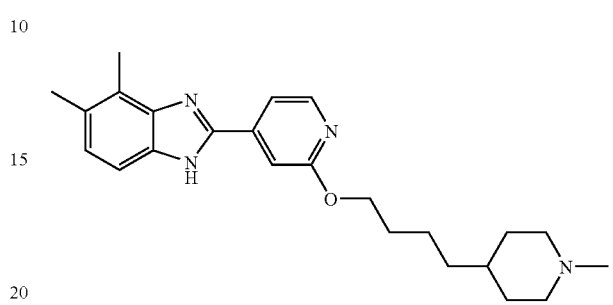

4,5-Dimethyl-2-{2-[4-(1-methyl-piperidin-4-yl)-butoxy]-pyridin-4-yl}-1H-benzoimidazole MS (electrospray): mass calculated for C$_{24}$H$_{32}$N$_4$O, 392.26; m/z found, 393.5 [M+H]$^+$.

Example 150

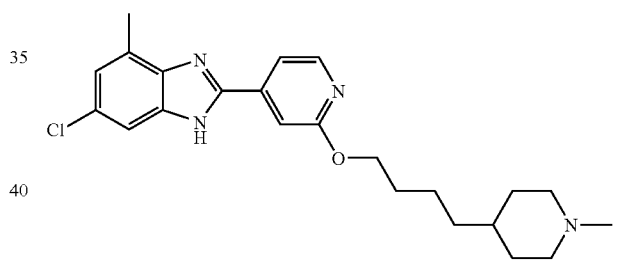

6-Chloro-4-methyl-2-{2-[4-(1-methyl-piperidin-4-yl)-butoxy]-pyridin-4-yl}-1H-benzoimidazole MS (electrospray): mass calculated for C$_{23}$H$_{29}$ClN$_4$O, 412.20 m/z found; 413.4 [M+H]$^+$.

Example 151

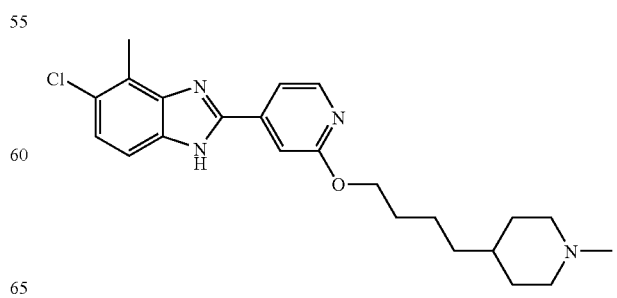

5-Chloro-4-methyl-2-{2-[4-(1-methyl-piperidin-4-yl)-butoxy]-pyridin-4-yl}-1H-benzoimidazole MS (electrospray): mass calculated for $C_{23}H_{29}ClN_4O$, 412.24; m/z found, 413.4 $[M+H]^+$.

Example 152

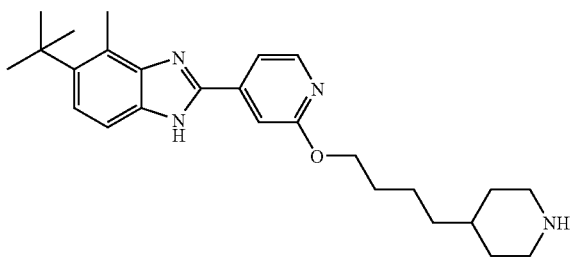

5-tert-Butyl-2-[2-(4-piperidin-4-yl-butoxy)-pyridin-4-yl]-1H-benzoimidazole

The title compound was prepared according to the methods described in Example 145, substituting 4-(4-hydroxy-butyl)-piperidine-1-carboxylic acid tert-butyl ester for 4-(1-methyl-piperidin-4-yl)-butan-1-ol to give 4-{4-[4-(5-tert-butyl-1H-benzoimidazol-2-yl)-pyridin-2-yloxy]-butyl}-piperidine-1-carboxylic acid tert-butyl ester. This intermediate was then converted to the title compound as described in Example 14. MS (electrospray): mass calculated for $C_{25}H_{34}N_4O$, 406.27; m/z found, 407.5 $[M+H]^+$.

Example 153

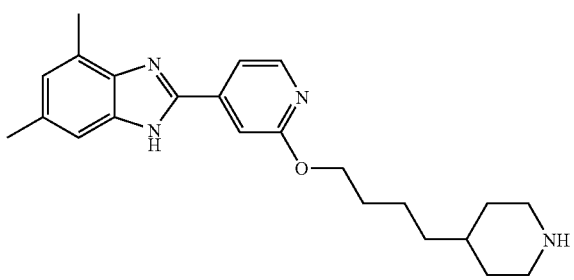

4,6-Dimethyl-2-[2-(4-piperidin-4-yl-butoxy)-pyridin-4-yl]-1H-benzoimidazole

The title compound was prepared according to the procedures as described in Example 152. MS (electrospray): mass calculated for $C_{23}H_{30}N_4O$, 378.24; m/z found, 379.5 $[M+H]^+$.

Example 154

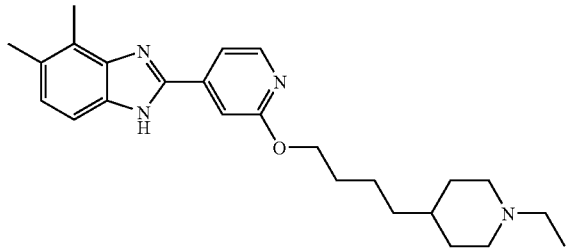

2-{2-[4-(1-Ethyl-piperidin-4-yl)-butoxy]-pyridin-4-yl}-4,5-dimethyl-1H-benzoimidazole The title compound was prepared according to the methods described in Example 90. MS (electrospray): mass calculated for $C_{25}H_{34}N_4O$, 406.27; m/z found, 407.4 $[M+H]^+$.

Example 155

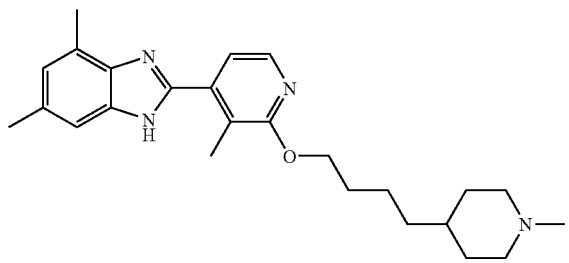

4,6-Dimethyl-2-{3-methyl-2-[4-(1-methyl-piperidin-4-yl)-butoxy]-pyridin-4-yl}-1H-benzoimidazole A. 3-Methyl-2-[4-(1-methyl-piperidin-4-yl)-butoxy]-isonicotinonitrile. To an oven dried flask under $N_2$ was added 2,2,6,6-tetramethylpiperidine (2.13 mL, 12.6 mmol 1.5 equiv) and THF (50 mL). The flask was cooled to −78° C. and n-butyllithium (2.5 M in hexanes, 5.03 mL, 12.6 mmol, 1.5 equiv) was added. The mixture was warmed to 0° C. for 1 h, and then was re-cooled to −78° C. A solution of 2-[4-(1-methyl-piperidin-4-yl)-butoxy]-isonicotinonitrile (2.3 g, 8.38 mmol, 1.0 equiv) in THF (15 mL) was added dropwise and the resulting mixture was stirred at −78° C. for 1 h. Methyl iodide (1.30 g, 9.22 mmol, 1.1 equiv) in THF (10 mL) was added dropwise. After 1 h, the reaction was quenched with satd. aq. $NaHCO_3$, warmed to rt, diluted with chloroform and washed with satd. aq. $NaHCO_3$. The organic layer was dried ($Na_2SO_4$), filtered, and concentrated. Purification by Method 2 afforded 405 mg of a mixture of 3-methyl-2-[4-(1-methyl-piperidin-4-yl)-butoxy]-isonicotinonitrile and other unidentified products. MS (electrospray): mass calculated for $C_{17}H_{25}N_3O$, 287.20; m/z found, 288.4 $[M+H]^+$.

B. 4,6-Dimethyl-2-{3-methyl-2-[4-(1-methyl-piperidin-4-yl)-butoxy]-pyridin-4-yl}-1H-benzoimidazole. To a stirred solution of impure 3-methyl-2-[4-(1-methyl-piperidin-4-yl)-butoxy]-isonicotinonitrile (283 mg) at 0° C. was added 1.5 M diisobutylaluminum hydride in toluene (1.32 mL). After 3 h, methanol (8 mL) and 1.0 M $H_2SO_4$ (5 mL) were added. The mixture was stirred for 30 min, then 1.0 M NaOH (10 mL) was added, followed by satd. aq. sodium potassium tartrate (40 mL) and dichloromethane (100 mL). After stirring for 30 min, the mixture was extracted with chloroform (3×50 mL) and the combined extracts were washed with brine, dried (Na$_2$SO$_4$), filtered, and concentrated. The residue was partially purified by Method 2 to afford 180 mg of a mixture of 2-(4-piperidin-4-yl-butoxy)-pyridine-4-carbaldehyde and several other unidentified products. A portion of the impure 2-(4-piperidin-4-yl-butoxy)-pyridine-4-carbaldehyde (19.5 mg), 3,5-dimethyl-benzene-1,2-diamine (9.2 mg), and Na$_2$S$_2$O$_5$ (16.6 mg) were stirred in DMF (3 mL) at 90° C. for 18 h. The reaction mixture was loaded directly on silica gel and purified by Method 2, which afforded 9.4 mg of the title compound. MS (electrospray): mass calculated for C$_{25}$H$_{34}$N$_4$O, 406.27; m/z found, 407.5 [M+H]$^+$. $^1$H NMR (400 MHz, CD$_3$OD): 8.06 (dd, J=5.3, 0.4 Hz, 1H), 7.23 (s, 1H), 7.13 (d, J=5.3 Hz, 1H), 6.94 (s, 1H), 4.36 (t, J=6.4 Hz, 2H), 2.92-2.81 (m, 2H), 2.56 (s, 3H), 2.43 (s, 3H), 2.33 (s, 3H), 2.24 (s, 3H), 2.07-1.94 (m, 2H), 1.87-1.67 (m, 4H), 1.60-1.46 (m, 2H), 1.40-1.15 (m, 5H).

The following compounds in Examples 156-157 were prepared according to the procedures described for Example 155.

Example 156

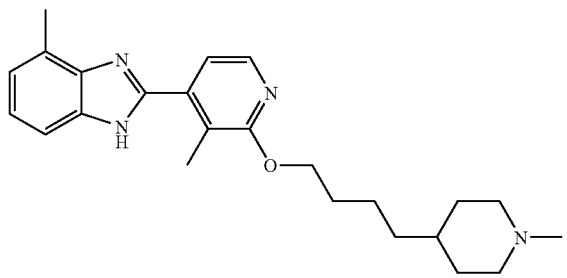

4-Methyl-2-{3-methyl-2-[4-(1-methyl-piperidin-4-yl)-butoxy]-pyridin-4-yl}-1H-benzoimidazole MS (electrospray): mass calculated for C$_{24}$H$_{32}$N$_4$O, 392.26; m/z found, 393.4 [M+H]$^+$.

Example 157

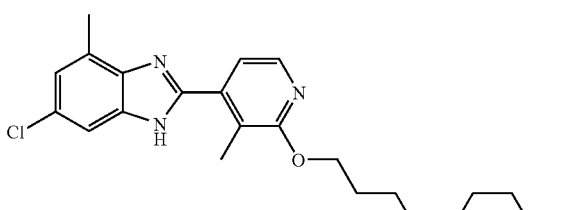

6-Chloro-4-methyl-2-{3-methyl-2-[4-(1-methyl-piperidin-4-yl)-butoxy]-pyridin-4-yl}-1H-benzoimidazole MS (electrospray): mass calculated for C$_{24}$H$_{31}$ClN$_4$O, 426.22; m/z found, 427.4 [M+H]$^+$.

Example 158

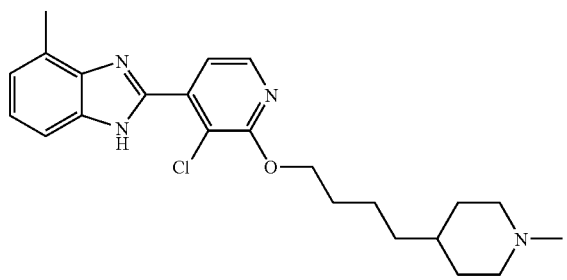

2-{3-Chloro-2-[4-(1-methyl-piperidin-4-yl)-butoxy]-pyridin-4-yl}-4-methyl-1H-benzoimidazole The title compound was prepared as described in Example 155, substituting hexachloroethane for methyl iodide. MS (electrospray): mass calculated for C$_{23}$H$_{29}$ClN$_4$O, 412.20; m/z found, 413.4 [M+H]$^+$.

The following compounds in Examples 159-164 were prepared according to the procedures described in Example 158.

Example 159

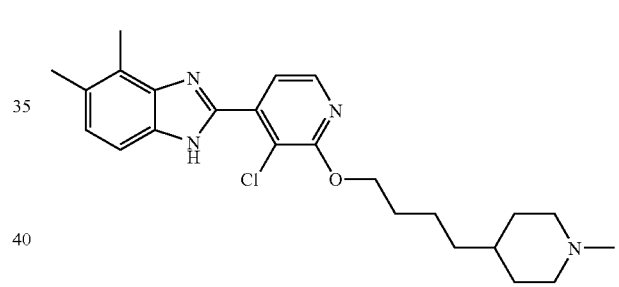

2-{3-Chloro-2-[4-(1-methyl-piperidin-4-yl)-butoxy]-pyridin-4-yl}-4,5-dimethyl-1H-benzoimidazole MS (electrospray): mass calculated for C$_{24}$H$_{31}$ClN$_4$O, 426.22; m/z found, 427.4 [M+H]$^+$.

Example 160

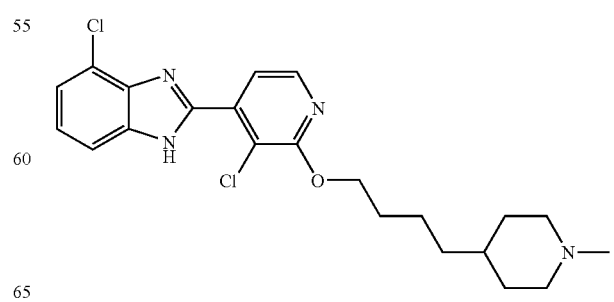

4-Chloro-2-{3-chloro-2-[4-(1-methyl-piperidin-4-yl)-butoxy]-pyridin-4-yl}-1H-benzoimidazole MS (electrospray): mass calculated for $C_{22}H_{26}Cl_2N_4O$, 432.15; m/z found, 433.3 [M+H]$^+$.

Example 161

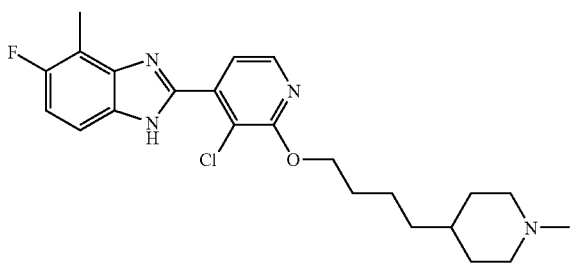

2-{3-Chloro-2-[4-(1-methyl-piperidin-4-yl)-butoxy]-pyridin-4-yl}-5-fluoro-4-methyl-1H-benzoimidazole MS (electrospray): mass calculated for $C_{23}H_{28}ClFN_4O$, 430.19; m/z found, 431.4 [M+H]$^+$.

Example 162

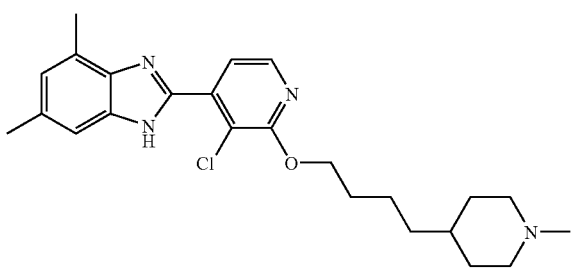

2-{3-Chloro-2-[4-(1-methyl-piperidin-4-yl)-butoxy]-pyridin-4-yl}-4,6-dimethyl-1H-benzoimidazole MS (electrospray): mass calculated for $C_{24}H_{31}ClN_4O$, 426.22; m/z found 427.4 [M+H]$^+$.

Example 163

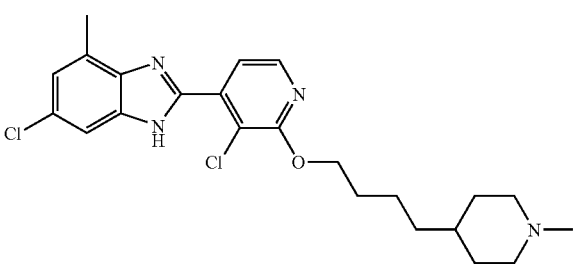

6-Chloro-2-{3-chloro-2-[4-(1-methyl-piperidin-4-yl)-butoxy]-pyridin-4-yl}-4-methyl-1H-benzoimidazole MS (electrospray): mass calculated for $C_{23}H_{28}Cl_2N_4O$, 446.16; m/z found, 446.4 [M+H]$^+$.

Example 164

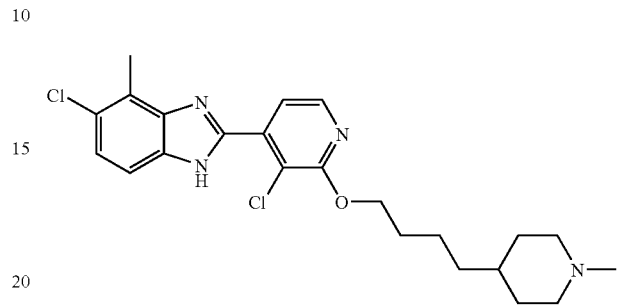

5-Chloro-2-{3-chloro-2-[4-(1-methyl-piperidin-4-yl)-butoxy]-pyridin-4-yl}-4-methyl-1H-benzoimidazole MS (electrospray): mass calculated for $C_{23}H_{28}Cl_2N_4O$, 446.16; m/z found, 446.4 [M+H]$^+$.

Example 165

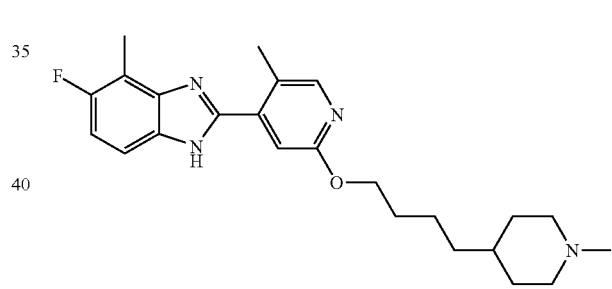

5-Fluoro-4-methyl-2-{5-methyl-2-[4-(1-methyl-piperidin-4-yl)-butoxy]-pyridin-4-yl}-1H-benzoimidazole A. 5-Bromo-2-[4-(1-methyl-piperidin-4-yl)-butoxy]-pyridine. To a solution of 4-(1-methyl-piperidin-4-yl)-butan-1-ol (14.9 g, 86.9 mmol, 1.0 equiv) in DMF (180 mL) at 0° C. was added sodium hydride (60% dispersion in oil 4.86 g, 122 mmol, 1.4 equiv). The mixture was warmed to rt for 1 h, and then was re-cooled to 0° C. A solution of 5-bromo-2-chloro-pyridine (20.6 g, 86.9 mmol, 1.0 equiv) in DMF (20 mL) was added dropwise. The mixture was stirred at rt for 18 h, then was diluted with water (100 mL) and satd. aq. NaHCO$_3$ (250 mL). The mixture was extracted with chloroform (3×100 mL) and the combined extracts were concentrated. Purification by Method 2 afforded 8.82 g of 5-bromo-2-[4-(1-methyl-piperidin-4-yl)-butoxy]-pyridine as a mixture with several unidentified impurities. MS (electrospray): mass calculated for $C_{15}H_{23}BrN_2O$, 326.10; m/z found, 327.3 [M+H]$^+$.

B. 5-Fluoro-4-methyl-2-{5-methyl-2-[4-(1-methyl-piperidin-4-yl)-butoxy]-pyridin-4-yl}-1H-benzoimidazole. To a solution of LDA (2.0 M in THF, 18.2 mL, 36.4 mmol, 2.2 equiv) at −78° C. in a oven dried 100 mL round bottom flask was added a solution of 5-bromo-2-[4-(1-methyl-piperidin-4-yl)-butoxy]-pyridine (5.40 g, 16.6 mmol, 1.0 equiv) in THF (20 mL) dropwise. The solution was stirred at −78° C. for 45 min, and then DMF (6.05 mL, 82.8 mmol, 5.0 equiv) was added dropwise. The solution was quenched with satd. aq. NaHCO₃ (25 mL) and extracted with chloroform (3×50 mL). The combined extracts were washed with brine and concentrated. The crude residue was diluted with ethanol (5 mL) and treated with sodium bisulfite (2.1 g). The precipitate that formed was collected by vacuum filtration and washed with diethyl ether. The solid was diluted with chloroform (50 mL) and washed with satd. aq. NaHCO₃ (50 mL). The organic layer was dried (Na₂SO₄), filtered and concentrated to afford 5-bromo-2-[4-(1-methyl-piperidin-4-yl)-butoxy]-pyridine-4-carbaldehyde as a mixture with several other unidentified products. A solution of this crude mixture in methanol (15 mL) was treated with conc. H₂SO₄ (1 mL) and the resulting solution was stirred for 14 h. The mixture was diluted with satd. aq. NaHCO₃ (25 mL) and extracted with chloroform (3×25 mL). The combined extracts were concentrated to provide 5-bromo-4-dimethoxymethyl-2-[4-(1-methyl-piperidin-4-yl)-butoxy]-pyridine. A −78° C. solution of the pyridine (2.0 g, 5.0 mmol, 1.0 equiv) in THF (50 mL) was treated with n-butyllithium (2.5 M in hexanes, 2.2 mL, 5.5 mmol, 1.1 equiv). The solution was stirred for 30 min, and then methyl iodide (0.312 g, 5.0 mmol, 1.0 equiv) was added. After 30 min, the reaction was quenched with satd. aq. NaHCO₃ (10 mL) and extracted with chloroform (3×25 mL). The combined extracts were dried (Na₂SO₄), filtered, and concentrated to afford 4-dimethoxymethyl-5-methyl-2-[4-(1-methyl-piperidin-4-yl)-butoxy]-pyridine as a crude mixture. A solution of 4-dimethoxymethyl-5-methyl-2-[4-(1-methyl-piperidin-4-yl)-butoxy]-pyridine (0.64 mg) in THF (100 mL) was treated with 1.0 M HCl (20 mL) and the mixture was stirred for 4 h. The mixture was diluted with satd. aq. NaHCO₃ and extracted with chloroform (3×100 mL). The combined extracts were dried (Na₂SO₄), filtered, and concentrated to provide 5-methyl-2-[4-(1-methyl-piperidin-4-yl)-butoxy]-pyridine-4-carbaldehyde. A portion of this aldehyde (110 mg), 4-fluoro-3-methyl-benzene-1,2-diamine (60 mg), and Na₂S₂O₅ (100 mg) were stirred in DMF (2 mL) at 90° C. for. 36 h. The reaction mixture was concentrated and purified by reverse phase HPLC to provide the title compound. MS (electrospray): mass calculated for $C_{24}H_{31}FN_4O$, 410.25; m/z found, 411.5 [M+H]⁺. ¹H NMR (400 MHz, CD₃OD): 8.17 (s, 1H), 7.54-7.43 (m, 1H), 7.19-7.05 (m, 2H), 4.34 (t, J=6.4 Hz, 2H), 3.53-3.43 (m, 2H), 3.04-2.89 (m, 2H), 2.84 (s, 3H), 2.53 (s, 3H), 2.43 (s, 3H), 2.06-1.95 (m, 2H), 1.85-1.76 (m, 2H), 1.64-1.29 (m, 7H).

The following compounds in Examples 166-168 were prepared according to the procedures described for Example 165.

Example 166

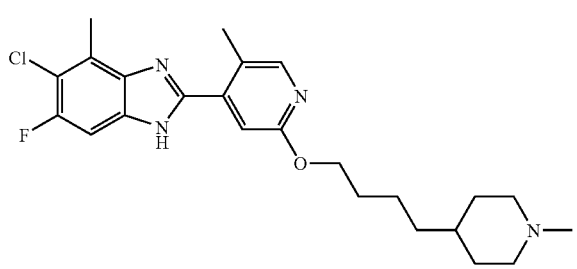

5-Chloro-6-fluoro-2-{5-methyl-2-[4-(1-methyl-piperidin-4-yl)-butoxy]-pyridin-4-yl}-1H-benzoimidazole MS (electrospray): mass calculated for $C_{23}H_{28}ClFN_4O$, 430.19; m/z found, 431.4 [M+H]⁺.

Example 167

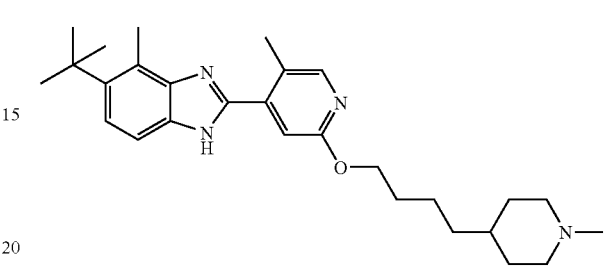

5-tert-Butyl-2-{5-methyl-2-[4-(1-methyl-piperidin-4-yl)-butoxy]-pyridin-4-yl}-1H-benzoimidazole MS (electrospray): mass calculated for $C_{27}H_{38}N_4O$, 434.30; m/z found, 435.5 [M+H]⁺.

Example 168

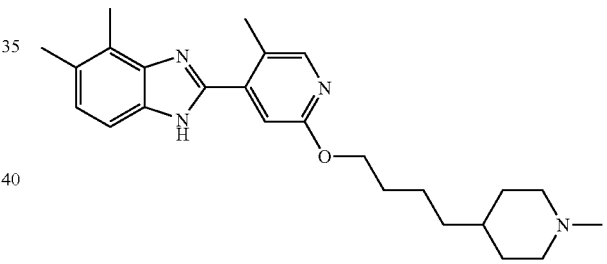

4,5-Dimethyl-2-{5-methyl-2-[4-(1-methyl-piperidin-4-yl)-butoxy]-pyridin-4-yl}-1H-benzoimidazole MS (electrospray): mass calculated for $C_{25}H_{34}N_4O$, 406.27; m/z found, 407.5 [M+H]⁺.

Example 169

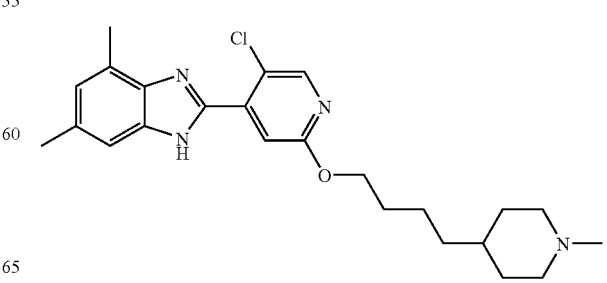

2-{5-Chloro-2-[4-(1-methyl-piperidin-4-yl)-butoxy]-pyridin-4-yl}-4,6-dimethyl-1H-benzoimidazole The title compound was prepared as described in Example 165, substituting hexachloroethane for methyl iodide. MS (electrospray): mass calculated for $C_{24}H_{31}ClN_4O$, 426.22; m/z found, 427.4 $[M+H]^+$.

The following compounds in Examples 170-172 were prepared according to the procedures described in Example 169.

Example 170

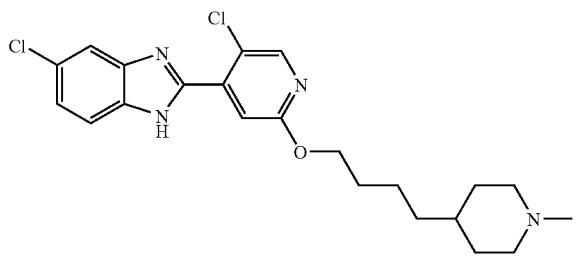

5-Chloro-2-{5-chloro-2-[4-(1-methyl-piperidin-4-yl)-butoxy]-pyridin-4-yl}-1H-benzoimidazole MS (electrospray): mass calculated for $C_{22}H_{26}Cl_2N_4O$, 432.15; m/z found 433.3 $[M+H]^+$.

Example 171

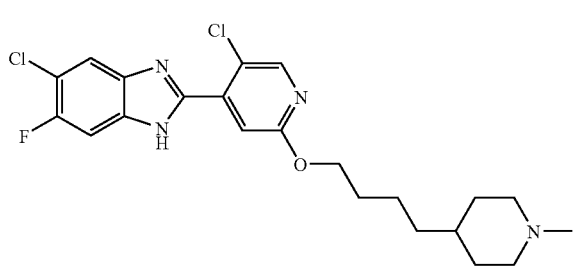

5-Chloro-2-{5-chloro-2-[4-(1-methyl-piperidin-4-yl)-butoxy]-pyridin-4-yl}-6-fluoro-1H-benzoimidazole MS (electrospray): mass calculated for $C_{22}H_{25}Cl_2FN_4O$, 450.14; m/z found 451.3 $[M+H]^+$.

Example 172

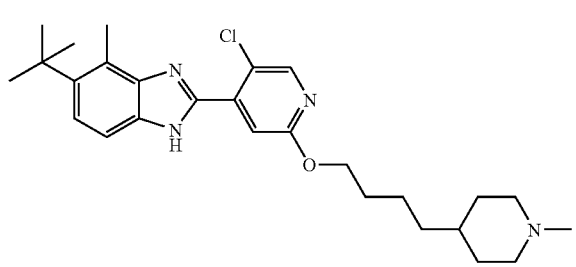

5-tert-Butyl-2-{5-chloro-2-[4-(1-methyl-piperidin-4-yl)-butoxy]-pyridin-4-yl}-1H-benzoimidazole MS (electrospray): mass calculated for $C_{26}H_{35}ClN_4O$, 454.25; m/z found 455.5 $[M+H]^+$.

The following compounds in Examples 173-175 were prepared according to the procedures described for Example 128.

Example 173

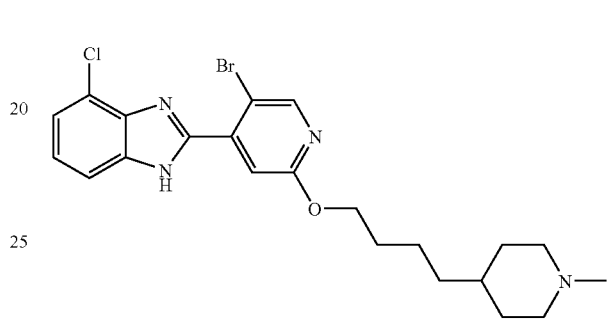

2-{5-Bromo-2-[4-(1-methyl-piperidin-4-yl)-butoxy]-pyridin-4-yl}-4-chloro-1H-benzoimidazole MS (electrospray): mass calculated for $C_{22}H_{26}BrClN_4O$, 476.10; m/z found 477.3 $[M+H]^+$.

Example 174

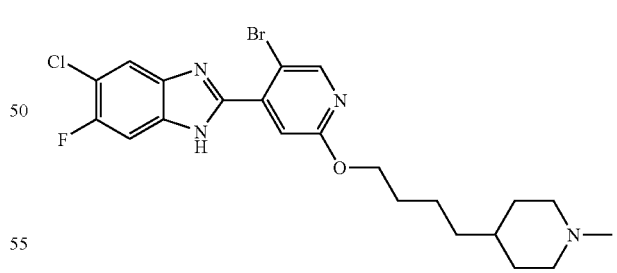

2-{5-Bromo-2-[4-(1-methyl-piperidin-4-yl)-butoxy]-pyridin-4-yl}-5-chloro-6-fluoro-1H-benzoimidazole MS (electrospray): mass calculated for $C_{22}H_{25}BrClFN_4O$, 494.09; m/z found 495.3 $[M+H]^+$.

Example 175

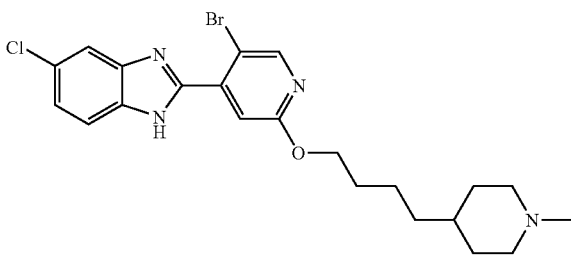

2-{5-Bromo-2-[4-(1-methyl-piperidin-4-yl)-butoxy]-pyridin-4-yl}-5-chloro-1H-benzoimidazole MS (electrospray): mass calculated for $C_{22}H_{26}BrClN_4O$, 476.10; m/z found 477.3 [M+H]$^+$.

Example 176

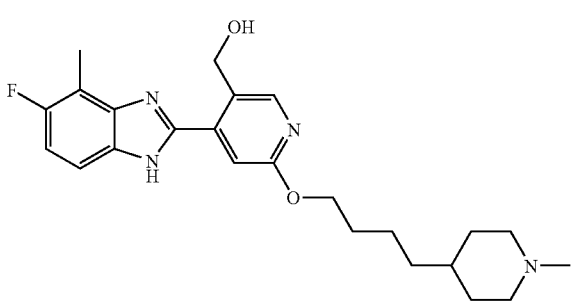

{2-(5-Fluoro-4-methyl-1H-benzoimidazol-2-yl)-5-[3-(1-methyl-piperidin-4-yl)-propoxy]-phenyl}-methanol A. 4-[3-(4-Bromo-3-[1,3]dioxan-2-yl-phenoxy)-Propyl]-1-methyl-piperidine. To a solution of 3-(1-methyl-piperidin-4-yl)-propan-1-ol (7.07 g, 45 mmol, 1.0 equiv) and methanesulfonyl chloride (4.18 mL, 54 mmol, 1.2 equiv) in dichloromethane (100 mL) at 0° C. was added triethylamine (9.41 mL, 68 mmol, 1.5 equiv). The reaction mixture, which was allowed to warm to rt, was stirred for 30 min and then poured into satd. aq. NaHCO$_3$. The aqueous mixture was extracted with chloroform and then ethyl acetate. The combined extracts were dried (Na$_2$SO$_4$), filtered, and concentrated. The residue was dissolved in acetonitrile (100 mL) and 4-bromo-3-[1,3]dioxan-2-yl-phenol (11.7 g, 45 mmol, 1.0 equiv) and cesium carbonate (29.2 mg, 90 mmol, 2.0 equiv) were added. The mixture was stirred at rt for 12 h, then warmed to 50° C. for 1.0 h. The mixture was poured into satd. aq. NaHCO$_3$ and extracted with ethyl acetate (2×) and chloroform. The combined extracts were dried (Na$_2$SO$_4$), filtered, and concentrated. Purification by Method 2 afforded 4.82 g (27%) of the title compound. $^1$H NMR (400 MHz, CD$_3$OD): 7.43 (d, J=8.8 Hz, 1H), 7.19 (d, J=3.1 Hz, 1H), 6.83 (dd, J=8.8, 3.1 Hz, 1H), 5.72 (s, 1H), 4.27-4.19 (m, 2H), 4.10-4.00 (m, 2H), 3.97 (t, J=6.4 Hz, 2H), 2.93-2.85 (m, 2H), 2.28 (s, 3H), 2.25-2.11 (m, 1H), 2.07-1.97 (m, 2H), 1.85-1.72 (m, 4H), 1.52-1.21 (m, 6H).

B. 2-{2-[1,3]Dioxan-2-yl-4-[3-(1-methyl-piperidin-4-yl)-propoxy]-phenyl}-5-fluoro-4-methyl-1H-benzoimidazole.

To a stirred solution of 4-[3-(4-bromo-3-[1,3]dioxan-2-yl-phenoxy)-propyl]-1-methyl-piperidine (4.82 g, 12.4 mmol, 1.0 equiv) in THF (62 mL) at −78° C. was added 2.5 M n-butyllithium in hexanes (22 mL, 55 mmol, 4.4 equiv). The resulting orange solution was stirred for 30 min then DMF (9.6 mL, 124 mmol, 10.0 equiv) was added. The solution was warmed to rt and stirred for 1.0 h then re-cooled to −78° C. and satd. aq. NaHCO$_3$ was added. The mixture was warmed to rt, poured into water, and extracted with ethyl acetate. The combined extracts were dried (Na$_2$SO$_4$), filtered, and concentrated. The crude residue was partially purified by Method 2. The resultant 2-[1,3]dioxan-2-yl-4-[3-(1-methyl-piperidin-4-yl)-propoxy]-benzaldehyde (491 mg, 1.41 mmol, 1.0 equiv) was stirred with 4-fluoro-3-methyl-benzene-1,2-diamine (198 mg, 1.41 mmol, 1.0 equiv) and Na$_2$S$_2$O$_5$ (350 mg, 1.84 mmol, 1.3 equiv) in DMF (7.0 mL) at 90° C. for 2 h. The mixture was loaded onto silica gel and purified by Method 2 to afford 509 mg (77%) of the title compound. MS (electrospray): mass calculated for $C_{27}H_{34}FN_3O_3$, 467.26; m/z found, 468.4 [M+H]$^+$. $^1$H NMR (400 MHz, CD$_3$OD): 7.62 (d, J=8.5 Hz, 1H), 7.44-7.37 (m, 1H), 7.35 (d, J=2.7 Hz, 1H), 7.09-6.99 (m, 2H), 5.97 (s, 1H), 4.19-4.13 (m, 2H), 4.09 (t, J=6.4 Hz, 2H), 3.95-3.86 (m, 2H), 2.95-2.87 (m, 2H), 2.53 (s, 3H), 2.30 (s, 3H), 2.22-1.99 (m, 3H), 1.93-1.76 (m, 4H), 1.51-1.22 (m, 6H).

C. {2-(5-Fluoro-4-methyl-1H-benzoimidazol-2-yl)-5-[3-(1-methyl-piperidin-4-yl)-propoxy]-phenyl}-methanol.

2-{2-[1,3]Dioxan-2-yl-4-[3-(1-methyl-piperidin-4-yl)-propoxy]-phenyl}-5-fluoro-4-methyl-1H-benzoimidazole (401 mg) and p-toluenesulfonic acid (1.0 g) were stirred in a solution of acetone (10 mL) and water (1.0 mL) at reflux for 16 h. The solution was poured into satd. aq. NaHCO$_3$ and extracted with ethyl acetate. The combined extracts were dried (Na$_2$SO$_4$), filtered, and concentrated. A portion of the crude residue (43.3 mg) was dissolved in ethanol (2.0 mL) and sodium borohydride (300 mg) was added. The mixture was stirred for 1.0 h and then poured into satd. aq. NaHCO$_3$. The aqueous mixture was extracted with ethyl acetate and the combined extracts were dried (Na$_2$SO$_4$), filtered, and concentrated. The residue was purified by Method 2 to afford 6.0 mg of the title compound. MS (electrospray): mass calculated for $C_{24}H_{30}FN_3O_2$, 411.23; m/z found, 412.4 [M+H]$^+$. $^1$H NMR (400 MHz, CD$_3$OD): 7.82 (d, J=8.6 Hz, 1H), 7.43-7.33 (m, 1H), 7.14-7.10 (m, 1H), 7.06-6.97 (m, 2H), 4.72 (s, 2H), 4.09 (t, J=6.3 Hz, 2H), 2.94-2.86 (m, 2H), 2.52 (s, 3H), 2.29 (s, 3H), 2.11-1.99 (m, 2H), 1.91-1.74 (m, 4H), 1.52-1.42 (m, 2H), 1.41-1.21 (m, 4H).

Example 177

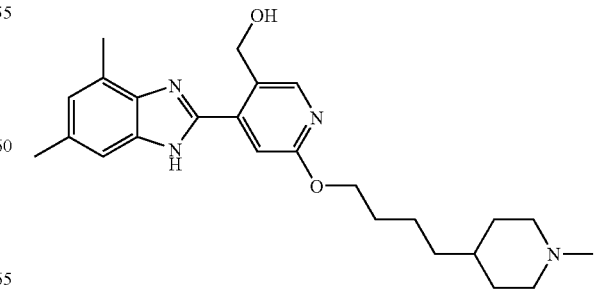

{4-(4,6-Dimethyl-1H-benzoimidazol-2-yl)-6-[4-(1-methyl-piperidin-4-yl)-butoxy]-pyridin-3-yl}-methanol 5-Bromo-4-dimethoxymethyl-2-[4-(1-methyl-piperidin-4-yl)-butoxy]-pyridine (0.5 g, 1.25 mmol, 1.0 equiv) was dissolved in THF (6 mL) and cooled to −78° C. A 2.5 M solution of n-butyllithium in hexanes (0.6 mL, 1.5 mmol, 1.2 equiv) was added dropwise. The solution was stirred for 45 min, and then DMF (0.55 mL, 1.25 mmol, 1.0 equiv) was added. After 1 h, sodium borohydride (38 mg, 1.36 mmol, 1.1 equiv) was added. The mixture was allowed to warm to −40° C. for 30 min, then was quenched with satd. aq. NaHCO$_3$ (10 mL). The mixture was extracted with chloroform (3×30 mL), and the combined extracts were dried (Na$_2$SO$_4$), filtered, and concentrated to afford {4-dimethoxymethyl-6-[4-(1-methyl-piperidin-4-yl)-butoxy]-pyridin-3-yl}-methanol as a crude mixture. This crude material (88 mg) was dissolved in THF (3 mL) and 1.0 M HCl (3 mL) was added portionwise over 3 h at 60° C. The mixture was cooled, satd. aq. NaHCO$_3$ was added, and the mixture was extracted with chloroform (3×30 mL). The combined extracts were dried (Na$_2$SO$_4$), filtered, and concentrated. A portion of the resulting crude 5-hydroxymethyl-2-[4-(1-methyl-piperidin-4-yl)-butoxy]-pyridine-4-carbaldehyde (33 mg), 3,5-dimethyl-benzene-1,2-diamine (22 mg), and Na$_2$S$_2$O$_5$ (36 mg) were stirred in DMF (2 mL) at 90° C. for 36 h. The reaction mixture was purified by Method 2 to afford 5.3 mg of the title compound. MS (electrospray): mass calculated for C$_{25}$H$_{34}$N$_4$O$_2$, 422.27; m/z found, 423.5 [M+H]$^+$. $^1$H NMR (400 MHz, CD$_3$OD): 8.21 (s, 1H), 7.30 (s, 1H), 7.23 (br s, 1H), 6.95 (br s, 1H), 4.68 (s, 2H), 4.34 (t, J=6.4 Hz, 2H), 2.95-2.82 (m, 2H), 2.57 (s, 3H), 2.44 (s, 3H), 2.27 (s, 3H), 2.11-1.98 (m, 2H), 1.86-1.68 (m, 4H), 1.57-1.44 (m, 2H), 1.39-1.15 (m, 5H).

Biological Examples

Binding Assay on Recombinant Human Histamine H$_4$ Receptor

SK-N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 s at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine H$_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, K$_i$ values were calculated, based on an experimentally determined K$_D$ value of 5 nM and a ligand concentration of 5 nM, according to Y. -C. Cheng and W. H. Prusoff (*Biochem. Pharmacol.* 1973, 22(23):3099-3108): K$_i$=(IC$_{50}$)/(1+([L]/(K$_D$)).

Binding Assay Results

TABLE

| EX | K$_i$ (nM) |
|---|---|
| 1 | 46 |
| 2 | 9 |
| 3 | 21 |
| 4 | 26 |
| 5 | 43 |
| 6 | 61 |
| 7 | 66 |
| 8 | 138 |
| 9 | 250 |
| 10 | 89 |
| 11 | 59 |
| 12 | 224 |
| 13 | 257 |
| 14 | 497 |
| 15 | 22 |
| 16 | 16 |
| 17 | 136 |
| 18 | 64 |
| 19 | 18 |
| 20 | 65 |
| 21 | 84 |
| 22 | 1 |
| 23 | 103 |
| 24 | 109 |
| 25 | 119 |
| 26 | 142 |
| 27 | 74 |
| 28 | 9 |
| 29 | 326 |
| 30 | 22 |
| 31 | 9 |
| 32 | 93 |
| 33 | 81 |
| 34 | 112 |
| 35 | 28 |
| 36 | 35 |
| 37 | 36 |
| 38 | 65 |
| 39 | 66 |
| 40 | 74 |
| 41 | 78 |
| 42 | 79 |
| 43 | 82 |
| 44 | 87 |
| 45 | 110 |
| 46 | 113 |
| 47 | 129 |
| 48 | 154 |
| 49 | 173 |
| 50 | 187 |
| 51 | 278 |
| 52 | 641 |
| 53 | 872 |
| 54 | 30 |
| 55 | 203 |
| 56 | 324 |
| 57 | 17 |
| 58 | 101 |
| 59 | 86 |
| 60 | 39 |
| 61 | 49 |
| 62 | 51 |
| 63 | 57 |
| 64 | 121 |
| 65 | 157 |
| 66 | 32 |
| 67 | 1 |
| 68 | 5 |
| 69 | 6 |
| 70 | 20 |
| 71 | 26 |
| 72 | 5 |
| 73 | 69 |
| 74 | 22 |

TABLE-continued

| EX | $K_i$ (nM) |
|---|---|
| 75 | 28 |
| 76 | 121 |
| 77 | 4 |
| 78 | 21 |
| 79 | 14 |
| 80 | 128 |
| 81 | 150 |
| 82 | 23 |
| 83 | 161 |
| 84 | 267 |
| 85 | 39 |
| 86 | 103 |
| 87 | 61 |
| 88 | 52 |
| 89 | 120 |
| 90 | 73 |
| 91 | 633 |
| 92 | 113 |
| 93 | 7 |
| 94 | 13 |
| 95 | 4 |
| 96 | 1 |
| 97 | 25 |
| 98 | 28 |
| 99 | 38 |
| 100 | 41 |
| 101 | 55 |
| 102 | 321 |
| 103 | 41 |
| 104 | 266 |
| 105 | 85 |
| 106 | 12 |
| 107 | 26 |
| 108 | 31 |
| 109 | 6 |
| 110 | 6 |
| 111 | 21 |
| 112 | 6 |
| 113 | 4 |
| 114 | 11 |
| 115 | 4 |
| 116 | 12 |
| 117 | 5 |
| 118 | 4 |
| 119 | 51 |
| 120 | 94 |
| 121 | 60 |
| 122 | 71 |
| 123 | 67 |
| 124 | 86 |
| 125 | 77 |
| 126 | 427 |
| 127 | 773 |
| 128 | 3 |
| 129 | 5 |
| 130 | 5 |
| 131 | 3 |
| 132 | 5 |
| 133 | 12 |
| 134 | 117 |
| 135 | 47 |
| 136 | 1 |
| 137 | 3 |
| 138 | 46 |
| 139 | 69 |
| 140 | 144 |
| 141 | 60 |
| 142 | 73 |
| 143 | 6 |
| 144 | 8 |
| 145 | 3 |
| 146 | 5 |
| 147 | 8 |
| 148 | 17 |
| 149 | 4 |
| 150 | 19 |

TABLE-continued

| EX | $K_i$ (nM) |
|---|---|
| 151 | 21 |
| 152 | 117 |
| 153 | 179 |
| 154 | 111 |
| 155 | 13 |
| 156 | 20 |
| 157 | 28 |
| 158 | 21 |
| 159 | 19 |
| 160 | 53 |
| 161 | 20 |
| 162 | 15 |
| 163 | 12 |
| 164 | 7 |
| 165 | 3 |
| 166 | 6 |
| 167 | 4 |
| 168 | 6 |
| 169 | 1 |
| 170 | 5 |
| 171 | 12 |
| 172 | 1 |
| 173 | 21 |
| 174 | 31 |
| 175 | 6 |
| 176 | 4 |
| 177 | 4 |

Mast Cell Chemotaxis Assay

Mast cell accumulation in mucosal epithelia is a well-known characteristic of allergic rhinitis and asthma. In addition, it is known that mast cell numbers increase in a number of inflammatory conditions. Some of this is due to chemotaxis of mast cells to the sites of inflammation. This chemotaxis to specific agents can be mimicked in vitro. Transwells (Costar, Cambridge, Mass.) of a pore size 8 μm are coated with 100 μL of 100 ng/mL human fibronectin (Sigma) for 2 h at room temperature. After removal of the fibronectin, 600 μL of RPMI with 5% BSA, in the presence of 10 μM histamine, is added to the bottom chamber. To test the various histamine receptor (HR) antagonists, 10 μM and/or 1 μM solutions of the test compounds are added to the top and bottom chambers. Mast cells ($2 \times 10^5$/well) are added to the top chamber. The plates are incubated for 3 h at 37° C. Transwells are removed and the cells in the bottom chamber are counted for sixty seconds using a flow cytometer. HR inhibition data are thus obtained.

Cell-type Distribution of $H_4$ Expression

RNA was prepared from the different cells using an RNeasy kit (Qiagen, Valencia, Calif.) according to the manufacturer's instructions. Total RNA was extracted from purified human cells using the RNeasy kit (Qiagen, Valencia, Calif.) and reverse transcribed to cDNA using the RT reaction kit (Invitrogen) according to the manufacturer's instructions. $H_4$ receptor RNA was detected by RT-PCR using human $H_4$ receptor-specific primers 5'-ATGCCAGATACTAATAG-CACA and 5'-CAGTCGGTCAGTATCTTCT. The amplified PCR band for $H_4$ receptor is 1170 bp.

Results

The RT-PCR results indicate that the $H_4$ receptor is expressed on mast cells, dendritic cells, basophils, and eosinophils. These positive results are consistent with the published literature (e.g. Oda et al., Nguyen et al., and Morse et al. in the Background section). Accumulation of mast cells and eosinophils in affected tissues is one of the principal characteristics of allergic rhinitis and asthma. Since $H_4$ receptor expression is found in these cell types, $H_4$ receptor signalling is likely to mediate the infiltration of mast cells and eosinophils in response to histamine. The following table reports the Cell-type Distribution of $H_4$ Expression by RT-PCR.

| Species | Cell Type | $H_4$ |
|---|---|---|
| Human | Eosinophils | + |
| | Immature Dendritic Cells | + |
| | Mature Dendritic Cells | + |
| | Mast Cells | + |
| | Basophils | + |
| | CD14$^+$ Monocytes | − |
| | CD4$^+$ T Cells | + |
| | CD8$^+$ T Cells | − |
| | B Cells | − |
| | Neutrophils | − |
| Mouse/(Rat) | Eosinophils | + |
| | Peritoneal Mast Cells (Rat) | + |
| | Bone Marrow-Derived Mast Cells | + |
| | Immature Dendritic Cells | + |
| | Mature Dendritic Cells | + |
| | Bone Marrow-Derived Macrophages | − |
| | Peritoneal Macrophages | − |
| | CD4$^+$ T Cells | − |
| | CD8$^+$ T Cells | − |
| | B Cells | − |

The Inhibition of Eosinophil Shape Change by Histamine $H_4$ Receptor Antagonists Eosinophil accumulation in sites of allergic reaction is a well-known characteristic of allergic rhinitis and asthma. This example demonstrates that histamine $H_4$ receptor antagonists can block the shape change response in human eosinophils in response to histamine. Shape change is a cellular characteristic that precedes eosinophil chemotaxis.

Methods

Human granulocytes were isolated from human blood by a Ficoll gradient. The red blood cells were lysed with 5-10× Qiagen lysis buffer at room temperature for 5-7 min. Granulocytes were harvested and washed once with FACS buffer. The cells were resuspended at a density of $2\times10^6$ cells/mL in reaction buffer. To test inhibition by specific histamine receptor antagonists, 90 μL of the cell suspension (~$2\times10^5$ cells) was incubated with 10 μM of one of the various test compound solutions. After 30 min, 11 μL of one of the various concentrations of histamine was added. Ten minutes later the cells were transferred to ice and fixed with 250 μL of ice-cold fixative buffer (2% formaldehyde) for 1 min. The shape change was quantitated using a gated autofluoescence forward scatter assay (GAFS) (S. A. Bryan et al., *Am. J. Respir. Crit. Care Med.* 2002, 165(12):1602-1609).

Results—Histamine Mediates Eosinophil Shape Change through $H_4$ Receptor

The change in shape of eosinophils is due to cytoskeletal changes that preceed chemotaxis and thus is a measure of chemotaxis. The data in the following table show that histamine induces a dose-dependent shape change in eosinophils. Histamine receptor (HR) antagonists were used to sort out which histamine receptor is responsible for the shape change. Antagonists specific for the histamine $H_1$ receptor (diphenhydramine) or the $H_2$ receptor (ranatidine) did not alter the histamine-induced shape change. However, a dual H3/$H_4$ antagonist (thioperamide) and a specific histamine $H_4$ receptor antagonist ((5-chloro-1H-indol-2-yl)-(4-methyl-piperazin-1-yl)-methanone, $K_i$=5 nM) inhibited histamine-induced eosinophil shape change with an $IC_{50}$ of 1.5 and 0.27 μM, respectively.

| Histamine | Fold Change | | | | |
|---|---|---|---|---|---|
| (μM): | 10 | 1 | 0.1 | 0.01 | 0 |
| No HR Antagonist | 1.34 | 1.31 | 1.21 | 1.01 | 1.00 |
| 10 μM $H_4$ Antagonist | 1.09 | 1.05 | 1.05 | 1.01 | 1.00 |
| 10 μM Thiop | 1.08 | 1.05 | 1.01 | 1.04 | 1.00 |
| 10 μM Diphen | 1.63 | 1.50 | 1.18 | 1.03 | 1.00 |
| 10 μM Ranat | 1.64 | 1.49 | 1.21 | 1.04 | 1.00 |

The Inhibition of Eosinophil Chemotaxis by Histamine $H_4$ Receptor Antagonists

Eosinophil accumulation in sites of allergic reaction is a well-known characteristic of allergic rhinitis and asthma. Eosinophils are purified from human blood with standard methods. Chemotaxis assays are carried out using transwells (Costar, Cambridge, Mass.) of a pore size 5 μm coated with 100 μL of 100 ng/mL human fibronectin (Sigma) for 2 h at room temperature. After removal of the fibronectin, 600 μL of RPMI with 5% BSA in the presence of histamine (ranging from 1.25-20 μM) is added to the bottom chamber. To test the various histamine receptor antagonists 10 μM of the test compounds can be added to the top and bottom chambers. Eosinophils will be added to the top chamber whereas histamine or chemotactic factors will be placed in the lower chamber. The plates are incubated for 3 h at 37° C. Transwells are removed and the number of cells in the bottom chamber can be counted for 60 s using a flow cytometer, or can be quantitated by using Giemsa staining.

The Inhibition of Zymosan-Induced Peritonitis in Mice by Histamine $H_4$ Receptor Antagonists It has been demonstrated that histamine $H_4$ receptor antagonists can block the peritonitis induced by zymosan, which is the insoluble polysaccharide component on the cell wall of *Saccharomyces cerevisiae*. This is commonly used to induce peritonitis in mice and appears to act in a mast cell-dependent manner. Compounds of the present invention can be tested in such a model to demonstrate their use as anti-inflammatory agents. At time 0 mice are given compound or PBS, either s.c. or p.o. Fifteen minutes later each mouse receives 1 mg zymosan A (Sigma) i.p. The mice are sacrificed 4 h later, and the peritoneal cavities are washed with 3 mL of PBS containing 3 mM EDTA. The number of migrated leukocytes is determined by taking an aliquot (100 μL) of the lavage fluid and diluting 1:10 in Turk's solution (0.01% crystal violet in 3% acetic acid). The samples are then vortexed, and 10 μL of the stained cell solution is placed in a Neubauer haemocytometer. Differential cell counts are performed using a light microscope (Olympus B061). In view of their chromatic characteristics and their nucleus and cytoplasm appearance, polymorphonuclear leukocytes (PMN; >95% neutrophils) can be easily identified. Treatment with zymosan increases the number of neutrophils, which is representative of an inflammatory response. Treatment with $H_4$ receptor antagonist blocks this incease.

Inhibition of Mast Cell Chemotaxis by $H_4$ Receptor Antagonist in an Animal Model of Asthma and Allergic Rhinitis An animal model is used to test the observation that mast cells accumulate in response to allergic inflammation and that this can be blocked by $H_4$ receptor antagonists. Compounds of the present invention can be tested in this model to demonstrate their use as treatments for allergic rhinitis or asthma. Mice are sensitized by intraperitoneal injection of ovalbumin/Alum (10 μg in 0.2 ml Al(OH)$_3$, 2%) on Day 0 and Day 14. On Day 21 through 23 mice are challenged by PBS or ovalbumin, and sacrificed 24 h after the last challenge on Day 24. A section of the trachea is removed and fixed in formalin. Paraffin embedding and longitudinal sectioning of tracheas are performed followed by staining of mast cells with toluidine blue. Alternatively, trachea are frozen in OCT for frozen sectioning, and mast cells are identified by IgE staining. Mast cells are quantified as sub-mucosal or sub-epithelial depending on their location within each tracheal section. Exposure to allergen should increase the number of sub-epithelial mast cells, and this effect is blocked by $H_4$ receptor antagonists.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A compound of formula (II):

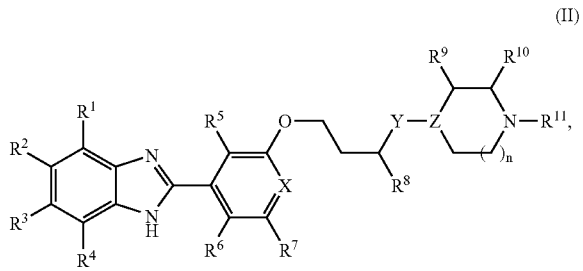

wherein
X is N;
Y is O, $NR^{12}$, or $CR^{12}R^{13}$;
Z is $CR^{14}$;
n is 1;
each of $R^{14}$ is, independently from other substituent assignments, H, $C_{1-4}$alkyl, $C_{2-5}$alkenyl, $C_{2-5}$alkynyl, $C_{3-6}$cycloalkyl, —$C_{1-4}$alkoxy, —$C_{1-4}$alkylamino, —$C_{1-4}$ alkylthio, —$C_{1-4}$alkylsulfonyl, —$OC_{3-6}$cycloalkyl, —$OCH_2Ph$, cyano, —$CF_3$, F, Cl, Br, I, nitro, —$OCF_3$, —$SCF_3$, —$OR^c$, —$SR^c$, —$S(O)R^c$, —$SO_2R^c$, —$C(O)R^c$, phenyl, benzyl, phenethyl, —$C(O)NR^aR^c$, —$C(O)OR^c$, —$NR^aR^b$, —$CH_2NR^aR^b$ or —$CH_2OR^c$; wherein each of $R^a$, $R^b$ and $R^c$ is, independently from other substituent assignments, selected from H, $C_{1-4}$alkyl, $C_{3-6}$cycloalkyl, phenyl, ($C_{3-6}$cycloalkyl)$C_{1-2}$alkyl-, benzyl and phenethyl, or $R^a$ and $R^b$ taken together with the nitrogen to which they are attached, form a 4-7 membered heterocyclic ring HetCyc1, wherein said ring HetCyc1 has 0 or 1 additional heteroatoms selected from O, S, >NH and >$NC_{1-6}$alkyl, and wherein any phenyl, phenethyl, benzyl, alkyl or cycloalkyl moiety in any of said $R^{1-4}$, $R^a$, $R^b$, $R^c$, and said ring HetCyc1 is optionally, and independently from other substituent assignments, substituted with 1, 2 or 3 substituents selected from $C_{1-3}$alkyl, halo, hydroxy, amino, and $C_{1-3}$alkoxy;
each of $R^{5-7}$ is, independently from other substituent assignments, H, $C_{1-6}$alkyl, F, Cl, Br, I, $CF_3$, —$OCF_3$, —$OR^c$, —$SR^c$, —$S(O)R^c$, $SO_2R^c$, $C_{1-4}$alkoxy cyano nitro, —$C(O)NR^aR^b$, —$C(O)$phenyl, —$C(O)C_{1-6}$alkyl, —$S(O)C_{1-4}$alkyl, or —$SO_2C_{1-4}$alkyl; or, $R^7$ and $R^6$ for a compound of formula (II) taken together with the carbon atoms to which they are attached form a cyclic structure Cyc2 selected from aryl, heteroaryl, 5- or 6-membered carbocycle, and 5- or 6-membered heterocycle with 1 or 2 heteroatoms, wherein said cyclic structure Cyc2 is, independently from other substituent assignments, substituted with 0, 1, or 2 substituents selected from $C_{1-3}$alkyl, halo, hydroxy, amino, and $C_{1-3}$alkoxy;
$R^8$ is H, $C_{1-6}$alkyl, $C_{1-4}$alkoxy, or OH;
each of $R^9$ and $R^{10}$ is, independently from other substituent assignments, H or $C_{1-6}$alkyl, or $R^9$ and $R^{10}$ taken together form a 5-6 membered cyclic structure Cyc3, wherein said cyclic structure Cyc3 is a 5- or 6-membered carbocycle or a 5- or 6-membered heterocycle with 1 or 2 heteroatoms, and wherein said cyclic structure Cyc3 is, independently from other substituent assignments, substituted with 0, 1, or 2 substituents selected from $C_{1-3}$alkyl, halo, hydroxy, amino, and $C_{1-3}$alkoxy;
$R^{11}$ is H, $C_{1-4}$alkyl;
each of $R^{12}$ and $R^{13}$ is, independently from other substituent assignments, H or $C_{1-4}$alkyl; or, when Y is $CR^{12}R^{13}$, $R^{12}$ and $R^{13}$ taken together with the carbon member to which they are attached form an optionally substituted cyclic structure Cyc4, wherein said cyclic structure Cyc4 is a 3- to 6-membered carbocycle or a 3- to 6-membered heterocycle with 0 or 1 additional heteroatoms, or $CR^{12}R^{13}$ is C=O;
$R^{14}$ is H, $C_{1-4}$alkyl, OH, or $C_{1-4}$alkoxy;
an enantiomer, diastereomer, racemate thereof, or a pharmaceutically acceptable salt, amide or ester thereof;
provided that:
when Y is O or $NR^{12}$, then $R^8$ is not OH or $C_{1-4}$alkoxy; and neither $R^1$ nor $R^4$ is $C(O)NH_2$.

2. A compound as in claim 1, wherein Y is $CR^{12}R^{13}$.

3. A compound as in claim 1, wherein Y is $CH_2$.

4. A compound as in claim 1, wherein Z is CH.

5. A compound as in claim 1, wherein $R^1$ is selected from the group consisting of H, methyl, ethyl, isopropyl, cyclopropyl, F, Cl, Br, cyano, phenyl, carboxymethyl, dimethylcarboxamido, and $CH_2OMe$.

6. A compound as in claim 1, wherein $R^1$ is H, methyl, F, or Cl.

7. A compound as in claim 1, wherein $R^2$ selected from the group consisting of H, methyl, ethyl, isopropyl, t-butyl, cyclopropyl, $CF_3$, $OCF_3$, F, Cl, Br, cyano, phenyl, carboxymethyl, dimethylcarboxamido, and benzoyl.

8. A compound as in claim 1, wherein $R^2$ is H, F, Cl, methyl, $CF_3$, $OCF_3$, or t-butyl.

9. A compound as in claim 1, wherein $R^3$ is selected from the group consisting of H, methyl, ethyl, isopropyl, t-butyl, cyclopropyl, $CF_3$, $OCF_3$, F, Cl, Br, cyano, phenyl, carboxymethyl, dimethylcarboxamido, and benzoyl.

10. A compound as in claim 1, wherein $R^3$ is H, F, Cl, methyl, $CF_3$, $OCF_3$, or t-butyl.

11. A compound as in claim 1, wherein $R^4$ is selected from the group consisting of H, methyl, ethyl, isopropyl, cyclopropyl, R, Cl, Br, cyano, phenyl, carboxymethyl, dimethylcarboxamido, and $CH_2OMe$.

12. A compound as in claim 1, wherein $R^4$ is H, methyl, F, or Cl.

13. A compound as in claim 1, wherein one or two of $R^{1-4}$ are not H.

14. A compound as in claim 1, wherein $R^5$ is H, F, Cl, methyl, or ethyl.

15. A compound as in claim 1, wherein $R^5$ is F, Cl, or methyl.

16. A compound as in claim 1, wherein $R^6$ is H, F, Cl, or methyl.

17. A compound as in claim 1, wherein $R^7$ is H, F, Cl, or methyl.

18. A compound as in claim 1, wherein $R^5$ is Cl or methyl.

19. A compound as in claim 1, wherein $R^8$ is H, methyl, or OH.

20. A compound as in claim 1, wherein $R^8$ is H.

21. A compound as in claim 1, wherein $R^9$ and $R^{10}$ are, independently, selected from the group consisting of
   a) H,
   b) methyl, ethyl, propyl, and isopropyl.

22. A compound as in claim 1, wherein each of $R^9$ and $R^{10}$ is, independently, H or methyl.

23. A compound as in claim 1, wherein $R^{11}$ is H, methyl, or ethyl.

24. A compound as in claim 1, wherein $R^{11}$ is methyl.

25. A compound selected from:
2-{5-Bromo-2-[4-(1-methyl-piperidin-4-yl)-butoxy]-pyridin-4-yl}-4-methyl-1H-benzoimidazole;
2-{5-Bromo-2-[4-(1-methyl-piperidin-4-yl)-butoxy]-pyridin-4-yl}-5-fluoro-4-methyl-1H-benzoimidazole;
2-{5-Bromo-2-[4-(1-methyl-piperidin-4-yl)-butoxy]-pyridin-4-yl}-6-chloro-4-methyl-1H-benzoimidazole;
2-{5-Bromo-2-[4-(1-methyl-piperidin-4-yl)-butoxy]-pyridin-4-yl}-4,6-dimethyl-1H-benzoimidazole;
2-{5-Bromo-2-[4-(1-methyl-piperidin-4-yl)-butoxy]-pyridin-4-yl}-4,5-dimethyl-1H-benzoimidazole;
2-{5-Bromo-2-[4-(1-methyl-piperidin-4-yl)-butoxy]-pyridin-4-yl}-5-chloro-4-methyl-1H-benzoimidazole;
2-{5-Bromo-2-[4-(1-methyl-piperidin-4-yl)-butoxy]-pyridin-4-yl}-5-tert-butyl-1H-benzoimidazole;
5-tert-Butyl-2-{2-[4-(1-methyl-piperidin-4-yl)-butoxy]-pyridin-4-yl}-1H-benzoimidazole;
2-{5-Chloro-2-[4-(1-methyl-piperidin-4-yl)-butoxy]-pyridin-4-yl}-5-fluoro-4-methyl-1H-benzoimidazole;
2-{5-Chloro-2-[4-(1-methyl-piperidin-4-yl)-butoxy]-pyridin-4-yl}-4,5-dimethyl-1H-benzoimidazole;
4,6-Dimethyl-2-{2-[4-(1-methyl-piperidin-4-yl)-butoxy]-pyridin-4-yl}-1H-benzoimidazole;
4-Methyl-2-{2-[4-(1-methyl-piperidin-4-yl)-butoxy]-pyridin-4-yl}-1H-benzoimidazole;
5-Fluoro-4-methyl-2-{2-[4-(1-methyl-piperidin-4-yl)-butoxy]-pyridin-4-yl}-1H-benzoimidazole;
4-Chloro-2-{2-[4-(1-methyl-piperidin-4-yl)-butoxy]-pyridin-4-yl}-1H-benzoimidazole;
4,5-Dimethyl-2-{2-[4-(1-methyl-piperidin-4-yl)-butoxy]-pyridin-4-yl}-1H-benzoimidazole;
6-Chloro-4-methyl-2-{2-[4-(1-methyl-piperidin-4-yl)-butoxy]-pyridin-4-yl}-1H-benzoimidazole;
5-Chloro-4-methyl-2-{2-[4-(1-methyl-piperidin-4-yl)-butoxy]-pyridin-4-yl}-1H-benzoimidazole;
5-tert-Butyl-2-[2-(4-piperidin-4-yl-butoxy)-pyridin-4-yl]-1H-benzoimidazole;
4,6-Dimethyl-2-[2-(4-piperidin-4-yl-butoxy)-pyridin-4-yl]-1H-benzoimidazole;
2-{2-[4-(1-methyl-piperidin-4-yl)-butoxy]-pyridin-4-yl}-4,5-dimethyl-1H-benzoimidazole;
4,6-Dimethyl-2-{3-methyl-2-[4-(1-methyl-piperidin-4-yl)-butoxy]-pyridin-4-yl}-1H-benzoimidazole;
4-Methyl-2-{3-methyl-2-[4-(1-methyl-piperidin-4-yl)-butoxy]-pyridin-4-yl}-1H-benzoimidazole;
6-Chloro-4-methyl-2-{3-methyl-2-[4-(1-methyl-piperidin-4-yl)-butoxy]-pyridin-4-yl}-1H-benzoimidazole;
2-{3-Chloro-2-[4-(1-methyl-piperidin-4-yl)-butoxy]-pyridin-4-yl}-4-methyl-1H-benzoimidazole;
2-{3-Chloro-2-[4-(1-methyl-piperidin-4-yl)-butoxy]-pyridin-4-yl}-4,5-dimethyl-1H-benzoimidazole;
4-Chloro-2-{3-chloro-2-[4-(1-methyl-piperidin-4-yl)-butoxy]-pyridin-4-yl}-1H-benzoimidazole;
2-{3-Chloro-2-[4-(1-methyl-piperidin-4-yl)-butoxy]-pyridin-4-yl}-5-fluoro-4-methyl-1H-benzoimidazole;
2-{3-Chloro-2-[4-(1-methyl-piperidin-4-yl)-butoxy]-pyridin-4-yl}-4,6-dimethyl-1H-benzoimidazole;
6-Chloro-2-{3-chloro-2-[4-(1-methyl-piperidin-4-yl)-butoxy]-pyridin-4-yl}-4-methyl-1H-benzoimidazole;
5-Chloro-2-{3-chloro-2-[4-(1-methyl-piperidin-4-yl)-butoxy]-pyridin-4-yl}-4-methyl-1H-benzoimidazole;
5-Fluoro-4-methyl-2-{5-methyl-2-[4-(1-methyl-piperidin-4-yl)-butoxy]-pyridin-4-yl}-1H-benzoimidazole;
5-Chloro-6-fluoro-2-{5-methyl-2-[4-(1-methyl-piperidin-4-yl)-butoxy]-pyridin-4-yl}-1H-benzoimidazole;
5-tert-Butyl-2-{5-methyl-2-[4-(1-methyl-piperidin-4-yl)-butoxy]-pyridin-4-yl}-1H-benzoimidazole;
4,5-Dimethyl-2-{5-methyl-2-[4-(1-methyl-piperidin-4-yl)-butoxy]-pyridin-4-yl}-1H-benzoimidazole;
2-{5-Chloro-2-[4-(1-methyl-piperidin-4-yl)-butoxy]-pyridin-4-yl}-4,6-dimethyl-1H-benzoimidazole;
5-Chloro-2-{5-chloro-2-[4-(1-methyl-piperidin-4-yl)-butoxy]-pyridin-4-yl}-1H-benzoimidazole;
5-Chloro-2-{5-chloro-2-[4-(1-methyl-piperidin-4-yl)-butoxy]-pyridin-4-yl}-6-fluoro-1H-benzoimidazole;
5-tert-Butyl-2-{5-chloro-2-[4-(1-methyl-piperidin-4-yl)-butoxy]-pyridin-4-yl}-1H-benzoimidazole;
2-{5-Bromo-2-[4-(1-methyl-piperidin-4-yl)-butoxy]-pyridin-4-yl}-4-chloro-1H-benzoimidazole;
2-{5-Bromo-2-[4-(1-methyl-piperidin-4-yl)-butoxy]-pyridin-4-yl}-5-chloro-6-fluoro-1H-benzoimidazole;
2-{5-Bromo-2-[4-(1-methyl-piperidin-4-yl)-butoxy]-pyridin-4-yl}-5-chloro-1H-benzoimidazole;
{4-(4,6-Dimethyl-1H-benzoimidazol-2-yl)-6-[4-(1-methyl-piperidin-4-yl)-butoxy]-pyridin-3-yl}-methanol,
and pharmaceutically acceptable salts of any of said compounds.

* * * * *

UNITED STATES PATENT AND TRADEMARK OFFICE
CERTIFICATE OF CORRECTION

PATENT NO. : 7,432,378 B2
APPLICATION NO. : 10/952989
DATED : October 7, 2008
INVENTOR(S) : James P. Edwards et al.

It is certified that error appears in the above-identified patent and that said Letters Patent is hereby corrected as shown below:

Claim 1, in column 119, line 50, that portion of the text reading "of $R^{14}$ is," should be changed to --of $R^{1-4}$ is,--.

Claim 9, in column 120, line 59, that portion of the text reading "of II, methyl, ethyl," should be changed to --of H, methyl, ethyl,--.

Claim 11, in column 120, line 66, that portion of the text reading "R, Cl, Br," should be changed to --F, Cl, Br,--.

Claim 12, in column 121, line 1, that portion of the text reading "wherein $R^4$ is II, methyl," should be changed to --wherein $R^4$ is H, methyl,--.

Claim 21, in column 121, lines 18-21, that portion of the text reading "consisting of a) H b) methyl, ethyl," should be changed to --consisting of H, methyl, ethyl,--.

Signed and Sealed this

Fourteenth Day of July, 2009

JOHN DOLL
*Acting Director of the United States Patent and Trademark Office*